US 7,459,162 B2
(12) United States Patent
Yang et al.

(10) Patent No.: US 7,459,162 B2
(45) Date of Patent: Dec. 2, 2008

(54) INFLUENZA HEMAGGLUTININ AND NEURAMINIDASE VARIANTS

(75) Inventors: Chin-Fen Yang, San Jose, CA (US); George Kemble, Saratoga, CA (US); Chongguang Liu, Fremont, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 11/368,246

(22) Filed: Mar. 6, 2006

(65) Prior Publication Data

US 2006/0252132 A1    Nov. 9, 2006

Related U.S. Application Data

(60) Provisional application No. 60/659,832, filed on Mar. 8, 2005.

(51) Int. Cl.
A61K 39/145 (2006.01)
A61K 39/12 (2006.01)
C12N 7/02 (2006.01)

(52) U.S. Cl. .......... 424/206.1; 435/239; 434/186.1; 434/199.1; 434/209.1

(58) Field of Classification Search .......... None
See application file for complete search history.

(56) References Cited

U.S. PATENT DOCUMENTS

| 3,992,522 | A | 11/1976 | Chanock et al. |
| 4,071,618 | A | 1/1978 | Konobe et al. |
| 4,634,666 | A | 1/1987 | Engleman et al. |
| 4,659,569 | A | 4/1987 | Mitsuhashi et al. |
| 5,166,057 | A | 11/1992 | Palese et al. |
| 5,690,937 | A | 11/1997 | Parkin |
| 5,716,821 | A | 2/1998 | Wertz et al. |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,922,326 | A | 7/1999 | Murphy |
| 6,033,886 | A | 3/2000 | Conzelmann |
| 6,090,391 | A | 7/2000 | Parkin |
| 6,146,642 | A | 11/2000 | Garcia-Sastre |
| 6,146,873 | A | 11/2000 | Kistner |
| 6,168,943 | B1 | 1/2001 | Rose |
| 7,037,707 | B2 | 5/2006 | Webster et al. |
| 2002/0119445 | A1 | 8/2002 | Parkin |
| 2002/0164770 | A1 | 11/2002 | Hoffmann |
| 2003/0035814 | A1 | 2/2003 | Kawaoka |
| 2003/0147916 | A1 | 8/2003 | Ferko |
| 2004/0029251 | A1 | 2/2004 | Hoffman |
| 2004/0137013 | A1 | 7/2004 | Katinger |
| 2005/0042229 | A1 | 2/2005 | Yang |
| 2005/0266026 | A1 | 12/2005 | Hoffmann |

FOREIGN PATENT DOCUMENTS

| EP | 0 702 085 | 3/1996 |
| EP | 0 863 202 | 9/1998 |
| EP | 0 864 645 | 9/1998 |
| EP | 0 780 475 | 6/1999 |
| EP | 1826269 A1 | 8/2007 |
| WO | WO-91-03552 | 3/1991 |
| WO | WO-93-21306 | 10/1993 |
| WO | WO-96-10632 | 4/1996 |
| WO | WO-96-34625 | 11/1996 |
| WO | WO-97-06270 | 2/1997 |
| WO | WO-97-12032 | 4/1997 |
| WO | WO-98-02530 | 1/1998 |
| WO | WO-98-13501 | 4/1998 |
| WO | WO-98-53078 | 11/1998 |
| WO | WO-99-02657 | 1/1999 |
| WO | WO-99-15672 | 4/1999 |
| WO | WO-00-53786 | 9/2000 |
| WO | WO-00-60050 | 10/2000 |

OTHER PUBLICATIONS

MMWR of Mar. 4, 2005, Update-Infuenza Activity-United States 2004-2005 Season.*
Daum et al, Influenza A (H3N2) Outbreak, Nepal, 2005, Emerging Infectious Diseases, vol. 11, No. 8, pp. 1186-1191.*
Banerjee and Barik, 1992, "Gene expression of vesicular stomatitis virus genome RNA", Virology. 188):417-28.
Baron and Barrett, 1997, "Rescue of Rinderpest Virus from Cloned cDNA", J. Virol. 71:1265-1271.
Beare et al., 1975, "Trials in Man with Live Recombinants Made from A/PR/8/34 (H0 N1) and Wild H3 N2 Influenza Viruses", Lancet 729-732.
Boyer et al., 1994, "Infectious transcripts and cDNA clones of RNA viruses", Virology. 198:415-26.
Brigden and Elliott, 1996, "Rescue of a Segmented Negative-Strand RNA Virus Entirely from Cloned Complementary DNAS", Proc. Natl. Acad. Sci. USA 93:15400-15404.
Buchholz et al., 1999 "Generation of Bovine Resp. Syncytial Virus (BRSV) from cDNA: BRSV NS2 Is Not Essential for Virus Replication in Tissue Culture . . . " J. Virol. 73:251-259.
Bukreyev et al., 1996, "Recovery of infectious respiratory syncytial virus expressing an additional, foreign gene", J Virol. 70(10):6634-41.
Castrucci et al., 1995, "Reverse genetics system. for generation of an influenza A virus mutant containing a deletion of the carboxyl-terminal M2..", J Virol. 69(5):2725-28.
Chen et al., 1999, "Influenza A virus NS1 protein targets poly (A)-binding protein II of the cellular 3'-end processing machinery", EMBO 18: 2273-2283.
Clarke et al., 2000, "Rescue of mumps virus from cDNAJ", J Virol. 74 (10:4831-38.

(Continued)

*Primary Examiner*—Bruce Campell
*Assistant Examiner*—Benjamin P Blumel

(57) ABSTRACT

Polypeptides, polynucleotides, methods, compositions, and vaccines comprising influenza hemagglutinin and neuraminidase variants are provided.

18 Claims, 50 Drawing Sheets

OTHER PUBLICATIONS

Collins et al., 1991, "Rescue of Synthetic Analogs of Respiratory Syncytial Virus Genomic RNA and Effect of Truncations.", Proc. Natl. Acad. Sci. USA 88:9663-9667.
Collins et al., 1995, "Production of infectious human respiratory syncytial virus from cloned cDNA confirms an essential role . . . " PNAS 92: 11563-1567.
Collins et al., 1996, "Parainfluenza Viruses", Fields Virology, Lippincott-Raven Publishers, Phila., pp. 1205-1241.
Conzelmann, 1996, "Genetic manipulation of non-segmented negative-strand RNA viruses", J Gen Virol. 77 (Pt 3):381-89.
Conzelmann et al., 1998, "Nonsegmented negative-strand RNA viruses: genetics and manipulation of viral genomes", Annu Rev Genet. 32:123-62.
Conzelmann et al., 1996, "Genetic engineering of animal RNA viruses"Trends Microbiol. 4(10):386-93.
Conzelmann et al., 1994, "Rescue of synthetic genomic RNA analogs of rabies virus by plasmid-encoded proteins", J Virol. 68(2):713-19.
De la Luna et al., 1993, "Influenza virus naked RNA can be expressed upon transfection into cells co-expressing the three subunits . . . " J. Gen. Virol. 74: 535-39.
De La Luna et al., 1995, "Influenza virus NS1 Protein Enhances the Rate of Translation Initiation of Viral mRNAs", J. of Virol. 69: 2427-2433.
De and Banerjee, 1985, "Requirements and Functions of Vesicular Stomatitis Virus L and NS Proteins in the Transcription..", Biochem. & Biophys. Res. Commun. 126:40-49.
De and Banerjee, 1993, "Rescue of synthetic analogs of genome RNA of human parainfluenza virus type 3", Virology, 96:344-48.
De and Banerjee, 1994, "Reverse genetics of negative strand RNA viruses," Indian J Biochem & Biophys. 31:367-76.
Dimock et al., 1993, "Rescue of synthetic analogs of genomic RNA and replicative-intermed. RNA of human parinfluenza virus type 3,", J Virol. 67(5):2772-78.
Dreher et al., 1984, "Mutant Viral RNAs Synthesized in vitro Show Altered Aminoacylation and Replicase Template Activities", Nature 311:171-175.
Dreher and Hall, 1988, "Mutational Analysis of the Sequence and Structural Requirements in Brome Mosaic Virus RNA for Minus Strand Promoter Activity", J. Mol. Biol. 201:31-40.
Dunn et al., 1995, "Transcription of a recombinant bunyavirus RNA template by transiently expressed bunyavirus proteins", Virology, 211:133-43.
Durbin et al., 1997, "Recovery of infectious Human Parainfluenza Virus Type 3 from cDNA", Virol. 235:323-332.
Elliot et al., 1997, Abstract # 96 10.sup.th International conference on Negative Strand Viruses.
Elliott et al., 1991, "Some highlights of virus research in 1990", J Gen Virol. 72:1761-79. Review.
Emerson and Yu, 1975, "Both NS and L Proteins are Required for in vitro RNA Synthesis by Vosicular Stomatitis Virus", J. Virol. 15:1348-1356.
Enami and Palese, 1991, "High-Efficiency Formation of Influenza Virus Transfectants", J. Virol. 65:2711-2713.
Enami et al., 1991, "An influenza virus containing nine different RNA segments", Virology. 185:291-98.
Fahey and Schooley, 1992, "Status of Immune-Based Therapies in HIV Infection and AIDS", Clin. Exp. Immunol. 88:1-5.
Fortes et al., 1994, "Influenza virus NS1 protein inhibits pre-mRNA splicing and blocks mRNA nucleocytoplasmic transport", EMBO J. 13: 704-712.
Garcia-Sastre A, Palese P, 1993. "Genetic manipulation of negative-strand RNA virus genomes", Annu Rev Microbiol. 47:765-90.
Garcin et al., 1995, "A highly recombinogenic system for the recovery of infectious sendai paramyxovirus from cDNA: generation of a novel . . . " EMBO J. 14: 6087-6094.
Goto et al.,1997, "Mutations Affecting the Sensitivity of the Influenza Virus Neuraminidase to 4-Guanidino-2,4-Dideoxy-2,3 Dehydro-N-Acetyineuraminic Acid", Virol. 238:265-72.
Grosfeld et al., 1995, "RNA replication by respiratory syncytial virus (RSV) is directed by the N., P., and L proteins: transcription . . . " J. Virol. 69(9):5677-86.

Hatada and Fukudo, 1992, "Binding of influenza A virus NS1 protein to dsRNA in vitro," J. of Gen. Virol. 73: 3325-3329.
He et al., 1997, "Recovery of Infectious SV5 from Cloned DNA and Expression of a Foreign Gene", Virol. 237:249-260.
Hoffman and Banerjee, 1997. "An Infectious Clone of Human Parainfluenza Virus Type 3", J. Virol. 71:4272-4277.
Huang et al., 1990, "Determination of Influenza virus proteins required for genome replication", J Virol. 64(11):5669-73.
Kaplan et al., 1985. "In vitro Synthesis of Infectious Poliovirus RNA", Proc. Natl. Acad. Sci. USA 82:8424-8428.
Kato et al., 1996, "Initiation of Sendai Virus Multiplication from Transfected cDNA or RNA with Negative or Positive Sense", Genes to Cells 1:569-579.
Kimura et al., 1993, "An in vivo study of the replication origin in the influenza virus complementary RNA", J Biochem (Tokyo) 113:88-92.
Kimura et al., 1992, "Transcription of a recombinant influenza virus RNA in cells that can express the influenza virus RNA polymerase . . . ", J Gen Virol. 73:1321-28.
Kobayashi et al., 1992, Reconstitution of influenza virus RNA polymerase from three subunits expressed using recombinant baculovirus system. Virus Res. 22:235-45.
Konarska et al., 1990, "Structure of RNAs replicated by the DNA-dependent T7 RNA polymerase", Cell. 63(3):609-18.
Krystal et al., 1986, "Expression of the Three Influenza Virus Polymerase Proteins in a Single Cell Allows Growth . . . ", Proc. Natl. Acad. Sci. USA 83:2709-2713.
Kunkel, 1985, "Rapid and Efficient Site-Specific Mutagenesis without Phenotypic Selection", Proc. Natl. Acad. Sci. USA 82:468-492.
Lamb et al., 1996, Fundamental Virology 3.sup.rd ed. Chapters 20 and 21.
Lawson et al., 1995, "Recombinant vesicular stomatitis viruses from DNA", Proc Natl Acad Sci U S A.92:4477-81.
Levis et al., 1986, "Deletion Mapping of Sindbis Virus DI RNAs Derived from cDNAs Defines the Sequences Essential for Replication and Packaging", Cell 44:137-145.
Luytjes et al., 1989, "Amplification, Expression, and Packaging of a Foreign Gene by Influenza Virus", Cell 59:1107-1113.
Mena et al., 1994, "Synthesis of biologically active influenza virus core proteins using a vaccinia virus-T7 RNA polymerase expression system", J Gen Virol. 75:2109-14.
Mena et al., 1996, "Rescue of a Synthetic Chloramphenicol Acetyltransferase RNA into Influenza Virus-Like Particles Obtained fr. Recombinant Plasmids", J. Virol. 70: 5016-5024.
Moyer et al., 1991, "Assembly and transcription of synthetic vesicular stomatitis virus nucleocapsids", J Virol. 65(5):2170-88.
Muster et al., 1991, "An influenza A virus containing influenza B virus 5' and 3' noncoding regions on the neuraminidase gene..:", Proc Natl Acad Sci USA 88:5177-81.
Naito and Ishihama, 1976, "Function and Structure of RNA Polymerase from Vesicular Stomatitis Virus", J. Biol. Chem. 251:4307-4314.
Nara et al., 1987, "Simple, Rapid, Quantitative, Syncytium-Forming Microrassay for the Detection of Human Immunodeficiency . . . ", AIDS Res. Hum. Retroviruses 3:283-302.
Nemeroff et al., 1998, "Influenza Virus NS1 Protein Interacts with the Cellular 30 kDa Subunit of CPSF and Inhibits 3' End Formation..", Mol. Cell 1:991-1000.
Neumann et al., 1994, "RNA Polymerase I-Mediated Expression of Influenza Viral RNA Molecules", Virol. 202:477-479.
Palese et al., 1996, "Negative-Strand RNA Viruses: Genetic Engineering and Applications", Proc. Natl. Acad. Sci. USA 93,11354-11358.
Park et al., 1991, "Rescue of a Foreign Gene by Sendai Virus ", Proc. Natl. Acad. Sci. USA 88:5537-5541.
Pattnaik et al., 1991, "Cells that express all five proteins of vesicular stomatitis virus from cloned cDNAs support replication.." Proc Natl Acad Sci USA 88:1379-83.
Peeters et al., 1999, "Rescue of Newcastle Disease Virus from Cloned cDNA: Evidence that Cleavability of the Fusion Protein . . . ", J. Virol. 73:5001-5009.

Pekosz et al., 1999, "Reverse genetics of negative-strand RNA viruses: closing the circle", Proc Natl Acad Sci USA. 96(16):8804-16.

Percy et al., 1994, "Expression of a foreign protein by influenza A virus", J Virol 68(7):4486-92.

Pleschka et al., 1996, "A Plasmid-Based Reverse Genetics System for Influenza A Virus", J. Virol. 70:4188-4192.

Qui et al., 1995. "The influenza virus NS1 protein binds to a specific region in human U6 snRNA and inhibits U6-U2 and U6-U4 snRNA..", RNA 1:304-16.

Zhang et al., "Persistence of four related human munodeficiency virus subtypes during the course of zidovudine therapy . . . ", J. Virol. 1994 68: 425-432.

Racaniello et al., 1981. "Cloned Poliovirus Complementary DNA is Infectious in Mammalian Cells", Science 214:916-919.

Radecke et al., 1995, "Rescue of measles viruses from cloned DNA", EMBO J. 14(23):5773-84.

Roberts and Rose, 1998, "Recovery of Negative-Strand RNA Viruses from Plasmid DNAs: a Positive Approach Revitalizes a Negative Field", Virol. 247:1-6.

Rose 1996, "Positive Strands to the Rescue Again: A Segmented Negative-Strand RNA Virus Derived from Cloned . . . ",PNAS USA 94:14998-15000.

Schlesinger, 1995. "RNA viruses as vectors for the expression of heterologous proteins", Mol Biotechnol. 3:155-65.

Schnell et al., 1994, "Infectious Rabies Viruses from Cloned cDNA", EMBO J. 13:4195-4203.

Seong et al., 1992, "A new method for reconstituting influenza polymerase and RNA in vitro: a study of the promoter elements for cRNA..", Virology 186:247-60.

Sidhu et al., 1995, "Rescue of synthetic measles virus minireplicons: measles genomic termini direct efficient expression . . . ", Virology. 208(2):800-07.

Szewczyk et al., 1988, "Purification, Thioredoxin Renaturation, and Reconstituted Activity of the Three Subunits of the Influenza..", Proc. Natl. Acad. Sci. USA 85:7907-7911.

Taylor et al., 1990, "Newcastle Disease Virus Fusion Protein Expressed in a Fowlpox Virus Recombinant Confers Protection in Chickens", J. Virol. 64:1441-1450.

Ward et al., 1988, "Direct Measurement of the Poliovirus RNA Polymerase Error Frequency in Vitro", J. Virol. 62:558-562.

Whelan et al., 1995, "Efficient recovery of infectious vesicular stomatitis virus entirely from cDNA clones", Proc.Natl.Acad.Sci. USA 92:8388-8392.

Yu et al., 1995, "Functional cDNA clones of the human respiratory syncytial (RS) virus N, P, and L proteins support replication . . . ", J Virol. 69(4):2412-19.

Yusoff et al., 1987, "Nucleotide Sequence Analysis of the L Gene of Newcastle Disease Virus: Homologies with Sendi and Vesicular Stomatitis..", Nucleic Acids Res. 15:3961-76.

Zaghouani et al., 1991, "Induction of antibodies to the envelope protein of the human immunodeficiency virus by immunization..", Proc. Natl. Acad Sci. USA 88:5645-5649.

Zaghouani et al., 1992, "Cells Expressing an H Chain to Gene Carrying a Viral T Cell Epitope Are Lysed by Specific Cytolytic T Cells", J. Immunol. 148:3604-3609.

Zhang and Air, 1994, "Expression of Functional Influenza Virus A Polymerase Proteins and Template from Cloned cDNAs..", Biochem. & Biophys. Res. Commun. 200:95-101.

Zobel et al., 1993, "RNA polymerase I catalysed transcription of insert viral cDNA", Nucleic Acids Res. 21(16):3607-14.

Enami et al., 1990, "Introduction of Site Specific Mutations into the Genome of Influenza Virus", Proc Natl Acad Sci USA 87: 3802-3805.

Yamanaka et al., 1991, "In vivo analysis of the promoter structure of the influenza virus RNA genome using a transfection system . . . ," Proc Natl Acad Sci USA 88: 5369-5373.

Belshe, 1995 "A Review of Attenuation of Influenza Viruses by Genetic manipulation", American Journal of Respiratory And Critical Care Medicine 152:S72-S75.

Brandt et al., 2001, "Molecular Determinants of Virulence, Cell Tropism, and Pathogenic Phenotype of Infectious Bursal Disease Virus", Journal of Virology 75(24):11974-11982.

Qiu et. al., 1994, "The influenza virus NS1 protein is a poly(A)-binding protein that inhibits nuclear export of mRNAs containing poly(A)", J Virol. 68(4):2425-32.

Maassab, "Adaptation and growth characteristics of influenza virus at 25 degrees C", Nature, 213:612-614 (1967).

Furminger, "Vaccine Production", Textbook of Influenza, pp. 324-332; (1996).

Subbarao et al., "The Attenuation Phenotype Conferred by the M Gene of the Influenza A/Ann Arbor/6/60 Cold-Adapted Virus (H2N2) on the . . . " Virus Res., 25:37-50; (1992).

Snyder et al., "Four Viral Genes Independently Contribute to Attenuation of Live Influenza A/Ann Arbor/6/60 (H2N2) Cold-Adapted . . . ", J. Virol., 62:488-95; (1988).

Parkin et al., "Temperature Sensitive Mutants of Influenza A Virus Generated by Reverse Genetics . . . ", Virus Res., 46:31-44; (1996).

Parkin N. et al., "Genetically Engineered Live Atenuated Influenza A Virus Vaccine Candidates", J. Virol., pp. 2772-2778; (1997).

Myrphy & Coelingh, "Principles Underlying the Development and Use of Live Attenuated Cold-Adapted Influenza A and B Virus Vaccines", Viral Immunol, 15:295-323; (2002).

Merten et al., "Production of influenza virus in Cell Cultures for Vaccine Preparation", Novel Strategies in Design and Production of Vaccines, pp. 141-151; (1996).

Maassab et al., "Evaluation of a Cold-Recombinant Influenza Virus Vaccine in Ferrets", J. of Infectious Diseases, 146:780-790; (1982).

Hoffman et al., "Eight-Plasmid Resue System for Influenza A Virus", International Congress Series, 1219:1007-1013; (2001).

Hoffman et al., "Eight-Plasmid System for Rapid Generation of Influenza Virus Vaccines", Vaccine, 20:3165-3170; (2002).

Herlocher et al., "Sequence Comparisons of A/AA/6/60 Influenza Viruses: Mutations Which May Contribute to Attenuation", Virus Research, 42:11-25; (1996).

Hoffman et al., "Ambisense" Approach for the Generation of Influenza A Virus: vRNA and mRNA Synthesis from One Template, Virology, 267:310-317; (2000).

Radecke et al., "Reverse Genetics Meets the Nonsegmented Negative-Strand RNA Viruses", Medical Virology, vol. 7: 49-63 (1997).

Katinger et al., "Attenuated Influenza Virus as a Vector for Mucosal Immunization against HIV-1", Vaccines, pp. 315-319, (1997).

Neumann, et al., "Genetic Engineering of Influenza and Other Negative-Strand RNA Viruses Containing Segmented Genomes," Advances in Virus Research, 1999; 53: 265-300.

Scholtissek, et al., "The Nucleoprotein as a Possible Major Factor in Determining Host Specificity of Influenza H3N2 Viruses," Virology, 1985; 147:287-294.

Bergmann, et al., 1995, "The relative amount of an influenza A virus segment present in the viral particle is not affected . . . ", J. of Gen. Virology, 76:3211-3215.

Ghendon, 1998, "Cold-Adapted, Live Influenza Vaccines Developed in Russia," Textbook of Influenza, Chapter 29, pp. 391-399.

Keitel, et al., 1998, "Live Cold-Adapted, Reassortant Influenza Vaccines (USA)," Textbook of Influenza, Chapter 28, pp. 373-390.

Hoffmann, Erich, Aufbau eines RNA-Polymerase I-Vektorsystems zur gezielten Mutagenese von Influenza A Viren, Gieben 1997 (Doctoral Dissertation).

Perez, Daniel R. et al., 1998 "The Matrix 1 Protein of Influenza A Virus Inhibits The Transcriptase Activity of a Model . . . ", Article No. VY989318, Virology, 249:52-61.

Xu, Xiyan, et al., 1999 "Genetic Characterization of the Pathogenic Influenza A /Goose/Guangdong/1/96 (H5N1) Virus: . . . ", Article ID viro. 1999.9820. Virology 261:15-19.

Zhou, Yan, et al., "Membrane-Anchored Incorporation of a Foreign Protein in Recombinant Influenza Virions", Article No. VY989169, Virology, 1998, vol. 246, pp. 83-94.

Erich Hoffman et al., 2000 "Characterization of the Influenza A Virus Gene Pool in Avian Species in Southern China: Was H6N1 . . . ?" J. Virology, 74(14):6309-6315.

Flick, et al., "Promoter elements in the influenza vRNA terminal structure," RNA, 1996; 2(10):1046-1057.

Govorkova, E.A., et al., "African Green Monkey Kidney (Vero) Cells Provide an Alternative Host Cell ..", J. of Virology, Am. Soc. for Microbiology, Aug. 1996, 70(8):5519-5524.

Guan, Yi, et al., "Molecular Characterization of H9N2 Influenza Viruses: Were They The Donors of the "Internal"..?", Proc. Natl. Acad. Sci., U.S.A. Aug. 1999, 96:9363-9367.

Erich Hoffman et al., 2002, "Rescue of influenza B virus from eight plasmids", PNAS 99: 11411-11416.

Hoffmann; 1997, "Generation of an RNA-Polymerase Vector Syst. for the Select. Mutagenesis...," Inaugural Dissertation of Sch. of Nat. Sciences, Justus Liebig U. Gieben.

Cox, et al.; "Identification of Sequence Changes in the Cold-Adapted, Live Attenuated Influenza Vaccine Strain, A/Ann Arbor/6/60 (H2N2)," Virology, 1988; 167: 554-567.

Belshe et al. 1998 , "The efficacy of live attenuated, cold-adapted, trivalent, intranasal influenza virus vaccine in children ," N Engl J Med 338:1405-12.

Boyce et al., 2001, "Safety and immunogenicity of adjuvanted and unadjuvanted subunit influenza vaccines administered intranasally to healthy adults", Vaccine 19:217-26.

Edwards et al., 1994, "A randomized controlled trial of cold adapted and inactivated vaccines for the prevention of influenza A disease", J Infect Dis 169:68-76.

Hoffmann et al. "Universal primer set for the full-length amplification of all influenza A viruses." Arch Virol. Dec. 2001;146(12):2275-89).

Li et al., 1999, "Recombinant influenza A virus vaccines for the pathogenic human A/Hong Kong/97 (H5N1) viruses," J. of Infectious Diseases, 179:1132-8.

Nichol et al. 1999, "Effectiveness of live, attenuated intranasal influenza virus vaccine in healthy, working adults: a randomized controlled trial", JAMA 282:137-44.

Hoffman et al.,2000, "Unidirectional RNA polymerase I-polymerase II transcription system for the generation of influenza A virus . . . ", J.I of Gen. Virology 81:2843-2847.

Hoffmann et al., 2000, "A DNA transfection system for generation of influenza A virus from eight plasmids", PNAS 97(11):6108-6113.

Subbarao et al., 1995, "Sequential addition of temperature-sensitive missense mutations into the PB2 gene of influenza A . . . ", J. of Virology 69(10):5969-5977.

Fodor et al., 1999, "Rescue of Influenza A Virus from Recombinant DNA", J. of Virology 73(11):9679-9682.

Neumann et al.. 1999, "Generation of influenza A viruses entirely from cloned cDNAs", PNAS 96(16):9345-9350.

Egorov et al., 1998, "Transfectant Influenza A Viruses with Long Deletions in the NS1 Protein Grow Efficiently in Vero Cells", J. of Virology 72(8):6437-6441.

Enami et al., 2000, "Characterization of Influenza Virus NS1 Protein by Using a Novel Helper-Virus Free Reverse Genetic System", J. of Virology 74(12):5556-5561.

Schickli et al., 2001, "Plasmid-only rescue of influenza A virus vaccine candidates", Philos Trans Society of London Ser B 356:1965-1973.

Basler et al., 1999, "Mutation of Neuraminidase Cysteine Residues Yields Temperature-Sensitive Influenza Viruses", J. of Virology 73(10):8095-8103.

Flandorger et al., 2003, "Chimeric Influenza A Viruses with a Functional Influenza B Virus Neuraminidase or Hemagglutinin", J. of Virology 77(17):9116-9123.

Martin et al., 1998, "Studies of the Binding Properties of Influenza Hemagglutinin Receptor-Site Mutants", Virology 241:101-111.

Nakajima et al., 2003, "Restriction of Amino Acid Change in Influenza A Virus H3HA: Comparison of Amino Acid Changes Observed . . . ", J. of Virology 77(18):10088-10098.

Xu et al., 1995 #AAB06964 (abstract only).

Xu et al., 1996, "Genetic Variation in Neuraminidase Genes of Influenza A (H3N2) Viruses", Virology 224:175-183.

Hillman Maurice R., 2000, "Vaccines in historic evolution and perspective: a narrative of vaccine discoveries", Vaccine 18:1436-1447.

Webby et al., 2004, "Responsiveness to a pandemic alert: use of reverse genetics for rapid development of influenza vaccines", Lancet 363:1099-1103.

Wareing, J.M., et al, 2001, "Immunogenic and Isotype-Specific Responses to Russian and US Cold-Adapted Influenza A Vaccine Donor . . . ", J. of Medical Virology 65:171-177.

Subbarao, Kanta et al., 2003, "Evaluation of a Genetically Modified Reassortant H5N1 Influenza A Virus Vaccine Candidate . . . " Virology 305:192-200.

GenBank AAX11495 Oct. 12, 2006.

GenBank AAT12674 March 26, 2005.

GenBank AAT12657 March 26, 2005.

* cited by examiner

SEQ ID NO:1 ca A/Shandong/9/93

Nucleotide Sequence of ca_A_Shandong_9_93_HA     Entire molecule length: 1745 bp

```
   1 caggggataa ttctattaac catgaagact atcattgctt tgagctacat
  51 tttatgtctg gttttcgctc aaaaacttcc cggaaatgac aacagcacag
 101 caacgctgtg cctgggacat catgcagtgc caaacggaac gctagtgaaa
 151 acaatcacga atgatcaaat tgaagtgact aatgctactg agttggttca
 201 gagttcctca acaggtagaa tatgcggcag tcctcaccga atccttgatg
 251 gaaaaaactg cacactgata gatgctctat gggagaccc tcattgtgat
 301 ggcttccaaa ataaggaatg ggacctttt gttgaacgca gcaaagctta
 351 cagcaactgt taccccttatg atgtgccgga ttatgcctcc cttaggtcac
 401 tagttgcctc atcaggcacc ctggagttta tcaatgaaga cttcaattgg
 451 actggagtcg ctcaggatgg gggaagctat gcttgcaaaa gaggatctgt
 501 taacagtttc tttagtagat tgaattggtt gcacaaatta gaatacaaat
 551 atccagcgct gaacgtgact atgccaaaca atggcaaatt tgacaaattg
 601 tacatttggg gggttcacca cccgagcacg gacagtgacc aaaccagcct
 651 atatgttcga gcatcaggga gagtcacagt ctctaccaaa agaagccaac
 701 aaactgtaac cccgaatatc gggtctagac cctgggtaag gggtcagtcc
 751 agtagaataa gcatctattg gacaatagta aaccgggag acatactttt
 801 gattaatagc acagggaatc taattgctcc tcggggttac ttcaaaatac
 851 gaaatgggaa aagctcaata atgaggtcag atgcacccat tggcaactgc
 901 agttctgaat gcatcactcc aaatggaagc attcccaatg acaaaccttt
 951 tcaaaatgta aacagaatca tatggggc ctgccccaga tatgttaagc
1001 aaaacactct gaaattggca acaggatgc ggaatgtacc agagaaacaa
1051 actagaggca tattcggcgc aatcgcaggt ttcatagaaa atggttggga
1101 gggaatggta gacggttggt acggtttcag gcatcaaaat tctgagggca
1151 caggacaagc agcagatctt aaaagcactc aagcagcaat cgaccaaatc
1201 aacgggaaac tgaataggtt aatcgagaaa acgaacgaga attccatca
1251 aatcgaaaaa gaattctcag aagtagaagg gagaattcag gacctcgaga
1301 aatatgttga agacactaaa atagatctct ggtcttacaa cgcggagctt
1351 cttgttgccc tggagaacca acatacaatt gatctaactg actcagaaat
1401 gaacaaactg tttgaaaaaa caaggaagca actgagggaa aatgctgagg
1451 acatgggcaa tggttgcttc aaaatatacc acaaatgtga caatgcctgc
1501 ataggagtcaa tcagaaatgg aacttatgac catgatgtat acagagacga
1551 agcattaaac aaccggttcc agatcaaagg tgttgagctg aagtcaggat
1601 acaaagatt gatcctatgg atttccttg ccatatcatg cttttttgctt
1651 tgtgttgttt tgctggggtt catcatgtgg gcctgccaaa aaggcaacat
1701 taggtgcaac atttgcattt gagtgcatta ttaaaaaca ccctg
```

SEQ ID NO:49

Amino Acid Sequence of ca_A_Shandong_9_93_HA Entire molecule length: 566 aa

```
  1 mktiialsyi lclvfaqklp gndnstatlc lghhavpngt lvktitndqi
 51 evtnatelvq ssstgricgs phrildgknc tlidallgdp hcdgfqnkew
101 dlfverskay sncypydvpd yaslrslvas sgtlefined fnwtgvaqdg
151 gsyackrgsv nsffsrlnwl hkleykypal nvtmpnngkf dklyiwgvhh
201 pstdsdqtsl yvrasgrvtv stkrsqqtvt pnigsrpwvr gqssrisiyw
251 tivkpgdill instgnliap rgyfkirngk ssimrsdapi gncssecitp
301 ngsipndkpf qnvnrityga cpryvkqntl klatgmrnvp ekqtrgifga
351 iagfiengwe gmvdgwygfr hqnsegtgqa adlkstqaai dqingklnrl
401 iektnekfhq iekefseveg riqdlekyve dtkidlwsyn aellvalenq
451 htidltdsem nklfektrkq lrenaedmgn gcfkiyhkcd nacigsirng
501 tydhdvyrde alnnrfqikg velksgykdw ilwisfaisc fllcvvllgf
551 imwacqkgni rcnici
```

Figure 1A

SEQ ID NO:2

Nucleotide Sequence of ca_A_Shandong_9_93_NA   Entire molecule length: 1429 bp

```
   1 aaagataata acaattggct ctgtttctct cactattgcc acaatatgct
  51 tccttatgca aattgccatc ctggtaacta ctgtaacatt gcacttcaag
 101 caatatgagt gcaactcccc cccaaacaac caagtaatgc tgtgtgaacc
 151 aacaataata gaaagaaaca taacagagat agtgtatctg accaacacca
 201 ccatagagaa agaaatatgc cccaaactag cagaatacag aaattggtca
 251 aagccgcaat gtaaaattac aggatttgca ccttttctta aggacaattc
 301 aattcggctt tcagctggtg gagacatttg ggtgacaaga gaaccttatg
 351 tgtcatgcga tcctggcaag tgttatcaat ttgcccttgg acagggaaca
 401 acactaaaca acaggcactc aaatgacaca gtacatgata ggacccctta
 451 tcgaacccta ttgatgaatg agttgggtgt tccatttcat ttgggaacca
 501 agcaagtgtg catagcatgg tccagctcaa gttgtcacga tggaaaagca
 551 tggctgcatg tttgtgtaac tgggcatgat gaaaatgcaa ctgctagctt
 601 catttacgat gggaggcttg tagatagtat tggttcatgg tccaaaaata
 651 tcctcaggac ccaggagtcg aatgcgttt gtatcaatgg aacttgtaca
 701 gtagtaatga ctgatggaag tgcttcagaa agagctgata ctaaaatact
 751 attcattgaa gaggggaaaa tcgttcatat tagcccattg tcaggaagtg
 801 ctcagcatgt cgaggagtgc tcctgttatc ctcgatatcc tggtgtcaga
 851 tgtgtctgca gagacaactg aaaggctcc aataggccca tcgtagatat
 901 aaatgtgaaa gattatagca ttgtttccag ttatgtgtgc tcaggacttg
 951 ttggagacac acccagaaaa acgacagct ccagcagtag ctattgccgg
1001 aatcctaaca atgagaaagg gagtcatgga gtgaaaggct gggcctttga
1051 tgatggaaat gacgtgtgga tgggaagaac gatcagcgag gagttacgct
1101 caggttatga aaccttcaaa gtcattggag gctggtccaa acctaactcc
1151 aaattgcaga taaataggca agtcatagtt gacagaggta ataggtccgg
1201 ttattctggt attttctctg ttgaaggcaa aagctgcatc aatcggtgct
1251 tttatgtgga gttgataagg ggaaggaaac aggaaactga agtctggtgg
1301 acctcaaaca gtattgttgt gttttgtggc acctcaggta catatggaac
1351 aggctcatgg ccctgatggg gcggacatca atctcatgcc tatataagct
1401 ttcgcaattt tagaaaaaaa ctccttgtt
```

SEQ ID NO:50

Amino Acid Sequence of ca_A_Shandong_9_93_NA Entire molecule length: 436 aa

```
   1 mqiailvttv tlhfkqyecn sppnnqvmlc eptiiernit eivyltntti
  51 ekeicpklae yrnwskpqck itgfapfskd nsirlsaggd iwvtrepyvs
 101 cdpgkcyqfa lgqgttlnnr hsndtvhdrt pyrtllmnel gvpfhlgtkq
 151 vciawssssc hdgkawlhvc vtghdenata sfiydgrlvd sigswsknil
 201 rtqesecvci ngtctvvmtd gsaseradtk ilfieegkiv hisplsgsaq
 251 hveecscypr ypgvrcvcrd nwkgsnrpiv dinvkdysiv ssyvcsglvg
 301 dtprkndsss ssycrnpnne kgshgvkgwa fddgndvwmg rtiseelrsg
 351 yetfkviggw skpnsklqin rqvivdrgnr sgysgifsve gkscinrcfy
 401 velirgrkqe tevwwtsnsi vvfcgtsgty gtgswp
```

Figure 1B

SEQ ID NO:3 ca A/Johannesburg/33/94-Like
Nucleotide Sequence of ca_A_Johannesburg_33_94_Like_HA Entire molecule length: 1755 bp

```
   1 agcaaaagca ggggataatt ctattaacca tgaagactat cattgctttg
  51 agctacattt tatgtctggt tttcgctcaa aaacttcccg gaaatgacaa
 101 cagcacagca acgctgtgcc tgggacacca tgcagtgcca aacggaacgc
 151 tagtgaaaac aatcacgaat gatcaaattg aagtgactaa tgctactgag
 201 ctggttcaga gttccccaac aggtagaata tgcgacagcc ctcaccgaat
 251 ccttgatgga aagaactgca cactgataga tgctctattg ggagaccctc
 301 attgtgatgg cttccaaaat aaggaatggg acctttttgt tgaacgcagc
 351 aaagcttaca gcaactgtta cccttatgat gtgccggatt atgcctccct
 401 taggtcacta gttgcctcat caggcaccct ggagtttatc aacgaaaact
 451 tcaattggac tggagtcgct caggatggga aaagctatgc ttgcaaaagg
 501 ggatctgtta acagtttctt tagtagattg aattggttgc acaaattaga
 551 atacaaatat ccagcgctga acgtgactat gccaaacaat ggcaaatttg
 601 acaaattgta catttggggg gttcaccacc cgagcacgga cagtgtccaa
 651 accagcctat atgtccgagc atcagggaga gtcacagtct ctaccaaaag
 701 aagccaacaa actgtaatcc cggatatcgg gtatagacca tgggtaaggg
 751 gtcagtccag tagaataagc atctattgga caatagtaaa accgggagac
 801 atacttttga ttaatagcac agggaatcta attgctcctc ggggttactt
 851 caaaatacga aatgggaaaa gctcaataat gaggtcagat gcacccattg
 901 gcaactgcag ttctgaatgc atcactccaa atggaagcat tcccaatgac
 951 aaaccttttc aaaatgtaaa caggatcaca tatggggcct gccccagata
1001 tgttaagcaa aacactctga aattggcaac agggatgcgg aatgtaccag
1051 agaaacaaac tagaggcata ttcggcgcaa tcgcaggttt catagaaaat
1101 ggttgggagg gaatggtaga cggttggtac ggtttcaggc atcaaaattc
1151 tgagggcaca ggacaagctg cagatcttaa aagcactcaa gcagcaatcg
1201 accaaatcaa cgggaaactg aataggttag tcgagaaaac gaacgagaaa
1251 ttccatcaaa tcgaaaaaga attctcagaa gtagaaggga gaattcagga
1301 cctcgagaaa tatgttgaag acactaaaat agatctctgg tcttacaatg
1351 cggaacttct tgttgctctg gagaaccaac atacaattga tctaactgac
1401 tcagaaatga acaaactgtt tgaaagaaca aggaagcaac tgagggaaaa
1451 tgctgaggac atgggcaatg gttgtttcaa aatataccac aaatgtgaca
1501 atgcctgcat agggtcaatc agaaatggaa cttatgacca tgatgtatac
1551 agagacgaag cattaaacaa ccggttccag atcaaaggtg ttgagctgaa
1601 gtcaggatac aaagattgga ttctatggat ttcctttgcc atatcgtgct
1651 ttttgctttg tgttgttttg cttgggttca tcatgtgggc ctgccaaaaa
1701 ggcaacatta ggtgcaacat ttgcatttga gtgcattaat taaaaacacc
1751 cttgt
```

SEQ ID NO:51

Amino Acid Sequence of ca_A_Johannesburg_33_94_Like_HA Entire molecule length: 566 aa

```
   1 mktiialsyi lclvfaqklp gndnstatlc lghhavpngt lvktitndqi
  51 evtnatelvq ssptgricds phrildgknc tlidallgdp hcdgfqnkew
 101 dlfverskay sncypydvpd yaslrslvas sgtlefinen fnwtgvaqdg
 151 ksyackrgsv nsffsrlnwl hkleykypal nvtmpnngkf dklyiwgvhh
 201 pstdsvqtsl yvrasgrvtv stkrsqqtvi pdigyrpwvr gqssrisiyw
 251 tivkpgdill instgnliap rgyfkirngk ssimrsdapi gncssecitp
 301 ngsipndkpf qnvnrityga cpryvkqntl klatgmrnvp ekqtrgifga
 351 iagfiengwe gmvdgwygfr hqnsegtgqa adlkstqqai dqingklnrl
 401 vektnekfhq iekefseveg riqdlekyve dtkidlwsyn aellvalenq
 451 htidltdsem nklfertrkq lrenaedmgn gcfkiyhkcd nacigsirng
 501 tydhdvyrde alnnrfqikg velksgykdw ilwisfaisc fllcvvllgf
 551 imwacqkgni rcnici
```

Figure 1C

SEQ ID NO:4

Nucleotide Sequence of ca_A_Johannesburg_33_94_Like_NA

Entire molecule length: 1354 bp

```
   1 gaaaatgaat ccaaatcaaa agataataac aattggctct gtttctctca
  51 ctattgccac aatatgcttc cttatgcaaa ttgccatcct ggtaactact
 101 gtaacattgc atttcaagca atatgagtgc aactcccccc caaacaacca
 151 agtaatgctg tgtgaaccaa caataataga aagaaacata acagagatag
 201 tgtatctgac caacaccacc atagagaaag aaatatgccc caaactagca
 251 gaatacagaa attggtcaaa gccgcaatgt aaaattacag gatttgcacc
 301 tttttctaag gacaattcaa ttcggctttc cgctggtgga gacatttggg
 351 tgacaagaga accttatgtg tcatgcgatc ctggcaagtg ttatcaattt
 401 gccctcggac agggaacaac actaaacaac aggcattcaa atgacacagt
 451 acatgatagg accccttatc gaaccctatt gatgaatgag ttgggtgttc
 501 catttcattt gggaaccaag caagtgtgca tagcatggtc cagctcaagt
 551 tgtcacgatg gaaaagcatg gctgcatgtt tgtgtaactg ggcatgatga
 601 aaatgcaact gctagcttca tttacgatgg gaggcttgta gatagtattg
 651 gttcatggtc caaaaatatc ctcaggaccc aggagtcgga atgcgtttgt
 701 atcaatggaa cttgtacagt agtaatgact gatggaagtg cttcagaaag
 751 agctgatact aaaatactat tcattgaaga ggggaaaatc gttcatatta
 801 gcccattgtc aggaagtgct cagcatgtcg aggagtgctc ctgttatcct
 851 cgatatcctg gtgtcagatg tgtctgcaga gacaactgga aaggctccaa
 901 taggcccatc gtagatataa atgtgaaaga ttatagcatt gtttccagtt
 951 atgtgtgctc aggacttgtt ggagacacac cagaaaaaa cgacagctcc
1001 agcagtagct attctggaa tcctaacaat gagaagggg gtcatggagt
1051 gaaaggctgg gcctttgatg atggaaatga cgtgtggatg ggaagaacga
1101 tcagcgagga gttacgctca ggttatgaaa ccttcaaagt cattggaggc
1151 tggtccaaac ctaactccaa attgcagata aataggcaag tcatagttga
1201 cagaggtaat aggtccggtt attctggtat tttctctgtt gaaggcaaaa
1251 gctgcatcaa tcggtgcttt tatgtggagt tgataagggg aaggaaacag
1301 gaaactgaag tctggtggac ctcaaacagt attgttgtgt tttgtggcac
1351 ttca
```

SEQ ID NO:52

Amino Acid Sequence of ca_A_Johannesburg_33_94_Like_NA
Entire molecule length: 451 aa

```
   1 kmnpnqkiit igsvsltiat icflmqiail vttvtlhfkq yecnsppnnq
  51 vmlceptiie rniteivylt nttiekeicp klaeyrnwsk pqckitgfap
 101 fskdnsirls aggdiwvtre pyvscdpgkc yqfalgqgtt lnnrhsndtv
 151 hdrtpyrtll mnelgvpfhl gtkqvciaws ssschdgkaw lhvcvtghde
 201 natasfiydg rlvdsigsws knilrtqese cvcingtctv vmtdgsaser
 251 adtkilfiee gkivhispls gsaqhveecs cyprypgvrc vcrdnwkgsn
 301 rpivdinvkd ysivssyvcs glvgdtprkn dssssycwn pnnekgghgv
 351 kgwafddgnd vwmgrtisee lrsgyetfkv iggwskpnsk lqinrqvivd
 401 rgnrsgysgi fsvegkscin rcfyvelirg rkqetevwwt snsivvfcgt
 451 s
```

Figure 1D

SEQ ID NO:5
ca A/Wuhan/395/95
Nucleotide Sequence of ca A/Wuhan/395/95 H3    Entire molecule length: 1762 bp

```
   1 agcaaaagca ggggataatt ctattaacca tgaagactat cattgctttg
  51 agctacattt tatgtctggt tttcgctcaa aaacttcccg gaaatgacaa
 101 cagcacggca acgctgtgcc tgggacacca tgcagtgcca aacggaacgc
 151 tagtgaaaac aatcacgaat gaccaaattg aagtgactaa tgctactgag
 201 ctggttcaga gttcctcaac aggtagaata tgcgacagtc ctcaccgaat
 251 ccttgatgga aaaaactgca cactgataga tgctctattg ggagaccctc
 301 attgtgatgg cttccaaaat aaggaatggg acctttttgt tgaacgcagc
 351 aaagcttaca gcaactgtta cccttatgat gtgccggatt atgcttccct
 401 taggtcacta gttgcctcat ccggcaccct ggagtttacc aatgaaggct
 451 tcaattggac tggagtcgct caggatggaa caagctatgc ttgcaaaagg
 501 ggatctgtta aaagtttctt tagtagattg aattggttgc acaaattaga
 551 atacaaatat ccagcactga acgtgactat gccaaacaat gacaaatttg
 601 acaaattgta catttggggg gttcaccacc cgagtacgga cagtgaccaa
 651 accagcatat atgttcaagc atcagggaga gtcacagtct ctaccaaaag
 701 aagccaacaa actgtaatcc cgaatatcgg gtctagaccc tgggtaaggg
 751 ggatctccag cagaataagc atctattgga caatagtaaa accgggagac
 801 atacttttga ttaacagcac agggaatcta attgctcctc ggggttactt
 851 caaaatacga agtgggaaaa gctcaataat gaggtcagat gcacccattg
 901 gcaactgcaa ttctgaatgc atcactccaa atggaagcat tcccaatgac
 951 aaaccttttc aaaatgtaaa caggatcaca tatggggcct gtcccagata
1001 tgttaagcaa aacactctga aattggcaac agggatgcgg aatgtaccag
1051 agaaacaaac tagaggcata ttcggcgcaa tcgcaggttt catagaaaat
1101 ggttgggagg gaatggtaga cggttggtac ggtttcaggc atcaaaattc
1151 tgagggcaca ggacaagcag cagatcttaa aagcactcaa gcagcaatca
1201 accaaatcaa cgggaaactg aataggttaa tcgagaaaac gaacgagaaa
1251 ttccatcaaa tcgaaaaaga attctcagaa gtagaaggga gaattcagga
1301 cctcgagaaa tatgttgaag acactaaaat agatctctgg tcttacaacg
1351 cggagcttct tgttgccctg gagaaccaac atacaattga tctaactgac
1401 tcagaaatga acaaactgtt tgaaagaaca aggaagcaac tgagggaaaa
1451 tgctgaggac atgggcaatg gttgcttcaa aatataccac aaatgtgaca
1501 atgcctgcat agggtcaatc agaaatggaa cttatgacca tgatgtatac
1551 agagacgaag cattaaacaa ccggttccag atcaaaggtg ttgagctgaa
1601 gtcaggatac aaagattgga tcctatggat ttcctttgcc atatcatgct
1651 tttgctttg tgttgttctg ctggggttca tcatgtgggc ctgccaaaaa
1701 ggcaacatta ggtgcaacat ttgcatttga gtgcattaat taaaaacacc
1751 cttgtttcta ct
```

SEQ ID NO:53

Amino Acid Sequence of ca A/Wuhan/395/95 H3 Entire molecule length: 566 aa

```
  1 mktiialsyi lclvfaqklp gndnstatlc lghhavpngt lvktitndqi
 51 evtnatelvq ssstgricds phrildgknc tlidallgdp hcdgfqnkew
101 dlfverskay sncypydvpd yaslrslvas sgtleftneg fnwtgvaqdg
151 tsyackrgsv ksffsrlnwl hkleykypal nvtmpnndkf dklyiwgvhh
201 pstdsdqtsi yvqasgrvtv stkrsqqtvi pnigsrpwvr gissrisiyw
251 tivkpgdill instgnliap rgyfkirsgk ssimrsdapi gncnsecitp
301 ngsipndkpf qnvnrityga cpryvkqntl klatgmrnvp ekqtrgifga
351 iagfiengwe gmvdgwygfr hqnsegtgqa adlkstqaai nqingklnrl
401 iektnekfhq iekefseveg riqdlekyve dtkidlwsyn aellvalenq
451 htidltdsem nklfertrkq lrenaedmgn gcfkiyhkcd nacigsirng
501 tydhdvyrde alnnrfqikg velksgykdw ilwisfaisc fllcvvllgf
551 imwacqkgni rcnici
```

Figure 1E

SEQ ID NO:6

Nucleotide Sequence of ca A/Wuhan/395/95 N2        Entire molecule length: 1451 bp

```
   1 agcaaaagca ggagtgaaaa tgaatccaaa tcaaaagata ataactattg
  51 gctctgtttc tctcactatt gccacaatat gcttccttat gcaaattgcc
 101 atcctggtaa ctactgtaac attacatttc aagcaatatg aatgcaactc
 151 ccccccaaac aaccaagtaa tgctgtgtga accaacaata atagaaagaa
 201 acataacaga gatagtgtat ctgaccaaca ccaccataga gaaggaaata
 251 tgccccaaac tagcagaata cagaaattgg tcaaagccgc aatgtaaaat
 301 tacaggattt gcacctttt ctaaggacaa ttcaattcgg ctttccgctg
 351 gtggggacat tgggtgaca agagaacctt atgtgtcatg cgatcctgac
 401 aagtgttatc aatttgccct tggacaggga acaacactaa acaacaggca
 451 ttcaaatgac acagtacatg ataggacccc ttatcgaacc ctattgatga
 501 atgagttggg tgttccattt catttgggaa ccaagcaagt gtgcatagca
 551 tggtccagct caagttgtca cgatggaaaa gcatggctgc atgtttgtgt
 601 aactgggcat gatgaaaatg caactgctag cttcatttac gatgggaggc
 651 ttgtagatag tattggttca tggtccaaaa aaatcctcag gacccaggag
 701 tcggaatgcg tttgtatcaa tggaacttgt acagtagtaa tgactgatgg
 751 aagtgcttca ggaagagctg atactaaaat actattcatt gaagagggga
 801 aaatcgttca tattagccca ttgtcaggaa gtgctcagca tgtcgaggag
 851 tgctcctgtt atcctcgata ttctggtgtc agatgtgtct gcagagacaa
 901 ctggaaaggc tccataggc ccatcgtaga tataaatgtg aaagattata
 951 gcattgtttc cagttatgtg tgctcaggac ttgttggaga cacacccaga
1001 aaaaacgaca gctccagcag tagccattgc ctgaatccta acaatgagga
1051 agggggtcat ggagtgaaag ctgggccctt tgatgatgga aatgacgtgt
1101 ggatgggaag aacgatcagc gagaagttac gctcaggtta tgaaaccttc
1151 aaagtcattg gaggctggtc aaacctaac tccaaattgc agataaatag
1201 acaagtcata gttgacagag gtaataggtc cggttattct ggtattttct
1251 ctgttgaagg caaaagctgc atcaatcggt gcttttatgt ggagttgata
1301 aggggaagga acaggaaac tgaagtctgg tggacctcaa acagtattgt
1351 tgtgttttgt ggcacctcag gtacatatgg aacaggctca tggcctgatg
1401 gggcggacat caatctcatg cctatataag ctttcgcaat tttagaaaaa
1451 a
```

SEQ ID NO:54

Amino Acid Sequence of ca A/Wuhan/395/95 N2        Entire molecule length: 469 aa

```
   1 mnpnqkiiti gsvsltiati cflmqiailv ttvtlhfkqy ecnsppnnqv
  51 mlceptiier niteivyltn ttiekeicpk laeyrnwskp qckitgfapf
 101 skdnsirlsa ggdiwvtrep yvscdpdkcy qfalgqgttl nnrhsndtvh
 151 drtpyrtllm nelgvpfhlg tkqvciawss sschdgkawl hvcvtghden
 201 atasfiydgr lvdsigswsk kilrtqesec vcingtctvv mtdgsasgra
 251 dtkilfieeg kivhisplsg saqhveecsc yprysgvrcv crdnwkgsnr
 301 pivdinvkdy sivssyvcsg lvgdtprknd ssssshclnp nneegghgvk
 351 gwafddgndv wmgrtisekl rsgyetfkvi ggwskpnskl qinrqvivdr
 401 gnrsgysgif svegkscinr cfyvelirgr kqetevwwts nsivvfcgts
 451 gtygtgswpd gadinlmpi
```

Figure 1F

SEQ ID NO:7 ca A/Sydney/05/97

Nucleotide Sequence of ca A/Sydney/05/97 H3 Entire molecule length: 1762 bp

```
   1 agcaaaagca ggggataatt ctattaacca tgaagactat cattgctttg
  51 agctacattt tatgtctggt tttcgctcaa aaaattcccg gaaatgacaa
 101 cagcacggca acgctgtgcc tgggacacca tgcagtgcca aacggaacgc
 151 tagtgaaaac aatcacgaat gaccaaattg aagtgactaa tgctactgag
 201 ctggttcaga gttcctcaac aggtagaata tgcgacagtc ctcaccgaat
 251 ccttgatgga gaaaactgca cactgataga tgctctattg ggagaccctc
 301 attgtgatgg cttccaaaat aaggaatggg accttttgt tgaacgcagc
 351 aaagcctaca gcaactgtta cccttatgat gtgccggatt atgcctccct
 401 taggtcacta gttgcctcat ccggcaccct ggagtttaac aatgaaagct
 451 tcaattggac tggagtcgct cagaatggaa caagctatgc ttgcaaaagg
 501 agttctatta aaagtttctt tagtagattg aattggttgc accaattaaa
 551 atacaaatat ccagcactga acgtgactat gccaaacaat gacaaatttg
 601 acaaattgta catttggggg gttcaccacc cgagtacgga cagtgaccaa
 651 accagcatat atgctcaagc atcagggaga gtcacagtct ccaccaaaag
 701 aagccaacaa actgtaatcc cgaatatcgg atctagaccc tgggtaaggg
 751 gtatctccag cagaataagc atccattgga caatagtaaa accgggagac
 801 atacttttga ttaacagcac agggaatcta attgctcctc ggggttactt
 851 caaaatacga agtgggaaaa gctcaataat gaggtcagat gcacccattg
 901 gcaaatgcaa ttctgaatgc atcactccaa atggaagcat tcccaatgac
 951 aaaccatttc aaaatgtaaa caggatcaca tatggggcct gtcccagata
1001 tgttaagcaa aacactctga aattggcaac agggatgcgg aatgtaccag
1051 agaaacaaac tagaggcata ttcggcgcaa tcgcaggttt catagaaaat
1101 ggttgggagg gaatggtaga cggttggtac ggtttcaggc atcaaaattc
1151 tgagggcaca ggacaagcag cagatcttaa aagcactcaa gcagcaatca
1201 accaaatcaa cgggaaactg aataggttaa tcgagaaaac gaacgagaaa
1251 ttccatcaaa ttgaaaaaga attctcagaa gtagaaggga gaattcagga
1301 cctcgagaaa tatgttgagg acactaaaat agatctctgg tcgtacaacg
1351 cggagcttct tgttgccctg gagaaccaac atacaattga tctaactgac
1401 tcagaaatga acaaactgtt tgaaagaaca aggaagcaac tgagggaaaa
1451 tgctgaggat atgggcaatg gttgtttcaa aatataccac aaatgtgaca
1501 atgcctgcat agggtcaatc agaaatggaa cttatgacca tgatgtatac
1551 agagacgaag cattaaacaa ccggttccag atcaaaggtg ttgagctgaa
1601 gtcaggatac aaagattgga tcctatggat ttcctttgcc atatcatgtt
1651 ttttgctttg tgttgttttg ctggggttca tcatgtgggc ctgccaaaaa
1701 ggcaacatta ggtgcaacat ttgcatttga gtgcattaat taaaaacacc
1751 cttgtttcta ct
```

SEQ ID NO:55

Amino Acid Sequence of ca A/Sydney/05/97 H3 Entire molecule length: 566 aa

```
   1 mktiialsyi lclvfaqkip gndnstatlc lghhavpngt lvktitndqi
  51 evtnatelvq ssstgricds phrildgenc tlidallgdp hcdgfqnkew
 101 dlfverskay sncypydvpd yaslrslvas sgtlefnnes fnwtgvaqng
 151 tsyackrssi ksffsrlnwl hqlkykypal nvtmpnndkf dklyiwgvhh
 201 pstdsdqtsi yaqasgrvtv stkrsqqtvi pnigsrpwvr gissrisihw
 251 tivkpgdill instgnliap rgyfkirsgk ssimrsdapi gkcnsecitp
 301 ngsipndkpf qnvnrityga cpryvkqntl klatgmrnvp ekqtrgifga
 351 iagfiengwe gmvdgwygfr hqnsegtgqa adlkstqaai nqingklnrl
 401 iektnekfhq iekefseveg riqdlekyve dtkidlwsyn aellvalenq
 451 htidltdsem nklfertrkq lrenaedmgn gcfkiyhkcd nacigsirng
 501 tydhdvyrde alnnrfqikg velksgykdw ilwisfaisc fllcvvllgf
 551 imwacqkgni rcnici
```

Figure 1G

SEQ ID NO:8

Nucleotide Sequence of ca A/Sydney/05/97 N2 Entire molecule length: 1467 bp

```
   1 agcaaaagca ggagtaaaga tgaatccaaa tcaaaagata ataacgattg
  51 gctctgtttc tctcactatt gccacaatat gcttccttat gcaaattgcc
 101 atcctggtaa ctactgtaac attgcatttc aagcaatatg aatgcagctc
 151 tcccccaaac aaccaagtaa tgctgtgtga accaacaata atagaaagaa
 201 acataacaga gatagtgtat ctgaccaaca ccaccataga gaaggaaata
 251 tgccccaaac tagcagaata cagaaattgg tcaaagccac aatgtaaaat
 301 tacaggattt gcaccttttt ctaaggacaa ttcaattcgg ctttccgctg
 351 gtggggacat ttgggtgaca agggaacctt atgtgtcgtg cgatcctgac
 401 aagtgttatc aatttgccct tggacaggga acaacactaa acaacaggca
 451 ttcaaatgac acagtacatg ataggacccc ttatcgaacc ctattgatga
 501 atgagttggg tgttccattt catttgggaa ccaagcaagt gtgcatagca
 551 tggtccagct caagttgtca cgatggaaaa gcatggctgc atgtttgtgt
 601 aactgggcat gatgaaaatg caactgctag cttcatttac gatgggaggc
 651 ttgtagatag tattggttca tggtccaaaa aaatcctcag gacccaggag
 701 tcggaatgcg tttgtatcaa tggaacttgt acagtagtaa tgactgatgg
 751 gagtgcttca ggaagagctg atactaaaat actattcatt gaggagggga
 801 aaatcgttca tatcagccca ctgtcaggaa gtgctcagca tgtcgaggag
 851 tgctcctgtt atcctcgata tcctggtgtc agatgtgtct gcagagacaa
 901 ctggaaaggc tccaataggc ccatcgtaga tataaatgta aaggattata
 951 gcattgtttc cagttatgtg tgctcaggac ttgttggaga cacacccaga
1001 aaaaacgaca gctccagcag tagtcattgc ctgaatccta acaatgagga
1051 agggggtcat ggagtgaaag gctgggcctt tgatgatgga aatgacgtgt
1101 ggatgggaag aacgatcagc gagaagttcc gctcaggtta tgaaaccttc
1151 aaagtcattg aaggctggtc caaacctaac tccaaattgc agataaatag
1201 gcaagtcata gttgacagag gtaataggtc cggttattct ggtattttct
1251 ctgttgaagg caaaagctgc atcaatcggt gcttttatgt ggagttgata
1301 aggggaagga aacaggaaac tgaagtctgg tggacctcaa acagtattgt
1351 tgtgttttgt ggcacctcag gtacatatgg aacaggctca tggcctgatg
1401 gggcggacat caatctcatg cctatataag ctttcgcaat tttagaaaaa
1451 aactccttgt ttctact
```

SEQ ID NO:56

Amino Acid Sequence of ca A/Sydney/05/97 N2 Entire molecule length: 469 aa

```
   1 mnpnqkiiti gsvsltiati cflmqiailv ttvtlhfkqy ecssppnnqv
  51 mlceptiier niteivyltn ttiekeicpk laeyrnwskp qckitgfapf
 101 skdnsirlsa ggdiwvtrep yvscdpdkcy qfalgqgttl nnrhsndtvh
 151 drtpyrtllm nelgvpfhlg tkqvciawss sschdgkawl hvcvtghden
 201 atasfiydgr lvdsigswsk kilrtqesec vcingtctvv mtdgsasgra
 251 dtkilfieeg kivhisplsg saqhveecsc yprypgvrcv crdnwkgsnr
 301 pivdinvkdy sivssyvcsg lvgdtprknd sssshclnp nneegghgvk
 351 gwafddgndv wmgrtisekf rsgyetfkvi egwskpnskl qinrqvivdr
 401 gnrsgysgif svegkscinr cfyvelirgr kqetevwwts nsivvfcgts
 451 gtygtgswpd gadinlmpi
```

Figure 1H

SEQ ID NO:9
ca A/Panama/2007/99
Nucleotide Sequence of ca A/Panama/2007/99 H3    Entire molecule length: 1762 bp

```
   1 agcaaaagca ggggataatt ctattaacca tgaagactat cattgctttg
  51 agctacattt tatgtctggt tttcgctcaa aaacttcccg gaaatgacaa
 101 cagcacggca acgctgtgcc tggggcacca tgcagtgtca aacggaacgc
 151 tagtgaaaac aatcacgaat gaccaaattg aagtgactaa tgctactgag
 201 ctggttcaga gttcctcaac aggtagaata tgcgacagtc ctcaccaaat
 251 ccttgatgga gaaaactgca cactaataga tgctctattg ggagaccctc
 301 attgtgatgg cttccaaaat aaggaatggg acctttttgt tgaacgcagc
 351 aaagcctaca gcaactgtta cccttatgat gtgccggatt atgcctccct
 401 taggtcacta gttgcctcat ccggcacact ggagtttaac aatgaaagct
 451 tcaattggac tggagtcgct cagaatggaa caagctctgc ttgcaaaagg
 501 ggatctaata aaagtttctt tagtagattg aattggttgc accaattaaa
 551 atacaaatat ccagcactga acgtgactat gccaaacaat gaaaaatttg
 601 acaaattgta catttggggg gttctccacc cgagtacgga cagtgaccaa
 651 atcagcctat atgctcaagc atcagggaga gtcacagtct ctaccaaaag
 701 aagccaacaa actgtaatcc cgaatatcgg atctagaccc tgggtaaggg
 751 gtgtctccag cagaataagc atctattgga caatagtaaa accgggagac
 801 atacttttga ttaacagcac agggaatcta attgctcctc ggggttactt
 851 caaaatacga agtgggaaaa gctcaataat gaggtcagat gcacccattg
 901 gcaaatgcaa ttctgaatgc atcactccaa atggaagcat tcccaatgac
 951 aaaccatttc aaaatgtaaa caggatcaca tatggggcct gtcccagata
1001 tgttaagcaa aacactctga aattggcaac agggatgcgg aatgtaccag
1051 agaaacaaac tagaggcata ttcggcgcaa tcgcgggttt catagaaaat
1101 ggttgggagg gaatggtgga cggttggtac ggtttcaggc atcaaaattc
1151 tgagggcaca ggacaagcag cagatcttaa aagcactcaa gcagcaatca
1201 accaaatcaa cgggaaactg aataggttaa tcgagaaaac gaacgagaaa
1251 ttccatcaaa ttgaaaaaga attctcagaa gtagaaggga gaattcagga
1301 cctcgagaaa tatgttgagg acactaaaat agatctctgg tcgtacaacg
1351 cggagcttct tgttgccctg gagaaccaac atacaattga tctaactgac
1401 tcagaaatga acaaactgtt tgaaagaaca aagaagcaac tgagggaaaa
1451 tgctgaggat atgggcaatg gttgtttcaa aatataccac aaatgtgaca
1501 atgcctgcat agggtcaatc agaaatggaa cttatgacca tgatgtatac
1551 agagacgaag cattaaacaa ccggttccag atcaaaggtg ttgagctgaa
1601 gtcaggatac aaagattgga tcctatggat ttcctttgcc atatcatgct
1651 ttttgctttg tgttgttttg ctggggttca tcatgtgggc ctgccaaaaa
1701 ggcaacatta ggtgcaacat ttgcatttga gtgcattaat taaaaacacc
1751 cttgtttcta ct
```

SEQ ID NO:57
Amino Acid Sequence of ca A/Panama/2007/99 H3 Entire molecule length: 566 aa

```
   1 mktiialsyi lclvfaqklp gndnstatlc lghhavsngt lvktitndqi
  51 evtnatelvq ssstgricds phqildgenc tlidallgdp hcdgfqnkew
 101 dlfverskay sncypydvpd yaslrslvas sgtlefnnes fnwtgvaqng
 151 tssackrgsn ksffsrlnwl hqlkykypal nvtmpnnekf dklyiwgvlh
 201 pstdsdqisl yaqasgrvtv stkrsqqtvi pnigsrpwvr gvssrisiyw
 251 tivkpgdill instgnliap rgyfkirsgk ssimrsdapi gkcnsecitp
 301 ngsipndkpf qnvnrityga cpryvkqntl klatgmrnvp ekqtrgifga
 351 iagfiengwe gmvdgwygfr hqnsegtgqa adlkstqaai nqingklnrl
 401 iektnekfhq iekefseveg riqdlekyve dtkidlwsyn aellvalenq
 451 htidltdsem nklfertkkq lrenaedmgn gcfkiyhkcd nacigsirng
 501 tydhdvyrde alnnrfqikg velksgykdw ilwisfaisc fllcvvllgf
 551 imwacqkgni rcnici
```

Figure 1I

SEQ ID NO:10
Nucleotide Sequence of ca A/Panama/2007/99 N2    Entire molecule length: 1466 bp

```
   1 agcaaaagca ggagtaaaga tgaatccaaa tcaaaagata ataacgattg
  51 gctctgtttc tctcactatt gccacaatat gcttccttat gcaaatagcc
 101 atcctggtaa ctactgtaac attgcatttc aagcaatatg aatgcaactc
 151 cccccaaac aaccaagtaa tgctgtgtga accaacaata atagaaagaa
 201 acataacaga gatagtgtat ctgaccaaca ccaccataga gaaggaaata
 251 tgccccaaac tagcagaata cagaaattgg tcaaagccgc aatgtaaaat
 301 tacaggattt gcaccttttt ctaaggataa ttcaattcgg ctttccgctg
 351 gtggggacat tgggtgaca agagaacctt atgtgtcatg cgatcctgac
 401 aagtgttatc aatttgccct tggacaggga acaacactaa acaacaggca
 451 ttcaaatgac acagtacatg ataggacccc ttatcgaacc ctattgatga
 501 atgagttggg tgttccattt catttgggaa ccaagcaagt gtgtatagca
 551 tggtccagct caagttgtca cgatggaaaa gcatggctgc atgtttgtgt
 601 aactgggcat gatgaaaatg caactgctag cttcatttac gatgggagac
 651 ttgtagatag tattggttca tggtccaaaa aaatcctcag gacccaggag
 701 tcggaatgcg tttgtatcaa tggaacttgt acagtagtaa tgactgatgg
 751 gagtgcttca ggaagagctg atactaaaat acttttcatt gaggaggga
 801 aaatcgttca tactagcaaa ttgtcaggaa gtgctcagca tgtcgaggag
 851 tgctcctgtt atcctcgata tcctggtgtc agatgtgtct gcagagacaa
 901 ctggaaaggc tccaataggc ccatcgtaga tataaatgta aaggattata
 951 gcattgtttc cagttatgtg tgctcaggac ttgttggaga cacacccaga
1001 aaaaacgaca gctccagcag tagccattgc ctggatccta acaatgaaga
1051 aggggtcat ggagtgaaag ctgggccttt gatgatgga aatgacgtgt
1101 ggatgggaag aacgatcagc gagaagtcac gctcaggtta tgaaaccttc
1151 aaggtcattg aaggctggtc aaacctaac tccaaattgc agataaatag
1201 gcaagtcata gttgaaagag gtaatatgtc cggttattct ggtattttct
1251 ctgttgaagg caaaagctgc atcaatcggt gcttttatgt ggagttgata
1301 aggggaagga acaggaaac tgaagtctgg tggacctcaa acagtattgt
1351 tgtgttttgt ggcacctcag gtacatatgg aacaggctca tggcctgatg
1401 gggcggacat caatctcatg cctatataag ctttcgcaat tttagaaaaa
1451 actccttgtt tctact
```

SEQ ID NO:58
Amino Acid Sequence of ca A/Panama/2007/99 N2    Entire molecule length: 469 aa

```
   1 mnpnqkiiti gsvsltiati cflmqiailv ttvtlhfkqy ecnsppnnqv
  51 mlceptiier niteivyltn ttiekeicpk laeyrnwskp qckitgfapf
 101 skdnsirlsa ggdiwvtrep yvscdpdkcy qfalgqgttl nnrhsndtvh
 151 drtpyrtllm nelgvpfhlg tkqvciawss sschdgkawl hvcvtghden
 201 atasfiydgr lvdsigswsk kilrtqesec vcingtctvv mtdgsasgra
 251 dtkilfieeg kivhtsklsg saqhveecsc yprypgvrcv crdnwkgsnr
 301 pivdinvkdy sivssyvcsg lvgdtprknd ssssshcldp nneegghgvk
 351 gwafddgndv wmgrtiseks rsgyetfkvi egwskpnskl qinrqviver
 401 gnmsgysgif svegkscinr cfyvelirgr kqetevwwts nsivvfcgts
 451 gtygtgswpd gadinlmpi
```

Figure 1J

SEQ ID NO:11 ca A/Wyoming/03/2003

Nucleotide Sequence of ca A/Wyoming/03/2003 H3  Entire molecule length: 1762 bp

```
   1 agcaaaagca ggggataatt ctattaacca tgaagactat cattgcttta
  51 agctacattc tatgtctggt tttctctcaa aagcttccg  gaaatgacaa
 101 cagcacggca acgctgtgcc ttgggcacca tgcagtacca aacggaacga
 151 tagtgaaaac aatcacgaat gaccaaattg aagttactaa tgctactgag
 201 ctggttcaga gttcctcaac aggtggaata tgcgacagtc ctcatcagat
 251 ccttgatgga gaaaactgca cactaataga tgctctattg ggagaccctc
 301 agtgtgatgg cttccaaaat aagaaatggg accttttgt  tgaacgcagc
 351 aaagcctaca gcaactgtta cccttatgat gtgccggatt atgcctccct
 401 taggtcacta gttgcctcat ccggcacact ggagtttaac aatgaaagct
 451 tcaattgggc tggagtcact cagaatggaa caagctctgc ttgcaaaagg
 501 agatctaata aagtttctt  tagtagattg aattggttga cccacttaaa
 551 atacaaatac ccagcattga acgtgactat gccaaacaat gaaaaatttg
 601 acaaattgta catttggggg gttcaccacc cggttacgga cagtgaccaa
 651 atcagcctat atgctcaagc atcaggaaga atcacagtct ctaccaaaag
 701 aagccaacaa actgtaatcc cgaatatcgg atatagaccc agggtaaggg
 751 atatctccag cagaataagc atctattgga caatagtaaa accgggagac
 801 atactttga  ttaacagcac aggaaatcta attgctcctc ggggttactt
 851 caaaatacga agtgggaaaa gctcaataat gagatcagat gcacccattg
 901 gcaaatgcaa ttctgaatgc atcactccaa atggaagcat tcccaatgac
 951 aaaccatttc aaaatgtaaa caggatcaca tatggggcct gtcccagata
1001 tgttaagcaa aacactctga aattggcaac agggatgcga atgtaccag
1051 agaaacaaac tagaggcata tttggcgcaa tcgcgggttt catagaaaat
1101 ggttgggagg gaatggtgga cggttggtac ggtttcaggc atcaaaattc
1151 tgagggcaca ggacaagcag cagatctcaa aagcactcaa gcagcaatca
1201 accaaatcaa tgggaaactg aataggttaa tcgggaaaac aaacgagaaa
1251 ttccatcaga ttgaaaaaga attctcagaa gtagaaggga gaattcagga
1301 cctcgagaaa tatgttgagg acactaaaat agatctctgg tcatacaacg
1351 cggagcttct gttgccctg  gaaaaccaac atacaattga tctaactgac
1401 tcagaaatga caaactgtt  tgaaagaaca aagaagcaac tgagggaaaa
1451 tgctgaggat atgggcaatg gttgtttcaa aatataccac aaatgtgaca
1501 atgcctgcat agagtcaatc agaaatggaa cttatgacca tgatgtatac
1551 agagatgaag cattaaacaa ccggttccag atcaaaggtg ttgagctgaa
1601 gtcaggatac aaagattgga tcctatggat ttcctttgcc atatcatgtt
1651 ttttgctttg tgttgctttg ttggggttca tcatgtgggc ctgccaaaaa
1701 ggcaacatta ggtgcaacat ttgcatttga gtgcattaat taaaaacacc
1751 cttgtttcta ct
```

SEQ ID NO:59

Amino Acid Sequence of ca A/Wyoming/03/2003 H3 Entire molecule length: 566 aa

```
  1 mktiialsyi lclvfsqklp gndnstatlc lghhavpngt ivktitndqi
 51 evtnatelvq ssstggicds phqildgenc tlidallgdp qcdgfqnkkw
101 dlfverskay sncypydvpd yaslrslvas sgtlefnnes fnwagvtqng
151 tssackrrsn ksffsrlnwl thlkykypal nvtmpnnekf dklyiwgvhh
201 pvtdsdqisl yaqasgritv stkrsqqtvi pnigyrprvr dissrisiyw
251 tivkpgdill instgnliap rgyfkirsgk ssimrsdapi gkcnsecitp
301 ngsipndkpf qnvnrityga cpryvkqntl klatgmrnvp ekqtrgifga
351 iagfiengwe gmvdgwygfr hqnsegtgqa adlkstqaai nqingklnrl
401 igktnekfhq iekefseveg riqdlekyve dtkidlwsyn aellvalenq
451 htidltdsem nklfertkkq lrenaedmgn gcfkiyhkcd naciesirng
501 tydhdvyrde alnnrfqikg velksgykdw ilwisfaisc fllcvallgf
551 imwacqkgni rcnici
```

Figure 1K

SEQ ID NO:12

Nucleotide Sequence of ca A/Wyoming/03/2003 N2   Entire molecule length: 1467 bp

```
   1 agcaaaagca ggagtaaaga tgaatccaaa tcaaaagata ataacgattg
  51 gctctgtttc cctcaccatt tccacaatat gcttcttcat gcaaattgcc
 101 atcctgataa ctactgtaac attgcatttc aagcaatatg aattcaactc
 151 ccccccaaac aaccaagtga tgctgtgtga accaacaata atagaaagaa
 201 acataacaga gatagtgtat ctgaccaaca ccaccataga gaaggaaata
 251 tgccccaaac tagcagaata cagaaattgg tcaaagccgc aatgtaacat
 301 tacaggattt gcaccttttt ctaaggacaa ttcgattcgg ctttccgctg
 351 gtggggacat ctgggtgaca agagaacctt atgtgtcatg cgatcctgac
 401 aagtgttatc aatttgccct tggacaggga acaacactaa acaacgtgca
 451 ttcaaatgac acagtacatg ataggacccc ttatcggacc ctattgatga
 501 atgagttggg tgttccattt catctgggga ccaagcaagt gtgcatagca
 551 tggtccagct caagttgtca cgatggaaaa gcatggctgc atgtttgtgt
 601 aacggggat gatgaaaatg caactgctag cttcatttac aatgggaggc
 651 ttgtagatag tattgtttca tggtccaaaa aaatcctcag gacccaggag
 701 tcagaatgcg tttgtatcaa tggaacttgt acagtagtaa tgactgatgg
 751 gagtgcttca ggaaaagctg atactaaaat actattcatt gaggagggga
 801 aaattgttca tactagcaca ttatcaggaa gtgctcagca tgtcgaggag
 851 tgctcctgtt atcctcgata tcctggtgtc agatgtgtct gcagagacaa
 901 ctggaaaggc tccataggc ccatcgtaga tataaacata aggattata
 951 gcattgtttc cagttatgtg tgctcaggac ttgttggaga cacacccaga
1001 aaaaacgaca gctccagcag tagccattgc ttggatccaa acaatgagga
1051 aggtggtcat ggagtgaaag gctgggcatt tgatgatgga atgacgtgt
1101 ggatgggaag aacgatcagc gagaagttac gctcaggata tgaaaccttc
1151 aaagtcattg aaggctggtc aaccctaac tccaaattgc agataaatag
1201 gcaagtcata gttgacagag gtaacaggtc cggttattct ggtattttct
1251 ctgttgaagg caaaagctgc atcaatcggt gcttttatgt ggagttgata
1301 aggggaagaa aacaggaaac tgaagtcttg tggacctcaa acagtattgt
1351 tgtgttttgt ggcacctcag gtacatatgg aacaggctca tggcctgatg
1401 gggcggacat caatctcatg cctatataag ctttcgcaat tttagaaaaa
1451 aactccttgt ttctact
```

SEQ ID NO:60

Amino Acid Sequence of ca A/Wyoming/03/2003 N2Entire molecule length: 469 aa

```
   1 mnpnqkiiti gsvsltisti cffmqiaili ttvtlhfkqy efnsppnnqv
  51 mlceptiier niteivyltn ttiekeicpk laeyrnwskp qcnitgfapf
 101 skdnsirlsa ggdiwvtrep yvscdpdkcy qfalgqgttl nnvhsndtvh
 151 drtpyrtllm nelgvpfhlg tkqvciawss sschdgkawl hvcvtgdden
 201 atasfiyngr lvdsivswsk kilrtqesec vcingtctvv mtdgsasgka
 251 dtkilfieeg kivhtstlsg saqhveecsc yprypgvrcv crdnwkgsnr
 301 pivdinikdy sivssyvcsg lvgdtprknd ssssshcldp nneegghgvk
 351 gwafddgndv wmgrtisekl rsgyetfkvi egwsnpnskl qinrqvivdr
 401 gnrsgysgif svegkscinr cfyvelirgr kqetevlwts nsivvfcgts
 451 gtygtgswpd gadinlmpi
```

Figure 1L

SEQ ID NO:13
ca A/Texas/36/91
Nucleotide Sequence of ca A/Texas/36/91 H1 Entire molecule length: 1778 bp

```
   1 agcaaaagca ggggaaaata aaaacaacca aaatgaaagc aaaactacta
  51 gtcctgttat gtgcatttac agctacatat gcagacacaa tatgtatagg
 101 ctaccatgcg aacaactcaa ccgacactgt tgacacagta cttgagaaga
 151 acgtgacagt gacacactct gtcaacctac ttgaggacag tcacaacgga
 201 aaactatgtc gactaaaggg aatagcccca ctacaattgg gtaattgcag
 251 cgttgccgga tggatcttag gaaacccaaa atgcgaatca ctgttttcta
 301 aggaatcatg gtcctacatt gcagaaacac caaaccctga gaatggaaca
 351 tgttacccag ggtatttcgc cgactatgag gaactgaggg agcaattgag
 401 ttcagtatca tcattcgaga gattcgaaat attccccaaa gaaagctcat
 451 ggcccaacca caccgtaacc aaaggagtaa cgacatcatg ctcccataat
 501 gggaaaagca gtttttacag aaatttgcta tggctgacga agaagaatgg
 551 cttgtaccca aatgtgagca agtcctatgt aaacaacaaa gagaaagaag
 601 tccttgtact atggggtgtt catcacccgt ctaacatagg ggaccaaagg
 651 gccatctatc atacagaaaa tgcttatgtc tctgtagtgt cttcacatta
 701 tagcagaaga ttcaccccag aaatagcaaa aagacccaaa gtaagagatc
 751 aagaaggaag aattaactac tactggactc tgctggaacc cggggacaca
 801 ataatatttg aggcaaatgg aaatctaata gcgccatggt atgctttcgc
 851 actgagtaga ggctttgggt caggaatcat cacctcaaac gcatcaatgg
 901 atgaatgtga cgcgaagtgt caaacacccc agggagctat aaacagtagt
 951 cttcctttcc agaatgtaca cccagtcaca ataggagagt gtccaaagta
1001 tgtcaggagt acaaaattaa ggatggttac aggactaagg aacatcccat
1051 ccattcaatc cagaggtttg tttggagcca ttgccggttt cattgaaggg
1101 gggtggactg gaatgataga tggatggtat ggttatcatc atcagaatga
1151 acaaggatct ggctatgctg cggaccaaaa aagcacacaa aatgccatta
1201 acgggattac aaacaaggtg aattctgtaa tcgagaaaat gaacactcaa
1251 ttcacagctg tgggcaaaga attcaacaaa ttagaaagaa ggatggaaaa
1301 cttaaataaa aaagttgatg atggatttct ggacatttgg acatataatg
1351 cagaattgtt ggttctactg gaaaatggaa ggactttgga ttttcatgac
1401 tcaaatgtga agaatctgta tgagaaagta aaaagccaat tgaagaataa
1451 tgccaaagaa atagggaacg ggtgttttga attctatcac aagtgtaaca
1501 atgaatgcat ggaaagtgtg aaaaatggaa cttatgacta tccaaaatat
1551 tccgaagaat caaagttaaa caggggaaaa attgatggag tgaaattgga
1601 atcaatggga gtctatcaga ttctggcgat ctactcaact gtcgccagtt
1651 cactggtgct tttggtctcc ctgggggcaa tcagcttctg gatgtgttct
1701 aatgggtctt tgcagtgtag aatatgcatc tgagaccaga atttcagaaa
1751 tataagaaaa aacacccttg tttctact
```

SEQ ID NO:61
Amino Acid Sequence of ca A/Texas/36/91 H1 Entire molecule length: 566 aa

```
  1 mkakllvllc aftatyadti cigyhannst dtvdtvlekn vtvthsvnll
 51 edshngklcr lkgiaplqlg ncsvagwilg npkceslfsk eswsyiaetp
101 npengtcypg yfadyeelre qlssvssfer feifpkessw pnhtvtkgvt
151 tscshngkss fyrnllwltk knglypnvsk syvnnkekev lvlwgvhhps
201 nigdqraiyh tenayvsvvs shysrrftpe iakrpkvrdq egrinyywtl
251 lepgdtiife angnliapwy afalsrgfgs giitsnasmd ecdakcqtpq
301 gainsslpfq nvhpvtigec pkyvrstklr mvtglrnips iqsrglfgai
351 agfieggwtg midgwygyhh qneqgsgyaa dqkstqnain gitnkvnsvi
401 ekmntqftav gkefnklerr menlnkkvdd gfldiwtyna ellvllengr
451 tldfhdsnvk nlyekvksql knnakeigng cfefyhkcnn ecmesvkngt
501 ydypkysees klnrgkidgv klesmgvyqi laiystvass lvllvslgai
551 sfwmcsngsl qcrici
```

Figure 1M

SEQ ID NO:14
Nucleotide Sequence of ca A/Texas/36/91 N1     Entire molecule length: 1463 bp

```
   1 agcaaaagca ggagtttaaa atgaatccaa atcaaaaaat aataatcata
  51 ggatcaatca gtatggcaat cggaataatt agtctaatat tgcaaatagg
 101 aaatattatt tcaatatggg ctagccactc aatccaaact ggaagtcaaa
 151 accacactgg aatatgcaac caaagaatca ttacatatga aaatagcacc
 201 tgggtgaatc aaacatatgt taatattaac aacactaatg ttgttgctgg
 251 aaaggacaaa acttcagtga cattggccgg caattcatct ctttgcccta
 301 tccgtgggtg ggctatatac acaaaagaca acagcataag aattggttcc
 351 aaggagatg tttttgtcat aagagagcct tttatatcat gttctcactt
 401 ggaatgcaga acctttttc tgacccaagg tgctctatta aatgacaagc
 451 attcaaatgg gaccgttaag gacagaagcc cttatagggc cttaatgagc
 501 tgtcctctag gtgaagctcc gtctccatac aattcaagat tgaatcagt
 551 tgcttggtca gcaagcgcat gccatgatgg catgggctgg ctaacaatcg
 601 gaatttctgg tccagataat ggagcagtgg ctgtactaaa atacaacggc
 651 ataatactg aaaccataaa aagttggaag aagcgaatat taagaacaca
 701 agagtctgaa tgtgtctgtg tgaacggttc atgttttacc ataatgaccg
 751 atggcccgag taatggggcc gcctcgtaca gaatcttcaa aatcgagaag
 801 gggaaggtta ctaaatcaat agagttggat gcacccaatt atcattacga
 851 ggaatgttcc tgttacccag acaccggcac agtgatgtgt gtgtgcaggg
 901 acaattggca cggttcaaat cgaccttggg tgtcttttaa tcaaaacctg
 951 gattatcaaa taggatacat ctgcagtggg gtgttcggtg acaatccgcg
1001 tcccaaagat ggagaaggca gctgtaatcc agtgactgtt gatggagcag
1051 acggagtaaa ggggttttca tacagatatg gtaatggtgt ttggatagga
1101 aggactaaaa gtaacagact cagaaaggga tttgagatga tttgggatcc
1151 taatggatgg acagataccg acagtgattt ctctgtgaaa caggatgtcg
1201 tggcaatgac tgattggtca gggtacagcg gaagtttcgt tcaacatcct
1251 gagctaacag gattggactg tatgagacct tgcttctggg ttgaattaat
1301 cagagggcga cctagagaaa atacaacaat ctggactagt gggagcagca
1351 tttcttttg tggcgtaaat agcgatactg caaactggtc ttggccagac
1401 ggtgccgagt tgccattcac cattgacaag tagtccgttg aaaaaaaact
1451 ccttgtttct act
```

SEQ ID NO:62
Amino Acid Sequence of ca A/Texas/36/91 N1     Entire molecule length: 470 aa

```
   1 mnpnqkiiii gsismaigii slilqignii siwashsiqt gsqnhtgicn
  51 qriityenst wvnqtyvnin ntnvvagkdk tsvtlagnss lcpirgwaiy
 101 tkdnsirigs kgdvfvirep fiscshlecr tffltqgall ndkhsngtvk
 151 drspyralms cplgeapspy nsrfesvaws asachdgmgw ltigisgpdn
 201 gavavlkyng iitetikswk krilrtqese cvcvngscft imtdgpsnga
 251 asyrifkiek gkvtksield apnyhyeecs cypdtgtvmc vcrdnwhgsn
 301 rpwvsfnqnl dyqigyicsg vfgdnprpkd gegscnpvtv dgadgvkgfs
 351 yrygngvwig rtksnrlrkg femiwdpngw tdtdsdfsvk qdvvamtdws
 401 gysgsfvqhp eltgldcmrp cfwvelirgr prenttiwts gssisfcgvn
 451 sdtanwswpd gaelpftidk
```

Figure 1N

SEQ ID NO:15
ca A/Shenzhen/227/95
Nucleotide Sequence of ca A/Shenzhen/227/95 H1 Entire molecule length: 1689 bp

```
   1 aaatgaaagc aaaactacta gtcctgttgt gtgcatttac agctacatat
  51 gcagacacaa tatgtatagg ctaccatgcg aacaactcaa ccgacactgt
 101 tgacacagta cttgagaaga acgtgacagt gacacactct gtcaacctac
 151 ttgaggacag tcacaacgga aaactatgcc gactaaaagg aacagcccca
 201 ctacaattgg gtaattgcag cgttgccgga tggatcttag gaaacccaga
 251 atgcgaatca ctgttttcta aggaatcatg gtcctacatt gcagaaacac
 301 caaaccctga gaatggaaca tgttacccag ggtatttcgc cgactatgag
 351 gaactgaggg agcaattgag ctcagtatca tcattcgaga gattcgaaat
 401 attccccaag gaaagctcat ggcccaaaca caccgtaacc aaaggagtga
 451 cggcatcatg ctcccataat gggaaaagca gtttttacaa aaatttgcta
 501 tggctgacgg aaaagaatgg cttgtaccca aatctgagca agtcctatgt
 551 aaacaacaag gagaaagaag tccttgtact atggggtgtt catcacccgt
 601 ctaacatagg ggaccaaagg gccatctatc atacagaaaa tgcttatgtc
 651 tctgtagtgt cttcacatta tagcagaaga ttcaccccag aaatagcaaa
 701 aagacccaaa gtaagaggtc aagaagggag aattaactac tactggactc
 751 tgctggaacc cggggacaca ataatatttg aggcaaatgg aaatctaata
 801 gcgccatggt acgctttcgc actgagtaga ggctttgggt caggaatcat
 851 cacctcaacc gcatcaatgg gtgaatgtga cgctaagtgt caaacacccc
 901 aaggagctat aaacagtagt cttccctttcc agaatgtaca cccagtcaca
 951 ataggagagt gtcccaagta tgtcaggagt acaaaattaa ggatggttac
1001 aggactaaga aacatcccat ccattcaatc tagaggtttg tttggagcca
1051 ttgccggttt cattgaaggg gggtggactg gaatgataga tggatggtat
1101 ggttatcatc atcagaatga acaaggatct ggctatgctg cagaccaaaa
1151 aagcacacaa aatgccattg atgggattac aaacaaggtg aattctgtaa
1201 tcgagaaaat gaacactcaa ttcacagctg taggcaaaga attcaacaaa
1251 ttagagagaa ggatggaaaa cttaaataag aaagttgatg atggatttct
1301 ggacatttgg acatataatg cagagttgtt ggttctcctg gaaaatggaa
1351 ggactttggg ttttcatgac tcaaatgtga agaatctgta tgagaaagta
1401 aaaaaccaat tgaagaataa tgccaaagaa atcgggaacg ggtgttttga
1451 attctatcac aagtgtaaca atgaatgcat ggaaagtgtg aaaaatggaa
1501 cttatgacta tccaaaatat tccgaagaat caaagttaaa cagggaaaaa
1551 attgatggag tgaaattgga atcaatggga gtctatcaga ttctggcgat
1601 ctactcaact gtcgccagtt cactggtgct tttggtctcc ctgggggcaa
1651 tcagtttctg gatgtgttct aatgggtctt tgcagtgta
```

SEQ ID NO:63
Amino Acid Sequence of ca A/Shenzhen/227/95 H1 Entire molecule length: 562 aa

```
   1 mkakllvllc aftatyadti cigyhannst dtvdtvlekn vtvthsvnll
  51 edshngklcr lkgtaplqlg ncsvagwilg npeceslfsk eswsyiaetp
 101 npengtcypg yfadyeelre qlssvssfer feifpkessw pkhtvtkgvt
 151 ascshngkss fyknllwlte knglypnlsk syvnnkekev lvlwgvhhps
 201 nigdqraiyh tenayvsvvs shysrrftpe iakrpkvrgq egrinyywtl
 251 lepgdtiife angnliapwy afalsrgfgs giitstasmg ecdakcqtpq
 301 gainsslpfq nvhpvtigec pkyvrstklr mvtglrnips iqsrglfgai
 351 agfieggwtg midgwygyhh qneqgsgyaa dqkstqnaid gitnkvnsvi
 401 ekmntqftav gkefnklerr menlnkkvdd gfldiwtyna ellvllengr
 451 tlgfhdsnvk nlyekvknql knnakeigng cfefyhkcnn ecmesvkngt
 501 ydypkysees klnrekidgv klesmgvyqi laiystvass lvllvslgai
 551 sfwmcsngsl qc
```

Figure 1O

SEQ ID NO:16
Nucleotide Sequence of ca A/Shenzhen/227/95 N1    Entire molecule length: 1447 bp

```
   1 agcaaaagca ggagtttaaa atgaatccaa atcaaaaaat aataaccatt
  51 ggatcaatca gtattgcaat tggaataatt agtctgatat tgcaaatagg
 101 aaatattatt tcaatatggg ctagccactc aatccaaact ggaagtcaaa
 151 accacactgg aatatgcaac caaagaatca ttacatatga aatagcacc
 201 tgggtaaatc aaacatatgt taatattaac aacactaatg ttgttgctgg
 251 aaaggacaaa acctcaatga cattggccgg caattcatct ctttgcccta
 301 tccgtggatg ggctatatac acaaaagaca acagcataag aattggttcc
 351 aaaggagatg ttttgtcat aagagagcct tttatatcat gttctcactt
 401 ggaatgcaga accttttttc tgacccaagg tgctctatta aatgacaagc
 451 attcaaatgg gaccgttaag gacagaagcc cttataggggc cttaatgagc
 501 tgtcctctag gtgaagctcc gtctccatac aattcaagat ttgaatcagt
 551 tgcttggtca gcaagcgcat gccatgatgg cttgggctgg ctaacaatcg
 601 gaatttctgg tccagataat ggggcagtgg ctgtactaaa atacaacggc
 651 ataataactg aaaccattaa aagttggaag aagcgaatat taagaacaca
 701 agagtctgaa tgtgtctgta tgaacggttc atgttttacc ataatgaccg
 751 atggcccgag taatggggcc gcatcgtaca gaatcttcaa aatcgagaag
 801 gggagagtta ctaaatcaat agagttggat gcacccaatt atcattacga
 851 ggaatgttca tgttacccag acaccggcac agtgatgtgt gtgtgcaggg
 901 acaattggca cggttcaaat cgaccttggg tgtcttttaa tcaaaacctg
 951 gattatcaaa taggatacat ctgcagtggg gtgttcggtg acaatccgcg
1001 tcccaaagat ggagaaggca gctgtaatcc agtgactgtt gatggagcag
1051 acggagtaaa ggggttttca tacagatatg gtaatggtgt ttggatagga
1101 aggactaaaa gtaacagact cagaaaggga tttgagatga tttgggatcc
1151 taatggatgg acagataccg acagtgattt ctcaatgaaa caggatatcg
1201 tggcaatgac tgattggtca gggtacagcg gaagttttgt tcaacatcct
1251 gagctaacag gattggactg tatgagacct tgctttgggg ttgaattagt
1301 cagagggcta cctagagaaa atacaacaat ctggactagt gggagcagca
1351 tttctttttg tggcgtaaat agcgatactg caaactggtc ttggccagac
1401 ggtgccgagt tgccattcac cattgacaag tagtccgttg aaaaaaa
```

SEQ ID NO:64
Amino Acid Sequence of ca A/Shenzhen/227/95 N1   Entire molecule length: 470 aa

```
   1 mnpnqkiiti gsisiaigii slilqignii siwashsiqt gsqnhtgicn
  51 qriityenst wvnqtyvnin ntnvvagkdk tsmtlagnss lcpirgwaiy
 101 tkdnsirigs kgdvfvirep fiscshlecr tffltqgall ndkhsngtvk
 151 drspyralms cplgeapspy nsrfesvaws asachdglgw ltigisgpdn
 201 gavavlkyng iitetikswk krilrtqese cvcmngscft imtdgpsnga
 251 asyrifkiek grvtksield apnyhyeecs cypdtgtvmc vcrdnwhgsn
 301 rpwvsfnqnl dyqigyicsg vfgdnprpkd gegscnpvtv dgadgvkgfs
 351 yrygngvwig rtksnrlrkg femiwdpngw tdtdsdfsmk qdivamtdws
 401 gysgsfvqhp eltgldcmrp cfwvelvrgl prenttiwts gssisfcgvn
 451 sdtanwswpd gaelpftidk
```

Figure 1P

SEQ ID NO:17
ca A/Beijing/262/95
Nucleotide Sequence of ca A/Beijing/262/95 H1 Entire molecule length: 1775 bp

```
   1 agcaaaagca ggggaaaata aaaacaacca aaatgaaagc aaaactacta
  51 gtcctgttat gtacatttac agctacatat gcagacacaa tatgtatagg
 101 ctaccatgcc aacaactcaa ccgacactgt tgacacagta cttgagaaga
 151 atgtgacagt gacacactct gtcaacctac ttgaggacag tcacaatgga
 201 aaactatgtc tactaaaagg aatagcccca ctacaattgg gtaattgcag
 251 cgttgccgga tggatcttag gaaacccaga atgcgaatca ctgatttcta
 301 aggaatcatg gtcctacatt gtagagacac caaaccctga gaatggaaca
 351 tgttacccag ggtatttcgc cgactatgag gaactgaggg agcaattgag
 401 ttcagtatca tcatttgaga gattcgaaat attccccaaa gaaagctcat
 451 ggcccaaaca caccgtaaca ggagtaacgg catcatgctc ccataatggg
 501 aaaagcagtt tttacagaaa tttgctatgg ctgacggaga agaatggctt
 551 gtacccaaat ctgagcaatt cctatgtgaa caacaaagag aaagaagtcc
 601 ttgtactatg ggtgttcat cacccatcta acatagggga ccaaagggcc
 651 atctatcata cagaaaacgc ttatgtctct gtagtgtctt cacattatag
 701 cagaagattc accccagaaa tagcaaaaag acccaaagta agaggtcagg
 751 aaggaagaat caactactac tggactctgc tggaacccgg ggacacaata
 801 atatttgagg caaatggaaa tctaatagcg ccatggtatg ctttcgcact
 851 gagtagaggc tttgggtcag gaatcatcac ctcaaatgca ccaatgaatg
 901 aatgtgatgc gaagtgtcaa acacctcagg gagctataaa cagtagtctt
 951 cctttccaga atgtacaccc agtcacaata ggagagtgtc caaagtatgt
1001 caggagtaca aaattaagga tggttacagg actaaggaat atcccatcca
1051 ttcaatccag aggtttgttt ggagccattg ccggtttcat tgaagggggg
1101 tggactggaa tgatggatgg gtggtatggt tatcatcatc agaatgagca
1151 aggatctggc tatgctgcag atcaaaaaag cacacaaaat gccattaacg
1201 ggattacaaa taaggtgaat tctgtaattg agaaaatgaa cactcaattc
1251 acagctgtgg gcaaagaatt caacaaatta gaaagaagga tggaaaactt
1301 aaataaaaaa gttgatgatg gatttctaga catttggaca tataatgcag
1351 aattgttggt tctactggaa aatgaaagga ctttggattt ccatgactca
1401 aatgtgaaga atctgtatga gaaagtgaaa agccaattaa agaataatgc
1451 caaagaaata gggaacgggt gttttgaatt ctatcacaag tgtaacaatg
1501 aatgcatgga aagtgtgaaa aatggaactt atgactatcc aaaatattcc
1551 gaagaatcaa agttaaacag ggagaaaatt gatggagtga aattggaatc
1601 aatgggagtc tatcagattc tggcgatcta ctcaactgtc gccagttcac
1651 tggttctttt ggtctccctg gggcaatca gcttctggat gtgttccaat
1701 gggtctttgc agtgtagaat atgcatctga gaccagaatt tcagaaatat
1751 aagaaaaaac acccttgttt ctact
```

SEQ ID NO:65
Amino Acid Sequence of ca A/Beijing/262/95 H1 Entire molecule length: 565 aa

```
   1 mkakllvllc tftatyadti cigyhannst dtvdtvlekn vtvthsvnll
  51 edshngklcl lkgiaplqlg ncsvagwilg npeceslisk eswsyivetp
 101 npengtcypg yfadyeelre qlssvssfer feifpkessw pkhtvtgvta
 151 scshngkssf yrnllwltek nglypnlsns yvnnkekevl vlwgvhhpsn
 201 igdqraiyht enayvsvvss hysrrftpei akrpkvrgqe grinyywtll
 251 epgdtiifea ngnliapwya falsrgfgsg iitsnapmne cdakcqtpqg
 301 ainsslpfqn vhpvtigecp kyvrstklrm vtglrnipsi qsrglfgaia
 351 gfieggwtgm mdgwygyhhq neqgsgyaad qkstqnaing itnkvnsvie
 401 kmntqftavg kefnklerrm enlnkkvddg fldiwtynae llvllenert
 451 ldfhdsnvkn lyekvksqlk nnakeigngc fefyhkcnne cmesvkngty
 501 dypkyseesk lnrekidgvk lesmgvyqil aiystvassl vllvslgais
 551 fwmcsngslq crici
```

Figure 1Q

SEQ ID NO:18
Nucleotide Sequence of ca A/Beijing/262/95 N1    Entire molecule length: 1463 bp

```
   1 agcaaaagca ggagtttaaa atgaatccaa atcaaaaaat aataaccatt
  51 ggatcaatca gtatagtaat cgggataatt agtctaatgt tgcaaatagg
 101 aaatattatt tcaatatggg ctagtcactc aatccaaact ggaagtcaaa
 151 accacactgg aatatgcaac caaagaatca tcacatatga aaatagcacc
 201 tgggtgaatc acacatatgt taatattaac aacactaatg ttgttgctgg
 251 aaaggacaaa acttcagtga cattggccgg caattcatca ctttgttcta
 301 tcagtggatg ggctatatac acaaaagaca acagcataag aattggttcc
 351 aaggagatg ttttttgtcat aagagagcct tttatatcat gttctcactt
 401 ggaatgcaga acctttttc tgacccaagg tgctctatta aatgacaaac
 451 attcaaatgg gaccgttaag gacagaagtc cttatagggc cttaatgagc
 501 tgtcctctag gcgaagctcc gtctccatat aattcaaagt ttgaatcagt
 551 tgcttggtca gcaagcgcat gtcatgatgg catgggctgg ttaacaatcg
 601 gaatttctgg tccagataat ggagcagtgg ctgtactaaa atacaacggc
 651 ataataactg aaaccataaa aagttggaaa aagcgaatat taagaacaca
 701 agagtctgaa tgtgtctgtg tgaacgggtc atgttttacc ataatgaccg
 751 atggcccgag taatgggcc gcctcgtaca aaatcttcaa gattgagaag
 801 gggaaggtta ctaaatcaat agagttgaat gcacccaatt ctcattatga
 851 ggaatgttcc tgttacccag acactggcac agtgatgtgt gtatgcaggg
 901 acaattggca cggttcaaat cgaccttggg tgtcttttaa tcaaaacctg
 951 gattatcaaa taggatacat ctgcagtggg gtgttcggtg acaatccgcg
1001 tcccaaagat ggagagggca gctgtaatcc agtgactgtt gatggagcag
1051 acggagtaaa ggggttttca tacagatatg gtaatggtgt tggatagga
1101 aggactaaaa gtaacagact cagaaaggga tttgagatga tttgggatcc
1151 taatggatgg acagataccg acagtgattt ctcagtgaaa caggatgttg
1201 tggcaatgac tgattggtca gggtacagcg gaagtttcgt tcaacatcct
1251 gagctaacag gattggactg tataagacct tgcttctggg ttgaattagt
1301 cagaggacgg cctagagaaa atacaacaat ctggactagt gggagcagca
1351 tttcttttg tggcgtaaat agtgatactg caaactggtc ttggccagac
1401 ggtgctgagt tgccattcac cattgacaag tagtccgttg aaaaaaaact
1451 ccttgtttct act
```

SEQ ID NO:66
Amino Acid Sequence of ca A/Beijing/262/95 N1    Entire molecule length: 470 aa

```
   1 mnpnqkiiti gsisivigii slmlqignii siwashsiqt gsqnhtgicn
  51 qriityenst wvnhtyvnin ntnvvagkdk tsvtlagnss lcsisgwaiy
 101 tkdnsirigs kgdvfvirep fiscshlecr tffltqgall ndkhsngtvk
 151 drspyralms cplgeapspy nskfesvaws asachdgmgw ltigisgpdn
 201 gavavlkyng iitetikswk krilrtqese cvcvngscft imtdgpsnga
 251 asykifkiek gkvtksieln apnshyeecs cypdtgtvmc vcrdnwhgsn
 301 rpwvsfnqnl dyqigyicsg vfgdnprpkd gegscnpvtv dgadgvkgfs
 351 yrygngvwig rtksnrlrkg femiwdpngw tdtdsdfsvk qdvvamtdws
 401 gysgsfvqhp eltgldcirp cfwvelvrgr prenttiwts gssisfcgvn
 451 sdtanwswpd gaelpftidk
```

Figure 1R

SEQ ID NO:19
ca A/New Caledonia/20/99
Nucleotide Sequence of ca A/New Caledonia/20/99 H1     Entire molecule length: 1775 bp

```
   1 agcaaaagca ggggaaaata aaaacaacca aaatgaaagc aaaactactg
  51 gtcctgttat gtacatttac agctacatat gcagacacaa tatgtatagg
 101 ctaccatgcc aacaactcaa ccgacactgt gacacagta  cttgagaaga
 151 atgtgacagt gacacactct gtcaacctac ttgaggacag tcacaatgga
 201 aaactatgtc tactaaaagg aatagcccca ctacaattgg gtaattgcag
 251 cgttgccgga tggatcttag gaaacccaga atgcgaatta ctgatttcca
 301 aggaatcatg gtcctacatt gtagaaacac caaatcctga gaatggaaca
 351 tgttacccag ggtatttcgc cgactatgag gaactgaggg agcaattgag
 401 ttcagtatct tcatttgaga gattcgaaat attccccaaa gaaagctcat
 451 ggcccaaaca caccgtaacc ggagtatcag catcatgctc ccataatggg
 501 aaaaacagtt tttacagaaa tttgctatgg ctgacgggga agaatggttt
 551 gtacccaaac ctgagcaagt cctatgtaaa caacaaagag aaagaagtcc
 601 ttgtactatg gggtgttcat cacccgccta acataggga  ccaaagggcc
 651 ctctatcata cagaaaatgc ttatgtctct gtagtgtctt cacattatag
 701 cagaagattc accccagaaa tagccaaaag acccaaagta agagatcagg
 751 aaggaagaat caactactac tggactctgc tggaacctgg ggatacaata
 801 atatttgagg caaatggaaa tctaatagcg ccatggtatg cttttgcact
 851 gagtagaggc tttggatcag gaatcatcac ctcaaatgca ccaatggatg
 901 aatgtgatgc gaagtgtcaa acacctcagg gagctataaa cagcagtctt
 951 cctttccaga atgtacaccc agtcacaata ggagagtgtc caaagtatgt
1001 caggagtgca aaattgagga tggttacagg actaaggaac atcccatcca
1051 ttcaatccag aggtttgttt ggagccattg ccggtttcat tgaaggggggg
1101 tggactggaa tggtagatgg gtggtatggt tatcatcatc agaatgagca
1151 aggatctggc tatgctgcag atcaaaaaag tacacaaaat gccattaacg
1201 ggattacaaa caaggtgaat tctgtaattg agaaaatgaa cactcaattc
1251 acagctgtgg gcaaagaatt caacaaattg gaaagaagga tggaaaactt
1301 aaataaaaaa gttgatgatg ggtttctaga catttggaca tataatgcag
1351 aattgttggt tctactggaa aatgaaagga ctttggattt ccatgactcc
1401 aatgtgaaga tctgtatga  gaaagtaaaa gccaattaa  agaataatgc
1451 caaagaaata ggaaacgggt gttttgaatt ctatcacaag tgtaacaatg
1501 aatgcatgga gagtgtgaaa aatggaactt atgactatcc aaaatattcc
1551 gaagaatcaa agttaaacag ggagaaaatt gatggagtga aattggaatc
1601 aatgggagtc tatcagattc tggcgatcta ctcaactgtc gccagttccc
1651 tggttctttt ggtctccctg ggggcaatca gcttctggat gtgttccaat
1701 gggtctttgc agtgtagaat atgcatctga gaccagaatt tcagaagtat
1751 aagaaaaaac acccttgttt ctact
```

SEQ ID NO:67
Amino Acid Sequence of ca A/ New Caledonia /20/99 H1     Entire molecule length: 565 aa

```
   1 mkakllvllc tftatyadti cigyhannst dtvdtvlekn vtvthsvnll
  51 edshngklcl lkgiaplqlg ncsvagwilg npecellisk eswsyivetp
 101 npengtcypg yfadyeelre qlssvssfer feifpkessw pkhtvtgvsa
 151 scshngknsf yrnllwltgk nglypnlsks yvnnkekevl vlwgvhhppn
 201 igdqralyht enayvsvvss hysrrftpei akrpkvrdqe grinyywtll
 251 epgdtiifea ngnliapwya falsrgfgsg iitsnapmde cdakcqtpqg
 301 ainsslpfqn vhpvtigecp kyvrsaklrm vtglrnipsi qsrglfgaia
 351 gfieggwtgm vdgwygyhhq neqgsgyaad qkstqnaing itnkvnsvie
 401 kmntqftavg kefnklerrm enlnkkvddg fldiwtynae llvllenert
 451 ldfhdsnvkn lyekvksqlk nnakeigngc fefyhkcnne cmesvkngty
 501 dypkyseesk lnrekidgvk lesmgvyqil aiystvassl vllvslgais
 551 fwmcsngslq crici
```

Figure 1S

SEQ ID NO:20
Nucleotide Sequence of ca A/New Caledonia/20/99 N1    Entire molecule length: 1463 bp

```
   1 agcaaaagca ggagtttaaa atgaatccaa atcaaaaaat aataaccatt
  51 ggatcaatca gtatagcaat cggaataatt agtctaatgt tgcaaatagg
 101 aaatattatt tcaatatggg ctagtcactc aatccaaact ggaagtcaaa
 151 accacactgg agtatgcaac caaagaatca tcacatatga aacagcacc
 201 tgggtgaatc acacatatgt taatattaac aacactaatg ttgttgctgg
 251 aaaggacaaa acttcagtga cattggccgg caattcatct ctttgttcta
 301 tcagtggatg ggctatatac acaaaagaca acagcataag aattggctcc
 351 aaggagatg ttttgtcat aagagaacct ttcatatcat gttctcactt
 401 ggaatgcaga accttttttc tgacccaagg tgctctatta aatgacaaac
 451 attcaaatgg gaccgttaag gacagaagtc cttatagggc cttaatgagc
 501 tgtcctctag gtgaagctcc gtccccatac aattcaaagt ttgaatcagt
 551 tgcatggtca gcaagcgcat gccatgatgg catgggctgg ttaacaatcg
 601 gaatttctgg tccagacaat ggagctgtgg ctgtactaaa atacaacggc
 651 ataataactg aaaccataaa aagttggaaa aagcgaatat taagaacaca
 701 agagtctgaa tgtgtctgtg tgaacgggtc atgtttcacc ataatgaccg
 751 atggcccgag taatggggcc gcctcgtaca aaatcttcaa gatcgaaaag
 801 gggaaggtta ctaaatcaat agagttgaat gcacccaatt ttcattatga
 851 ggaatgttcc tgttacccag acactggcac agtgatgtgt gtatgcaggg
 901 acaactggca tggttcaaat cgaccttggg tgtcttttaa tcaaaacctg
 951 gattatcaaa taggatacat ctgcagtggg gtgttcggtg acaatccgcg
1001 tcccaaagat ggagagggca gctgtaatcc agtgactgtt gatggagcag
1051 acggagtaaa ggggttttca tacaaatatg gtaatggtgt tggataggga
1101 aggactaaaa gtaacagact agaaaggggg tttgagatga tttgggatcc
1151 taatggatgg acagataccg acagtgattt ctcagtgaaa caggatgttg
1201 tggcaataac tgattggtca gggtacagcg gaagtttcgt tcaacatcct
1251 gagttaacag gattggactg tataagacct tgcttctggg ttgagttagt
1301 cagaggactg cctagagaaa atacaacaat ctggactagt gggagcagca
1351 tttctttttg tggcgtaaat agtgatactg caaactggtc ttggccagac
1401 ggtgctgagt tgccgttcac cattgacaag tagttcgttg aaaaaaaact
1451 ccttgtttct act
```

SEQ ID NO:68
Amino Acid Sequence of ca A/New Caledonia/20/99 N1    Entire molecule length: 470 aa

```
   1 mnpnqkiiti gsisiaigii slmlqignii siwashsiqt gsqnhtgvcn
  51 qriityenst wvnhtyvnin ntnvvagkdk tsvtlagnss lcsisgwaiy
 101 tkdnsirigs kgdvfvirep fiscshlecr tffltqgall ndkhsngtvk
 151 drspyralms cplgeapspy nskfesvaws asachdgmgw ltigisgpdn
 201 gavavlkyng iitetikswk krilrtqese cvcvngscft imtdgpsnga
 251 asykifkiek gkvtksieln apnfhyeecs cypdtgtvmc vcrdnwhgsn
 301 rpwvsfnqnl dyqigyicsg vfgdnprpkd gegscnpvtv dgadvkgfs
 351 ykygngvwig rtksnrlrkg femiwdpngw tdtdsdfsvk qdvvaitdws
 401 gysgsfvqhp eltgldcirp cfwvelvrgl prenttiwts gssisfcgvn
 451 sdtanwswpd gaelpftidk
```

Figure 1T

SEQ ID NO:21
ca B/Ann Arbor/1/94
Nucleotide Sequence of ca B/Ann Arbor/1/94 HA     Entire molecule length: 1879 bp

```
   1 agcagaagca gagcattttc taatatccac aaaatgaagg caataattgt
  51 actactcatg gtagtaacat ccaacgcaga tcgaatctgc actgggataa
 101 catcttcaaa ctcacctcat gtggtcaaaa cagctactca aggggaagtc
 151 aatgtgactg gtgtgatacc actgacaaca acaccaacaa aatctcattt
 201 tgcaaatctc aaaggaacaa agaccagagg gaaactatgc ccaaactgtc
 251 tcaactgcac agatctggat gtggccttgg gcagaccaat gtgtataggg
 301 atcacacctt cggcaaaagc ttcaatactc cacgaagtca gacctgttac
 351 atccgggtgc tttcctataa tgcacgacag aacaaaaatc agacagctac
 401 ccaatcttct cagaggatat gaacatatca gattatcaac ccataacgtt
 451 atcaacgcag aaagggcacc aggaggaccc tacagacttg gaacctcagg
 501 atcttgccct aacgttacca gtagaagcgg attcttcgca acaatggctt
 551 gggctgtccc aagggacaac aaaacagcaa cgaacccact aacagtagaa
 601 gtaccataca tttgtacaaa aggagaagac caaattactg tttgggggtt
 651 ccattctgat aacaaaatcc aaatgaaaaa cctctatgga gactcaaatc
 701 ctcaaaagtt cacctcatct gccaatggaa taaccacaca ttatgtttct
 751 cagattggtg gcttcccaaa tcaaacagaa gacggagggc taccacaaag
 801 cggcagaatt gttgttgatt acatggtgca aaaacctggg aaaacaggaa
 851 caattgtcta tcaaagaggt gttttgttgc ctcaaaaggt gtggtgtgca
 901 agtggcagga gcaaggtaat aaaagggtcc ttgcctttaa ttggtgaagc
 951 agattgcctt cacgaaaaat acggtggatt aaacaaaagc aagccttact
1001 acacaggaga acatgcaaaa gccataggaa attgcccaat atgggtgaaa
1051 acacctttaa agcttgccaa tggaaccaaa tatagacctc ccgcaaaact
1101 attaaaggaa aagggtttct tcggagctat tgctggtttc ttagaaggag
1151 gatgggaagg aatgattgca ggttggcacg gatacacatc tcatggagca
1201 catggggtgg cagtggcagc agaccttaag agtacgcaag aagccataaa
1251 caagataaca aaaaatctca attctttgag tgagctagaa gtaaagaatc
1301 ttcaaagact aagtggtgcc atggatgaac tccacaacga aatactcgag
1351 ctggatgaga aagtggatga tctcagagct gacacaataa gctcgcaaat
1401 agagcttgca gtcttgcttt ccaatgaagg aataataaac agtgaagatg
1451 agcatctatt ggcacttgag agaaaactaa agaaaatgct gggtccctct
1501 gctgtagaca tagggaatgg atgcttcgaa accaaacaca agtgcaacca
1551 gacctgctta gacaggatag ctgctggcac ctttaatgca ggagaatttt
1601 ctcttcccac ttttgattca ctgaatatta ctgctgcatc tttaaatgat
1651 gatggattgg ataatcatac tatactgctc tactactcaa ctgcggcttc
1701 tagtttggct gtaacattga tgatagctat ttttattgtt tatatggtct
1751 ccagagacaa tgtttcttgc tccatctgtc tatagggaaa attgagccct
1801 gtattttcct ttattgtggt gcttgtttgc ttgttgccat tacagagaaa
1851 cgttattgaa aaatgctctt gttactact
```

SEQ ID NO:69

Amino Acid Sequence of ca B/Ann Arbor/1/94 HA Entire molecule length: 583 aa

```
   1 mkaiivllmv vtsnadrict gitssnsphv vktatqgevn vtgviplttt
  51 ptkshfanlk gtktrgklcp nclnctdldv algrpmcigi tpsakasilh
 101 evrpvtsgcf pimhdrtkir qlpnllrgye hirlsthnvi naerapggpy
 151 rlgtsgscpn vtsrsgffat mawavprdnk tatnpltvev pyictkgedq
 201 itvwgfhsdn kiqmknlygd snpqkftssa ngitthyvsq iggfpnqted
 251 gglpqsgriv vdymvqkpgk tgtivyqrgv llpqkvwcas grskvikgsl
 301 pligeadclh ekygglnksk pyytgehaka igncpiwvkt plklangtky
 351 rppakllkek gffgaiagfl eggwegmiag whgytshgah gvavaadlks
 401 tqeainkitk nlnslselev knlqrlsgam delhneilel dekvddlrad
 451 tissqielav llsnegiins edehllaler klkkmlgpsa vdigngcfet
 501 khkcnqtcld riaagtfnag efslptfdsl nitaaslndd gldnhtilly
 551 ystaasslav tlmiaifivy mvsrdnvscs icl
```

Figure 1U

SEQ ID NO:22

Nucleotide Sequence of ca B/Ann Arbor/1/94 NA Entire molecule length: 1554 bp

```
   1 agcagaagca gagcatcttc tcaaaactga agtaaagagg ccaaaaatga
  51 acaatgctac cttcaactat acaaacgtta accctatttc tcacatcagg
 101 gggagtgtta ttatcactat atgtgtcagc cttactgtca tacttattgt
 151 attcggatat attgctaaaa ttttcaccaa aaataattgc accaacaacg
 201 tcgttggact gcgcgaacgc atcaaatgtt caggctgtga accattctgc
 251 aacaaaagag atgaaattcc ttcccccaga accggagtgg acatacccc
 301 gtttatcttg ccagggttca accttccaga aagcactctt aattagccct
 351 catagatttg gagaagccaa aggaaactca gctcccttga taataaggga
 401 accttttatt gcttgtggac caaaggagtg caaacacttt gctctaaccc
 451 attatgcagc tcaaccaggg ggatactaca atggaacaag agaggacaga
 501 aacaagctga ggcatctgat ttcagtcaac ttaggcaaaa tcccaactgt
 551 agaaaactcc attttccata tggcagcttg gagtggatcc gcatgccatg
 601 atggtagaga atggacatat atcggagttg atggtcctga cagtaatgca
 651 ttgatcaaaa taaaatatgg agaagcatac actgacacat accattccta
 701 tgcaaacaac atcctaagaa cacaagaaag tgcctgcaat tgcatcgggg
 751 gagattgtta tcttatgata actgatggct cagcttcagg aattagtaaa
 801 tgcagattcc ttaagatccg agagggtcga ataataaaag aaatatttcc
 851 aacaggaagg gtagagcaca ctgaagaatg cacatgcgga tttgccagca
 901 acaaaaccat agaatgtgcc tgtagagata acagttacac agcaaaaaga
 951 ccctttgtca aattaaatgt ggagactgat acagctgaaa taagattgat
1001 gtgcacagag acttatttgg acacccccag accagatgat ggaagcataa
1051 cagggccttg cgaatctaat ggggacaaag ggagtggagg tgtcaaggga
1101 ggatttgttc atcaaagaat ggcatccaag attggaagat ggtactcccg
1151 aacgatgtct aaaactaaaa gaatggggat ggaactgtat gtcaagtatg
1201 atggagaccc atggactgac agtgacgccc ttgctcctag tggagtaatg
1251 gtctcaatgg aagaacctgg ttggtactct ttcggcttcg aaataaaaga
1301 taagaaatgt gatgtcccct gtattgggat agagatggta catgatggtg
1351 gaaaaaggac ttggcactca gcagcaacag ccatttactg tttaatgggc
1401 tcaggacagt tgctatggga cactgtcaca ggtgttaata tggctctgta
1451 atggaggaat ggttgaatct gttctaaacc ctttgttcct attttatttg
1501 aacaattgtc cttactggac ttaattgttt ctgaaaaatg ctcttgttac
1551 tact
```

SEQ ID NO:70

Amino Acid Sequence of ca B/Ann Arbor/1/94 NA Entire molecule length: 465 aa

```
   1 mlpstiqtlt lfltsggvll slyvsallsy llysdillkf spkiiaptts
  51 ldcanasnvq avnhsatkem kflppepewt yprlscqgst fqkallisph
 101 rfgeakgnsa pliirepfia cgpkeckhfa lthyaaqpgg yyngtredrn
 151 klrhlisvnl gkiptvensi fhmaawsgsa chdgrewtyi gvdgpdsnal
 201 ikikygeayt dtyhsyanni lrtqesacnc iggdcylmit dgsasgiskc
 251 rflkiregri ikeifptgrv ehteectcgf asnktiecac rdnsytakrp
 301 fvklnvetdt aeirlmctet yldtprpddg sitgpcesng dkgsggvkgg
 351 fvhqrmaski grwysrtmsk tkrmgmelyv kydgdpwtds dalapsgvmv
 401 smeepgwysf gfeikdkkcd vpcigiemvh dggkrtwhsa ataiyclmgs
 451 gqllwdtvtg vnmal
```

Figure 1V

SEQ ID NO:23
ca B/Yamanashi/166/98
Nucleotide Sequence of ca B/Yamanashi/166/98 HA          Entire molecule length: 1881 bp

```
   1 agcagaagca gagcattttc taatatccac aaaatgaagg caataattgt
  51 actactcatg gtagtaacat ccaatgcaga tcgaatctgc actgggataa
 101 catcgtcaaa ctcacctcat gtggtcaaaa cagctactca aggggaggtc
 151 aatgtgactg tgtgatacc actgacaaca acaccaacaa aatctcattt
 201 tgcaaatctc aaaggaacaa agaccagagg gaaactatgc ccaacctgtc
 251 tcaactgcac agatctggat gtggccttag cagaccaat gtgtgtgggg
 301 gtcacacctt cggcaaaagc ttcaatactc cacgaagtca ggcctgttac
 351 atccggatgc tttcctataa tgcacgacag aacaaaaatc agacagctac
 401 ccaatcttct cagaggatat gaaaaaatca gattatcaac ccaaatcgtt
 451 atcaacgcag aaaaggcacc aggaggaccc tacagacttg aacctcagg
 501 atcttgccct aacgctacca gtagaagcgg atttttcgca acaatggctt
 551 gggctgtccc aaaggacaac aacaaaacag caacgaatcc actaacagta
 601 gaagtaccac acatctgtac aaaagaagaa gaccaaatta ctgtttgggg
 651 gttccattct gatgacaaaa cccaaatgaa aaacctctat ggagactcaa
 701 atcctcaaaa gttcacctca tctgctaatg gagtaaccac acattatgtt
 751 tctcagattg gcggcttccc ggatcaaaca gaagacggag ggctaccaca
 801 aagcggcaga attgttgttg attacatggt gcaaaaacct gggaaaacag
 851 gaacaattgt ctatcaaaga ggtattttgt tgcctcaaaa ggtgtggtgc
 901 gcgagtggca ggagcaaagt aataaaaggg tccttgcctt taattggtga
 951 agcagattgc cttcacgaaa aatacggtgg attaaacaaa agcaagcctt
1001 actacacagg agaacatgca aaagccatag gaattgccc aatatgggtg
1051 aaaacaccct tgaagcttgc caatggaacc aaatatagac ctcctgcaaa
1101 actattaaag gaaagggggtt tcttcggagc tattgctggt ttcttagaag
1151 gaggatggga aggaatgatt gcaggttggc acggatacac atctcacgga
1201 gcacatggag tggcagtggc agcagaccct aagagtacgc aagaagccat
1251 aaacaagata acaaaaaatc tcaattcttt gagtgagcta gaagtaaaga
1301 atcttcaaag actaagtggt gccatggatg aactccacaa cgaaatactc
1351 gagctggatg agaagtgga tgatctcaga gctgcacaa taagctcaca
1401 aatagaactt gcagtcttgc tttccaacga aggaataata aacagtgaag
1451 atgagcatct attggcactt gagagaaaac taaagaaaat gctgggtccc
1501 tctgctgtag acatagggaa tggatgcttc gaaccaaac acaagtgcaa
1551 ccagacctgc ttagacagga tagctgctgg cacctttaat gcaggagaat
1601 tttctcttcc cactttttgat tcactgaata ttactgctgc atctttaaat
1651 gatgatggat tggataacca tactatactg ctctactact caactgctgc
1701 ttctagtttg gctgtaacat tgatgatagc tattttat ttgtttatatga
1751 tctccagaga caatgtttct tgctccatct gtctatagg aaattaagcc
1801 ctgtatttc ctttattgta gtgcttgttt gcttgttatc attacaaaga
1851 aacgttattg aaaaatgctc ttgttactac t
```

SEQ ID NO:71
Amino Acid Sequence of ca B/Yamanashi/166/98 HA          Entire molecule length: 584 aa

```
   1 mkaiivllmv vtsnadrict gitssnsphv vktatqgevn vtgviplttt
  51 ptkshfanlk gtktrgklcp tclnctdldv algrpmcvgv tpsakasilh
 101 evrpvtsgcf pimhdrtkir qlpnllrgye kirlstqivi naekapggpy
 151 rlgtsgscpn atsrsgffat mawavpkdnn ktatnpltve vphictkeed
 201 qitvwgfhsd dktqmknlyg dsnpqkftss angvtthyvs qiggfpdqte
 251 dgglpqsgri vvdymvqkpg ktgtivyqrg illpqkvwca sgrskvikgs
 301 lpligeadcl hekygglnks kpyytgehak aigncpiwvk tplklangtk
 351 yrppakllke rgffgaiagf leggwegmia gwhgytshga hgvavaadlk
 401 stqeainkit knlnslsele vknlqrlsga mdelhneile ldekvddlra
 451 dtissqiela vllsnegiin sedehllale rklkkmlgps avdigngcfe
 501 tkhkcnqtcl driaagtfna gefslptfds lnitaaslnd dgldnhtill
 551 yystaasslav vtlmiaifiv ymisrdnvsc sicl
```

Figure 1W

SEQ ID NO:24
Nucleotide Sequence of ca B/Yamanashi/166/98 NA    Entire molecule length: 1557 bp

```
   1 agcagaagca gagcatcttc tcaaaactga ggcaaatagg ccaaaaatga
  51 acaatgctac cttcaactat acaaacgtta ccctatttc tcacatcagg
 101 gggagtgtta ttatcactat atgtgtcagc ttcactgtca tacttactat
 151 attcggatat attgctaaaa ttttcaccaa cagaaataac tgcaccaaca
 201 atgccattga attgtgcaaa cgcatcaaat gttcaggctg tgaaccgttc
 251 tgcaacaaaa ggggtgacac ttcctctccc agaaccggag tggacatacc
 301 ctcgtttatc ttgcccgggc tcaacctttc agaaagcact cctaattagc
 351 cctcatagat tcggagaaac caaggaaac tcagctccct tgataataag
 401 ggaacctttt attgcttgtg gaccaaagga atgcagacac tttgctctaa
 451 cccattatgc agcccaacca gggggatact acaatggaac aagagaagac
 501 agaaacaagc tgaggcatct aatttcagtc aaattgggca aatcccaac
 551 agtagaaaac tccattttcc acatggcagc ttggagcggg tccgcatgcc
 601 atgatggtag agaatggaca tatatcggag ttgatggccc tgacagtaat
 651 gcattgctca aaataaaata tggagaagca tatactgaca cataccattc
 701 ctatgcaaac aacatcctaa gaacacaaga aagtgcctgc aattgcatcg
 751 ggggagattg ttatcttatg ataactgatg gctcagcttc agggattagt
 801 gaatgcagat ttcttaagat tcgagagggc cgaataataa aagaaatatt
 851 tccaacagga agagtagaac atactgaaga atgcacatgc ggatttgcca
 901 gcaataaaac catagaatgt gcctgtagag ataacagtta cacagcaaaa
 951 agacccttg tcaaattaaa tgtggagact gatacagcag aaataagatt
1001 gatgtgcaca gagacttact tggacacccc cagaccagat gatggaagca
1051 taacagggcc ttgtgaatct aatggggata aagggagtgg aggcatcaag
1101 ggaggatttg ttcatcaaag aatggcatcc aagattggaa ggtggtactc
1151 tcgaacgatg tctaaaacta aaggatggg gatgggactg tatgtcaagt
1201 atgatggaga cccatggatt gacagtgatg cccttactct tagcggagta
1251 atggtttcaa tggaagaacc tggttggtat tcctttggct tcgaaataaa
1301 agataagaaa tgtgatgtcc cctgtattgg gatagagatg gtacatgatg
1351 gtggaaagaa gacttggcac tcagcagcaa cagccattta ctgtttaatg
1401 ggctcaggac aactgctatg ggacactgtc acaggcgttg atatggctct
1451 gtaatggagg aatggttgag tctgttctaa ccccttgtt cctatttgt
1501 ttgaacaatt gtccttactg aacttaattg tttctgaaaa atgctcttgt
1551 tactact
```

SEQ ID NO:72
Amino Acid Sequence of ca B/Yamanashi/166/98 NA      Entire molecule length: 466 aa

```
   1 mlpstiqtlt lfltsggvll slyvsaslsy llysdillkf spteitaptm
  51 plncanasnv qavnrsatkg vtlplpepew typrlscpgs tfqkallisp
 101 hrfgetkgns apliirepfi acgpkecrhf althyaaqpg gyyngtredr
 151 nklrhlisvk lgkiptvens ifhmaawsgs achdgrewty igvdgpdsna
 201 llkikygeay tdtyhsyann ilrtqesacn ciggdcylmi tdgsasgise
 251 crflkiregr iikeifptgr vehteectcg fasnktieca crdnsytakr
 301 pfvklnvetd taeirlmcte tyldtprpdd gsitgpcesn gdkgsggikg
 351 gfvhqrmask igrwysrtms ktkrmgmgly vkydgdpwid sdaltlsgvm
 401 vsmeepgwys fgfeikdkkc dvpcigiemv hdggkktwhs aataiyclmg
 451 sgqllwdtvt gvdmal
```

Figure 1X

SEQ ID NO:25
ca B/Johannesburg/5/99
Nucleotide Sequence of ca B_Johannesburg_5_99_HA  Entire molecule length: 1882 bp

```
   1 agcagaagca gagcattttc taatatccac aaaatgaagg caataattgt
  51 actactcatg gtagtaacat ccaatgcaga tcgaatctgc actgggataa
 101 catcgtcaaa ctcacctcat gtggtcaaaa cagctactca aggggaggtc
 151 aatgtgactg gtgcgatacc attgacaaca acaccaacaa aatctcattt
 201 tgcaaatctc aaaggaacaa agaccagagg gaaactatgc ccaacctgtc
 251 tcaactgcac agatctggat gtggccttgg gcagaccaat gtgtgtgggg
 301 atcacacctt cggcaaaagc ttcaatactc cacgaagtca gacctgttac
 351 atccggatgc tttcctataa tgcacgacag aacaaaaatc agacagctac
 401 ccaatcttct cagaggatat gaaaaaatca gattatcaac ccaaaacgtt
 451 atcaacgcag aaaaggcacc aggaggaccc tacagacttg gaacttcagg
 501 atcttgccct aacgctacca gtaaaagcgg atttttcgca acaatggctt
 551 gggctgtccc aagggacaac aacaaaacag caacgaatcc actaacagta
 601 gaagtaccac acatctgtac aaaagaagaa gaccaaatta ctgtttgggg
 651 gttccattct gatgacaaaa cccaaatgaa aaacctctat ggagactcaa
 701 atcctcaaaa gttcacctca tctgctaatg gaataaccac acattatgtt
 751 tctcagattg gcggcttccc ggaccaaaca gaagacggag ggctaccaca
 801 aagcggcaga attgttgttg attacatggt gcaaaaacct gggaaaacag
 851 gaacaattgt ctatcaaaga gggatcttgt tgcctcaaaa ggtgtggtgc
 901 gcgagtggca ggagcaaagt aataaaaggg tccttgcctt taattggtga
 951 agcagattgc cttcacgaaa aatacggtgg attaaacaaa agcaagcctt
1001 actacacagg agaacatgca aaagccatag gaaattgccc aatatgggtg
1051 aaaacacctt tgaagcttgc caatggaacc aagtatagac ctcctgcaaa
1101 actattaaag gaaaggggtt tcttcggagc tattgctggt ttcttagaag
1151 gaggatggga aggaatgatt gcaggttggc acggatacac atctcacgga
1201 gcacacggag tggcagtggc agcagacctt aagagtacgc aagaagccat
1251 aaacaagata acaaaaaatc tcaattcttt gagtgagtta gaagtaaaga
1301 accttcaaag actaagtggt gccatggatg aactccataa cgaaatactc
1351 gagctggatg agaaagtgga tgatctcaga gctgacacaa taagctcaca
1401 aatagaactt gcagtcttgc tttccaacga aggaataata aacagtgaag
1451 atgagcatct attggcactt gagagaaaac taaagaagat gctgggtccc
1501 tctgctatag acatagggaa tggatgcttc gaaaccaaac acaagtgcaa
1551 ccagacctgc ttagacagga tagctgctgg cacctttaat gcaggagaat
1601 tttctcttcc cacttttgat tcactgaaca ttactgctgc atctttaaat
1651 gatgatggat tggataacca tactatactg ctctactact caactgctgc
1701 ttctagtttg gctgtaacat tgatgatagc tatttttatt gtttatatga
1751 tctccagaga caatgtttct tgctccatct gtctataagg aaaattaagc
1801 cctgtatttt cctttattgt agtgcttgtt tgcttgttat cattacaaag
1851 aaacgttatt gaaaaatgct cttgttacta ct
```

SEQ ID NO:73
Amino Acid Sequence of ca B_Johannesburg_5_99_HA Entire molecule length: 584 aa

```
   1 mkaiivllmv vtsnadrict gitssnsphv vktatqgevn vtgaipltt t
  51 ptkshfanlk gtktrgklcp tclnctdldv algrpmcvgi tpsakasilh
 101 evrpvtsgcf pimhdrtkir qlpnllrgye kirlstqnvi naekapggpy
 151 rlgtsgscpn atsksgffat mawavprdnn ktatnpltve vphictkeed
 201 qitvwgfhsd dktqmknlyg dsnpqkftss angitthyvs qiggfpdqte
 251 dgglpqsgri vvdymvqkpg ktgtivyqrg illpqkvwca sgrskvikgs
 301 lpligeadcl hekygglnks kpyytgehak aigncpiwvk tplklangtk
 351 yrppakllke rgffgaiagf leggwegmia gwhgytshga hgvavaadlk
 401 stqeainkit knlnslsele vknlqrlsga mdelhneile ldekvddlra
 451 dtissqiela vllsnegiin sedehllale rklkkmlgps aidigngcfe
 501 tkhkcnqtcl driaagtfna gefslptfds lnitaaslnd dgldnhtill
 551 yystaassla vtlmiaifiv ymisrdnvsc sicl
```

Figure 1Y

SEQ ID NO:26

Nucleotide Sequence of ca B_Johannesburg_5_99_NA Entire molecule length: 1557 bp

```
   1 agcagaagca gagcatcttc tcaaaactga ggcaaatagg ccaaaaatga
  51 acaatgctac cctcaactat acaaacgtta accctattcc tcacatcagg
 101 gggagtgtta ttatcactat atgtgtcagc ttcactgtca tacttactat
 151 attcggatat attgctaaaa ttttcaccaa cagaaataac tgcaccagca
 201 atgcccttgg attgtgcaaa cgcatcaaat gttcaggctg tgaaccgttc
 251 tgcaacaaaa ggggtgacac ttcttctccc agaaccggag tggacatacc
 301 cgcgtttatc ttgcccgggc tcaacctttc agaaagcact cctaattagc
 351 cctcatagat tcggagaaac caaaggaaac tcagctccct tgataataag
 401 ggaacctttt attgcttgtg gaccaaagga atgcaaacac tttgctctaa
 451 cccattatgc agcccaacca gggggatact acaatggaac aagagaagac
 501 agaaacaagc taaggcatct aatttcagtc aaatttggta aaatcccaac
 551 agtagaaaac tccattttcc acatggcagc atggagcggg tccgcatgcc
 601 atgatggtaa agaatggaca tatatcggag ttgatggccc tgacagtaat
 651 gcattgctca aaataaaata tggagaagca tatactgaca cataccattc
 701 ctatgcaaac aacatcctaa gaacacaaga aagtgcctgc aattgcatcg
 751 ggggaaattg ttatcttatg ataactgatg gctcagcttc aggtattagt
 801 gagtgcagat ttcttaagat tcgagagggc cgaataataa aagaaatatt
 851 tccaacagga agagtaaaac atactgaaga atgcacatgc ggatttgcca
 901 gcaataaaac catagaatgt gcctgtagag ataacagtta cacagcaaaa
 951 agaccctttg tcaaattaaa tgtggagact gatacagcag aaataagatt
1001 gatgtgcaca gagacttatt tggacacccc cagaccagat gatggaagca
1051 taacagggcc ttgtgaatct aatggggata aagggagtgg aggcatcaag
1101 ggaggatttg ttcatcaaag aatggcatcc aagattggaa ggtggtactc
1151 tcgaacaatg tctaaaacta aaaggatggg gatgggactg tatgtcaagt
1201 atgatggaga cccatggact gacagtgatg cccttgctct tagtggagta
1251 atggtttcaa tggaagaacc tggttggtac tcctttggct tcgaaataaa
1301 agataagaaa tgtgatgtcc cctgtattgg gatagagatg gtacatgatg
1351 gtggaaagga gacttggcac tcagcagcaa cagccattta ctgtttaatg
1401 ggctcaggac aactgctatg ggacactgtc acaggtgttg atatggctct
1451 gtaatggagg aatggttgag tctgttctaa accctttgtt cctatttgt
1501 ttgaacaatt gtccttactg aacttaattg tttctgaaaa atgctcttgt
1551 tactact
```

SEQ ID NO:74

Amino Acid Sequence of ca B_Johannesburg_5_99_NA Entire molecule length: 466 aa

```
   1 mlpstiqtlt lfltsggvll slyvsaslsy llysdillkf spteitapam
  51 pldcanasnv qavnrsatkg vtlllpepew typrlscpgs tfqkallisp
 101 hrfgetkgns apliirepfi acgpkeckhf althyaaqpg gyyngtredr
 151 nklrhlisvk fgkiptvens ifhmaawsgs achdgkewty igvdgpdsna
 201 llkikygeay tdtyhsyann ilrtqesacn ciggncylmi tdgsasgise
 251 crflkiregr iikeifptgr vkhteectcg fasnktieca crdnsytakr
 301 pfvklnvetd taeirlmcte tyldtprpdd gsitgpcesn gdkgsggikg
 351 gfvhqrmask igrwysrtms ktkrmgmgly vkydgdpwtd sdalalsgvm
 401 vsmeepgwys fgfeikdkkc dvpcigiemv hdggketwhs aataiyclmg
 451 sgqllwdtvt gvdmal
```

Figure 1Z

SEQ ID NO:27
ca B/Victoria/504/2000
Nucleotide Sequence of ca B/Victoria/504/2000 HA   Entire molecule length: 1879 bp

```
   1 agcagaagca gagcattttc taatatccac aaaatgaagg caataattgt
  51 actactcatg gtagtaacat ccaacgcaga tcgaatctgc actgggataa
 101 catcttcaaa ctcacctcat gtggtcaaaa cagctactca aggggaagtc
 151 aatgtgactg gtgtgatacc actgacaaca acaccaacaa aatctcattt
 201 tgcaaatctc aaaggaacaa agaccagagg gaaactatgc ccaaactgtc
 251 tcaactgcac agatctggat gtggccttgg gcagaccaat gtgtataggg
 301 atcacacctt cggcaaaagc ttcaatactc cacgaagtca gacctgttac
 351 atccgggtgc tttcctataa tgcacgacag aacaaaaatc agacagctac
 401 ccaatcttct cagaggatat gaacatatca gattatcaac ccataacgtt
 451 atcaacgcag aaagggcacc aggaggaccc tacagacttg gaacctcagg
 501 atcttgccct aacgttacca gtagaagcgg attcttcgca acaatggctt
 551 gggctgtccc aagggacaac aaaacagcaa cgaacccact aacagtagaa
 601 gtaccataca tttgtacaaa aggagaagac caaattactg tttgggggtt
 651 ccattctgat aacaaaatcc aaatgaaaaa cctctatgga gactcaaatc
 701 ctcaaaagtt cacctcatct gccaatggaa taaccacaca ttatgtttct
 751 cagattggtg gcttcccaaa tcaaacagaa gacggagggc taccacaaag
 801 cggcagaatt gttgttgatt acatggtgca aaaacctggg aaaacaggaa
 851 caattgtcta tcaaagaggt gttttgttgc ctcaaaaggt gtggtgtgca
 901 agtggcagga gcaaggtaat aaaagggtcc ttgcctttaa ttggtgaagc
 951 agattgcctt cacgaaaaat acggtggatt aaacaaaagc aagccttact
1001 acacaggaga acatgcaaaa gccataggaa attgcccaat atgggtgaaa
1051 acacctttaa agcttgccaa tggaaccaaa tatagacctc ccgcaaaact
1101 attaaggaa agggtttct tcggagctat tgctggtttc ttagaaggag
1151 gatgggaagg aatgattgca ggttggcacg gatacacatc tcatggagca
1201 catggggtgg cagtggcagc agaccttaag agtacgcaag aagccataaa
1251 caagataaca aaaatctca attctttgag tgagctagaa gtaaagaatc
1301 ttcaaagact aagtggtgcc atggatgaac tccacaacga aatactcgag
1351 ctggatgaga agtggatga tctcagagct gacacaataa gctcgcaaat
1401 agagcttgca gtcttgcttt ccaatgaagg aataataaac agtgaagatg
1451 agcatctatt ggcacttgag agaaaactaa agaaaatgct gggtccctct
1501 gctgtagaca tagggaatgg atgcttcgaa accaaacaca gtgcaaccca
1551 gacctgctta gacaggatag ctgctggcac ctttaatgca ggagaattt
1601 ctcttcccac ttttgattca ctgaatatta ctgctgcatc tttaaatgat
1651 gatggattgg ataatcatac tatactgctc tactactcaa ctgcggcttc
1701 tagtttggct gtaacattga tgatagctat ttttattgtt tatatggtct
1751 ccagagacaa tgtttcttgc tccatctgtc tagggaaa attgagccct
1801 gtattttcct ttattgtggt gcttgtttgc ttgttgccat tacagagaaa
1851 cgttattgaa aatgctctt gttactact
```

SEQ ID NO:75
Amino Acid Sequence of ca B/Victoria/504/2000 HA          Entire molecule length: 583 aa

```
  1 mkaiivllmv vtsnadrict gitssnsphv vktatqgevn vtgviplttt
 51 ptkshfanlk gtktrgklcp nclnctdldv algrpmcigi tpsakasilh
101 evrpvtsgcf pimhdrtkir qlpnllrgye hirlsthnvi naerapggpy
151 rlgtsgscpn vtsrsgffat mawavprdnk tatnpltvev pyictkgedq
201 itvwgfhsdn kiqmknlygd snpqkftssa ngitthyvsq iggfpnqted
251 gglpqsgriv vdymvqkpgk tgtivyqrgv llpqkvwcas grskvikgsl
301 pligeadclh ekygglnksk pyytgehaka igncpiwvkt plklangtky
351 rppakllkek gffgaiagfl eggwegmiag whgytshgah gvavaadlks
401 tqeainkitk nlnslselev knlqrlsgam delhneilel dekvddlrad
451 tissqielav llsnegiins edehllaler klkkmlgpsa vdigngcfet
501 khkcnqtcld riaagtfnag efslptfdsl nitaaslndd gldnhtilly
551 ystaasslav tlmiaifivy mvsrdnvscs icl
```

Figure 1AA

SEQ ID NO:28
Nucleotide Sequence of ca B/Victoria/504/2000 NA   Entire molecule length: 1554 bp

```
   1 agcagaagca gagcatcttc tcaaaactga agtaaagagg ccaaaaatga
  51 acaatgctac cttcaactat acaaacgtta accctatttc tcacatcagg
 101 gggagtgtta ttatcactat atgtgtcagc cttactgtca tacttattgt
 151 attcggatat attgctaaaa ttttcaccaa aaataattgc accaacaacg
 201 tcgttggact gcgcgaacgc atcaaatgtt caggctgtga accattctgc
 251 aacaaaagag atgaaattcc ttcccccaga accggagtgg acatacccc
 301 gtttatcttg ccagggttca accttccaga aagcactctt aattagccct
 351 catagatttg agaagccaa aggaaactca gctcccttga taataaggga
 401 accttttatt gcttgtggac caaaggagtg caaacacttt gctctaaccc
 451 attatgcagc tcaaccaggg ggatactaca atggaacaag agaggacaga
 501 aacaagctga ggcatctgat ttcagtcaac ttaggcaaaa tcccaactgt
 551 agaaaactcc attttccata tggcagcttg gagtggatcc gcatgccatg
 601 atggtagaga atggacatat atcggagttg atggtcctga cagtaatgca
 651 ttgatcaaaa taaaatatgg agaagcatac actgacacat accattccta
 701 tgcaaacaac atcctaagaa cacaagaaag tgcctgcaat tgcatcgggg
 751 gagattgtta tcttatgata actgatggct cagcttcagg aattagtaaa
 801 tgcagattcc ttaagatccg agagggtcga ataataaaag aaatatttcc
 851 aacaggaagg gtagagcaca ctgaagaatg cacatgcgga tttgccagca
 901 acaaaaccat agaatgtgcc tgtagagata cagttacac agcaaaaaga
 951 ccctttgtca aattaaatgt ggagactgat acagctgaaa taagattgat
1001 gtgcacagag acttatttgg acaccccag accagatgat ggaagcataa
1051 cagggccttg cgaatctaat ggggacaaag ggagtggagg tgtcaaggga
1101 ggatttgttc atcaaagaat ggcatccaag attggaagat ggtactcccg
1151 aacgatgtct aaaactaaaa gaatggggat ggaactgtat gtcaagtatg
1201 atggagaccc atggactgac agtgacgccc ttgctcctag tggagtaatg
1251 gtctcaatgg aagaacctgg ttggtactct tcggcttcg aaataaaaga
1301 taagaaatgt gatgtcccct gtattgggat agagatggta catgatggtg
1351 gaaaaaggac ttggcactca gcagcaacag ccatttactg tttaatgggc
1401 tcaggacagt tgctatggga cactgtcaca ggtgttaata tggctctgta
1451 atggaggaat ggttgaatct gttctaaacc ctttgttcct attttatttg
1501 aacaattgtc cttactggac ttaattgttt ctgaaaaatg ctcttgttac
1551 tact
```

SEQ ID NO:76
Amino Acid Sequence of ca B/Victoria/504/2000 NA    Entire molecule length: 465 aa

```
  1 mlpstiqtlt lfltsggvll slyvsallsy llysdillkf spkiiaptts
 51 ldcanasnvq avnhsatkem kflppepewt yprlscqgst fqkallisph
101 rfgeakgnsa pliirepfia cgpkeckhfa lthyaaqpgg yyngtredrn
151 klrhlisvnl gkiptvensi fhmaawsgsa chdgrewtyi gvdgpdsnal
201 ikikygeayt dtyhsyanni lrtqesacnc iggdcylmit dgsasgiskc
251 rflkiregri ikeifptgrv ehteectcgf asnktiecac rdnsytakrp
301 fvklnvetdt aeirlmctet yldtprpddg sitgpcesng dkgsggvkgg
351 fvhqrmaski grwysrtmsk tkrmgmelyv kydgdpwtds dalapsgvmv
401 smeepgwysf gfeikdkkcd vpcigiemvh dggkrtwhsa ataiyclmgs
451 gqllwdtvtg vnmal
```

Figure 1AB

SEQ ID NO:29
ca B/Hong Kong/330/01
Nucleotide Sequence of ca B/Hong Kong/330/01 HA Entire molecule length: 1885 bp

```
   1 agcagaagca gagcattttc taatatccac aaaatgaagg caataattgt
  51 actactcatg gtagtaacat ccaatgcaga tcgaatctgc actggaataa
 101 catcgtcaaa ctcaccccat gtggtcaaaa ctgctactca aggggaagtc
 151 aatgtgactg gtgtgatacc actgacaaca acacccacca aatctcattt
 201 tgcaaatctc aaaggaacaa aaaccagagg gaaactatgc ccaaaatgtc
 251 tcaactgcac agatctggac gtggccttgg gcagaccaaa atgcacgggg
 301 aacatacctt cggcaaaagt ttcaatactc catgaagtaa gacctgttac
 351 atctgggtgc tttcctataa tgcacgacag aacaaaaatt agacagctgc
 401 ccaatcttct cagaggatac gaacgtatca ggttatcaaa ccataacgtt
 451 atcaatgcag aaaaagcacc aggaggaccc tacaaaattg gaacctcagg
 501 gtcttgccct aacgttacca atggaaacgg attcttcgca acaatggctt
 551 gggctgtccc aaaaaacgaa aacaacaaaa cagcaacaaa ttcattaaca
 601 atagaagtac catacatttg tacagaagga gaagaccaaa ttaccgtttg
 651 gggttccac tctgatagcg aaacccaaat ggcaaaactc tatggagact
 701 caaagcctca gaagttcact tcatctgcta acggagtgac cacacattac
 751 gtttcacaga ttggtggctt cccaaatcaa acagaagacg gaggactacc
 801 acaaagtggt agaattgttg ttgattacat ggtgcaaaaa tctggaaaaa
 851 caggaacaat tacctatcaa agaggtattt tattgcctca aaaagtgtgg
 901 tgcgcaagtg gcaggagcaa ggtaataaaa ggatccttgc ctttaattgg
 951 agaagcagat tgcctccacg aaaaatacgg tggattaaac aaaagcaagc
1001 cttactatac aggggaacat gcaaaagcca taggaaattg cccaatatgg
1051 gtgaaaacac ccttgaagct ggccaatgga accaaatata gacctcctgc
1101 aaaactatta aaggaaaggg gtttcttcgg agctattgct ggtttcttag
1151 aaggaggatg ggaaggaatg attgcaggtt ggcacggata cacatcccat
1201 ggagcacatg gagtagcagt ggcagcagac cttaagagta ctcaagaagc
1251 cataaacaag atcacaaaaa atctcaactc tttgagtgag ctggaagtaa
1301 agaatcttca aagactaagc ggagccatgg atgaactcca caacgaaata
1351 ctagaactag atgagaaagt ggatgatctc agagctgata caataagctc
1401 gcaaatagaa ctcgcagtct tgctttccaa tgaaggaata ataaacagtg
1451 aagatgagca tctcttggcg cttgaaagaa aactgaagaa aatgctgggc
1501 ccctctgctg tagagatagg gaatggatgc ttcgaaacca aacacaagtg
1551 caaccagacc tgcctcgata gaatagctgc tggcaccttt aatgcaggag
1601 aattttctct ccccaccttt gattcactaa atattactgc tgcatcttta
1651 aatgacgatg gattggataa tcatactata ctgctttact actcaactgc
1701 tgcttccagt ttggctgtaa cattgatgat agctatcttt gttgtttata
1751 tggtctccag agacaatgtt tcttgttcca tctgtctata aggaaagtta
1801 agccccgtat tttcctttat tgtagtactt gtttgcttgt tatcattaca
1851 aaaaaacgtt attgaaaaat gctcttgtta ctact
```

SEQ ID NO:77

Amino Acid Sequence of ca B/Hong Kong/330/01 HA Entire molecule length: 585 aa

```
   1 mkaiivllmv vtsnadrict gitssnsphv vktatqgevn vtgviplttt
  51 ptkshfanlk gtktrgklcp kclnctdldv algrpkctgn ipsakvsilh
 101 evrpvtsgcf pimhdrtkir qlpnllrgye rirlsnhnvi naekapggpy
 151 kigtsgscpn vtngngffat mawavpknen nktatnslti evpyictege
 201 dqitvwgfhs dsetqmakly gdskpqkfts sangvtthyv sqiggfpnqt
 251 edgglpqsgr ivvdymvqks gktgtityqr gillpqkvwc asgrskvikg
 301 slpligeadc lhekygglnk skpyytgeha kaigncpiwv ktplklangt
 351 kyrppakllk ergffgaiag fleggwegmi agwhgytshg ahgvavaadl
 401 kstqeainki tknlnslsel evknlqrlsg amdelhneil eldekvddlr
 451 adtissqiel avllsnegii nsedehllal erklkkmlgp saveigngcf
 501 etkhkcnqtc ldriaagtfn agefslptfd slnitaasln ddgldnhtil
 551 lyystaassl avtlmiaifv vymvsrdnvs csicl
```

Figure 1AC

SEQ ID NO:30
Nucleotide Sequence of ca B/Hong Kong/330/01 NA  Entire molecule length: 1544 bp

```
   1 agcagagcat cttctcaaaa ctgaagcaaa taggccaaaa tgaacaatgc
  51 taccctcaac tatacaaaca ttaaccctat ttctcacatc aggggggagtg
 101 ttattatcac tatatgtgtc agccttactg tcatacttac tgtattcgga
 151 tatattgcta aaatttttcac caacaaaaat aattgcacca acaacgtcgt
 201 tggactccgc gaacgcatca aattttcagg ccgtgaacca ttctgcaaca
 251 aaagagatga catttcttct cccagaaccg gagtggacat accctcgttt
 301 atcttgccag ggttcaacct ttcaaaaagc actcctaatt agccctcata
 351 gattcggaga agccaaagga aactcagctc ccttgataat aagggaacct
 401 tttattgctt gtggaccaaa ggagtgtaaa cactttgctc taacccatta
 451 tgcagctcaa ccagggggat actacaatgg aacaagagag gacagaaaca
 501 agctgaggca tctgatttca gtcaacttag gcaaaatacc aactgtagaa
 551 aactccatt tccacatggc agcttggagt gggtccgcat gccatgatgg
 601 tagagagtgg acttatatcg gagttgatgg ccctgacagt aatgcattga
 651 tcaaaataaa atatggagaa gcatacactg acacatacca ttcctatgca
 701 aacaacatcc taagaacaca agaaagtgcc tgcaactgca tcggggagga
 751 ttgttatctt atgataactg atggctcagc ttcaggaatt agtaaatgca
 801 gattccttaa gattcgagag ggtcgaatag taaaagaaat atttccaaca
 851 ggaagagtag agcatactga agaatgcaca tgcggatttg ccagcaataa
 901 aaccatagaa tgtgcctgta gagataacag ttacacagca aaaagaccct
 951 ttgtcaaatt aaatgtggaa actgatacag cagaaataag attgatgtgc
1001 acagagactt atttggacac ccccagacca gatgatggaa gcataacagg
1051 gccttgcgaa tctaatgggg acaaagggag tggaggtatc aagggaggat
1101 ttgtccatca aagaatggca tccaagattg gaagatggta ctctcgaacg
1151 atgtctaaaa ctaaagaat ggggatggaa ctgtatgtca agtatgatgg
1201 agacccatgg actgacagtg atgcccttgc tcctagtgga gtaatggtct
1251 caatagaaga acctggttgg tattctttcg gcttcgaaat aaaagataag
1301 aaatgcgatg tccctgtat tgggatagag atggtacacg atggtggaaa
1351 aacaacttgg cactcagcag caacagccat ttactgttta atgggctcag
1401 gacagttgct atgggacact atcacaggtg ttgatatggc tctgtaatgg
1451 aggaatggtt gaatctgttc taaacccttt gttcctattt tgtttgaaca
1501 attgtcctta ctggacttaa ttgtttctga aaaatgctct tgtt
```

SEQ ID NO:78
Amino Acid Sequence of ca B/Hong Kong/330/01 NA  Entire molecule length: 466 aa

```
  1 mlpstiqtlt lfltsggvll slyvsallsy llysdillkf sptkiiaptt
 51 sldsanasnf qavnhsatke mtfllpepew typrlscqgs tfqkallisp
101 hrfgeakgns apliirepfi acgpkeckhf althyaaqpg gyyngtredr
151 nklrhlisvn lgkiptvens ifhmaawsgs achdgrewty igvdgpdsna
201 likikygeay tdtyhsyann ilrtqesacn ciggdcylmi tdgsasgisk
251 crflkiregr ivkeifptgr vehteectcg fasnktieca crdnsytakr
301 pfvklnvetd taeirlmcte tyldtprpdd gsitgpcesn gdkgsggikg
351 gfvhqrmask igrwysrtms ktkrmgmely vkydgdpwtd sdalapsgvm
401 vsieepgwys fgfeikdkkc dvpcigiemv hdggkttwhs aataiyclmg
451 sgqllwdtit gvdmal
```

Figure 1AD

SEQ ID NO:31
ca B/Brisbane/32/2002
Nucleotide Sequence of ca B_Brisbane_32_2002_HA          Entire molecule length: 1885 bp

```
   1 agcagaagca gagcattttc taatatccac aaaatgaagg caataattgt
  51 actactcatg gtagtaacat ccaatgcaga tcgaatctgc actgggataa
 101 catcgtcaaa ctcaccccat gtggtcaaaa ctgctactca aggggaggtc
 151 aatgtgactg gtgtgatacc actgacaaca cacccacca aatctcattt
 201 tgcaaatctc aaaggaacaa aaccagagg gaaactatgc ccaaaatgcc
 251 tcaactgcac agatctggac gtggccttgg cagaccaaa atgcacgggg
 301 aacatacct cggcaaaagt ttcaatactc catgaagtca gacctgttac
 351 atctgggtgc tttcctataa tgcacgacag aacaaaaatt agacagctgc
 401 ccaatcttct cagaggatac gaacatatca ggttatcaac tcataacgtt
 451 atcaatgcag aaaaggcacc aggaggaccc tacaaaattg gaacctcagg
 501 gtcttgccct aacgttacca atggaaacgg atttttcgca acaatggctt
 551 gggccgtccc aaaaaacgac aacaacaaaa cagcaacaaa ttcattaaca
 601 atagaagtac catacatttg tacagaagga gaagaccaaa ttaccgtttg
 651 ggggttccac tctgataacg aagcccaaat ggcaaactc tatggggact
 701 caaagcccca gaagttcacc tcatctgcca acggagtgac cacacattac
 751 gtttcacaga ttggtggctt cccaaatcaa acagaagacg gaggactacc
 801 acaaagtggt agaattgttg ttgattacat ggtgcaaaaa tctgggaaaa
 851 caggaacaat tacctatcaa agaggtattt tattgcctca aaaagtgtgg
 901 tgcgcaagtg gcaggagcaa ggtaataaaa ggatccttgc ctttaattgg
 951 agaagcagat tgcctccacg aaaaatacgg tggattaaac aaaagcaagc
1001 cttactacac aggggaacat gcaaaggcca taggaaattg cccaatatgg
1051 gtgaaaacac ccttgaagct ggccaatgga accaaatata gacctcctgc
1101 aaaactatta aaggaaagag gtttcttcgg agctattgct ggtttcttag
1151 aaggaggatg ggaaggaatg attgcaggtt ggcacggata cacatcccat
1201 ggggcacatg gagtagcagt ggcagcagac cttaagagta ctcaagaagc
1251 cataaacaag ataacaaaaa atctcaactc tttgagtgag ctggaagtaa
1301 agaatcttca aagactaagc ggtgccatgg atgaactcca caacgaaata
1351 ctagaactag acgagaaagt ggatgatctc agagctgata caataagctc
1401 acaaatagaa ctcgcagtct tgctttccaa tgaaggaata ataaacagtg
1451 aagatgagca tctcttggcg cttgaaagaa agctgaagaa aatgctgggc
1501 ccctctgctg tagagatagg aatggatgc ttcgaaacca acacaagtg
1551 caaccagacc tgtctcgaca gaatagctgc tggtaccttt gatgcaggag
1601 aatttctct ccccactttt gattcactga atattactgc tgcatcttta
1651 aatgacgatg gattggataa tcatactata ctgctttact actcaactgc
1701 tgcctccagt ttggctgtaa cattgatgat agctatcttt gttgtttata
1751 tggtctccag agacaatgtt tcttgctcca tctgtctata aggaaagtta
1801 agccctgtat tttcctttat tgtagtgctt gtttgcttgt taccattaca
1851 aaaaacgtt attgaaaaat gctcttgtta ctact
```

SEQ ID NO:79
Amino Acid Sequence of ca B_Brisbane_32_2002_HA          Entire molecule length: 585 aa

```
   1 mkaiivllmv vtsnadrict gitssnsphv vktatqgevn vtgviplttt
  51 ptkshfanlk gtktrgklcp kclnctdldv algrpkctgn ipsakvsilh
 101 evrpvtsgcf pimhdrtkir qlpnllrgye hirlsthnvi naekapggpy
 151 kigtsgscpn vtngngffat mawavpkndn nktatnslti evpyictege
 201 dqitvwgfhs dneaqmakly gdskpqkfts sangvtthyv sqiggfpnqt
 251 edgglpqsgr ivvdymvqks gktgtityqr gillpqkvwc asgrskvikg
 301 slpligeadc lhekygglnk skpyytgeha kaigncpiwv ktplklangt
 351 kyrppakllk ergffgaiag fleggwegmi agwhgytshg ahgvavaadl
 401 kstqeainki tknlnslsel evknlqrlsg amdelhneil eldekvddlr
 451 adtissqiel avllsnegii nsedehllal erklkkmlgp saveigngcf
 501 etkhkcnqtc ldriaagtfd agefslptfd slnitaasln ddgldnhtil
 551 lyystaassl avtlmiaifv vymvsrdnvs csicl
```

Figure 1AE

SEQ ID NO:32

Nucleotide Sequence of ca B_Brisbane_32_2002_NA    Entire molecule length: 1557 bp

```
   1 agcagaagca gagcatcttc tcaaaactga ggcaaatagg ccaaaaatga
  51 acaatgctac cttcaactat acaaacgtta accctatttc tcacatcagg
 101 gggagtatta ttatcactat atgtgtcagc ttcattgtca tacttactat
 151 attcggatat attgctaaaa ttctcaccaa cagaaataac tgcaccaaca
 201 atgccattgg attgtgcaaa cgcatcaaat gttcaggctg tgaaccgttc
 251 tgcaacaaaa ggggtgacac ttcttctccc agaaccagag tggacatacc
 301 cgcgtttatc ttgcccgggc tcaacctttc agaaagcact cctaattagc
 351 cctcatagat cggagaaaca caaggaaac tcagctccct tgataataag
 401 ggaaccttt attgcttgtg gaccaaagga atgcaaacac tttgctctaa
 451 cccattatgc agcccaacca ggggatact acaatggaac aagaggagac
 501 agaaacaagc tgaggcatct aatttcagtc aaattgggca aatcccaac
 551 agtagaaaac tccatttcc acatggcagc atggagcggg tccgcatgcc
 601 atgatggtaa agaatggaca tatatcggag ttgatggccc tgacaataat
 651 gcattgctca aaataaaata tggagaagca tatactgaca cataccattc
 701 ctatgcaaac aacatcctaa gaacacaaga aagtgcctgc aattgcatcg
 751 ggggaaattg ttatcttatg ataactgatg gctcagcttc aggtattagt
 801 gaatgcagat ttcttaaaat tcgagagggc cgaataataa agaaaatatt
 851 tccaacagga agagtaaaac atactgaaga atgcacatgc ggatttgcca
 901 gcaataagac catagaatgt gcctgtagag ataacagtta cacagcaaaa
 951 agaccctttg tcaaattaaa cgtggagact gatacagcag aaataagatt
1001 gatgtgcaca gagacttatt tggacacccc cagaccagat gatggaagca
1051 taacagggcc ttgtgaatct aatgggggaca aagggagtgg aggcatcaag
1101 ggaggatttg ttcatcaaag aatggcatcc aagattggaa ggtggtactc
1151 tcgaacgatg tctaaaacta aaggatggg gatgggactg tatgtcaagt
1201 atgatggaga cccatgggct gacagtgatg cccttgctct tagtggagta
1251 atggtttcaa tggaagaacc tggttggtac tcctttggct tcgaaataaa
1301 agataagaaa tgtgatgtcc cctgtattgg aatagagatg gtacatgatg
1351 gtggaaaga gacttggcac tcagcagcaa cagccattta ctgtttaatg
1401 ggctcaggac agctgctgtg ggacactgtc acaggtgttg atatggctct
1451 gtaatggagg aatggttgag tctgttctaa accctttgtt cctatttgt
1501 ttgaacaatt gtccttactg aacttaattg tttctgaaaa atgctcttgt
1551 tactact
```

SEQ ID NO:80

Amino Acid Sequence of ca B_Brisbane_32_2002_NA    Entire molecule length: 466 aa

```
  1 mlpstiqtlt lfltsggvll slyvsaslsy llysdillkf spteitaptm
 51 pldcanasnv qavnrsatkg vtlllpepew typrlscpgs tfqkallisp
101 hrfgetkgns apliirepfi acgpkeckhf althyaaqpg gyyngtrgdr
151 nklrhlisvk lgkiptvens ifhmaawsgs achdgkewty igvdgpdnna
201 llkikygeay tdtyhsyann ilrtqesacn ciggncylmi tdgsasgise
251 crflkiregr iikeifptgr vkhteectcg fasnktieca crdnsytakr
301 pfvklnvetd taeirlmcte tyldtprpdd gsitgpcesn gdksggikg
351 gfvhqrmask igrwysrtms ktkrmgmgly vkydgdpwad sdalalsgvm
401 vsmeepgwys fgfeikdkkc dvpcigiemv hdggketwhs aataiyclmg
451 sgqllwdtvt gvdmal
```

Figure 1AF

SEQ ID NO:33
ca B/Jilin/20/2003
Nucleotide Sequence of ca B/Jilin/20/03 HA Entire molecule length: 1853 bp

```
   1 tctaatatcc acaaaatgaa ggcaataatt gtactactca tggtagtaac
  51 atccaatgca gatcgaatct gcactgggat aacatcttca aactcacctc
 101 atgtggtcaa aacagctact caaggggagg tcaatgtgac tggtgtaata
 151 ccactgacaa caacaccaac aaaatcttat tttgcaaatc tcaaaggaac
 201 aaggaccaga gggaaactat gtccagactg tctcaactgt acagatctgg
 251 atgtggcctt gggcagacca atgtgtgtgg ggaccacacc ttcggcaaaa
 301 gcttcaatac tccacgaagt cagacctgtt acatccgggt gctttcctat
 351 aatgcacgac agaacaaaaa tcagacaact acccaatctt ctcagaggat
 401 atgaaaatat cagattatca acccaaaacg ttatcgatgc agaaaatgca
 451 ccaggaggac cctacagact tggaacctca ggatcttgcc ctaacgctac
 501 cagtaaaagc ggatttttcg caacaatggc ttgggctgtc ccaaaggaca
 551 acaacaaaaa tgcaacgaac ccactaacag tagaagtacc atacgtttgt
 601 acagaagggg aagaccaaat tactgtttgg gggttccatt cagataacaa
 651 aaccccaatg aagaacctct atggagactc aaatcctcaa aagttcacct
 701 catctgctaa tggagtaacc acacattatg tttctcagat tggcggcttc
 751 ccagctcaaa cagaagacga aggactacca caaagcggca gaattgttgt
 801 tgattacatg gtgcaaaaac ctaggaaaac aggaacaatt gtctatcaaa
 851 gaggtgtttt gttgcctcaa aaggtgtggt gcgcgagtgg caggagcaaa
 901 gtaataaaag ggtccttgcc tttaattggt gaagcagatt gccttcatga
 951 aaaatacggt ggattaaaca aaagcaagcc ttactacaca ggagaacatg
1001 caaaagccat aggaaattgc ccaatatggg tgaaaacacc tttgaagctt
1051 gccaatggaa ccaaatatag acctcctgca aaactattaa aggaaagggg
1101 tttcttcgga gctattgctg gtttcctaga aggaggatgg gaaggaatga
1151 ttgcaggttg gcacggatac acatctcacg gagcacatgg agtggcagtg
1201 gcggcagacc ttaagagtac gcaagaagct ataaacaaga taacaaaaaa
1251 tctcaattct ttgagtgagc tagaagtaaa gaatcttcaa agactaagtg
1301 gtgccatgga tgaactccac aacgaaatac tcgagctgga tgagaaagtg
1351 gatgatctca gagctgacac tataagctcg caaatagaac ttgcagtctt
1401 gctttccaat gaaggaataa taaacagtga agatgagcat ctattggcac
1451 ttgagagaaa actaaagaaa atgctgggtc cctctgctgt agacatagga
1501 aatggatgct tcgaaaccaa acacaagtgc aaccagacct gcttagacag
1551 gatagctgct ggcaccttta atgcaggaga attttctctc cccacttttg
1601 attcactgaa cattactgct gcatctttaa atgatgatgg attggataac
1651 catactatac tgctctatta ctcaactgct gcttctagtt tggctgtaac
1701 attgatgcta gctattttta ttgtttatat ggtctccaga gacaacgttt
1751 catgctccat ctgtctataa ggaagattaa gccttgtatt ttcctttatt
1801 gtagtgcttg tttgcttgtc atcattacaa agaaacgtta ttgaaaaatg
1851 ctc
```

SEQ ID NO:81

Amino Acid Sequence of ca B/Jilin/20/03 HA Entire molecule length: 584 aa

```
   1 mkaiivllmv vtsnadrict gitssnsphv vktatqgevn vtgvipltttt
  51 ptksyfanlk gtrtrgklcp dclnctdldv algrpmcvgt tpsakasilh
 101 evrpvtsgcf pimhdrtkir qlpnllrgye nirlstqnvi daenapggpy
 151 rlgtsgscpn atsksgffat mawavpkdnn knatnpltve vpyvcteged
 201 qitvwgfhsd nktpmknlyg dsnpqkftss angvtthyvs qiggfpaqte
 251 deglpqsgri vvdymvqkpr ktgtivyqrg vllpqkvwca sgrskvikgs
 301 lpligeadcl hekygglnks kpyytgehak aigncpiwvk tplklangtk
 351 yrppakllke rgffgaiagf leggwegmia gwhgytshga hgvavaadlk
 401 stqeainkit knlnslsele vknlqrlsga mdelhneile ldekvddlra
 451 dtissqiela vllsnegiin sedehllale rklkkmlgps avdigngcfe
 501 tkhkcnqtcl driaagtfna gefslptfds lnitaaslnd dgldnhtill
 551 yystaassla vtlmlaifiv ymvsrdnvsc sicl
```

Figure 1AG

SEQ ID NO:34
Nucleotide Sequence of ca B/Jilin/20/03 NA Entire molecule length: 1529 bp

```
   1 tctcaaaact gaggcaaata ggccaaaaat gaacaatgct accctcaact
  51 atacaaacgt taaccctatt cctcacatca gggggagtgt tattatcact
 101 atatgtgtca gcttcactgt catacttact atattcggat atattgctaa
 151 aattttcaac aacagaaata actgcaccaa caatgccatt ggattgtgca
 201 aacgcatcaa atgttcaggc tgtgaaccgt tctgcaacaa aagggggtgac
 251 acttcttctc ccagaaccgg agtggacata cccgcgttta tcttgcccgg
 301 gctcaacctt tcagaaagca ctcctaatta gccctcatag attcggagaa
 351 accaaaggaa actcagctcc cttgataata agggaacctt ttattgcttg
 401 tggaccaaag gaatgcaaac actttgctct aacccattat gcagcccaac
 451 caggggggata ctacaatgga acaaaagaag acagaaacaa gctgaggcat
 501 ctaatttcag tcaaattggg caaaatccca acagtagaaa actccatttt
 551 ccacatggca gcatggagcg ggtccgcatg ccatgatggt aaagaatgga
 601 catatatcgg agttgatggc cctgacagta atgcattgct caaaataaaa
 651 tatggagaag catatactga cacataccat tcctatgcaa acaacatcct
 701 aagaacacaa gaaagtgcct gcaattgcat cggggggaaat tgttatctta
 751 tgataactga tggctcagct tcaggtatta gtgagtgcag atttcttaag
 801 attcgagagg gccgaataat aaaagaaata tttccaacag gaagagtaaa
 851 acatactgaa gaatgcacat gcggatttgc cagcaataaa accatagaat
 901 gtgcctgtag agataacagt tacacagcaa aagacccctt tgtcaaatta
 951 aatgtggaga ctgatacagc agaaataaga ttgatgtgca cagagactta
1001 tttggacacc cccagaccag atgatggaag cataacaggg ccttgtgaat
1051 ctaatgggaa taaagggagt ggaggcatca agggaggatt tgttcatcaa
1101 agaatggcat ccaaaattgg aaggtggtac tctcgaacaa tgtctaaaac
1151 caaaaggatg ggaatgggac tgtatgtcaa gtatgatgga gacccatgga
1201 ctgacagtga tgcccttgct cttagtggag taatggtttc aatggaagaa
1251 cctggttggt actcatttgg cttcgaaata aaagataaga aatgtgatgt
1301 cccctgtatt gggatagaga tggtacatga tggtggaaag agacttggc
1351 actcagcagc aacagccatt tactgtttaa tgggctcagg acaactgttg
1401 tgggacactg tcacaggtgt tgatatggct ctgtaatggg ggaatggttg
1451 agtctgttct aaacccttg ttcctatttt gtttgaacaa ttgtccttgc
1501 tgaacttaat tgtttctgaa aaatgctct
```

SEQ ID NO:82
Amino Acid Sequence of ca B/Jilin/20/03 NA    Entire molecule length: 466 aa

```
  1 mlpstiqtlt lfltsggvll slyvsaslsy llysdillkf stteitaptm
 51 pldcanasnv qavnrsatkg vtlllpepew typrlscpgs tfqkallisp
101 hrfgetkgns apliirepfi acgpkeckhf althyaaqpg gyyngtkedr
151 nklrhlisvk lgkiptvens ifhmaawsgs achdgkewty igvdgpdsna
201 llkikygeay tdtyhsyann ilrtqesacn ciggncylmi tdgsasgise
251 crflkiregr iikeifptgr vkhteectcg fasnktieca crdnsytakr
301 pfvklnvetd taeirlmcte tyldtprpdd gsitgpcesn gnkgsggikg
351 gfvhqrmask igrwysrtms ktkrmgmgly vkydgdpwtd sdalalsgvm
401 vsmeepgwys fgfeikdkkc dvpcigiemv hdggketwhs aataiyclmg
451 sgqllwdtvt gvdmal
```

SEQ ID NO:35
Nucleotide Sequence of wt_A_California_7_04_HA         Entire molecule length: 1721 bp

```
   1 ctattaacca tgaagactat cattgctttg agctacattc tatgtctggt
  51 tttcgctcaa aaacttcccg gaaatgacaa cagcacggca acgctgtgcc
 101 tgggcacca tgcagtacca aacgaacga tagtgaaaac aatcacgaat
 151 gaccaaattg aagttactaa tgctactgag ctggttcaga gttcctcaac
 201 aggtggaata tgcgacagtc ctcatcagat ccttgatgga gaaactgca
 251 cactaataga tgctctattg ggagaccctc agtgtgatgg cttccaaaat
 301 aagaaatggg acctttttgt tgaacgcagc aaagcctaca gcaactgtta
 351 cccttatgat gtgccggatt atgcctccct taggtcacta gttgcctcat
 401 ccggcacact ggagtttaac aatgaaagct tcaattggac tggagtcact
 451 caaaatggaa caagctcttc ttgcaaaagg agatctaata acagtttctt
 501 tagtagattg aattggttga cccatttaaa attcaaatac ccagcattga
 551 acgtgactat gccaaacaat gaaaatttg acaaattgta catttggggg
 601 gttcaccacc cgggtacgaa caatgaccaa atcagcctat atactcaagc
 651 atcaggaaga atcacagtct ctaccaaaag aagccaacaa actgtaatcc
 701 cgaatatcgg atctagaccc agggtaaggg atatccccag cagaataagc
 751 atctattgga caatagtaaa accgggagac atacttttga ttaacagcac
 801 agggaatcta attgctcctc ggggttactt caaaatacga agtgggaaaa
 851 gctcaataat gagatcagat gcacccattg gcaaatgcaa ttctgaatgc
 901 atcactccaa atggaagcat tcccaatgac aaaccatttc aaaatgtaaa
 951 caggatcaca tatgggggcct gtcccagata tgttaagcaa aacactctga
1001 aattggcaac agggatgcga aatgtaccag agaaacaaac tagaggcata
1051 tttggcgcaa tcgcgggttt catagaaaat ggttgggagg gaatggtgga
1101 tggttggtac ggtttcaggc atcaaaattc tgagggaata ggacaagcag
1151 cagatctcaa aagcactcaa gcagcaatca accaaatcaa tgggaagctg
1201 aataggttga tcgggaaaac caacgagaaa ttccatcaga ttgaaaaaga
1251 attctcagaa gtagaaggga gaattcagga cctcgagaaa tatgttgagg
1301 acactaaaat agatctctgg tcatacaacg cggagcttct tgttgccctg
1351 gagaaccaac atacaattga tctaactgac tcagaaatga caaactgtt
1401 tgaaagaaca aagaagcaac tgagggaaaa tgctgaggat atgggcaatg
1451 gttgtttcaa aatataccac aaatgtgaca atgcctgcat agggtcaatc
1501 agaaatggaa cttatgacca tgatgtatac agagatgaag cattaaacaa
1551 ccggttccag atcaaaggtg ttgagctgaa gtcaggatac aaagattgga
1601 tcctatggat ttcctttgcc atatcatgtt ttttgctttg tgttgctttg
1651 ttggggttca tcatgtgggc ctgccaaaaa ggcaacatta ggtgcaacat
1701 ttgcatttga gtgcattaat t
```

SEQ ID NO:83
Amino Acid Sequence of wt_A_California_7_04_HA         Entire molecule length: 566 aa

```
   1 mktiialsyi lclvfaqklp gndnstatlc lghhavpngt ivktitndqi
  51 evtnatelvq ssstggicds phqildgenc tlidallgdp qcdgfqnkkw
 101 dlfverskay sncypydvpd yaslrslvas sgtlefnnes fnwtgvtqng
 151 tssckrrsn nsffsrlnwl thlkfkypal nvtmpnnekf dklyiwgvhh
 201 pgtnndqisl ytqasgritv stkrsqqtvi pnigsrprvr dipsrisiyw
 251 tivkpgdill instgnliap rgyfkirsgk ssimrsdapi gkcnsecitp
 301 ngsipndkpf qnvrityga cpryvkqntl klatgmrnvp ekqtrgifga
 351 iagfiengwe gmvdgwygfr hqnsegigqa adlkstqaai nqingklnrl
 401 igktnekfhq iekefseveg riqdlekyve dtkidlwsyn aellvalenq
 451 htidltdsem nklfertkkq lrenaedmgn gcfkiyhkcd nacigsirng
 501 tydhdvyrde alnnrfqikg velksgykdw ilwisfaisc fllcvallgf
 551 imwacqkgni rcnici
```

Figure 1AI

SEQ ID NO:36

Nucleotide Sequence of wt_A_California_7_04_NA      Entire molecule length: 1426 bp

```
   1 atgaatccaa atcaaaagat aataacgatt ggctctgttt ctctcaccat
  51 ttccacaata tgcttcttta tgcaaattgc catcttgata actactgtaa
 101 cattgcattt caagcaatat gaattcaact ccccccaaa caaccaagtg
 151 atgctgtgtg aaccaacaat aatagaaaga acataacag agatagtgta
 201 tctgaccaac accaccatag agaaggaaat atgccccaaa ctagcagaat
 251 acagaaattg gtcaaagccg caatgtgaca ttacaggatt tgcacctttt
 301 tctaaggaca attcgattag gctttccgct ggtggggaca tctgggtgac
 351 aagagaacct tatgtgtcat gcgatcctga caaatgttat caatttgccc
 401 ttggacaggg aacaacacta aacaacgtgc attcaaatga cacagtacat
 451 gataggaccc cttatcggac cctattgatg aatgagttag gtgttccatt
 501 tcatctgggg actaagcaag tgtgcatagc atggtccagc tcaagttgtc
 551 acgatggaaa agcatggctg catgtttgtg taacggggga tgataaaaat
 601 gcaactgcta gcttcattta caatgggagg cttgtagata gtattgtttc
 651 atggtccaaa gaaatcctca gaacccagga gtcagaatgc gtttgtatca
 701 atggaacttg tacagtagta atgactgatg ggagtgcttc aggaaaagct
 751 gatactaaaa tactattcat tgaggagggg aaaatcgttc atactagcac
 801 attgtcagga agtgcccagc atgtcgagga gtgctcctgc tatcctcgat
 851 atcctggtgt cagatgtgtc tgcagagaca actggaaagg ctccaatagg
 901 cccatcgtag atataaacat aaaggattat agcattgttt ccagttatgt
 951 gtgctcagga cttgttggag acacacccag aaaaaacgac agctccagca
1001 gtagccattg cttggatcct aacaatgaag aaggtggtca tggagtgaaa
1051 ggctgggcct tgatgatgg aaatgacgtg tggatgggaa gaacgatcag
1101 cgagaagtta cgctcaggat atgaaacctt caaagtcatt gaaggctggt
1151 ccaaccctaa ttccaaattg cagataaata ggcaagtcat agttgacaga
1201 ggtaataggt ccggttattc tggtattttc tctgttgaag gcaaaagctg
1251 catcaatcgg tgcttttatg tggagttgat aaggggaaga aagaggaaa
1301 ctgaagtctt gtggacctca aacagtattg ttgtgtttg tggcacctca
1351 ggtacatatg gaacaggctc atggcctgat ggggcggaca tcaatctcat
1401 gcctatataa gctttcgcaa ttttag
```

SEQ ID NO:84

Amino Acid Sequence of wt_A_California_7_04_NA      Entire molecule length: 469 aa

```
   1 mnpnqkiiti gsvsltisti cffmqiaili ttvtlhfkqy efnsppnnqv
  51 mlceptiier niteivyltn ttiekeicpk laeyrnwskp qcditgfapf
 101 skdnsirlsa ggdiwvtrep yvscdpdkcy qfalgqgttl nnvhsndtvh
 151 drtpyrtllm nelgvpfhlg tkqvciawss sschdgkawl hvcvtgddkn
 201 atasfiyngr lvdsivswsk eilrtqesec vcingtctvv mtdgsasgka
 251 dtkilfieeg kivhtstlsg saqhveecsc yprypgvrcv crdnwkgsnr
 301 pivdinikdy sivssyvcsg lvgdtprknd sssshcldp nneegghgvk
 351 gwafddgndv wmgrtisekl rsgyetfkvi egwsnpnskl qinrqvivdr
 401 gnrsgysgif svegkscinr cfyvelirgr keetevlwts nsivvfcgts
 451 gtygtgswpd gadinlmpi
```

Figure 1AJ

SEQ ID NO:37
Nucleotide sequence of ca A/Sandai-H/F4962/02 H3 (Fujian-like strain)  Entire molecule
length: 1736 bp

```
   1 gataattcta ttaaccatga agactatcat tgctttgagc tacattctat
  51 gtctggtttt cgctcaaaag cttcccggaa atgacaacag cacggcaacg
 101 ctgtgccttg ggcaccatgc agtaccaaac ggaacgatag tgaaaacaat
 151 cacgaatgac caaattgaag ttactaatgc tactgagctg gttcagagtt
 201 cctcaacagg tggaatatgc gacagccctc atcagatcct tgatggagaa
 251 aactgcacac taatagatgc tctattggga gaccctcagt gtgatggctt
 301 ccaaaataag aaatgggacc tttttgttga acgcagcaaa gcctacagca
 351 actgttaccc ttatgatgtg ccggattatg cctcccttag gtcactagtt
 401 gcctcatccg gcacactgga gtttaacaat gaaagcttca attggactgg
 451 agtcactcag aatggaacaa gctctgcttg caaaaggaga tctaataaaa
 501 gtttctttag tagattgaat tggttgaccc acttaaaata caaatacccca
 551 gcattgaacg tgactatgcc aaacaatgaa aaatttgaca aattgtacat
 601 ttgggggggtt caccacccgg gtacggacag tgaccaaatc agcctatatg
 651 ctcaagcatc aggaagaatc acagtctcta ccaaaagaag ccaacaaact
 701 gtaatcccga atatcggatc tagacccagg gtaagggatg tctccagcag
 751 aataagcatc tattggacaa tagtaaaacc gggagacata cttttgatta
 801 acagcacagg gaatctaatt gctcctcggg gttacttcaa aatacgaagt
 851 gggaaaagct caataatgag atcagatgca cccattggca aatgcaattc
 901 tgaatgcatc actccaaatg gaagcattcc caatgacaaa ccatttcaaa
 951 atgtaaacag gatcacatat ggggcctgtc ccagatatgt aagcaaaac
1001 actctgaaat tggcaacagg gatgcgaaat gtaccagaga acaaaactag
1051 aggcatattt ggcgcaatcg cgggtttcat agaaaatggt tgggagggaa
1101 tggtggacgg ttggtacggt ttcaggcatc aaaattctga gggcacagga
1151 caagcagcag atctcaaaag cactcaagca gcaatcaacc aaatcaatgg
1201 gaaactgaat aggttaatcg ggaaaacaaa cgagaaattc catcagattg
1251 aaaagaatt ctcagaagta aagggagaa ttcaggacct cgagaaatat
1301 gttgaggaca ctaaaataga tctctggtca tacaacgcgg agcttcttgt
1351 tgccctggag aaccaacata caattgatct aactgactca gaaatgaaca
1401 aactgtttga aagaacaaag aagcaactga gggaaaatgc tgaggatatg
1451 ggcaatggtt gtttcaaaat ataccacaaa tgtgacaatg cctgcataga
1501 gtcaatcaga aatggaactt atgaccatga tgtatacaga gatgaagcat
1551 taaacaaccg gttccagatc aaaggtgttg agctgaagtc aggatacaaa
1601 gattggatcc tatggatttc ctttgccata tcatgttttt tgctttgtgt
1651 tgctttgttg gggtcatca tgtgggcctg ccaaaaaggc aacattaggt
1701 gcaacatttg catttgagtg cattaattaa aaacac
```

SEQ ID NO:85
Amino acid sequence of ca A/Sandai-H/F4962/02 H3 (Fujian-like strain)  Entire molecule
length: 550 aa

```
   1 qklpgndnst atlclghhav pngtivktit ndqievtnat elvqssstgg
  51 icdsphqild genctlidal lgdpqcdgfq nkkwdlfver skaysncypy
 101 dvpdyaslrs lvassgtlef nnesfnwtgv tqngtssack rrsnksffsr
 151 lnwlthlkyk ypalnvtmpn nekfdklyiw gvhhpgtdsd qislyaqasg
 201 ritvstkrsq qtvipnigsr prvrdvssri siywtivkpg dillinstgn
 251 liaprgyfki rsgkssimrs dapigkcnse citpngsipn dkpfqnvnri
 301 tygacpryvk qntlklatgm rnvpekqtrg ifgaiagfie ngwegmvdgw
 351 ygfrhqnseg tgqaadlkst qaainqingk lnrligktne kfhqiekefs
 401 evegriqdle kyvedtkidl wsynaellva lenqhtidlt dsemnklfer
 451 tkkqlrenae dmgngcfkiy hkcdnacies irngtydhdv yrdealnnrf
 501 qikgvelksg ykdwilwisf aiscfllcva llgfimwacq kgnircnici
```

Figure 1AK

SEQ ID NO:38

Nucleotide sequence of ca A/Sandai-H/F4962/02 N2 (Fujian-like strain)  Entire molecule
length: 1438 bp

```
   1 atgaatccaa atcaaaagat aataacgatt ggctctgttt ccctcaccat
  51 ttccacaata tgcttcttca tgcaaattgc catcctgata actactgtaa
 101 cattgcattt caagcaatat gaattcaact ccccccaaa caaccaagtg
 151 atgctgtgtg aaccaacaat aatagaaaga aacataacag agatagtgta
 201 tctgaccaac accaccatag agaaggaaat atgccccaaa ctagcagaat
 251 acagaaattg gtcaaagccg caatgtaaca ttacaggatt gcacctttt
 301 tctaaggaca attcgattcg ctttccgct ggtggggaca tctgggtgac
 351 aagacaacct tatgtgtcat gcgatcctga caagtgttat caatttgccc
 401 ttggaaaggg aacaacacta acaacgtgc attcaaatga cacagtacat
 451 gataggaccc cttatcggac cctattgatg aatgagttgg gtgttccatt
 501 tcatctgggg accaagcaag tgtgcatagc atggtccagc tcaagttgtc
 551 acgatggaaa agcatggctg catgtttgtg taacggggga tgatgaaaat
 601 gcaactgcta gcttcattta caatgggagg cttgtagata gtattgtttc
 651 atggtccaaa aaaatcctca ggacccagga gtcagaatgc gtttgtatca
 701 atggaacttg tacagtagta atgactgatg ggagtgcttc aggaaaagct
 751 gatactaaaa tactattcat tgaggagggg aaaattgttc atactagcac
 801 attatcagga agtgctcagc atgtcgagga gtgctcctgt tatcctcgat
 851 atcctggtgt cagatgtgtc tgcagagaca actggaaagg ctccaatagg
 901 cccatcgtag atataaacat aaaggattat agcattgttt ccagttatgt
 951 gtgctcagga cttgttggag acacacccag aaaaaacgac agctccagca
1001 gtagccattg cttggatcca acaatgagg aaggtggtta tggagtgaaa
1051 ggctgggctt tgatgatgg aaatgacgtg tggatgggaa gaacgatcag
1101 cgagaagtta cgctcaggat atgaaacctt caaagtcatt gaaggctggt
1151 ccaaccctaa ctccaaattg cagataaata ggcaagtcat agttgacaga
1201 ggtaacaggt ccggttattc tggtattttc tctgttgaag caaaagctg
1251 catcaatcgg tgcttttatg tggagttgat aaggggaaga aaacaggaaa
1301 ctgaagtctt gtggacctca aacagtattg ttgtgttttg tggcacctca
1351 ggtacatatg aacaggctc atggcctgat ggggcggaca tcaatctcat
1401 gcctatataa gctttcgcaa ttttagaaaa aaactcct
```

SEQ ID NO:86

Amino acid sequence of ca A/Sandai-H/F4962/02 N2 (Fujian-like strain)  Entire molecule
length: 469 aa

```
   1 mnpnqkiiti gsvsltisti cffmqiaili ttvtlhfkqy efnsppnnqv
  51 mlceptiier niteivyltn ttiekeicpk laeyrnwskp qcnitgfapf
 101 skdnsirlsa ggdiwvtrqp yvscdpdkcy qfalgkgttl nnvhsndtvh
 151 drtpyrtllm nelgvpfhlg tkqvciawss sschdgkawl hvcvtgdden
 201 atasfiyngr lvdsivswsk kilrtqesec vcingtctvv mtdgsasgka
 251 dtkilfieeg kivhtstlsg saqhveecsc yprypgvrcv crdnwkgsnr
 301 pivdinikdy sivssyvcsg lvgdtprknd ssssshcldp nneeggygvk
 351 gwafddgndv wmgrtisekl rsgyetfkvi egwsnpnskl qinrqvivdr
 401 gnrsgysgif svegkscinr cfyvelirgr kqetevlwts nsivvfcgts
 451 gtygtgswpd gadinlmpi
```

Figure 1AL

SEQ ID NO:39
Nucleotide sequence of ca A/Wellington/1/04 H3 (Fujian-like strain)   Entire molecule length: 1723 bp

```
   1 ttctattaac catgaagact atcattgctt tgagctacat tctatgtctg
  51 gttttcgctc aaaaacttcc cggaaatgac aacagcacgg caacgctgtg
 101 ccttgggcac catgcagtac caaacggaac gatagtgaaa acaatcacga
 151 atgaccaaat tgaagttact aatgctactg agctggttca gagttcctca
 201 acaggtggaa tatgcgacag tcctcatcag atccttgatg gagaaaactg
 251 cacactaata gatgcttctat tgggagaccc tcagtgtgat ggcttccaaa
 301 ataagaaatg ggacctttt gttgaacgca gcaaagccta cagcaactgt
 351 taccct tatg atgtgccgga ttatgcctcc cttaggtcac tagttgcctc
 401 atccggcaca ctggagttta caatgaaag cttcaattgg actggagtca
 451 ctcaaaatgg aacaagctct gcttgcaaaa ggagatctaa taaaagtttc
 501 tttagtagat tgaattggtt gacccactta aaattcaaat cccagcatt
 551 gaacgtgact atgccaaaca atgaaaaatt tgacaaattg tacatttggg
 601 gggttcacca cccgggtacg gacaatgacc aaatcaacct atatgttcaa
 651 gcatcaggaa gaatcacagt ctctaccaaa agaagccaac aaactgtaat
 701 cccgaatatc ggatctagac ccagagtaag ggatgtcccc agcagaataa
 751 gcatctattg gacaatagta aaaccgggag acatactttt gattagcagc
 801 acagggaatc taattgctcc tcggggttac ttcaaaatac gaagtgggaa
 851 aagctcaata atgagatcag atgcacccat tggcaaatgc aattctgaat
 901 gcatcactcc aaatggaagc attcccaatg acaaaccatt tcaaaatgta
 951 aacaggatca catatgggc ctgtcccaga tatgttaagc aaaacactct
1001 gaaattggca acagggatgc gaaatgtacc agagaaacaa actagaggca
1051 tatttggcgc·aatcgcgggt ttcatagaaa atggttggga gggaatggtg
1101 gacggttggt acggtttcag gcatcaaaat tctgagggaa caggacaagc
1151 agcagatctc aaaagcactc aagcagcaat caaccaaatc aatgggaagc
1201 tgaataggtt gatcgggaaa acaaacgaga attccatca gattgaaaaa
1251 gaattctcag aagtagaagg gagaattcag gacctcgaga aatatgttga
1301 ggacactaaa atagatctct ggtcatacaa cgcggagctt cttgttgccc
1351 tggagaacca acatacaatt gatctaactg actcagaaat gaacaaactg
1401 tttgaaagaa caaagaagca actgagggaa atgctgagg atatgggcaa
1451 tggttgtttc aaaatatacc acaaatgtga caatgcctgc ataggtcaa
1501 tcagaaatgg aacttatgac catgatgtat acagagatga agcattaaac
1551 aaccggttcc agatcaaagg tgttgagctg aagtcaggat acaaagattg
1601 gatcctatgg atttcctttg ccatatcatg ttttttgctt tgtgttgctt
1651 tgttggggtt catcatgtgg gcctgccaaa aaggcaacat taggtgcaac
1701 atttgcattt gagtgcatta att
```

SEQ ID NO:87
Amino acid sequence of ca A/Wellington/1/04 H3 (Fujian-like strain)   Entire molecule length: 550 aa

```
   1 qklpgndnst atlclghhav pngtivktit ndqievtnat elvqssstgg
  51 icdsphqild genctlidal lgdpqcdgfq nkkwdlfver skaysncypy
 101 dvpdyaslrs lvassgtlef nnesfnwtgv tqngtssack rrsnksffsr
 151 lnwlthlkfk ypalnvtmpn nekfdklyiw gvhhpgtdnd qinlyvqasg
 201 ritvstkrsq qtvipnigsr prvrdvpsri siywtivkpg dillisstgn
 251 liaprgyfki rsgkssimrs dapigkcnse citpngsipn dkpfqnvnri
 301 tygacpryvk qntlklatgm rnvpekqtrg ifgaiagfie ngwegmvdgw
 351 ygfrhqnseg tgqaadlkst qaainqingk lnrligktne kfhqiekefs
 401 evegriqdle kyvedtkidl wsynaellva lenqhtidlt dsemnklfer
 451 tkkqlrenae dmgngcfkiy hkcdnacigs irngtydhdv yrdealnnrf
 501 qikgvelksg ykdwilwisf aiscfllcva llgfimwacq kgnircnici
```

Figure 1AM

SEQ ID NO:40

Nucleotide sequence of ca A/Wellington/1/04 N2 (Fujian-like strain)   Entire molecule length: 1428 bp

```
   1 aaatgaatcc aaatcaaaag ataataacga ttggctctgt ttctctcacc
  51 atttccacaa tatgcttctt catgcaaatt gccatcttga taactactgt
 101 aacattgcat ttcaagcaat atgaattcaa ctccccccca aacaaccaag
 151 tgatgctgtg tgaaccaaca ataatagaaa gaaacataac agagatagtg
 201 tatctgacca acaccaccat agagaaggaa atatgcccca actagcaga
 251 atacagaaat tggtcaaagc cgcaatgtga cattacagga tttgcacctt
 301 tttctaagga caattcgatt aggctttccg ctggtgggga catctgggtg
 351 acaagagaac cttatgtgtc atgcgatcct gacaagtgtt atcaatttgc
 401 ccttggacag ggaacaacac taaacaacgt gcattcaaat gacacagtac
 451 atgataggac cccttatcgg accctattga tgaatgagtt aggtgttcca
 501 tttcatctgg ggaccaagca agtgtgcata gcatggtcca gctcaagttg
 551 tcacgatgga aaagcatggc tgcatgtttg tgtaacgggg atgataaaa
 601 atgcaactgc tagcttcatt tacaatggga ggcttgtaga tagtattgtt
 651 tcatggtcca aaaaaatcct caggacccag gagtcagaat gcgtttgtat
 701 caatggaact tgtacagtag taatgactga tgggagtgct tcaggaaaag
 751 ctgatactaa aatactattc attgaggagg ggaaaatcgt tcatactagc
 801 acattgtcag gaagtgctca gcatgtcgag gagtgctcct gctatcctcg
 851 atatcctggt gtcagatgtg tctgcagaga caactggaaa ggctccaata
 901 ggcccatcgt agatataaac ataaggatt atagcattgt tccagttat
 951 gtgtgctcag gacttgttgg agacacaccc agaaaaaacg acagctccag
1001 cagtagccat tgcttggatc ctaacaatga agaaggtggt catggagtga
1051 aaggctgggc ctttgatgat ggaaatgacg tgtggatggg aagaacgatc
1101 agcgagaagt tacgctcagg atatgaaacc ttcaaagtca ttgaaggctg
1151 gtccaaccct aattccaaat tgcagataaa taggcaagtc atagttgaca
1201 gaggtaatag gtccggttat tctggtattt tctctgttga aggcaaaagc
1251 tgcatcaatc ggtgctttta tgtggagttg ataaggggaa gaaaagagga
1301 aactaaagtc ttgtggacct caaacagtat tgttgtgttt tgtggcacct
1351 caggtacata tggaacaggc tcatggcctg atggggcgga catcaatctc
1401 atgcctatat aagctttcgc aattttag
```

SEQ ID NO:88

Amino acid sequence of ca A/Wellington/1/04 N2 (Fujian-like strain)   Entire molecule length: 469 aa

```
   1 mnpnqkiiti gsvsltisti cffmqiaili ttvtlhfkqy efnsppnnqv
  51 mlceptiier niteivyltn ttiekeicpk laeyrnwskp qcditgfapf
 101 skdnsirlsa ggdiwvtrep yvscdpdkcy qfalgqgttl nnvhsndtvh
 151 drtpyrtllm nelgvpfhlg tkqvciawss sschdgkawl hvcvtgddkn
 201 atasfiyngr lvdsivswsk kilrtqesec vcingtctvv mtdgsasgka
 251 dtkilfieeg kivhtstlsg saqhveecsc yprypgvrcv crdnwkgsnr
 301 pivdinikdy sivssyvcsg lvgdtprknd ssssshcldp nneegghgvk
 351 gwafddgndv wmgrtisekl rsgyetfkvi egwsnpnskl qinrqvivdr
 401 gnrsgysgif svegkscinr cfyvelirgr keetkvlwts nsivvfcgts
 451 gtygtgswpd gadinlmpi
```

Figure 1AN

SEQ ID NO:41

Nucleotide sequence of ca A/Malalysia/1/04_1 H3 (Fujian-like strain)   Entire molecule length: 1724 bp

```
   1 attctattaa ccatgaagac tatcattgct ttgagctaca ttctatgtct
  51 ggttttcgct caaaaacttc ccggaaatga acacagcacg gcaacgctgt
 101 gccttgggca ccatgcagta ccaaacggaa caatagtgaa aacaatcacg
 151 aatgaccaaa ttgaagttac taatgctact gagctggttc agaattcctc
 201 aacaggtgga atatgcgaca gtcctcatca gatccttgat ggagaaaact
 251 gcacactaat agatgctcta tgggagacc ctcagtgtga tggcttccaa
 301 aataagaaat gggaccttt tgttgaacgc agcaaggcct acagcaactg
 351 ttacccttat gatgtgccgg attatgcctc ccttaggtca ctagttgcct
 401 catccggcac actggagttt aacaatgaaa gcttcaattg gactggagtc
 451 actcaaaatg gaacaagctc tgcttgcaaa aggagatcta ataaaagttt
 501 ctttagtaga ttgaattggt tgacccactt aaaattcaaa tacccagcat
 551 tgaacgtgac tatgccaaac aatgaaaaat tgacaaatt gtacatttgg
 601 ggggttcacc acccgggtac ggactatgac caaatccgcc tatatgctca
 651 agcatcagga agaatcacag tctctaccaa aagaagccaa caaactgtaa
 701 tcccgaatat cggatctaga cccagggtaa gggatatccc cagcagaata
 751 agcatctatt ggacaatagt aaaaccggga gacatacttt tgattaacag
 801 cacagggaat ctaattgctc ctcggggtta cttcaaaata cgaagtggga
 851 aaagctcaat aatgagatca gatgcaccca ttggcaaatg caattctgaa
 901 tgcatcactc caaatggaag cattcccaat gacaaaccat tcaaaatgt
 951 aaacaggatc acatatgggg cctgtcccag atatgttaag caaaacactc
1001 tgaaattggc aacagggatg cgaaacgtac cagagaaaca aactagaggc
1051 atatttggcg caatcgcggg tttcatagaa aatggttggg agggaatggt
1101 ggacggttgg tacggtttca ggcatcaaaa ttctgaggga acaggacaag
1151 cagcagatct caaaagcact caagcagcaa tcaaccaaat caatgggaag
1201 ctgaataggt tgatcgggaa aacaaacgag aaattccatc agattgaaaa
1251 agaattctca gaagtagaag ggagaattca ggacctcgag aaatatgttg
1301 aggacactaa aatagatctc tggtcataca cgcggagct tcttgttgcc
1351 ctggagaacc aacatacaat tgatctaact gactcagaaa tgaacaaact
1401 gtttgaaaga acaaagaagc aactgaggga aaatgctgag gatatgggca
1451 atggttgttt caaaatatac cacaaatgtg acaatgcctg cataggtca
1501 atcagaaatg gaacttatga ccatgatgta tacagagatg aagcattaaa
1551 caaccggttc cagatcaaag gtgttgagct gaagtcagga tacaaagatt
1601 ggatcctatg gatttccttt gccatatcat gttttttgct ttgtgttgct
1651 ttgtcggggt tcatcatgtg ggcctgccaa aaaggcaaca ttaggtgcaa
1701 catttgcatt tgagtgcatt aatt
```

SEQ ID NO:89

Amino acid sequence of ca A/Malalysia/1/04_1 H3 (Fujian-like strain)   Entire molecule length: 550 aa

```
   1 qklpgndnst atlclghhav pngtivktit ndqievtnat elvqnsstgg
  51 icdsphqild genctlidal lgdpqcdgfq nkkwdlfver skaysncypy
 101 dvpdyaslrs lvassgtlef nnesfnwtgv tqngtssack rrsnksffsr
 151 lnwlthlkfk ypalnvtmpn nekfdklyiw gvhhpgtdyd qirlyaqasg
 201 ritvstkrsq qtvipnigsr prvrdipsri siywtivkpg dillinstgn
 251 liaprgyfki rsgkssimrs dapigkcnse citpngsipn dkpfqnvnri
 301 tygacpryvk qntlklatgm rnvpekqtrg ifgaiagfie ngwegmvdgw
 351 ygfrhqnseg tgqaadlkst qaainqingk lnrligktne kfhqiekefs
 401 evegriqdle kyvedtkidl wsynaellva lenqhtidlt dsemnklfer
 451 tkkqlrenae dmgngcfkiy hkcdnacigs irngtydhdv yrdealnnrf
 501 qikgvelksg ykdwilwisf aiscfllcva lsgfimwacq kgnircnici
```

Figure 1AO

SEQ ID NO:42
Nucleotide sequence of ca A/Malaysia/1/04_1 N2 (Fujian-like strain)   Entire molecule length: 1426 bp

```
   1 atgaatccaa atcaaaagat aataacgatt ggctctgttt ctctcaccat
  51 ttccacaata tgcttcttca tgcaaattgc catcttgata actactgtaa
 101 cattgcattt caagcaatat gaattcaact cccccccaaa caaccaagtg
 151 atgctgtgtg aaccaacaat aatagaaaga acataacag agatagtgta
 201 tctgaccaac accaccatag agaaggaaat atgccccaaa ctagcagaat
 251 acagaaattg gtcaaagccg caatgtgaca ttacaggatt gcacctttt
 301 tctaaggaca attcgattag gctttccgct ggtggggaca tctgggtgac
 351 aagagaacct tatgtgtcat gcgatcctga caagtgttat caatttgccc
 401 ttggacaggg aacaacacta acaacgtgc attcaaatga cacagtacat
 451 gataggaccc cttatcggac cctattgatg aatgagttag tgttccatt
 501 tcatctgggg accaagcaag tgtgcatagc atggtccagc tcaagttgtc
 551 acgatggaaa agcatggctg catgtttgtg taacggggga tgataaaaat
 601 gcaactgcta gcttcattta caatgggagg cttgtagata gtattgtttc
 651 atggtccaaa aaatcctca ggacccagga gtcagaatgc gtttgtatca
 701 atggaacttg tacagtagta atgactgatg ggagtgcttc aggaaaagct
 751 gatactaaaa tactattcat tgaggagggg aaaatcgttc atactagcac
 801 attgtcagga agtgctcagc atgtcgagga gtgctcctgc tatcctcgat
 851 atcctggtgt cagatgtgtc tgcagagaca actggaaagg ctccaatagg
 901 cccatcgtag atataaacat aaaggattat agcattgttt ccagttatgt
 951 gtgctcagga cttgttggag acacacccag aaaaaacgac agctccagca
1001 gtagccattg cttggatcct aacaatgaag aaggtggtca tggagtgaaa
1051 ggctgggcct ttgatgatgg aaatgacgtg tggatgggaa gaacgatcag
1101 cgagaagtta cgctcaggat atgaaaacct caaagtcatt gaaggctggt
1151 ccaaccctaa ttccaaattg cagataaata ggcaagtcat agttgacaga
1201 ggtaataggt ccggttactc tggtattttc tctgttgaag gcaaaagctg
1251 catcaatcgg tgcttttatg tggagttgat aaggggaaga aagagaaaa
1301 ctgaagtctt gtggacctca aacagtattg ttgtgtttg tggcacctca
1351 ggtacatatg aacaggctc atggcctgat ggggcggaca tcaatctcat
1401 gcctatataa gctttcgcaa ttttag
```

SEQ ID NO:90
Amino acid sequence of ca A/Malaysia/1/04_1 N2 (Fujian-like strain)   Entire molecule length: 469 aa

```
   1 mnpnqkiiti gsvsltisti cffmqiaili ttvtlhfkqy efnsppnnqv
  51 mlceptiier niteivyltn ttiekeicpk laeyrnwskp qcditgfapf
 101 skdnsirlsa ggdiwvtrep yvscdpdkcy qfalgqggttl nnvhsndtvh
 151 drtpyrtllm nelgvpfhlg tkqvciawss sschdgkawl hvcvtgddkn
 201 atasfiyngr lvdsivswsk kilrtqesec vcingtctvv mtdgsasgka
 251 dtkilfieeg kivhtstlsg saqhveecsc yprypgvrcv crdnwkgsnr
 301 pivdinikdy sivssyvcsg lvgdtprknd sssshcldp nneegghgvk
 351 gwafddgndv wmgrtisekl rsgyetfkvi egwsnpnskl qinrqvivdr
 401 gnrsgysgif svegkscinr cfyvelirgr kektevlwts nsivvfcgts
 451 gtygtgswpd gadinlmpi
```

Figure 1AP

SEQ ID NO:43
Nucleotide sequence of ca A/Malaysia/1/04_2 H3 (Fujian-like strain)   Entire molecule length: 1724 bp

```
   1 attctattaa ccatgaagac tatcattgct ttgagctaca ttctatgtct
  51 ggttttcgct caaaaacttc ccggaaatga acagcacg gcaacgctgt
 101 gccttgggca ccatgcagta ccaaacggaa caatagtgaa aacaatcacg
 151 aatgaccaaa ttgaagttac taatgctact gagctggttc agaattcctc
 201 aacaggtgga atatgcgaca gtcctcatca gatccttgat ggagaaaact
 251 gcacactaat agatgctcta tgggagacc ctcagtgtga tggcttccaa
 301 aataagaaat gggacctttt tgttgaacgc agcaaggcct acagcaactg
 351 ttacccttat gatgtgccgg attatgcctc ccttaggtca ctagttgcct
 401 catccggcac actggagttt aacaatgaaa gcttcaattg gactggagtc
 451 actcaaaatg gaacaagctc tgcttgcaaa aggagatcta ataaaagttt
 501 ctttagtaga ttgaattggt tgacccactt aaaattcaaa tacccagcat
 551 tgaacgtgac tatgccaaac aatgaaaaat ttgacaaatt gtacatttgg
 601 ggggttcacc acccggttac ggactatgac caaatcagcc tatatgctca
 651 agcatcagga agaatcacag tctctaccaa agaagccaa caaactgtaa
 701 tcccgaatat cggatctaga cccagggtaa gggatatccc cagcagaata
 751 agcatctatt ggacaatagt aaaaccggga gacatacttt tgattaacag
 801 cacagggaat ctaattgctc ctcggggtta cttcaaaata cgaagtggga
 851 aaagctcaat aatgagatca gatgcaccca ttggcaaatg caattctgaa
 901 tgcatcactc caaatggaag cattcccaat gacaaaccat ttcaaaatgt
 951 aaacaggatc acatatgggg cctgtcccag atatgttaag caaaacactc
1001 tgaaattggc aacagggatg cgaaacgtac cagagaaaca aactagaggc
1051 atatttggcg caatcgcggg tttcatagaa atggttggg agggaatggt
1101 ggacggttgg tacggtttca ggcatcaaaa ttctgaggga caggacaag
1151 cagcagatct caaaagcact caagcagcaa tcaaccaaat caatgggaag
1201 ctgaataggt tgatcgggaa aacaaacgag aaattccatc agattgaaaa
1251 agaattctca gaagtagaag ggagaattca ggacctcgag aaatatgttg
1301 aggacactaa aatagatctc tggtcataca cgcggagct tcttgttgcc
1351 ctggagaacc aacatacaat tgatctaact gactcagaaa tgaacaaact
1401 gtttgaaaga acaaagaagc aactgaggga aaatgctgag gatatgggca
1451 atggttgttt caaaatatac cacaaatgtg acaatgcctg catagggtca
1501 atcagaaatg gaacttatga ccatgatgta tacagagatg aagcattaaa
1551 caaccggttc cagatcaaag tgttgagct gaagtcagga tacaaagatt
1601 ggatcctatg gatttccttt gccatatcat gtttttgct ttgtgttgct
1651 ttgtcggggt tcatcatgtg ggcctgccaa aaaggcaaca ttaggtgcaa
1701 catttgcatt tgagtgcatt aatt
```

SEQ ID NO:91
Amino acid sequence of ca A/Malaysia/1/04_2 H3 (Fujian-like strain)  Entire molecule length: 550 aa

```
   1 qklpgndnst atlclghhav pngtivktit ndqievtnat elvqnsstgg
  51 icdsphqild genctlidal lgdpqcdgfq nkkwdlfver skaysncypy
 101 dvpdyaslrs lvassgtlef nnesfnwtgv tqngtssack rrsnksffsr
 151 lnwlthlkfk ypalnvtmpn nekfdklyiw gvhhpvtdyd qislyaqasg
 201 ritvstkrsq qtvipnigsr prvrdipsri siywtivkpg dillinstgn
 251 liaprgyfki rsgkssimrs dapigkcnse citpngsipn dkpfqnvnri
 301 tygacpryvk qntlklatgm rnvpekqtrg ifgaiagfie ngwegmvdgw
 351 ygfrhqnseg tgqaadlkst qaainqingk lnrligktne kfhqiekefs
 401 evegriqdle kyvedtkidl wsynaellva lenqhtidlt dsemnklfer
 451 tkkqlrenae dmgngcfkiy hkcdnacigs irngtydhdv yrdealnnrf
 501 qikgvelksg ykdwilwisf aiscfllcva lsgfimwacq kgnircnici
```

Figure 1AQ

SEQ ID NO:44

Nucleotide sequence of ca A/Malaysia/1/04_2 N2 (Fujian-like strain)  Entire molecule length: 1427 bp

```
   1 aatgaatcca aatcaaaaga taataacgat tggctctgtt tctctcacca
  51 tttccacaat atgcttcttc atgcaaattg ccatcttgat aactactgta
 101 acattgcatt tcaagcaata tgaattcaac tcccccccaa acaaccaagt
 151 gatgctgtgt gaaccaacaa taatagaaag aaacataaca gagatagtgt
 201 atctgaccaa caccaccata gagaaggaaa tatgcccccaa actagcagaa
 251 tacagaaatt ggtcaaagcc gcaatgtgac attacaggat tgcacctttt
 301 ttctaaggac aattcgatta ggctttccgc tggtggggac atctgggtga
 351 caagagaacc ttatgtgtca tgcgatcctg acaagtgtta tcaatttgcc
 401 cttggacagg gaacaacact aaacaacgtg cattcaaatg acacagtaca
 451 tgataggacc ccttatcgga ccctattgat gaatgagtta ggtgttccat
 501 ttcatctggg gaccaagcaa gtgtgcatag catggtccag ctcaagttgt
 551 cacgatggaa aagcatggct gcatgtttgt gtaacggggg atgataaaaa
 601 tgcaactgct agcttcattt acaatgggag gcttgtagat agtattgttt
 651 catggtccaa aaaaatcctc aggacccagg agtcagaatg cgtttgtatc
 701 aatggaactt gtacagtagt aatgactgat gggagtgctt caggaaaagc
 751 tgatactaaa atactattca ttgaggaggg aaaatcgtt catactagca
 801 cattgtcagg aagtgctcag catgtcgagg agtgctcctg ctatcctcga
 851 tatcctggtg tcagatgtgt ctgcagagac aactggaaag ctccaatag
 901 gcccatcgta gatataaaca taaaggatta tagcattgtt tccagttatg
 951 tgtgctcagg acttgttgga gacacaccca gaaaaaacga cagctccagc
1001 agtagccatt gcttggatcc taacaatgaa gaaggtggtc atggagtgaa
1051 aggctgggcc tttgatgatg gaaatgacgt gtggatggga agaacgatca
1101 gcgagaagtt acgctcagga tatgaaacct tcaaagtcat tgaaggctgg
1151 tccaacccta attccaaatt gcagataaat aggcaagtca tagttgacag
1201 aggtaatagg tccggttact ctggtatttt ctctgttgaa ggcaaaagct
1251 gcatcaatcg gtgcttttat gtggagttga taggggaag aaaagagaaa
1301 actgaagtct tgtggacctc aaacagtatt gttgtgtttt gtggcacctc
1351 aggtacatat ggaacaggct catggcctga tggggcggac atcaatctca
1401 tgcctatata agctttcgca attttag
```

SEQ ID NO:92

Amino acid sequence of ca A/Malaysia/1/04_2 N2 (Fujian-like strain)  Entire molecule length: 469 aa

```
   1 mnpnqkiiti gsvsltisti cffmqiaili ttvtlhfkqy efnsppnnqv
  51 mlceptiier niteivyltn ttiekeicpk laeyrnwskp qcditgfapf
 101 skdnsirlsa ggdiwvtrep yvscdpdkcy qfalgqgttl nnvhsndtvh
 151 drtpyrtllm nelgvpfhlg tkqvciawss sschdgkawl hvcvtgddkn
 201 atasfiyngr lvdsivswsk kilrtqesec vcingtctvv mtdgsasgka
 251 dtkilfieeg kivhtstlsg saqhveecsc yprypgvrcv crdnwkgsnr
 301 pivdinikdy sivssyvcsg lvgdtprknd sssshcldp nneegghgvk
 351 gwafddgndv wmgrtisekl rsgyetfkvi egwsnpnskl qinrqvivdr
 401 gnrsgysgif svegkscinr cfyvelirgr kektevlwts nsivvfcgts
 451 gtygtgswpd gadinlmpi
```

Figure 1AR

SEQ ID NO:45

Nucleotide sequence of ca B/Jiangshu/10/03 HA (Shanhai-like strain) Entire molecule length: 1870 bp

```
   1 gcagaagcag agcattttct aatatccaca aaatgaaggc aataattgta
  51 ctactcatgg tagtaacatc caatgcagat cgaatctgca ctgggataac
 101 atcttcaaac tcacctcatg tggtcaaaac agctactcaa ggggaggtca
 151 atgtgactgg tgtaatacca ctgacaacaa caccaacaaa atcttatttt
 201 gcaaatctca aaggaacaag gaccagaggg aaactatgtc cagactgtct
 251 caactgtaca gatctggatg tggccttggg cagaccaatg tgtgtgggga
 301 ccacaccttc ggcaaaagct tcaatactcc acgaagtcag acctgttaca
 351 tccgggtgct ttcctataat gcacgacaga acaaaaatca gacaactacc
 401 caatcttctc agaggatatg aaaatatcag attatcaacc caaaacgtta
 451 tcgatgcaga aaatgcacca ggaggaccct acagacttgg aacctcaaga
 501 tcttgcccta acgctaccag taaaagcgga tttttcgcaa caatggcttg
 551 ggctgtccca aaggacaaca acaaaaatgc aacgaaccca ctaacagtag
 601 aagtaccata cgtttgtaca gaaggggaag accaaattac tgtttggggg
 651 ttccattcag ataacaaaac ccaaatgaag aacctctatg gagactcaaa
 701 tcctcaaaag ttcacctcat ctgctaatgg agtaaccaca cattatgttt
 751 ctcagattgg cggcttccca gctcaaacag aagacgaagg actaccacaa
 801 agcggcagaa ttgttgttga ttacatggtg caaaaaccta gaaaaacagg
 851 aacaattgtc tatcaaagag gtgttttgtt gcctcaaaag gtgtggtgcg
 901 cgagtggcag gagcaaagta ataaaagggt ccttgccttt aattggtgaa
 951 gcagattgcc ttcatgaaaa atacggtgga ttaaacaaaa gcaagcctta
1001 ctacacagga gaacatgcaa aagccatagg aaattgccca atatgggtga
1051 aaacaccttt gaagcttgcc aatggaacca aatatagacc tcctgcaaaa
1101 ctattaaagg aaaggggttt cttcggagct attgctggtt tcctagaagg
1151 aggatgggaa ggaatgattg caggttggca cggatacaca tctcacggag
1201 cacatggagt ggcagtggcg gcagacctta agagtacgca agaagctata
1251 aacaagataa caaaaaatct caattctttg agtgagctag aagtaaagaa
1301 tcttcaaaga ctaagtggtg ccatggatga actccacaac gaaatactcg
1351 agctggatga gaaagtggat gatctcagag ctgacactat aagctcgcaa
1401 atagaacttg cagtcttgct ttccaatgaa ggaataataa acagtgaaga
1451 tgagcatcta ttggcacttg agagaaaact aaagaaaatg ctgggtccct
1501 ctgctgtaga cataggaaat ggatgcttcg aaaccaaaca caagtgcaac
1551 cagacctgct tagacaggat agctgctggc acctttaatg caggagaatt
1601 ttctctcccc acttttgatt cactgaacat tactgctgca tctttaaatg
1651 atgatggatt ggataaccat actatactgc tctattactc aactgctgct
1701 tctagtttgg ctgtaacatt gatgctagct atttttattg tttatatggt
1751 ctccagagac aacgtttcat gctccatctg tctataagga agattaagcc
1801 ttgtattttc ctttattgta gtgcttgttt gcttgtcatc attacaaaga
1851 aacgttattg aaaaatgctc
```

SEQ ID NO:93
Amino acid sequence of ca B/Jiangshu/10/03 HA(Shanghai-like strain) Entire molecule length: 569 aa

```
   1 drictgitss nsphvvktat qgevnvtgvi pltttptksy fanlkgtrtr
  51 gklcpdclnc tdldvalgrp mcvgttpsak asilhevrpv tsgcfpimhd
 101 rtkirqlpnl lrgyenirls tqnvidaena pggpyrlgts rscpnatsks
 151 gffatmawav pkdnnknatn pltvevpyvc tegedqitvw gfhsdnktqm
 201 knlygdsnpq kftssangvt thyvsqiggf paqtedeglp qsgrivvdym
 251 vqkprktgti vyqrgvllpq kvwcasgrsk vikgslplig eadclhekyg
 301 glnkskpyyt gehakaignc piwvktplkl angtkyrppa kllkergffg
 351 aiagfleggw egmiagwhgy tshgahgvav aadlkstqea inkitknlns
 401 lselevknlq rlsgamdelh neileldekv ddlradtiss qielavllsn
 451 egiinsedeh llalerklkk mlgpsavdig ngcfetkhkc nqtcldriaa
 501 gtfnagefsl ptfdslnita aslnddgldn htillyysta asslavtlml
 551 aifivymvsr dnvscsicl
```

Figure 1AS

SEQ ID NO:46
Nucleotide sequence of ca B/Jiangshu/10/03 NA (Shanghai-like strain) Entire molecule length: 1536 bp

```
   1 aagcagagca tcttctcaaa actgaggcaa ataggccaaa aatgaacaat
  51 gctaccctca actatacaaa cgttaaccct attcctcaca tcaggggag
 101 tgttattatc actatatgtg tcagcttcac tgtcatactt actatattcg
 151 gatatattgc taaaattttc aacaacagaa acaactgcac caacaatgcc
 201 attggattgt gcaaacgcat caaatgttca ggctgtgaac cgttctgcaa
 251 caaaggggt gacacttctt ctcccagaac cggagtggac atacccgcgt
 301 ttatcttgcc cgggctcaac ctttcagaaa gcactcctaa ttagccctca
 351 tagattcgga gaaccaaag gaaactcagc tcccttgata ataagggaac
 401 cttttattgc ttgtggacca aaggaatgca aacactttgc tctaacccat
 451 tatgcagccc aaccagggg atactacaat ggaacaagag aagacagaaa
 501 caagctgagg catctaattt cagtcaaatt gggcaaaatc ccaacagtag
 551 aaaactccat tttccacatg gcagcatgga gcgggtccgc atgccatgat
 601 ggtaaagaat ggacatatat cggagttgat ggccctgaca gtaatgcatt
 651 gctcaaaata aatatggag aagcatatac tgacacatac cattcctatg
 701 caaacaacat cctaagaaca caagaaagtg cctgcaattg catcggggga
 751 aattgttatc ttatgataac tgatggctca gcttcaggta ttagtgagtg
 801 cagatttctt aagattcgag agggccgaat aataaaagaa atatttccaa
 851 caggaagagt aaaacatact gaagaatgca catgcggatt tgccagcaat
 901 aaaaccatag aatgtgcctg tagagataac agttacacag caaaaagacc
 951 ctttgtcaaa ttaaatgtgg agactgatac agcagaaata agattgatgt
1001 gcacagagac ttatttggac accccccagac cagatgatgg aagtataaca
1051 gggccttgtg aatctaatgg gaataaaggg agtggaggca tcaagggagg
1101 atttgttcat caaagaatgg catccaaaat tggaaggtgg tactctcgaa
1151 caatgtctaa aaccaaaagg atgggaatgg gactgtatgt caagtatgat
1201 ggagacccat ggactgacag tgatgccctt gctcttagtg gagtaatggt
1251 ttcaatggaa gaacctggtt ggtactcatt tggcttcgaa ataaaagata
1301 agaaatgtga tgtccccctgt attgggatag atggtaca tgatggtgga
1351 aaggagactt ggcactcagc agcaacagcc atttactgtt taatgggctc
1401 aggacaactg ttgtgggaca ctgtcacagg tgttgatatg gctctgtaat
1451 gggggaatgg ttgagtctgt tctaaaccct tgttcctat tttgtttgaa
1501 caattgtcct tgctgaactt aattgtttct gaaaaa
```

SEQ ID NO:94
Amino acid sequence of ca B/Jiangshu/10/03 NA (Shanghai-like strain)Entire molecule length: 466 aa

```
   1 mlpstiqtlt lfltsggvll slyvsaslsy llysdillkf sttettaptm
  51 pldcanasnv qavnrsatkg vtlllpepew typrlscpgs tfqkallisp
 101 hrfgetkgns apliirepfi acgpkeckhf althyaaqpg gyyngtredr
 151 nklrhlisvk lgkiptvens ifhmaawsgs achdgkewty igvdgpdsna
 201 llkikygeay tdtyhsyann ilrtqesacn ciggncylmi tdgsasgise
 251 crflkiregr iikeifptgr vkhteectcg fasnktieca crdnsytakr
 301 pfvklnvetd taeirlmcte tyldtprpdd gsitgpcesn gnkgsggikg
 351 gfvhqrmask igrwysrtms ktkrmgmgly vkydgdpwtd sdalalsgvm
 401 vsmeepgwys fgfeikdkkc dvpcigiemv hdggketwhs aataiyclmg
 451 sgqllwdtvt gvdmal
```

SEQ ID NO:47
Nucleotide sequence of ca B/Shanghai/361/02 HA (Shanghai-like strain)    Entire molecule
length: 1846 bp

```
   1 tctaatatcc acaaaatgaa ggcaataatt gtactactca tggtagtaac
  51 atccaacgca gatcgaatct gcactgggat aacatcttca aactcacctc
 101 atgtggtcaa aacagctact caaggggagg tcaatgtgac tggtgtgata
 151 ccactgacaa caactccaat aaaatctcat tttgcaaatc tcaaaggaac
 201 aaggactaga gggaaactat gcccagattg tctcaactgc acagatctgg
 251 atgtggcctt gggcagacca atgtgtgtgg ggaccacacc ttcggcaaaa
 301 gcttcaatac tccacgaagt cagacctgtt catccgggt gctttcctat
 351 aatgcacgac agaacaaaaa tcagacaact acccaatctt ctcagaggat
 401 atgaaaatat caggttatca acccaaaacg ttatcgatgc agaaaaggcc
 451 ctaggaggac cctacagact ggaacctca ggatcttgcc ctaacgccac
 501 cagtaaaagc ggatttttcg caacaatggc ttgggctgtc caaaggaca
 551 acaacaaaaa tgcaacgaac ccactaacag tagaagtacc atacatctgt
 601 acagaagggg aagaccaaat tactgtttgg gggttccatt cagatgacaa
 651 aacccaaatg aaaaacctct atggagactc aaatcctcaa aagttcacct
 701 catctgctaa tggagtaacc acacattatg tttctcagat tggcggcttc
 751 ccagatcaaa cagaagacgg aggactacca caaagcggca gaattgttgt
 801 tgattacatg gtgcaaaaac ctgggaaaac aggaacaatt gtctatcaaa
 851 gaggtgtttt gttgcctcaa aaggtgtggt gcgcgagtgg caggagcaaa
 901 gtaataaaag gtccttgcc tttaattggt gaagcagatt gccttcatga
 951 aaaatacggt gggttaaaca aaagcaagcc ttactacaca ggagaacatg
1001 caaaagccat aggaaattgc ccaatatggg tgaaaacacc tttgaagctt
1051 gccaatggaa ccaaatatag acctcctgca aaactattaa aggaaagggg
1101 tttcttcgga gctattgctg gttcctaga aggaggatgg gaaggaatga
1151 ttgcaggttg gcacggatac acatctcacg gagcacatgg agtggcagtg
1201 gcggcagacc ttaagagtac gcaagaagct ataaacaaga taacaaaaaa
1251 tctcaattct ttgagtgagc tagaagtaaa gaatcttcaa agactaagtg
1301 gtgccatgga tgaactccac aacgaaatac tcgagctgga tgagaaagtg
1351 gatgatctca gagctgacac tataagctcg caaatagaac ttgcagtctt
1401 gctttccaac gaaggaataa taaacagtga agatgagcat ctattggcac
1451 ttgagagaaa actaaagaaa atgctgggtc cctctgctgt agacatagga
1501 aatggatgct cgaaaccaa acacaagtgc aaccagacct gcttagacag
1551 gatagctgct ggcacctta atgcaggaga attttctctc cccactttg
1601 attcactgaa cattactgct gcatctttaa atgatgatgg attggataac
1651 catactatat tgctctatta ctcaactgct gcttctagtt tggctgtaac
1701 attgatgcta gctattttta ttgtttatat ggtctccaga gacaacgttt
1751 catgctccat ctgtctataa gggagattaa gccttgtatt ttcctttatt
1801 gtagtgcttg tttgcttgtc atcattacaa agaaacgtta ttgaaa
```

SEQ ID NO:95
Amino acid sequence of ca B/Shanghai/361/02 HA (Shanghai-like strain)    Entire molecule
length: 569 aa

```
   1 drictgitss nsphvvktat qgevnvtgvi pltttpiksh fanlkgtrtr
  51 gklcpdclnc tdldvalgrp mcvgttpsak asilhevrpv tsgcfpimhd
 101 rtkirqlpnl lrgyenirls tqnvidaeka lggpyrlgts gscpnatsks
 151 gffatmawav pkdnnknatn pltvevpyic tegedqitvw gfhsddktqm
 201 knlygdsnpq kftssangvt thyvsqiggf pdqtedgglp qsgrivvdym
 251 vqkpgktgti vyqrgvllpq kvwcasgrsk vikgslplig eadclhekyg
 301 glnkskpyyt gehakaignc piwvktplkl angtkyrppa kllkergffg
 351 aiagfleggw egmiagwhgy tshgahgvav aadlkstqea inkitknlns
 401 lselevknlq rlsgamdelh neileldekv ddlradtiss qielavllsn
 451 egiinsedeh llalerklkk mlgpsavdig ngcfetkhkc nqtcldriaa
 501 gtfnagefsl ptfdslnita aslnddgldn htillyysta asslavtlml
 551 aifivymvsr dnvscsicl
```

Figure 1AU

SEQ ID NO:48

Nucleotide sequence of ca B/Shanghai/361/02 NA (Shanghai-like strain)     Entire molecule
length: 1520 bp

```
   1 ctcaaaactg aggcaaatag gccaaaaatg aacaatgcta ccctcaacta
  51 tacaaacgtt aaccctattc ctcacatcag ggggagtgtt attatcacta
 101 tatgtgtcag cttcactgtc atacttacta tattcggata tattgctaaa
 151 attttcaaca acagaaataa ctgcaccaac aatgccattg gattgtgcaa
 201 acgcatcaaa tgttcaggct gtgaaccgtt ctgcaacaaa agggtgaca
 251 cttcttctcc cagaaccgga gtggacatac ccgcgtttat cttgcccggg
 301 ctcaaccttt cagaaagcac tcctaattag ccctcataga ttcggagaaa
 351 ccaaaggaaa ctcagctccc ttgataataa gggaaccttt tattgcttgt
 401 ggaccaaagg aatgcaaaca ctttgctcta acccattatg cagcccaacc
 451 aggggatac tacaatggaa caagagaaga caggaacaag ctgaggcatc
 501 taatttcagt caaattgggc aaaatcccaa cagtagaaaa ctccattttc
 551 cacatggcag catggagcgg gtccgcatgc catgatggta agaatggac
 601 atatatcgga gttgatgcc ctgacagtaa tgcattgctc aaaataaaat
 651 atggagaagc atatactgac ataccatt cctatgcaaa caacatccta
 701 agaacacaag aaagtgcctg caattgcatc gggaaatt gttatcttat
 751 gataactgat ggctcagctt caggtattag tgagtgcaga tttcttaaga
 801 ttcgagaggg ccgaataata aaagaaatat ttccaacagg aagagtaaaa
 851 catactgaag aatgcacatg cggatttgcc agcaataaaa ccatagaatg
 901 tgcctgtagg ataacagtt acacagcaaa aagacccttt gtcaaattaa
 951 atgtggagac tgatacagca gaataagat tgatgtgcac agagacttat
1001 ttggacaccc ccagaccaga tgatggaagc ataacagggc cttgtgaatc
1051 taatgggaat aaagggagtg gaggcatcaa gggaggattt gttcatcaaa
1101 gaatggcatc caaaattgga aggtggtact ctcgaacaat gtctaaaacc
1151 aaaaggatgg gaatgggact gtatgtcaag tatgatggag acccatggat
1201 tgacagtgat gcccttgctc ttagtggagt aatggtttca atggaagaac
1251 ctggttggta ctcatttggc ttcgaaataa aagataagaa atgtgatgtc
1301 ccctgtattg ggatagagat ggtacatgat ggtggaaagg agacttggca
1351 ctcagcagca acagccattt actgtttaat gggctcagga cagctgctgt
1401 gggacactgt cacaggtgtt gatatggctc tgtaatggag aatggttga
1451 gtctgttcta aacccttgt tcctattttg tttgaacaat tgtccttact
1501 gaacttaatt gtttctgaaa
```

SEQ ID NO:96

Amino acid sequence of ca B/Shanghai/361/02 NA (Shanghai-like strain)     Entire molecule
length: 466 aa

```
  1 mlpstiqtlt lfltsggvll slyvsaslsy llysdillkf stteitaptm
 51 pldcanasnv qavnrsatkg vtlllpepew typrlscpgs tfqkallisp
101 hrfgetkgns apliirepfi acgpkeckhf althyaaqpg gyyngtredr
151 nklrhlisvk lgkiptvens ifhmaawsgs achdgkewty igvdgpdsna
201 llkikygeay tdtyhsyann ilrtqesacn ciggncylmi tdgsasgise
251 crflkiregr iikeifptgr vkhteectcg fasnktieca crdnsytakr
301 pfvklnvetd taeirlmcte tyldtprpdd gsitgpcesn gnkgsggikg
351 gfvhqrmask igrwysrtms ktkrmgmgly vkydgdpwid sdalalsgvm
401 vsmeepgwys fgfeikdkkc dvpcigiemv hdggketwhs aataiyclmg
451 sgqllwdtvt gvdmal
```

Figure 1AV

Figure 2A

| SEQ ID NO | HA or NA | Strain Name |
|---|---|---|
| SEQ ID NO:1 and 49 | HA | ca A/Shandong/9/93 |
| SEQ ID NO:2 and 50 | NA | ca A/Shandong/9/93 |
| SEQ ID NO:3 and 51 | HA | ca A/Johannesburg/33/94-Like |
| SEQ ID NO:4 and 52 | NA | ca A/Johannesburg/33/94-Like |
| SEQ ID NO:5 and 53 | HA (H3) | ca A/Wuhan/395/95 |
| SEQ ID NO:6 and 54 | NA (N2) | ca A/Wuhan/395/95 |
| SEQ ID NO:7 and 55 | HA (H3) | ca A/Sydney/05/97 |
| SEQ ID NO:8 and 56 | NA (N2) | ca A/Sydney/05/97 |
| SEQ ID NO:9 and 57 | HA (H3) | ca A/Panama/2007/99 |
| SEQ ID NO:10 and 58 | NA (N2) | ca A/Panama/2007/99 |
| SEQ ID NO:11 and 59 | HA (H3) | ca A/Wyoming/03/2003 |
| SEQ ID NO:12 and 60 | NA (N2) | ca A/Wyoming/03/2003 |
| SEQ ID NO:13 and 61 | HA (H1) | ca A/Texas/36/91 |
| SEQ ID NO:14 and 62 | NA (N1) | ca A/Texas/36/91 |
| SEQ ID NO:15 and 63 | HA (H1) | ca A/Shenzhen/227/95 |
| SEQ ID NO:16 and 64 | NA (N1) | ca A/Shenzhen/227/95 |
| SEQ ID NO:17 and 65 | HA (H1) | ca A/Beijing/262/95 |
| SEQ ID NO:18 and 66 | NA (N1) | ca A/Beijing/262/95 |
| SEQ ID NO:19 and 67 | HA (H1) | ca A/New Caledonia/20/99 |
| SEQ ID NO:20 and 68 | NA (N1) | ca A/New Caledonia/20/99 |
| SEQ ID NO:21 and 69 | HA | ca B/Ann Arbor/1/94 |
| SEQ ID NO:22 and 70 | NA | ca B/Ann Arbor/1/94 |
| SEQ ID NO:23 and 71 | HA | ca B/Yamanashi/166/98 |
| SEQ ID NO:24 and 72 | NA | ca B/Yamanashi/166/98 |
| SEQ ID NO:25 and 73 | HA | ca B/Johannesburg/5/99 |
| SEQ ID NO:26 and 74 | NA | ca B/Johannesburg/5/99 |
| SEQ ID NO:27 and 75 | HA | ca B/Victoria/504/2000 |
| SEQ ID NO:28 and 76 | NA | ca B/Victoria/504/2000 |
| SEQ ID NO:29 and 77 | HA | ca B/Hong Kong/330/01 |
| SEQ ID NO:30 and 78 | NA | ca B/Hong Kong/330/01 |
| SEQ ID NO:31 and 79 | HA | ca B/Brisbane/32/2002 |
| SEQ ID NO:32 and 80 | NA | ca B/Brisbane/32/2002 |
| SEQ ID NO:33 and 81 | HA | ca B/Jilin/20/2003 |
| SEQ ID NO:34 and 82 | NA | ca B/Jilin/20/2003 |
| SEQ ID NO:35 and 83 | HA | wt/A/California/7/04 |
| SEQ ID NO:36 and 84 | NA | wt/A/California/7/04 |
| SEQ ID NO:37 and 85 | HA (H3) | ca A/Sandai-H/F4962/02 |
| SEQ ID NO:38 and 86 | NA (N2) | ca A/Sandai-H/F4962/02 |
| SEQ ID NO:39 and 87 | HA (H3) | ca A/Wellington/1/04 |
| SEQ ID NO:40 and 88 | NA (N2) | ca A/Wellington/1/04 |
| SEQ ID NO:41 and 89 | HA (H3) | ca A/Malalysia/1/04_1 |
| SEQ ID NO:42 and 90 | NA (N2) | ca A/Malalysia/1/04_1 |
| SEQ ID NO:43 and 91 | HA (H3) | ca A/Malaysia/1/04_2 |
| SEQ ID NO:44 and 92 | NA (N2) | ca A/Malaysia/1/04_2 |
| SEQ ID NO:45 and 93 | HA | ca B/Jiangshu/10/03 |

| SEQ ID NO:46 and 94 | NA | ca B/Jiangshu/10/03 |
| SEQ ID NO:47 and 95 | HA | ca B/Shanghai/361/02 |
| SEQ ID NO:48 and 96 | NA | ca B/Shanghai/361/02 |

Figure 2B

SEQUENCE LISTING

```
<160> NUMBER OF SEQ ID NOS: 96

<210> SEQ ID NO 1
<211> LENGTH: 1745
<212> TYPE: DNA
<213> ORGANISM: influenza A virus

<400> SEQUENCE: 1
caggggataa ttctattaac catgaagact atcattgctt tgagctacat tttatgtctg      60
gttttcgctc aaaaacttcc cggaaatgac aacagcacag caacgctgtg cctgggacat     120
catgcagtgc caaacggaac gctagtgaaa acaatcacga atgatcaaat tgaagtgact     180
aatgctactg agttggttca gagttcctca acaggtagaa tatgcggcag tcctcaccga     240
```

-continued

```
atccttgatg gaaaaaactg cacactgata gatgctctat tgggagaccc tcattgtgat    300
ggcttccaaa ataaggaatg ggaccttttt gttgaacgca gcaaagctta cagcaactgt    360
taccctt atg atgtgccgga ttatgcctcc cttaggtcac tagttgcctc atcaggcacc    420
ctggagttta tcaatgaaga cttcaattgg actggagtcg ctcaggatgg gggaagctat    480
gcttgcaaaa gaggatctgt taacagtttc tttagtagat tgaattggtt gcacaaatta    540
gaatacaaat atccagcgct gaacgtgact atgccaaaca atggcaaatt tgacaaattg    600
tacatttggg gggttcacca cccgagcacg gacagtgacc aaaccagcct atatgttcga    660
gcatcaggga gagtcacagt ctctaccaaa agaagccaac aaactgtaac cccgaatatc    720
gggtctagac cctgggtaag ggtcagtcc agtagaataa gcatctattg gacaatagta    780
aaaccgggag acatactttt gattaatagc acagggaatc taattgctcc tcggggttac    840
ttcaaaatac gaaatgggaa aagctcaata atgaggtcag atgcacccat tggcaactgc    900
agttctgaat gcatcactcc aaatggaagc attcccaatg acaaaccttt tcaaaatgta    960
aacagaatca catatggggc ctgccccaga tatgttaagc aaaacactct gaaattggca   1020
acagggatgc ggaatgtacc agagaaacaa actagaggca tattcggcgc aatcgcaggt   1080
ttcatagaaa atggttggga gggaatggta gacggttggt acggtttcag gcatcaaaat   1140
tctgagggca caggacaagc agcagatctt aaaagcactc aagcagcaat cgaccaaatc   1200
aacgggaaac tgaataggtt aatcgagaaa acgaacgaga aattccatca aatcgaaaaa   1260
gaattctcag aagtagaagg gagaattcag gacctcgaga aatatgttga agacactaaa   1320
atagatctct ggtcttacaa cgcggagctt cttgttgccc tggagaacca acatacaatt   1380
gatctaactg actcagaaat gaacaaactg tttgaaaaaa caaggaagca actgagggaa   1440
aatgctgagg acatgggcaa tggttgcttc aaaatatacc acaaatgtga caatgcctgc   1500
atagggtcaa tcagaaatgg aacttatgac catgatgtat acagagacga agcattaaac   1560
aaccggttcc agatcaaagg tgttgagctg aagtcaggat acaaagattg gatcctatgg   1620
atttcctttg ccatatcatg ctttttgctt tgtgttgttt tgctggggtt catcatgtgg   1680
gcctgccaaa aaggcaacat taggtgcaac atttgcattt gagtgcatta attaaaaaca   1740
ccctg                                                               1745
```

```

<210> SEQ ID NO 2
<211> LENGTH: 1429
<212> TYPE: DNA
<213> ORGANISM: influenza A virus

<400> SEQUENCE: 2
```

```
aaagataata acaattggct ctgtttctct cactattgcc acaatatgct tccttatgca     60
aattgccatc ctggtaacta ctgtaacatt gcacttcaag caatatgagt gcaactcccc    120
cccaaacaac caagtaatgc tgtgtgaacc aacaataata gaaagaaaca taacagagat    180
agtgtatctg accaacacca ccatagagaa agaaatatgc cccaaactag cagaatacag    240
aaattggtca aagccgcaat gtaaaattac aggatttgca cctttttcta aggacaattc    300
aattcggctt tcagctggtg gagacatttg ggtgacaaga gaaccttatg tgtcatgcga    360
tcctggcaag tgttatcaat ttgcccttgg acagggaaca acactaaaca acaggcactc    420
aaatgacaca gtacatgata ggacccctta tcgaacccta ttgatgaatg agttgggtgt    480
tccatttcat ttgggaacca agcaagtgtg catagcatgg tccagctcaa gttgtcacga    540
tggaaaagca tggctgcatg tttgtgtaac tgggcatgat gaaaatgcaa ctgctagctt    600
```

-continued

```
catttacgat gggaggcttg tagatagtat tggttcatgg tccaaaaata tcctcaggac      660
ccaggagtcg gaatgcgttt gtatcaatgg aacttgtaca gtagtaatga ctgatggaag      720
tgcttcagaa agagctgata ctaaaatact attcattgaa gaggggaaaa tcgttcatat      780
tagcccattg tcaggaagtg ctcagcatgt cgaggagtgc tcctgttatc ctcgatatcc      840
tggtgtcaga tgtgtctgca gagacaactg gaaaggctcc aataggccca tcgtagatat      900
aaatgtgaaa gattatagca ttgtttccag ttatgtgtgc tcaggacttg ttggagacac      960
acccagaaaa aacgacagct ccagcagtag ctattgccgg aatcctaaca atgagaaagg     1020
gagtcatgga gtgaaaggct gggcctttga tgatggaaat gacgtgtgga tgggaagaac     1080
gatcagcgag gagttacgct caggttatga aaccttcaaa gtcattggag ctggtccaa      1140 acctaactcc aaattgcaga taaataggca agtcatagtt gacagaggta ataggtccgg     1200
ttattctggt atttttctctg ttgaaggcaa aagctgcatc aatcggtgct tttatgtgga    1260
gttgataagg ggaaggaaac aggaaactga agtctggtgg acctcaaaca gtattgttgt     1320
gttttgtggc acctcaggta catatggaac aggctcatgg ccctgatggg gcggacatca     1380
atctcatgcc tatataagct tcgcaattt tagaaaaaaa ctccttgtt                   1429
```

<210> SEQ ID NO 3
<211> LENGTH: 1755
<212> TYPE: DNA
<213> ORGANISM: influenza A virus

<400> SEQUENCE: 3

```
agcaaaagca gggataatt ctattaacca tgaagactat cattgctttg agctacattt       60
tatgtctggt tttcgctcaa aaacttcccg gaaatgacaa cagcacagca acgctgtgcc     120
tgggacacca tgcagtgcca acggaacgc tagtgaaaac aatcacgaat gatcaaattg      180
aagtgactaa tgctactgag ctggttcaga gttccccaac aggtagaata tgcgacagcc     240
ctcaccgaat ccttgatgga agaactgca cactgataga tgctctattg ggagaccctc     300
attgtgatgg cttccaaaat aaggaatggg acctttttgt tgaacgcagc aaagcttaca    360
gcaactgtta cccttatgat gtgccggatt atgcctccct aggtcacta gttgcctcat     420 caggcaccct ggagtttatc aacgaaaact tcaattggac tggagtcgct caggatggga    480
aaagctatgc ttgcaaaagg ggatctgtta acagtttctt tagtagattg aattggttgc     540
acaaattaga atacaaatat ccagcgctga acgtgactat gccaaacaat ggcaaatttg    600
acaaattgta catttggggg gttcaccacc cgagcacgga cagtgtccaa accagcctat    660
atgtccgagc atcagggaga gtcacagtct ctaccaaaag aagccaacaa actgtaatcc    720
cggatatcgg gtatagacca tgggtaaggg gtcagtccag tagaataagc atctattgga    780
caatagtaaa accgggagac atactttga ttaatagcac agggaatcta attgctcctc    840
ggggttactt caaaatacga aatgggaaaa gctcaataat gaggtcagat gcacccattg    900
gcaactgcag ttctgaatgc atcactccaa atggaagcat tcccaatgac aaacctttc     960 aaaatgtaaa caggatcaca tatgggcct gcccagata tgttaagcaa aacactctga    1020
aattggcaac agggatgcgg aatgtaccag agaaacaaac tagaggcata ttcggcgcaa   1080
tcgcaggttt catagaaaat ggttgggagg gaatggtaga cggttggtac ggtttcaggc    1140
atcaaaattc tgagggcaca ggacaagctg cagatcttaa aagcactcaa gcagcaatcg    1200
accaaatcaa cgggaaactg aataggttag tcgagaaaac gaacgagaaa ttccatcaaa    1260
```

-continued

```
tcgaaaaaga attctcagaa gtagaaggga gaattcagga cctcgagaaa tatgttgaag    1320
acactaaaat agatctctgg tcttacaatg cggaacttct tgttgctctg gagaaccaac    1380
atacaattga tctaactgac tcagaaatga acaaactgtt tgaaagaaca aggaagcaac    1440
tgagggaaaa tgctgaggac atgggcaatg gttgtttcaa atataccac aaatgtgaca     1500 atgcctgcat agggtcaatc agaaatgaa cttatgacca tgatgtatac agagacgaag     1560
cattaaacaa ccggttccag atcaaaggtg ttgagctgaa gtcaggatac aaagattgga    1620
ttctatggat ttcctttgcc atatcgtgct ttttgctttg tgttgttttg cttgggttca    1680
tcatgtgggc ctgccaaaaa ggcaacatta ggtgcaacat ttgcatttga gtgcattaat    1740
taaaaacacc cttgt                                                     1755

<210> SEQ ID NO 4
<211> LENGTH: 1354
<212> TYPE: DNA
<213> ORGANISM: influenza A virus

<400> SEQUENCE: 4
gaaaatgaat ccaaatcaaa agataataac aattggctct gtttctctca ctattgccac       60
aatatgcttc cttatgcaaa ttgccatcct ggtaactact gtaacattgc atttcaagca      120
atatgagtgc aactccccc caaacaacca agtaatgctg tgtgaaccaa caataataga      180
aagaaacata acagagatag tgtatctgac caacaccacc atagagaaag aaatatgccc      240
caaactagca gaatacagaa attggtcaaa gccgcaatgt aaaattacag gatttgcacc      300
tttttctaag gacaattcaa ttcggctttc cgctggtgga gacatttggg tgacaagaga      360
accttatgtg tcatgcgatc ctggcaagtg ttatcaattt gccctcggac agggaacaac      420
actaaacaac aggcattcaa atgacacagt acatgatagg ccccttatc gaaccctatt      480 gatgaatgag ttgggtgttc catttcattt gggaaccaag caagtgtgca tagcatggtc      540
cagctcaagt tgtcacgatg gaaaagcatg gctgcatgtt tgtgtaactg gcatgatga       600 aaatgcaact gctagcttca tttacgatgg gaggcttgta gatagtattg gttcatggtc      660
caaaaatatc ctcaggaccc aggagtcgga atgcgtttgt atcaatggaa cttgtacagt      720
agtaatgact gatggaagtg cttcagaaag agctgatact aaaatactat tcattgaaga      780
ggggaaaatc gttcatatta gcccattgtc aggaagtgct cagcatgtcg aggagtgctc      840
ctgttatcct cgatatcctg tgtcagatg tgtctgcaga gacaactgga aaggctccaa      900
taggcccatc gtagatataa atgtgaaaga ttatagcatt gtttccagtt atgtgtgctc      960
aggacttgtt ggagacacac ccagaaaaaa cgacagctcc agcagtagct attgctggaa     1020
tcctaacaat gagaaagggg gtcatggagt gaaaggctgg gcctttgatg atggaaatga     1080
cgtgtggatg ggaagaacga tcagcgagga gttacgctca ggttatgaaa ccttcaaagt     1140
cattggaggc tggtccaaac taactccaa attgcagata aataggcaag tcatagttga      1200
cagaggtaat aggtccggtt attctggtat tttctctgtt gaaggcaaaa gctgcatcaa     1260
tcggtgcttt tatgtggagt tgataagggg aaggaaacag gaaactgaag tctggtggac     1320
ctcaaacagt attgttgtgt tttgtggcac ttca                                 1354

<210> SEQ ID NO 5
<211> LENGTH: 1762
<212> TYPE: DNA
<213> ORGANISM: influenza A virus

<400> SEQUENCE: 5
```

```
agcaaaagca gggataatt ctattaacca tgaagactat cattgctttg agctacattt      60
tatgtctggt tttcgctcaa aaacttcccg gaaatgacaa cagcacggca acgctgtgcc    120
tgggacacca tgcagtgcca acggaacgc tagtgaaaac aatcacgaat gaccaaattg     180
aagtgactaa tgctactgag ctggttcaga gttcctcaac aggtagaata tgcgacagtc    240
ctcaccgaat ccttgatgga aaaaactgca cactgataga tgctctattg ggagaccctc    300
attgtgatgg cttccaaaat aaggaatggg accttttttgt tgaacgcagc aaagcttaca   360
gcaactgtta cccttatgat gtgccggatt atgcttccct taggtcacta gttgcctcat    420
ccggcaccct ggagtttacc aatgaaggct tcaattggac tggagtcgct caggatggaa    480
caagctatgc ttgcaaaagg ggatctgtta aagtttctt tagtagattg aattggttgc     540
acaaattaga atacaaatat ccagcactga acgtgactat gccaaacaat gacaaatttg    600
acaaattgta catttggggg gttcaccacc cgagtacgga cagtgaccaa accagcatat    660
atgttcaagc atcagggaga gtcacagtct ctaccaaaag aagccaacaa actgtaatcc    720
cgaatatcgg gtctagaccc tgggtaaggg ggatctccag cagaataagc atctattgga    780
caatagtaaa accgggagac atactttga ttaacagcac agggaatcta attgctcctc     840
ggggttactt caaaatacga agtgggaaaa gctcaataat gaggtcagat gcacccattg    900
gcaactgcaa ttctgaatgc atcactccaa atggaagcat tcccaatgac aaacctttc     960
aaaatgtaaa caggatcaca tatgggcct gtcccagata tgttaagcaa acactctga     1020
aattggcaac agggatgcgg aatgtaccag agaaacaaac tagaggcata ttcggcgcaa    1080
tcgcaggttt catagaaaat ggttgggagg aatggtaga cggttggtac ggtttcaggc     1140
atcaaaattc tgagggcaca ggacaagcag cagatcttaa aagcactcaa gcagcaatca    1200
accaaatcaa cgggaaactg aataggttaa tcgagaaaac gaacgagaaa ttccatcaaa    1260
tcgaaaaga attctcagaa gtagaaggga gaattcagga cctcgagaaa tatgttgaag    1320
acactaaaat agatctctgg tcttacaacg cggagcttct tgttgccctg gagaaccaac    1380
atacaattga tctaactgac tcagaaatga acaaactgtt tgaaagaaca aggaagcaac    1440
tgagggaaaa tgctgaggac atgggcaatg gttgcttcaa aatataccac aaatgtgaca    1500
atgcctgcat agggtcaatc agaaatggaa cttatgacca tgatgtatac agagacgaag    1560
cattaaacaa ccggttccag atcaaggtg ttgagctgaa gtcaggatac aaagattgga    1620
tcctatggat ttcctttgcc atatcatgct ttttgctttg tgttgttctg ctggggttca    1680
tcatgtgggc ctgccaaaaa ggcaacatta ggtgcaacat ttgcatttga gtgcattaat    1740
taaaaacacc cttgtttcta ct                                              1762
```

<210> SEQ ID NO 6
<211> LENGTH: 1451
<212> TYPE: DNA
<213> ORGANISM: influenza A virus

<400> SEQUENCE: 6

```
agcaaaagca ggagtgaaaa tgaatccaaa tcaaaagata taactattg gctctgtttc      60
tctcactatt gccacaatat gcttccttat gcaaattgcc atcctggtaa ctactgtaac    120
attacatttc aagcaatatg aatgcaactc ccccccaaac aaccaagtaa tgctgtgtga    180
accaacaata atagaagaa acataacaga gatagtgtat ctgaccaaca ccaccataga    240
gaaggaaata tgccccaaac tagcagaata cagaaattgg tcaaagccgc aatgtaaaat    300
```

-continued

```
tacaggattt gcacctttt ctaaggacaa ttcaattcgg ctttccgctg gtggggacat      360
ttgggtgaca agagaaccatt atgtgtcatg cgatcctgac aagtgttatc aatttgccct    420
tggacaggga acaacactaa acaacaggca ttcaaatgac acagtacatg ataggacccc    480
ttatcgaacc ctattgatga atgagttggg tgttccattt catttgggaa ccaagcaagt    540
gtgcatagca tggtccagct caagttgtca cgatggaaaa gcatggctgc atgtttgtgt    600
aactgggcat gatgaaaatg caactgctag cttcatttac gatgggaggc ttgtagatag    660
tattggttca tggtccaaaa aaatcctcag acccaggag tcggaatgcg tttgtatcaa     720
tggaacttgt acagtagtaa tgactgatgg aagtgcttca ggaagagctg atactaaaat    780
actattcatt gaagagggga aaatcgttca tattagccca ttgtcaggaa gtgctcagca    840
tgtcgaggag tgctcctgtt atcctcgata ttctggtgtc agatgtgtct gcagagacaa    900
ctggaaaggc tccaataggc ccatcgtaga tataaatgtg aaagattata gcattgtttc    960
cagttatgtg tgctcaggac ttgttggaga cacacccaga aaaaacgaca gctccagcag   1020
tagccattgc ctgaatccta caatgagga aggggtcat ggagtgaaag ctgggcctt      1080 tgatgatgga aatgacgtgt ggatgggaag aacgatcagc gagaagttac gctcaggtta   1140
tgaaaccttc aaagtcattg gaggctggtc caaacctaac tccaaattgc agataaatag   1200
acaagtcata gttgacagag gtaataggtc cggttattct ggtatttct ctgttgaagg    1260 caaaagctgc atcaatcggt gcttttatgt ggagttgata aggggaagga aacaggaaac    1320
tgaagtctgg tggaccctcaa acagtattgt tgtgttttgt ggcacctcag gtacatatgg   1380
aacaggctca tggcctgatg gggcggacat caatctcatg cctatataag ctttcgcaat    1440
tttagaaaaa a                                                         1451

<210> SEQ ID NO 7
<211> LENGTH: 1762
<212> TYPE: DNA
<213> ORGANISM: influenza A virus

<400> SEQUENCE: 7
agcaaaagca ggggataatt ctattaacca tgaagactat cattgctttg agctacattt      60
tatgtctggt tttcgctcaa aaaattcccg gaaatgacaa cagcacggca acgtgtgcc     120 tgggacacca tgcagtgcca acggaacgc tagtgaaaac aatcacgaat gaccaaattg     180
aagtgactaa tgctactgag ctggttcaga gttcctcaac aggtagaata tgcgacagtc    240
ctcaccgaat ccttgatgga gaaaactgca cactgataga tgctctattg ggagaccctc    300
attgtgatgg cttccaaaat aaggaatggg accttttgt tgaacgcagc aaagcctaca    360
gcaactgtta cccttatgat gtgccggatt atgcctccct taggtcacta gttgcctcat   420
ccggcaccct ggagtttaac aatgaaagct tcaattggac tggagtcgct cagaatggaa   480
caagctatgc ttgcaaaagg agttctatta aagtttctt tagtagattg aattggttgc    540
accaattaaa atacaaatat ccagcactga acgtgactat gccaaacaat gacaaatttg   600
acaaattgta catttggggg gttcaccacc cgagtacgga cagtgaccaa ccagcatat    660 atgctcaagc atcagggaga gtcacagtct ccaccaaaag aagccaacaa actgtaatcc    720
cgaatatcgg atctagaccc tgggtaaggg gtatctccag cagaataagc atccattgga   780
caatagtaaa accgggagac atacttttga ttaacagcac agggaatcta attgctcctc   840 gggttactt caaatacga agtgggaaaa gctcaataat gaggtcagat gcacccattg   900
gcaaatgcaa ttctgaatgc atcactccaa atggaagcat tcccaatgac aaaccatttc   960
```

```
aaaatgtaaa caggatcaca tatggggcct gtcccagata tgttaagcaa aacactctga    1020
aattggcaac agggatgcgg aatgtaccag agaaacaaac tagaggcata ttcggcgcaa    1080
tcgcaggttt catagaaaat ggttgggagg gaatggtaga cggttggtac ggtttcaggc    1140
atcaaaattc tgagggcaca ggacaagcag cagatcttaa aagcactcaa gcagcaatca    1200
accaaatcaa cggaaactg aataggttaa tcgagaaaac gaacgagaaa ttccatcaaa    1260
ttgaaaaaga attctcagaa gtagaaggga gaattcagga cctcgagaaa tatgttgagg    1320
acactaaaat agatctctgg tcgtacaacg cggagcttct tgttgccctg agaaccaac    1380 atacaattga tctaactgac tcagaaatga acaaactgtt tgaaagaaca aggaagcaac    1440
tgagggaaaa tgctgaggat atgggcaatg gttgtttcaa aatataccac aaatgtgaca    1500
atgcctgcat agggtcaatc agaaatggaa cttatgacca tgatgtatac agagacgaag    1560
cattaaacaa ccggttccag atcaaaggtg ttgagctgaa gtcaggatac aaagattgga    1620
tcctatggat ttcctttgcc atatcatgtt ttttgctttg tgttgttttg ctggggttca    1680
tcatgtgggc ctgccaaaaa ggcaacatta ggtgcaacat ttgcatttga gtgcattaat    1740
taaaaacacc cttgtttcta ct                                            1762

<210> SEQ ID NO 8
<211> LENGTH: 1467
<212> TYPE: DNA
<213> ORGANISM: influenza A virus

<400> SEQUENCE: 8
agcaaaagca ggagtaaaga tgaatccaaa tcaaaagata ataacgattg gctctgtttc    60
tctcactatt gccacaatat gcttccttat gcaaattgcc atcctggtaa ctactgtaac    120
attgcatttc aagcaatatg aatgcagctc tcccccaaac aaccaagtaa tgctgtgtga    180
accaacaata atagaaagaa acataacaga gatagtgtat ctgaccaaca ccaccataga    240
gaaggaaata tgccccaaac tagcagaata cagaaattgg tcaaagccac aatgtaaaat    300
tacaggattt gcaccttttt ctaaggacaa ttcaattcgg cttccgctg gtggggacat    360 ttgggtgaca agggaacctt atgtgtcgtg cgatcctgac aagtgttatc aatttgccct    420
tggacaggga acaacactaa acaacaggca ttcaaatgac acagtacatg ataggacccc    480
ttatcgaacc ctattgatga atgagttggg tgttccattt catttgggaa ccaagcaagt    540
gtgcatagca tggtccagct caagttgtca cgatggaaaa gcatggctgc atgtttgtgt    600
aactgggcat gatgaaaatg caactgctag cttcatttac gatgggaggc ttgtagatag    660
tattggttca tggtccaaaa aaatcctcag acccaggag tcggaatgcg tttgtatcaa    720
tggaacttgt acagtagtaa tgactgatgg gagtgcttca ggaagagctg atactaaaat    780
actattcatt gaggagggga aaatcgttca tatcagccca ctgtcaggaa gtgctcagca    840
tgtcgaggag tgctcctgtt atcctcgata tcctggtgtc agatgtgtct gcagagacaa    900
ctggaaaggc tccaataggc ccatcgtaga tataaatgta aaggattata gcattgtttc    960
cagttatgtg tgctcaggac ttgttggaga cacacccaga aaaacgaca gctccagcag    1020 tagtcattgc ctgaatccta caatgaggaa gggggtcat ggagtgaaag ctgggcctt    1080 tgatgatgga aatgacgtgt ggatgggaag aacgatcagc gagaagttcc gctcaggtta    1140
tgaaaccttc aaagtcattg aaggctggtc caaacctaac tccaaattgc agataaaatag    1200 gcaagtcata gttgacagag gtaataggtc cggttattct ggtattttct ctgttgaagg    1260
```

-continued

```
caaaagctgc atcaatcggt gcttttatgt ggagttgata aggggaagga aacaggaaac    1320
tgaagtctgg tggacctcaa acagtattgt tgtgttttgt ggcacctcag gtacatatgg    1380
aacaggctca tggcctgatg gggcggacat caatctcatg cctatataag ctttcgcaat    1440
tttagaaaaa aactccttgt ttctact                                        1467

<210> SEQ ID NO 9
<211> LENGTH: 1762
<212> TYPE: DNA
<213> ORGANISM: influenza A virus

<400> SEQUENCE: 9
agcaaaagca ggggataatt ctattaacca tgaagactat cattgctttg agctacattt      60
tatgtctggt tttcgctcaa aaacttcccg gaaatgacaa cagcacggca acgctgtgcc     120
tggggcacca tgcagtgtca acggaacgc tagtgaaaac aatcacgaat gaccaaattg      180
aagtgactaa tgctactgag ctggttcaga gttcctcaac aggtagaata tgcgacagtc     240
ctcaccaaat ccttgatgga gaaaactgca cactaataga tgctctattg ggagaccctc     300
attgtgatgg cttccaaaat aaggaatggg acctttttgt tgaacgcagc aaagcctaca     360
gcaactgtta cccttatgat gtgccggatt atgcctccct taggtcacta gttgcctcat     420
ccggcacact ggagtttaac aatgaaagct tcaattggac tggagtcgct cagaatggaa     480
caagctctgc ttgcaaaagg ggatctaata aaagtttctt tagtagattg aattggttgc     540
accaattaaa atacaaatat ccagcactga acgtgactat gccaaacaat gaaaaatttg     600
acaaattgta catttggggg gttctccacc cgagtacgga cagtgaccaa atcagcctat     660
atgctcaagc atcagggaga gtcacagtct ctaccaaaag aagccaacaa actgtaatcc     720
cgaatatcgg atctagaccc tgggtaaggg gtgtctccag cagaataagc atctattgga     780
caatagtaaa accgggagac atactttga ttaacagcac agggaatcta attgctcctc      840
ggggttactt caaaatacga agtgggaaaa gctcaataat gaggtcagat gcacccattg     900
gcaaatgcaa ttctgaatgc atcactccaa atggaagcat tcccaatgac aaaccatttc     960
aaaatgtaaa caggatcaca tatggggcct gtcccagata tgttaagcaa aacactctga    1020
aattggcaac agggatgcgg aatgtaccag agaaacaaac tagaggcata ttcggcgcaa    1080
tcgcgggttt catagaaaat ggttgggagg gaatggtgga cggttggtac ggtttcaggc    1140
atcaaaattc tgagggcaca ggacaagcag cagatcttaa aagcactcaa gcagcaatca    1200
accaaatcaa cgggaaactg aataggttaa tcgagaaaac gaacgagaaa ttccatcaaa    1260
ttgaaaaaga attctcagaa gtagaaggga aattcagga cctcgagaaa tatgttgagg    1320
acactaaaat agatctctgg tcgtacaacg cggagcttct tgttgccctg gagaaccaac    1380
atacaattga tctaactgac tcagaaatga acaaactgtt tgaaagaaca aagaagcaac    1440
tgagggaaaa tgctgaggat atgggcaatg gttgtttcaa atataccac aaatgtgaca    1500 atgcctgcat agggtcaatc agaaatggaa cttatgacca tgatgtatac agagacgaag    1560
cattaaacaa ccggttccag atcaaggtg ttgagctgaa gtcaggatac aaagattgga    1620
tcctatggat tccctttgcc atatcatgct ttttgctttg tgttgttttg ctggggttca    1680
tcatgtgggc ctgccaaaaa ggcaacatta ggtgcaacat ttgcatttga gtgcattaat    1740
taaaaacacc cttgtttcta ct                                            1762

<210> SEQ ID NO 10
<211> LENGTH: 1466
```

<212> TYPE: DNA
<213> ORGANISM: influenza A virus

<400> SEQUENCE: 10

```
agcaaaagca ggagtaaaga tgaatccaaa tcaaaagata taacgattg gctctgtttc      60
tctcactatt gccacaatat gcttccttat gcaaatagcc atcctggtaa ctactgtaac    120
attgcatttc aagcaatatg aatgcaactc ccccccaaac aaccaagtaa tgctgtgtga    180
accaacaata atagaaagaa acataacaga gatagtgtat ctgaccaaca ccaccataga    240
gaaggaaata tgccccaaac tagcagaata cagaaattgg tcaaagccgc aatgtaaaat    300
tacaggattt gcaccttttt ctaaggataa ttcaattcgg ctttccgctg gtggggacat    360
ttgggtgaca agagaacctt atgtgtcatg cgatcctgac aagtgttatc aatttgccct    420
tggacaggga acaacactaa acaacaggca ttcaaatgac acagtacatg ataggacccc    480
ttatcgaacc ctattgatga atgagttggg tgttccattt catttgggaa ccaagcaagt    540
gtgtatagca tggtccagct caagttgtca cgatggaaaa gcatggctgc atgtttgtgt    600
aactgggcat gatgaaaatg caactgctag cttcatttac gatgggagac ttgtagatag    660
tattggttca tggtccaaaa aaatcctcag gacccaggag tcggaatgcg tttgtatcaa    720
tggaacttgt acagtagtaa tgactgatgg agtgcttca ggaagagctg atactaaaat    780
acttttcatt gaggagggga aaatcgttca tactagcaaa ttgtcaggaa gtgctcagca    840
tgtcgaggag tgctcctgtt atcctcgata tcctggtgtc agatgtgtct gcagagacaa    900
ctggaaaggc tccaataggc ccatcgtaga tataaatgta aaggattata gcattgtttc    960
cagttatgtg tgctcaggac ttgttggaga cacacccaga aaaacgaca gctccagcag   1020
tagccattgc ctggatccta acaatgaaga aggggggtcat ggagtgaaag ctgggcctt   1080
tgatgatgga aatgacgtgt ggatgggaag aacgatcagc gagaagtcac gctcaggtta   1140
tgaaaccttc aaggtcattg aaggctggtc caaacctaac tccaaattgc agataaaatag   1200
gcaagtcata gttgaaagag gtaatatgtc cggttattct ggtattttct ctgttgaagg   1260
caaaagctgc atcaatcggt gcttttatgt ggagttgata aggggaagga acaggaaac   1320
tgaagtctgg tggaccctcaa acagtattgt tgtgttttgt ggcacctcag gtacatatgg   1380
aacaggctca tggcctgatg gggcggacat caatctcatg cctatataag ctttcgcaat   1440
tttagaaaaa actccttgtt tctact                                        1466
```

<210> SEQ ID NO 11
<211> LENGTH: 1762
<212> TYPE: DNA
<213> ORGANISM: influenza A virus

<400> SEQUENCE: 11

```
agcaaaagca gggataatt ctattaacca tgaagactat cattgcttta agctacattc       60
tatgtctggt tttctctcaa aagcttcccg gaaatgacaa cagcacggca acgctgtgcc     120
ttgggcacca tgcagtacca acgaacga tagtgaaaac aatcacgaat gaccaaattg     180
aagttactaa tgctactgag ctggttcaga gttcctcaac aggtggaata tgcgacagtc     240
ctcatcagat ccttgatgga gaaaactgca cactaataga tgctctattg ggagaccctc     300
agtgtgatgg cttccaaaat aagaaatggg acctttttgt tgaacgcagc aaagcctaca     360
gcaactgtta cccttatgat gtgccggatt atgcctccct taggtcacta gttgcctcat     420
ccggcacact ggagtttaac aatgaaagct tcaattgggc tggagtcact cagaatggaa     480
```

```
caagctctgc ttgcaaaagg agatctaata aaagtttctt tagtagattg aattggttga      540
cccacttaaa atacaaatac ccagcattga acgtgactat gccaaacaat gaaaaatttg      600
acaaattgta catttggggg gttcaccacc cggttacgga cagtgaccaa atcagcctat      660
atgctcaagc atcaggaaga atcacagtct ctaccaaaag aagccaacaa actgtaatcc      720
cgaatatcgg atatagaccc agggtaaggg atatctccag cagaataagc atctattgga      780
caatagtaaa accgggagac atacttttga ttaacagcac aggaaatcta attgctcctc      840
ggggttactt caaaatacga agtgggaaaa gctcaataat gagatcagat gcacccattg      900
gcaaatgcaa ttctgaatgc atcactccaa atggaagcat tcccaatgac aaaccatttc      960
aaaatgtaaa caggatcaca tatgggcct gtcccagata tgttaagcaa acactctga     1020 aattggcaac agggatgcga atgtaccag agaaacaaac tagaggcata tttggcgcaa     1080
tcgcgggttt catagaaaat ggttgggagg gaatggtgga cggttggtac ggtttcaggc     1140
atcaaaattc tgagggcaca ggacaagcag cagatctcaa aagcactcaa gcagcaatca     1200
accaaatcaa tgggaaactg aataggttaa tcgggaaaac aaacgagaaa ttccatcaga     1260
ttgaaaaaga attctcagaa gtagaaggga gaattcagga cctcgagaaa tatgttgagg     1320
acactaaaat agatctctgg tcatacaacg cggagcttct tgttgccctg gaaaaccaac     1380
atacaattga tctaactgac tcagaaatga caaactgtt tgaaagaaca agaagcaac      1440 tgagggaaaa tgctgaggat atgggcaatg gttgtttcaa aatataccac aaatgtgaca     1500
atgcctgcat agagtcaatc agaaatgaa cttatgacca tgatgtatac agagatgaag     1560
cattaaacaa ccggttccag atcaaggtg ttgagctgaa gtcaggatac aaagattgga     1620
tcctatggat ttcctttgcc atatcatgtt ttttgctttg tgttgctttg ttggggttca     1680
tcatgtgggc ctgccaaaaa ggcaacatta ggtgcaacat ttgcatttga gtgcattaat     1740
taaaaacacc cttgtttcta ct                                             1762

<210> SEQ ID NO 12
<211> LENGTH: 1467
<212> TYPE: DNA
<213> ORGANISM: influenza A virus

<400> SEQUENCE: 12
agcaaaagca ggagtaaaga tgaatccaaa tcaaaagata taacgattg gctctgtttc       60 cctcaccatt tccacaatat gcttcttcat gcaaattgcc atcctgataa ctactgtaac      120
attgcatttc aagcaatatg aattcaactc cccccaaac aaccaagtga tgctgtgtga      180
accaacaata atagaaagaa acataacaga gatagtgtat ctgaccaaca ccaccataga      240
gaaggaaata tgccccaaac tagcagaata cagaaattgg tcaaagccgc aatgtaacat      300
tacaggattt gcaccttttt ctaaggacaa ttcgattcgg ctttccgctg gtggggacat      360
ctgggtgaca agagaacctt atgtgtcatg cgatcctgac aagtgttatc aatttgccct      420
tggacaggga acaacactaa acaacgtgca ttcaaatgac acagtacatg ataggacccc      480
ttatcggacc ctattgatga atgagttggg tgttccattt catctgggga ccaagcaagt      540
gtgcatagca tggtccagct caagttgtca cgatggaaaa gcatggctgc atgtttgtgt      600 aacggggat gatgaaaatg caactgctag cttcattac aatgggaggc ttgtagatag      660
tattgtttca tggtccaaaa aaatcctcag acccaggag tcagaatgcg tttgtatcaa      720
tggaacttgt acagtagtaa tgactgatgg gagtgcttca ggaaaagctg atactaaaat      780
actattcatt gaggagggga aaattgttca tactagcaca ttatcaggaa gtgctcagca      840
```

```
tgtcgaggag tgctcctgtt atcctcgata tcctggtgtc agatgtgtct gcagagacaa      900
ctggaaaggc tccaataggc ccatcgtaga tataaacata aaggattata gcattgtttc      960
cagttatgtg tgctcaggac ttgttggaga cacacccaga aaaaacgaca gctccagcag     1020
tagccattgc ttggatccaa acaatgagga aggtggtcat ggagtgaaag ctgggcatt      1080 tgatgatgga aatgacgtgt ggatgggaag aacgatcagc gagaagttac gctcaggata     1140
tgaaaccttc aaagtcattg aaggctggtc caaccctaac tccaaattgc agataaatag     1200
gcaagtcata gttgacagag gtaacaggtc cggttattct ggtatttttc tgttgaagg      1260 caaaagctgc atcaatcggt gcttttatgt ggagttgata aggggaagaa acaggaaac     1320 tgaagtcttg tggaccctcaa acagtattgt tgtgttttgt ggcacctcag gtacatatgg    1380
aacaggctca tggcctgatg gggcggacat caatctcatg cctatataag ctttcgcaat    1440
tttagaaaaa aactccttgt ttctact                                         1467

<210> SEQ ID NO 13
<211> LENGTH: 1778
<212> TYPE: DNA
<213> ORGANISM: influenza A virus

<400> SEQUENCE: 13
agcaaaagca ggggaaaata aaacaacca aatgaaagc aaaactacta gtcctgttat        60
gtgcatttac agctacatat gcagacacaa tatgtatagg ctaccatgcg aacaactcaa     120
ccgacactgt tgacacagta cttgagaaga acgtgacagt gacacactct gtcaacctac     180
ttgaggacag tcacaacgga aaactatgtc gactaaaggg aatagcccca ctacaattgg     240
gtaattgcag cgttgccgga tggatcttag gaaacccaaa atgcgaatca ctgttttcta     300
aggaatcatg gtcctacatt gcagaaacac caaaccctga gatggaaca tgttacccag      360 ggtatttcgc cgactatgag gaactgaggg agcaattgag ttcagtatca tcattcgaga    420
gattcgaaat attccccaaa gaaagctcat ggcccaacca caccgtaacc aaaggagtaa    480
cgacatcatg ctcccataat gggaaaagca gttttttacag aaatttgcta tggctgacga    540
agaagaatgg cttgtaccca atgtgagca gtcctatgt aaacaacaaa gagaagaag       600 tccttgtact atggggtgtt catcacccgt ctaacatagg ggaccaaagg gccatctatc    660
atacagaaaa tgcttatgtc tctgtagtgt cttcacatta tagcagaaga ttcaccccag    720
aaatagcaaa aagacccaaa gtaagagatc aagaaggaag aattaactac tactggactc    780
tgctggaacc cggggacaca ataatatttg aggcaaatgg aaatctaata gcgccatggt    840
atgctttcgc actgagtaga ggctttgggt caggaatcat cacctcaaac gcatcaatgg    900
atgaatgtga cgcgaagtgt caaacacccc agggagctat aaacagtagt cttcctttcc    960
agaatgtaca cccagtcaca ataggagagt gtccaaagta tgtcaggagt acaaaattaa     1020
ggatggttac aggactaagg aacatcccat ccattcaatc cagaggttg tttggagcca     1080 ttgccggttt cattgaaggg gggtggactg gaatgataga tggatggtat ggttatcatc     1140
atcagaatga acaaggatct ggctatgctg cggaccaaaa aagcacacaa atgccatta     1200 acggattac aaaacaaggtg aattctgtaa tcgagaaaat gaacactcaa ttcacagctg    1260
tgggcaaaga attcaacaaa ttagaaagaa ggatggaaaaa cttaaataaa aaagttgatg    1320
atggatttct ggcatttggg acatataatg cagaattgtt ggttctactg gaaaatggaa     1380
ggactttgga ttttcatgac tcaaatgtga agaatctgta tgaaagta aaaagccaat      1440
```

```
tgaagaataa tgccaaagaa atagggaacg ggtgttttga attctatcac aagtgtaaca    1500
atgaatgcat ggaaagtgtg aaaaatggaa cttatgacta tccaaaatat tccgaagaat    1560
caaagttaaa caggggaaaa attgatgag tgaaattgga atcaatggga gtctatcaga     1620
ttctggcgat ctactcaact gtcgccagtt cactggtgct tttggtctcc ctgggggcaa    1680
tcagcttctg gatgtgttct aatgggtctt tgcagtgtag aatatgcatc tgagaccaga    1740
atttcagaaa tataagaaaa aacacccttg tttctact                            1778

<210> SEQ ID NO 14
<211> LENGTH: 1463
<212> TYPE: DNA
<213> ORGANISM: influenza A virus

<400> SEQUENCE: 14
agcaaaagca ggagtttaaa atgaatccaa atcaaaaaat aataatcata ggatcaatca     60
gtatggcaat cggaataatt agtctaatat tgcaaatagg aaatattatt tcaatatggg    120
ctagccactc aatccaaact ggaagtcaaa accacactgg aatatgcaac caagaatca    180 ttacatatga aaatagcacc tgggtgaatc aaacatatgt taatattaac aacactaatg    240
ttgttgctgg aaaggacaaa acttcagtga cattggccgg caattcatct ctttgcccta    300
tccgtgggtg ggctatatac acaaaagaca acagcataag aattggttcc aaaggagatg    360
tttttgtcat aagagagcct tttatatcat gttctcactt ggaatgcaga accttttttc    420
tgacccaagg tgctctatta atgacaagc attcaaatgg accgttaag acagaagcc      480 cttatagggc cttaatgagc tgtcctctag gtgaagctcc gtctccatac aattcaagat    540 tgaatcagt tgcttggtca gcaagcgcat gccatgatgg catgggctgg ctaacaatcg    600
gaatttctgg tccagataat ggagcagtgg ctgtactaaa atacaacggc ataataactg    660
aaaccataaa aagttggaag aagcgaatat taagaacaca agagtctgaa tgtgtctgtg    720
tgaacggttc atgtttttacc ataatgaccg atggcccgag taatgggcc gcctcgtaca    780 gaatcttcaa aatcgagaag gggaaggtta ctaaatcaat agagttggat gcacccaatt    840
atcattacga ggaatgttcc tgttacccag acaccggcac agtgatgtgt gtgtgcaggg    900
acaattggca cggttcaaat cgaccttggg tgtcttttaa tcaaaacctg gattatcaaa    960
taggatacat ctgcagtggg gtgttcggtg acaatccgcg tcccaaagat ggagaaggca   1020
gctgtaatcc agtgactgtt gatggagcag acggagtaaa ggggttttca tacagatatg   1080
gtaatggtgt ttgatagga aggactaaaa gtaacagact cagaaaggga tttgagatga   1140
tttgggatcc taatggatgg acagataccg cagtgatttt ctctgtgaaa caggatgtcg   1200
tggcaatgac tgattggtca gggtacagcg gaagtttcgt tcaacatcct gagctaacag   1260
gattggactg tatgagacct tgcttctggg ttgaattaat cagagggcga cctagagaaa   1320
atacaacaat ctggactagt gggagcagca tttcttttttg tggcgtaaat agcgatactg   1380
caaactggtc ttggccagac ggtgccgagt tgccattcac cattgacaag tagtccgttg   1440
aaaaaaaact ccttgtttct act                                           1463

<210> SEQ ID NO 15
<211> LENGTH: 1689
<212> TYPE: DNA
<213> ORGANISM: influenza A virus

<400> SEQUENCE: 15
aaatgaaagc aaaactacta gtcctgttg

```
tatgtatagg ctaccatgcg aacaactcaa ccgacactgt tgacacagta cttgagaaga      120
acgtgacagt gacacactct gtcaacctac ttgaggacag tcacaacgga aaactatgcc      180
gactaaaagg aacagcccca ctacaattgg gtaattgcag cgttgccgga tggatcttag      240
gaaacccaga atgcgaatca ctgttttcta aggaatcatg gtcctacatt gcagaaacac      300
caaaccctga aatggaaaca tgttacccag gtatttcgc cgactatgag gaactgaggg      360
agcaattgag ctcagtatca tcattcgaga gattcgaaat attccccaag gaaagctcat      420
ggcccaaaca caccgtaacc aaaggagtga cggcatcatg ctcccataat gggaaaagca      480
gtttttacaa aaatttgcta tggctgacgg aaaagaatgg cttgtaccca aatctgagca      540
agtcctatgt aaacaacaag gagaaagaag tccttgtact atggggtgtt catcacccgt      600
ctaacatagg ggaccaaagg gccatctatc atacagaaaa tgcttatgtc tctgtagtgt      660
cttcacatta tagcagaaga ttcacccag aaatagcaaa aagacccaaa gtaagaggtc      720
aagaagggag aattaactac tactggactc tgctggaacc cggggacaca ataatatttg      780
aggcaaatgg aaatctaata gcgccatggt acgctttcgc actgagtaga ggctttgggt      840
caggaatcat cacctcaacc gcatcaatgg gtgaatgtga cgctaagtgt caaacacccc      900
aaggagctat aaacagtagt cttcctttcc agaatgtaca cccagtcaca ataggagagt      960
gtcccaagta tgtcaggagt acaaaattaa ggatggttac aggactaaga aacatcccat     1020
ccattcaatc tagaggtttg tttgagcca ttgccggttt cattgaaggg gggtggactg     1080
gaatgataga tggatggtat ggttatcatc atcagaatga acaaggatct ggctatgctg     1140
cagaccaaaa aagcacacaa aatgccattg atgggattac aaacaaggtg aattctgtaa     1200
tcgagaaaat gaacactcaa ttcacagctg taggcaaaga attcaacaaa ttagagagaa     1260
ggatggaaaa cttaaataag aaagttgatg atggatttct ggacatttgg acatataatg     1320
cagagttgtt ggttctcctg gaaaatggaa ggacttggg ttttcatgac tcaaatgtga     1380
agaatctgta tgagaaagta aaaaaccaat tgaagaataa tgccaaagaa atcgggaacg     1440
ggtgttttga attctatcac aagtgtaaca atgaatgcat ggaaagtgtg aaaaatggaa     1500
cttatgacta tccaaaatat tccgaagaat caaagttaaa cagggaaaaa attgatggag     1560
tgaaattgga atcaatggga gtctatcaga ttctggcgat ctactcaact gtcgccagtt     1620
cactggtgct tttggtctcc ctgggggcaa tcagtttctg gatgtgttct aatgggtctt     1680
tgcagtgta                                                             1689
```

<210> SEQ ID NO 16
<211> LENGTH: 1447
<212> TYPE: DNA
<213> ORGANISM: influenza A virus

<400> SEQUENCE: 16

```
agcaaaagca ggagtttaaa atgaatccaa atcaaaaaat aataaccatt ggatcaatca       60
gtattgcaat tggaataatt agtctgtatt tgcaaatagg aaatattatt tcaatatggg      120
ctagccactc aatccaaact ggaagtcaaa accacactgg aatatgcaac caaagaatca      180
ttacatatga aaatagcacc tgggtaaatc aacatatgt taatattaac aacactaatg      240
ttgttgctgg aaaggacaaa acctcaatga cattggccgg caattcatct ctttgcccta      300
tccgtggatg ggctatatac acaaaagaca acagcataag aattggttcc aaaggagatg      360 ttttttgtcat aagagagcct tttatatcat gttctcactt ggaatgcaga acctttttc      420
```

-continued

```
tgacccaagg tgctctatta aatgacaagc attcaaatgg gaccgttaag gacagaagcc      480 cttataggc cttaatgagc tgtcctctag gtgaagctcc gtctccatac aattcaagat       540
ttgaatcagt tgcttggtca gcaagcgcat gccatgatgg cttgggctgg ctaacaatcg      600
gaatttctgg tccagataat ggggcagtgg ctgtactaaa atacaacggc ataataactg      660
aaaccattaa aagttggaag aagcgaatat taagaacaca agagtctgaa tgtgtctgta     720
tgaacggttc atgttttacc ataatgaccg atggcccgag taatggggcc gcatcgtaca     780
gaatcttcaa aatcgagaag gggagagtta ctaaatcaat agagttggat gcacccaatt     840
atcattacga ggaatgttca tgttacccag acaccggcac agtgatgtgt gtgtgcaggg     900
acaattggca cggttcaaat cgaccttggg tgtcttttaa tcaaaacctg gattatcaaa     960
taggatacat ctgcagtggg gtgttcggtg acaatccgcg tcccaaagat ggagaaggca    1020
gctgtaatcc agtgactgtt gatggagcag acggagtaaa ggggttttca tacagatatg    1080
gtaatggtgt ttggatagga aggactaaaa gtaacagact cagaaaggga tttgagatga    1140
tttgggatcc taatggatgg acagataccg acagtgattt ctcaatgaaa caggatatcg    1200
tggcaatgac tgattggtca gggtacagcg gaagttttgt tcaacatcct gagctaacag    1260
gattggactg tatgagacct tgcttttggg ttgaattagt cagagggcta cctagagaaa    1320
atacaacaat ctggactagt gggagcagca tttcttttgt ggcgtaaat agcgatactg     1380 caaactggtc ttggccagac ggtgccgagt tgccattcac cattgacaag tagtccgttg    1440
aaaaaaa                                                               1447
```

<210> SEQ ID NO 17
<211> LENGTH: 1775
<212> TYPE: DNA
<213> ORGANISM: influenza A virus

<400> SEQUENCE: 17

```
agcaaaagca ggggaaaata aaaacaacca aaatgaaagc aaaactacta gtcctgttat      60
gtacatttac agctacatat gcagacacaa tatgtatagg ctaccatgcc aacaactcaa     120
ccgacactgt tgacacagta cttgagaaga atgtgacagt gacacactct gtcaacctac     180
ttgaggacag tcacaatgga aaactatgtc tactaaaagg aatagcccca ctacaattgg     240
gtaattgcag cgttgccgga tggatcttag gaaacccaga atgcgaatca ctgatttcta    300
aggaatcatg tcctacatt gtagagacac caaaccctga gaatggaaca tgttacccag     360
ggtatttcgc cgactatgag gaactgaggg agcaattgag ttcagtatca tcatttgaga    420
gattcgaaat attccccaaa gaaagctcat ggcccaaaca caccgtaaca ggagtaacgg     480
catcatgctc ccataatggg aaaagcagtt tttacagaaa tttgctatgg ctgacggaga    540
agaatggctt gtacccaaat ctgagcaatt cctatgtgaa caacaaagag aaagaagtcc    600
ttgtactatg gggtgttcat cacccatcta acataggggg ccaagggggcc atctatcata    660 cagaaaacgc ttatgtctct gtagtgtctt cacattatag cagaagattc accccagaaa    720
tagcaaaaag acccaaagta agaggtcagg aaggaagaat caactactac tggactctgc    780
tggaacccgg ggacacaata atatttgagg caaatggaaa tctaatagcg ccatggtatg    840 cttcgcact gagtagaggc tttgggtcag gaatcatcac ctcaaatgca ccaatgaatg    900
aatgtgatgc gaagtgtcaa acacctcagg gagctataaa cagtagtctt cctttccaga    960
atgtacaccc agtcacaata ggagagtgtc caaagtatgt caggagtaca aaattaagga    1020
tggttacagg actaaggaat atcccatcca ttcaatccag aggtttgttt ggagccattg    1080
```

-continued

```
ccggtttcat tgaagggggg tggactggaa tgatggatgg gtggtatggt tatcatcatc    1140
agaatgagca aggatctggc tatgctgcag atcaaaaaag cacacaaaat gccattaacg    1200
ggattacaaa taaggtgaat tctgtaattg agaaaatgaa cactcaattc acagctgtgg    1260
gcaaagaatt caacaaatta gaaagaagga tggaaaactt aaataaaaaa gttgatgatg    1320
gatttctaga catttggaca tataatgcag aattgttggt tctactggaa atgaaagga    1380 ctttggattt ccatgactca aatgtgaaga atctgtatga aaagtgaaa agccaattaa    1440 agaataatgc caaagaaata gggaacgggt gttttgaatt ctatcacaag tgtaacaatg    1500
aatgcatgga aagtgtgaaa atggaactt atgactatcc aaaatattcc gaagaatcaa    1560
agttaaacag ggagaaaatt gatggagtga aattggaatc aatgggagtc tatcagattc    1620
tggcgatcta ctcaactgtc gccagttcac tggttctttt ggtctccctg ggggcaatca    1680
gcttctggat gtgttccaat gggtctttgc agtgtagaat atgcatctga accagaatt    1740 tcagaaatat aagaaaaaac acccttgttt ctact    1775
```

<210> SEQ ID NO 18
<211> LENGTH: 1463
<212> TYPE: DNA
<213> ORGANISM: influenza A virus

<400> SEQUENCE: 18

```
agcaaaagca ggagtttaaa atgaatccaa atcaaaaaat aataaccatt ggatcaatca     60
gtatagtaat cgggataatt agtctaatgt tgcaaatagg aaatattatt tcaatatggg    120
ctagtcactc aatccaaact ggaagtcaaa accacactgg aatatgcaac caaagaatca    180
tcacatatga aaatagcacc tgggtgaatc acacatatgt taatattaac aacactaatg    240
ttgttgctgg aaaggacaaa acttcagtga cattggccgg caattcatca ctttgttcta    300
tcagtggatg ggctatatac acaaaagaca cagcataag aattggttcc aaaggagatg    360
tttttgtcat aagagagcct tttatatcat gttctcactt ggaatgcaga acctttttc    420 tgacccaagg tgctctatta atgacaaac attcaaatgg accgttaag acagaagtc    480 cttatagggc cttaatgagc tgtcctctag gcgaagctcc gtctccatat aattcaaagt    540
ttgaatcagt tgcttggtca gcaagcgcat gtcatgatgg catgggctgg ttaacaatcg    600
gaatttctgg tccagataat ggagcagtgg ctgtactaaa atacaacggc ataataactg    660
aaaccataaa aagttggaaa aagcgaatat taagaacaca agagtctgaa tgtgtctgtg    720
tgaacgggtc atgtttacc ataatgaccg atggcccgag taatgggcc gcctcgtaca    780 aaatcttcaa gattgagaag gggaaggtta ctaaatcaat agagttgaat gcacccaatt    840
ctcattatga ggaatgttcc tgttacccag acactggcac agtgatgtgt gtatgcaggg    900
acaattggca cggttcaaat cgaccttggg tgtcttttaa tcaaaacctg gattatcaaa    960
taggatacat ctgcagtggg gtgttcggtg acaatccgcg tcccaaagat ggagagggca   1020
gctgtaatcc agtgactgtt gatggagcag acggagtaaa ggggttttca tacagatatg   1080
gtaatggtgt ttggatagga aggactaaaa gtaacagact cagaaaggga tttgagatga   1140
tttgggatcc taatgatgg acagataccg acagtgattt ctcagtgaaa caggatgttg   1200
tggcaatgac tgattggtca gggtacagcg gaagtttcgt tcaacatcct gagctaacag   1260
gattggactg tataagacct tgcttctggg ttgaattagt cagaggacgg cctagagaa    1320 atacaacaat ctggactagt gggagcagca tttcttttg tggcgtaaat agtgatactg    1380
```

-continued

| caaactggtc | ttggccagac | ggtgctgagt | tgccattcac | cattgacaag | tagtccgttg | 1440 |
| aaaaaaaact | ccttgtttct | act | | | | 1463 |

<210> SEQ ID NO 19
<211> LENGTH: 1775
<212> TYPE: DNA
<213> ORGANISM: influenza A virus

<400> SEQUENCE: 19

| agcaaaagca | ggggaaaata | aaaacaacca | aaatgaaagc | aaaactactg | gtcctgttat | 60 |
| gtacatttac | agctacatat | gcagacacaa | tatgtatagg | ctaccatgcc | aacaactcaa | 120 |
| ccgacactgt | tgacacagta | cttgagaaga | atgtgacagt | gacacactct | gtcaacctac | 180 |
| ttgaggacag | tcacaatgga | aaactatgtc | tactaaaagg | aatagcccca | ctacaattgg | 240 |
| gtaattgcag | cgttgccgga | tggatcttag | gaaacccaga | atgcgaatta | ctgatttcca | 300 |
| aggaatcatg | gtcctacatt | gtagaaacac | caaatcctga | gatggaaca | tgttacccag | 360 |
| ggtatttcgc | cgactatgag | gaactgaggg | agcaattgag | ttcagtatct | tcatttgaga | 420 |
| gattcgaaat | attccccaaa | gaaagctcat | ggcccaaaca | caccgtaacc | ggagtatcag | 480 |
| catcatgctc | ccataatggg | aaaaacagtt | tttacagaaa | tttgctatgg | ctgacgggga | 540 |
| agaatggttt | gtacccaaac | ctgagcaagt | cctatgtaaa | caacaaagag | aaagaagtcc | 600 |
| ttgtactatg | gggtgttcat | cacccgccta | acataggga | ccaagggcc | ctctatcata | 660 |
| cagaaaatgc | ttatgtctct | gtagtgtctt | cacattatag | cagaagattc | accccagaaa | 720 |
| tagccaaaag | acccaaagta | agagatcagg | aaggaagaat | caactactac | tggactctgc | 780 |
| tggaacctgg | ggatacaata | atatttgagg | caaatgaaa | tctaatagcg | ccatggtatg | 840 |
| cttttgcact | gagtagaggc | tttggatcag | gaatcatcac | ctcaaatgca | ccaatggatg | 900 |
| aatgtgatgc | gaagtgtcaa | acacctcagg | agctataaaa | cagcagtctt | cctttccaga | 960 |
| atgtacaccc | agtcacaata | ggagagtgtc | caaagtatgt | caggagtgca | aaattgagga | 1020 |
| tggttacagg | actaaggaac | atcccatcca | ttcaatccag | aggtttgttt | ggagccattg | 1080 |
| ccggtttcat | tgaagggggg | tggactggaa | tggtagatgg | gtggtatggt | tatcatcatc | 1140 |
| agaatgagca | aggatctggc | tatgctgcag | atcaaaaag | tacacaaaat | gccattaacg | 1200 |
| ggattacaaa | caaggtgaat | tctgtaattg | agaaaatgaa | cactcaattc | acagctgtgg | 1260 |
| gcaaagaatt | caacaaattg | gaagaagga | tggaaaactt | aaataaaaaa | gttgatgatg | 1320 |
| ggtttctaga | catttggaca | tataatgcag | aattgttggt | tctactggaa | aatgaaagga | 1380 |
| ctttggattt | ccatgactcc | aatgtgaaga | atctgtatga | gaaagtaaaa | agccaattaa | 1440 |
| agaataatgc | caaagaaata | ggaaacgggt | gttttgaatt | ctatcacaag | tgtaacaatg | 1500 |
| aatgcatgga | gagtgtgaaa | aatggaactt | atgactatcc | aaaatattcc | gaagaatcaa | 1560 |
| agttaaacag | ggagaaaatt | gatggagtga | aattggaatc | aatgggagtc | tatcagattc | 1620 |
| tggcgatcta | ctcaactgtc | gccagttccc | tggttctttt | ggtctccctg | ggggcaatca | 1680 |
| gcttctggat | gtgttccaat | gggtctttgc | agtgtagaat | atgcatctga | gaccagaatt | 1740 |
| tcagaagtat | aagaaaaaac | acccttgttt | ctact | | | 1775 |

<210> SEQ ID NO 20
<211> LENGTH: 1463
<212> TYPE: DNA
<213> ORGANISM: influenza A virus

<400> SEQUENCE: 20

-continued

```
agcaaaagca ggagtttaaa atgaatccaa atcaaaaaat aataaccatt ggatcaatca      60
gtatagcaat cggaataatt agtctaatgt tgcaaatagg aaatattatt tcaatatggg     120
ctagtcactc aatccaaact ggaagtcaaa accacactgg agtatgcaac caaagaatca     180
tcacatatga aaacagcacc tgggtgaatc acacatatgt taatattaac aacactaatg     240
ttgttgctgg aaaggacaaa acttcagtga cattggccgg caattcatct ctttgttcta     300
tcagtggatg ggctatatac acaaaagaca acagcataag aattggctcc aaaggagatg     360
tttttgtcat aagagaacct ttcatatcat gttctcactt ggaatgcaga acctttttc      420
tgacccaagg tgctctatta aatgacaaac attcaaatgg gaccgttaag gacagaagtc     480
cttatagggc cttaatgagc tgtcctctag gtgaagctcc gtccccatac aattcaaagt     540
ttgaatcagt tgcatggtca gcaagcgcat gccatgatgg catgggctgg ttaacaatcg     600
gaatttctgg tccagacaat ggagctgtgg ctgtactaaa atacaacggc ataataactg     660
aaaccataaa aagttggaaa aagcgaatat taagaacaca agagtctgaa tgtgtctgtg     720
tgaacgggtc atgtttcacc ataatgaccg atggcccgag taatggggcc gcctcgtaca     780
aaatcttcaa gatcgaaaag ggaaggtta ctaaatcaat agagttgaat gcacccaatt      840
ttcattatga ggaatgttcc tgttacccag acactggcac agtgatgtgt gtatgcaggg     900
acaactggca tggttcaaat cgaccttggg tgtcttttaa tcaaaacctg gattatcaaa     960
taggatacat ctgcagtggg gtgttcggtg acaatccgcg tcccaaagat ggagagggca    1020
gctgtaatcc agtgactgtt gatggagcag acggagtaaa ggggttttca tacaaatatg    1080
gtaatggtgt ttggatagga aggactaaaa gtaacagact tagaaagggg tttgagatga    1140
tttgggatcc taatggatgg acagataccg acagtgattt ctcagtgaaa caggatgttg    1200
tggcaataac tgattggtca gggtacagcg gaagtttcgt tcaacatcct gagttaacag    1260
gattggactg tataagacct tgcttctggg ttgagttagt cagaggactg cctagagaaa    1320
atacaacaat ctggactagt gggagcagca tttctttttg tggcgtaaat agtgatactg    1380
caaactggtc ttggccagac ggtgctgagt tgccgttcac cattgacaag tagttcgttg    1440
aaaaaaaact ccttgtttct act                                            1463
```

<210> SEQ ID NO 21
<211> LENGTH: 1879
<212> TYPE: DNA
<213> ORGANISM: influenza B virus

<400> SEQUENCE: 21

```
agcagaagca gagcattttc taatatccac aaaatgaagg caataattgt actactcatg      60
gtagtaacat ccaacgcaga tcgaatctgc actgggataa catcttcaaa ctcacctcat     120
gtggtcaaaa cagctactca aggggaagtc aatgtgactg gtgtgatacc actgacaaca     180
acaccaacaa aatctcattt tgcaaatctc aaaggaacaa agaccagagg gaaactatgc     240
ccaaactgtc tcaactgcac agatctggat gtggccttgg gcagaccaat gtgtataggg     300
atcacacctt cggcaaaagc ttcaatactc cacgaagtca gacctgttac atccgggtgc     360
tttcctataa tgcacgacag aacaaaaatc agacagctac ccaatcttct cagaggatat     420
gaacatatca gattatcaac ccataacgtt atcaacgcag aaagggcacc aggaggaccc     480
tacagacttg gaacctcagg atcttgccct aacgttacca gtagaagcgg attcttcgca     540
acaatggctt gggctgtccc aagggacaac aaaacagcaa cgaacccact aacagtagaa     600
```

-continued

```
gtaccataca tttgtacaaa aggagaagac caaattactg tttgggggtt ccattctgat    660
aacaaaatcc aaatgaaaaa cctctatgga gactcaaatc ctcaaaagtt cacctcatct    720
gccaatggaa taaccacaca ttatgttct cagattggtg gcttcccaaa tcaaacagaa    780
gacggagggc taccacaaag cggcagaatt gttgttgatt acatggtgca aaaacctggg    840
aaaacaggaa caattgtcta tcaaagaggt gttttgttgc ctcaaaaggt gtggtgtgca    900
agtggcagga gcaaggtaat aaagggtcc ttgcctttaa ttggtgaagc agattgcctt    960
cacgaaaaat acggtggatt aaacaaaagc aagccttact acacaggaga acatgcaaaa   1020
gccataggaa attgcccaat atgggtgaaa acacctttaa agcttgccaa tggaaccaaa   1080
tatagacctc ccgcaaaact attaaaggaa aagggtttct tcggagctat tgctggtttc   1140
ttagaaggag gatgggaagg aatgattgca ggttggcacg gatacacatc tcatggagca   1200
catggggtgg cagtggcagc agaccttaag agtacgcaag aagccataaa caagataaca   1260
aaaaatctca attctttgag tgagctagaa gtaaagaatc ttcaaagact aagtggtgcc   1320
atggatgaac tccacaacga aatactcgag ctggatgaga agtggatga tctcagagct   1380 gacacaataa gctcgcaaat agagcttgca gtcttgcttt ccaatgaagg aataataaac   1440
agtgaagatg agcatctatt ggcacttgag agaaaactaa agaaaatgct gggtccctct   1500
gctgtagaca tagggaatgg atgcttcgaa accaaacaca agtgcaacca gacctgctta   1560
gacaggatag ctgctggcac ctttaatgca ggagaatttt ctcttcccac ttttgattca   1620
ctgaatatta ctgctgcatc tttaaatgat gatggattgg ataatcatac tatactgctc   1680
tactactcaa ctgcggcttc tagtttggct gtaacattga tgatagctat ttttattgtt   1740
tatatggtct ccagagacaa tgtttcttgc tccatctgtc tatagggaaa attgagccct   1800
gtattttcct ttattgtggt gcttgtttgc ttgttgccat tacagagaaa cgttattgaa   1860
aaatgctctt gttactact                                               1879
```

```
<210> SEQ ID NO 22
<211> LENGTH: 1554
<212> TYPE: DNA
<213> ORGANISM: influenza B virus

<400> SEQUENCE: 22
```

```
agcagaagca gagcatcttc tcaaaactga agtaaagagg ccaaaaatga acaatgctac     60
cttcaactat acaaacgtta accctatttc tcacatcagg gggagtgtta ttatcactat    120
atgtgtcagc cttactgtca tacttattgt attcggatat attgctaaaa ttttcaccaa    180
aaataattgc accaacaacg tcgttggact gcgcgaacgc atcaaatgtt caggctgtga    240
accattctgc aacaaaagag atgaaattcc ttcccccaga accggagtgg ataacccccc    300
gtttatcttg ccagggttca accttccaga aagcactctt aattagccct catagatttg    360
gagaagccaa aggaaactca gctcccttga taataaggga accttttatt gcttgtggac    420
caaaggagtg caaacacttt gctctaaccc attatgcagc tcaaccaggg ggatactaca    480
atggaacaag agaggacaga aacaagctga ggcatctgat tcagtcaac ttaggcaaaa    540 tcccaactgt agaaaactcc attttccata tggcagcttg gagtggatcc gcatgccatg    600
atggtagaga atggacatat atcggagttg atggtcctga cagtaatgca ttgatcaaaa    660
taaaatatgg agaagcatac actgacacat accattccta tgcaaacaac atcctaagaa    720
cacaagaaag tgcctgcaat tgcatcgggg gagattgtta tcttatgata actgatggct    780
cagcttcagg aattagtaaa tgcagattcc ttaagatccg agagggtcga ataataaaag    840
```

-continued

```
aaatatttcc aacaggaagg gtagagcaca ctgaagaatg cacatgcgga tttgccagca     900
acaaaaccat agaatgtgcc tgtagagata acagttacac agcaaaaaga ccctttgtca     960
aattaaatgt ggagactgat acagctgaaa taagattgat gtgcacagag acttatttgg    1020
acacccccag accagatgat ggaagcataa cagggccttg cgaatctaat ggggacaaag    1080
ggagtggagg tgtcaaggga ggatttgttc atcaaagaat ggcatccaag attggaagat    1140
ggtactcccg aacgatgtct aaaactaaaa gaatggggat ggaactgtat gtcaagtatg    1200
atggagaccc atggactgac agtgacgccc ttgctcctag tggagtaatg gtctcaatgg    1260
aagaacctgg ttggtactct ttcggcttcg aaataaaaga taagaaatgt gatgtcccct    1320
gtattgggat agagatggta catgatggtg gaaaaaggac ttggcactca gcagcaacag    1380
ccatttactg tttaatgggc tcaggacagt tgctatggga cactgtcaca ggtgttaata    1440
tggctctgta atggaggaat ggttgaatct gttctaaacc ctttgttcct attttatttg    1500
aacaattgtc cttactggac ttaattgttt ctgaaaaatg ctcttgttac tact          1554
```

<210> SEQ ID NO 23
<211> LENGTH: 1881
<212> TYPE: DNA
<213> ORGANISM: influenza B virus

<400> SEQUENCE: 23

```
agcagaagca gagcattttc taatatccac aaaatgaagg caataattgt actactcatg      60
gtagtaacat ccaatgcaga tcgaatctgc actgggataa catcgtcaaa ctcacctcat     120
gtggtcaaaa cagctactca aggggaggtc aatgtgactg gtgtgatacc actgacaaca     180
acaccaacaa aatctcattt tgcaaatctc aaaggaacaa agaccagagg gaaactatgc     240
ccaacctgtc tcaactgcac agatctggat gtggccttag gcagaccaat gtgtgtgggg     300
gtcacacctt cggcaaaagc ttcaatactc cacgaagtca ggcctgttac atccggatgc     360
tttcctataa tgcacgacag aacaaaaatc agacagctac ccaatcttct cagaggatat     420
gaaaaaatca gattatcaac ccaaatcgtt atcaacgcag aaaaggcacc aggaggaccc     480
tacagacttg gaacctcagg atcttgccct aacgctacca gtagaagcgg atttttcgca     540
acaatggctt gggctgtccc aaaggacaac aacaaaacag caacgaatcc actaacagta     600
gaagtaccac acatctgtac aaaagaagaa gaccaaatta ctgtttgggg gttccattct     660
gatgacaaaa cccaaatgaa aaacctctat ggagactcaa atcctcaaaa gttcacctca     720
tctgctaatg gagtaaccac acattatgtt tctcagattg gcggcttccc ggatcaaaca     780
gaagacggag ggctaccaca aagcggcaga attgttgttg attacatggt gcaaaaacct     840
gggaaaacag gaacaattgt ctatcaaaga ggtattttgt tgcctcaaaa ggtgtggtgc     900
gcgagtggca ggagcaaagt aataaaaggg tccttgcctt taattggtga agcagattgc     960
cttcacgaaa aatacggtgg attaaacaaa agcaagcctt actacacagg agaacatgca    1020
aaagccatag gaaattgccc aatatgggtg aaaacacctt tgaagcttgc caatggaacc    1080
aaatatagac ctcctgcaaa actattaaag gaaagggggtt tcttcggagc tattgctggt   1140
ttcttagaag gaggatggga aggaatgatt gcaggttggc acggatacac atctcacgga    1200
gcacatggag tggcagtggc agcagacctt aagagtacgc aagaagccat aaacaagata    1260
acaaaaaatc tcaattcttt gagtgagcta gaagtaaaga atcttcaaag actaagtggt    1320
gccatggatg aactccacaa cgaaatactc gagctggatg agaaagtgga tgatctcaga    1380
```

```
gctgacacaa taagctcaca aatagaactt gcagtcttgc tttccaacga aggaataata    1440
aacagtgaag atgagcatct attggcactt gagagaaaac taaagaaaat gctgggtccc    1500
tctgctgtag acatagggaa tggatgcttc gaaaccaaac acaagtgcaa ccagacctgc    1560
ttagacagga tagctgctgg cacctttaat gcaggagaat tttctcttcc cacttttgat    1620
tcactgaata ttactgctgc atctttaaat gatgatggat tggataacca tactatactg    1680
ctctactact caactgctgc ttctagtttg gctgtaacat tgatgatagc tatttttatt    1740
gtttatatga tctccagaga caatgtttct tgctccatct gtctataggg aaattaagcc    1800
ctgtattttc ctttattgta gtgcttgttt gcttgttatc attacaaaga aacgttattg    1860
aaaaatgctc ttgttactac t                                              1881

<210> SEQ ID NO 24
<211> LENGTH: 1557
<212> TYPE: DNA
<213> ORGANISM: influenza B virus

<400> SEQUENCE: 24
agcagaagca gagcatcttc tcaaaactga ggcaaatagg ccaaaaatga caatgctac      60 cttcaactat acaaacgtta accctatttc tcacatcagg gggagtgtta ttatcactat     120
atgtgtcagc ttcactgtca tacttactat attcggatat attgctaaaa ttttcaccaa     180
cagaaataac tgcaccaaca atgccattga attgtgcaaa cgcatcaaat gttcaggctg     240
tgaaccgttc tgcaacaaaa ggggtgacac ttcctctccc agaaccggag tggacatacc     300
ctcgtttatc ttgcccgggc tcaacctttc agaaagcact cctaattagc cctcatagat     360
tcggagaaac caaggaaac tcagctccct tgataataag ggaaccttt attgcttgtg      420 gaccaaagga atgcagacac tttgctctaa cccattatgc agcccaacca ggggatact       480 acaatggaac aagagaagac agaaacaagc tgaggcatct aatttcagtc aaattgggca      540
aaatcccaac agtagaaaac tccatttcc acatggcagc ttggagcggg tccgcatgcc      600
atgatggtag agaatggaca tatatcggag ttgatggccc tgacagtaat gcattgctca      660
aaataaaata tggagaagca tatactgaca catacaattc ctatgcaaac aacatcctaa      720
gaacacaaga aagtgcctgc aattgcatcg ggggagattg ttatcttatg ataactgatg      780
gctcagcttc aggattagt gaatgcagat ttcttaagat tcgagagggc cgaataataa      840
aagaaatatt tccaacagga agagtagaac atactgaaga atgcacatgc ggatttgcca      900
gcaataaaac catagaatgt gcctgtagag ataacagtta cacagcaaaa agacctttg      960 tcaaattaaa tgtggagact gatacagcag aaataagatt gatgtgcaca gagacttact     1020
tggacacccc cagaccagat gatggaagca taacaggcc ttgtgaatct aatgggata      1080 aagggagtgg aggcatcaag ggaggatttg ttcatcaaag aatggcatcc aagattggaa     1140
ggtggtactc tcgaacgatg tctaaaacta aaaggatggg gatgggactg tatgtcaagt     1200
atgatggaga cccatggatt gacagtgatg cccttactct agcggagta atggtttcaa      1260 tggaagaacc tggttggtat tcctttggct tcgaaataaa agataagaaa tgtgatgtcc     1320
cctgtattgg gatagagatg gtacatgatg gtggaaagaa gacttggcac tcagcagcaa     1380
cagccattta ctgtttaatg ggctcaggac aactgctatg ggacactgtc acaggcgttg      1440
atatggctct gtaatggagg aatggttgag tctgttctaa acccttttgtt cctattttgt      1500 ttgaacaatt gtccttactg aacttaattg tttctgaaaa atgctcttgt tactact        1557
```

<210> SEQ ID NO 25
<211> LENGTH: 1882
<212> TYPE: DNA
<213> ORGANISM: influenza B virus

<400> SEQUENCE: 25

```
agcagaagca gagcattttc taatatccac aaaatgaagg caataattgt actactcatg      60
gtagtaacat ccaatgcaga tcgaatctgc actgggataa catcgtcaaa ctcacctcat     120
gtggtcaaaa cagctactca aggggaggtc aatgtgactg gtgcgatacc attgacaaca    180
acaccaacaa aatctcattt tgcaaatctc aaaggaacaa agaccagagg gaaactatgc    240
ccaacctgtc tcaactgcac agatctggat gtggccttgg cagaccaat gtgtgtgggg     300
atcacacctt cggcaaaagc ttcaatactc acgaagtca gacctgttac atccggatgc     360
tttcctataa tgcacgacag aacaaaaatc agacagctac ccaatcttct cagaggatat    420
gaaaaaatca gattatcaac ccaaaacgtt atcaacgcag aaaaggcacc aggaggaccc    480
tacagacttg aacttcagg atcttgccct aacgctacca gtaaaagcgg atttttcgca     540
acaatggctt gggctgtccc aagggacaac aacaaaacag caacgaatcc actaacagta    600
gaagtaccac acatctgtac aaaagaagaa gaccaaatta ctgtttgggg gttccattct    660
gatgacaaaa cccaaatgaa aaacctctat ggagactcaa atcctcaaaa gttcacctca    720
tctgctaatg gaataaccac acattatgtt tctcagattg gcggcttccc ggaccaaaca    780
gaagacggag gctaccaca agcggcaga attgttgttg attacatggt gcaaaaaccct    840
gggaaaacag gaacaattgt ctatcaaaga gggatcttgt tgcctcaaaa ggtgtggtgc    900
gcgagtggca ggagcaaagt aataaaaggg tccttgcctt taattggtga agcagattgc    960
cttcacgaaa atacggtgg attaaacaaa gcaagcctt actacacagg agaacatgca    1020
aaagccatag gaaattgccc aatatgggtg aaaacacctt tgaagcttgc caatggaacc    1080
aagtatagac tcctgcaaa actattaaag gaagggggtt tcttcggagc tattgctggt    1140
ttcttagaag gaggatggga aggaatgatt gcaggttggc acggatacac atctcacgga    1200
gcacacgag tggcagtggc agcagacctt aagagtacgc aagaagccat aaacaagata    1260
acaaaaaatc tcaattcttt gagtgagtta gaagtaaaga accttcaaag actaagtggt    1320
gccatggatg aactccataa cgaaatactc gagctggatg agaaagtgga tgatctcaga    1380
gctgacacaa taagctcaca aatagaactt gcagtcttgc tttccaacga aggaataata    1440
aacagtgaag atgagcatct attggcactt gagagaaaac taagaagat gctgggtccc    1500
tctgctatag acataggaa tggatgcttc gaaaccaaac acaagtgcaa ccagacctgc    1560
ttagacagga tagctgctgg caccttaat gcagagaat tttctcttcc cacttttgat    1620
tcactgaaca ttactgctgc atctttaaat gatgatggat tggataacca tactatactg    1680
ctctactact caactgctgc ttcagtttg gctgtaacat tgatgatagc tatttttatt    1740
gtttatatga tctccagaga caatgtttct tgctccatct gtctataagg aaaattaagc    1800
cctgtatttt cctttattgt agtgcttgtt tgcttgttat cattacaaag aaacgttatt    1860
gaaaaatgct cttgttacta ct                                            1882
```

<210> SEQ ID NO 26
<211> LENGTH: 1557
<212> TYPE: DNA
<213> ORGANISM: influenza B virus

<400> SEQUENCE: 26

-continued

```
agcagaagca gagcatcttc tcaaaactga ggcaaatagg ccaaaaatga acaatgctac      60
cctcaactat acaaacgtta accctattcc tcacatcagg gggagtgtta ttatcactat     120
atgtgtcagc ttcactgtca tacttactat attcggatat attgctaaaa ttttcaccaa     180
cagaaataac tgcaccagca atgcccttgg attgtgcaaa cgcatcaaat gttcaggctg     240
tgaaccgttc tgcaacaaaa ggggtgacac ttcttctccc agaaccggag tggacatacc     300
cgcgtttatc ttgcccgggc tcaacctttc agaaagcact cctaattagc cctcatagat     360
tcggagaaac caaaggaaac tcagctccct tgataataag ggaacctttt attgcttgtg     420
gaccaaagga atgcaaacac tttgctctaa cccattatgc agcccaacca ggggggatact    480 acaatggaac aagagaagac agaaacaagc taaggcatct aatttcagtc aaatttggta     540
aaatcccaac agtagaaaac tccattttcc acatggcagc atggagcggg tccgcatgcc     600
atgatggtaa agaatggaca tatatcggag ttgatggccc tgacagtaat gcattgctca     660
aaataaaata tggagaagca tatactgaca cataccattc ctatgcaaac aacatcctaa     720
gaacacaaga aagtgcctgc aattgcatcg gggaaattg ttatcttatg ataactgatg      780
gctcagcttc aggtattagt gagtgcagat ttcttaagat tcgagagggc cgaataataa     840
aagaaatatt tccaacagga agagtaaaac atactgaaga atgcacatgc ggatttgcca     900
gcaataaaac catagaatgt gcctgtagag ataacagtta cacagcaaaa agaccctttg     960
tcaaattaaa tgtggagact gatacagcag aaataagatt gatgtgcaca gagacttatt    1020
tggacacccc cagaccagat gatggaagca taacagggcc ttgtgaatct aatggggata    1080
aagggagtgg aggcatcaag ggaggatttg ttcatcaaag aatggcatcc aagattggaa    1140
ggtggtactc tcgaacaatg tctaaaacta aaaggatggg gatgggactg tatgtcaagt    1200
atgatggaga cccatggact gacagtgatg cccttgctct tagtggagta atggtttcaa    1260
tggaagaacc tggttggtac tcctttggct tcgaaataaa agataagaaa tgtgatgtcc    1320
cctgtattgg gatagagatg gtacatgatg gtggaaagga gacttggcac tcagcagcaa    1380
cagccattta ctgtttaatg ggctcaggac aactgctatg ggacactgtc acaggtgttg    1440
atatggctct gtaatggagg aatggttgag tctgttctaa accctttgtt cctattttgt    1500
ttgaacaatt gtccttactg aacttaattg tttctgaaaa atgctcttgt tactact       1557

<210> SEQ ID NO 27
<211> LENGTH: 1879
<212> TYPE: DNA
<213> ORGANISM: influenza B virus
<400> SEQUENCE: 27
agcagaagca gagcattttc taatatccac aaaatgaagg caataattgt actactcatg      60
gtagtaacat ccaacgcaga tcgaatctgc actgggataa catcttcaaa ctcacctcat     120
gtggtcaaaa cagctactca aggggaagtc aatgtgactg gtgtgatacc actgacaaca     180
acaccaacaa aatctcattt tgcaaatctc aaaggaacaa agaccagagg gaaactatgc     240
ccaaactgtc tcaactgcac agatctggat gtggccttgg gcagaccaat gtgtataggg     300
atcacacctt cggcaaaagc ttcaatactc cacgaagtca gacctgttac atccgggtgc     360
tttcctataa tgcacgacag aacaaaaatc agacagctac ccaatcttct cagaggatat     420
gaacatatca gattatcaac ccataacgtt atcaacgcag aaagggcacc aggaggaccc     480
tacagacttg gaacctcagg atcttgccct aacgttacca gtagaagcgg attcttcgca     540
acaatggctt gggctgtccc aagggacaac aaaacagcaa cgaacccact aacagtagaa     600
```

-continued

```
gtaccataca tttgtacaaa aggagaagac caaattactg tttgggggtt ccattctgat    660
aacaaaatcc aaatgaaaaa cctctatgga gactcaaatc ctcaaaagtt cacctcatct    720
gccaatggaa taaccacaca ttatgttttct cagattggtg gcttcccaaa tcaaacagaa   780
gacggagggc taccacaaag cggcagaatt gttgttgatt acatggtgca aaaacctggg    840
aaaacaggaa caattgtcta tcaaagaggt gttttgttgc ctcaaaaggt gtggtgtgca    900
agtggcagga gcaaggtaat aaaagggtcc ttgcctttaa ttggtgaagc agattgcctt    960
cacgaaaaat acggtggatt aaacaaaagc aagccttact acacaggaga acatgcaaaa    1020
gccataggaa attgcccaat atgggtgaaa acaccttttaa agcttgccaa tggaaccaaa   1080
tatagacctc ccgcaaaact attaaaggaa aagggtttct tcggagctat tgctggtttc    1140
ttagaaggag gatgggaagg aatgattgca ggttggcacg gatacacatc tcatggagca    1200
catggggtgg cagtggcagc agaccttaag agtacgcaag aagccataaa caagataaca    1260
aaaaatctca attctttgag tgagctagaa gtaaagaatc ttcaaagact aagtggtgcc    1320
atggatgaac tccacaacga atactcgag ctggatgaga aagtggatga tctcagagct     1380
gacacaataa gctcgcaaat agagcttgca gtcttgcttt ccaatgaagg aataataaac    1440
agtgaagatg agcatctatt ggcacttgag agaaaaactaa agaaaatgct gggtccctct    1500
gctgtagaca tagggaatgg atgcttcgaa accaaacaca agtgcaacca gacctgctta    1560
gacaggatag ctgctggcac ctttaatgca ggagaatttt ctcttcccac ttttgattca    1620
ctgaatatta ctgctgcatc tttaaatgat gatggattgg ataatcatac tatactgctc    1680
tactactcaa ctgcggcttc tagtttggct gtaacattga tgatagctat ttttattgtt    1740
tatatggtct ccagagacaa tgtttcttgc tccatctgtc tatagggaaa attgagccct    1800
gtattttcct ttattgtggt gcttgtttgc ttgttgccat tacagagaaa cgttattgaa    1860
aaatgctctt gttactact                                                1879
```

<210> SEQ ID NO 28
<211> LENGTH: 1554
<212> TYPE: DNA
<213> ORGANISM: influenza B virus

<400> SEQUENCE: 28

```
agcagaagca gagcatcttc tcaaaactga agtaaagagg ccaaaaatga acaatgctac     60
cttcaactat acaaacgtta accctatttc tcacatcagg gggagtgtta ttatcactat    120
atgtgtcagc cttactgtca tacttattgt attcggatat attgctaaaa ttttcaccaa    180
aaataattgc accaacaacg tcgttggact gcgcgaacgc atcaaatgtt caggctgtga    240
accattctgc aacaaaagag atgaaattcc ttcccccaga accggagtgg acataccccc    300
gtttatcttg ccagggttca accttccaga aagcactctt aattagccct catagatttg    360
gagaagccaa aggaaactca gctcccttga taataaggga accttttatt gcttgtggac    420
caaaggagtg caaacacttt gctctaaccc attatgcagc tcaaccaggg ggatactaca    480
atggaacaag agaggacaga aacaagctga ggcatctgat ttcagtcaac ttaggcaaaa    540
tcccaactgt agaaaactcc atttttccata tggcagcttg gagtggatcc gcatgccatg    600
atggtagaga atggacatat atcggagttg atggtcctga cagtaatgca ttgatcaaaa    660
taaaatatgg agaagcatac actgacacat accattccta tgcaacaac atcctaagaa    720
cacaagaaag tgcctgcaat tgcatcgggg gagattgtta tcttatgata actgatggct    780
```

-continued

```
cagcttcagg aattagtaaa tgcagattcc ttaagatccg agagggtcga ataataaaag    840
aaatatttcc aacaggaagg gtagagcaca ctgaagaatg cacatgcgga tttgccagca    900
acaaaaccat agaatgtgcc tgtagagata acagttacac agcaaaaaga ccctttgtca    960
aattaaatgt ggagactgat acagctgaaa taagattgat gtgcacagag acttatttgg   1020
acacccccag accagatgat ggaagcataa cagggccttg cgaatctaat ggggacaaag   1080
ggagtggagg tgtcaaggga ggatttgttc atcaaagaat ggcatccaag attggaagat   1140
ggtactcccg aacgatgtct aaaactaaaa gaatggggat ggaactgtat gtcaagtatg   1200
atggagaccc atggactgac agtgacgccc ttgctcctag tggagtaatg gtctcaatgg   1260
aagaacctgg ttggtactct ttcggcttcg aaataaaaga taagaaatgt gatgtcccct   1320
gtattgggat agagatggta catgatggtg gaaaaaggac ttggcactca gcagcaacag   1380
ccatttactg tttaatgggc tcaggacagt tgctatggga cactgtcaca ggtgttaata   1440
tggctctgta atggaggaat ggttgaatct gttctaaacc ctttgttcct attttatttg   1500
aacaattgtc cttactggac ttaattgttt ctgaaaaatg ctcttgttac tact         1554
```

<210> SEQ ID NO 29
<211> LENGTH: 1885
<212> TYPE: DNA
<213> ORGANISM: influenza B virus

<400> SEQUENCE: 29

```
agcagaagca gagcattttc taatatccac aaaatgaagg caataattgt actactcatg     60
gtagtaacat ccaatgcaga tcgaatctgc actggaataa catcgtcaaa ctcacccccat   120 gtggtcaaaa ctgctactca aggggaagtc aatgtgactg gtgtgatacc actgacaaca    180
acacccacca aatctcattt tgcaaatctc aaaggaacaa aaaccagagg gaaactatgc    240
ccaaaatgtc tcaactgcac agatctggac gtggccttgg gcagaccaaa atgcacgggg    300
aacatacctt cggcaaaagt ttcaatactc catgaagtaa gacctgttac atctgggtgc    360
tttcctataa tgcacgacag aacaaaaatt agacagctgc ccaatcttct cagaggatac    420
gaacgtatca ggttatcaaa ccataacgtt atcaatgcag aaaaagcacc aggaggaccc    480
tacaaaattg gaacctcagg gtcttgccct aacgttacca atggaaacgg attcttcgca    540
acaatggctt gggctgtccc aaaaaacgaa aacaacaaaa cagcaacaaa ttcattaaca    600
atagaagtac catacatttg tacagaagga gaagaccaaa ttaccgtttg gggttccac     660 tctgatagcg aaacccaaat ggcaaaactc tatggagact caaagcctca gaagttcact    720
tcatctgcta acggagtgac cacacattac gtttcacaga ttggtggctt cccaaatcaa    780
acagaagacg gaggactacc acaaagtggt agaattgttg ttgattacat ggtgcaaaaa    840
tctggaaaaa caggaacaat tacctatcaa agaggtattt tattgcctca aaaagtgtgg    900
tgcgcaagtg gcaggagcaa ggtaataaaa ggatccttgc ctttaattgg agaagcagat    960
tgcctccacg aaaaatacgg tggattaaac aaaagcaagc cttactatac aggggaacat   1020
gcaaaagcca taggaaattg cccaatatgg gtgaaaacac ccttgaagct ggccaatgga   1080
accaaatata gacctcctgc aaaactatta aaggaaaggg gtttcttcgg agctattgct   1140
ggtttcttag aaggaggatg ggaaggaatg attgcaggtt ggcacggata cacatcccat   1200
ggagcacatg gagtagcagt ggcagcagac cttaagagta ctcaagaagc cataaacaag   1260
atcacaaaaa atctcaactc tttgagtgag ctggaagtaa agaatcttca aagactaagc   1320
ggagccatgg atgaactcca caacgaaata ctagaactag atgagaaagt ggatgatctc   1380
```

-continued

```
agagctgata caataagctc gcaaatagaa ctcgcagtct tgctttccaa tgaaggaata   1440
ataaacagtg aagatgagca tctcttggcg cttgaaagaa aactgaagaa aatgctgggc   1500
ccctctgctg tagagatagg gaatggatgc ttcgaaacca aacacaagtg caaccagacc   1560
tgcctcgata gaatagctgc tggcaccttt aatgcaggag aattttctct ccccaccttt   1620
gattcactaa atattactgc tgcatcttta aatgacgatg gattggataa tcatactata   1680
ctgctttact actcaactgc tgcttccagt ttggctgtaa cattgatgat agctatcttt   1740
gttgtttata tggtctccag agacaatgtt tcttgttcca tctgtctata aggaaagtta   1800
agccccgtat tttcctttat tgtagtactt gtttgcttgt tatcattaca aaaaaacgtt   1860
attgaaaaat gctcttgtta ctact                                          1885
```

<210> SEQ ID NO 30
<211> LENGTH: 1544
<212> TYPE: DNA
<213> ORGANISM: influenza B virus

<400> SEQUENCE: 30

```
agcagagcat cttctcaaaa ctgaagcaaa taggccaaaa tgaacaatgc taccctcaac     60
tatacaaaca ttaaccctat ttctcacatc agggggagtg ttattatcac tatatgtgtc    120
agccttactg tcatacttac tgtattcgga tatattgcta aaattttcac caacaaaaat    180
aattgcacca acaacgtcgt tggactccgc gaacgcatca aattttcagg ccgtgaacca    240
ttctgcaaca aaagagatga catttcttct cccagaaccg gagtggacat accctcgttt    300
atcttgccag ggttcaacct ttcaaaaagc actcctaatt agccctcata gattcggaga    360
agccaaagga aactcagctc ccttgataat aagggaacct tttattgctt gtggaccaaa    420
ggagtgtaaa cactttgctc taacccatta tgcagctcaa ccagggggat actacaatgg    480
aacaagagag gacagaaaca agctgaggca tctgatttca gtcaacttag gcaaaatacc    540
aactgtagaa aactccattt tccacatggc agcttggagt gggtccgcat gccatgatgg    600
tagagagtgg acttatatcg gagttgatgg ccctgacagt aatgcattga tcaaaataaa    660
atatggagaa gcatacactg acacatacca ttcctatgca aacaacatcc taagaacaca    720
agaaagtgcc tgcaactgca tcgggggaga ttgttatctt atgataactg atggctcagc    780
ttcaggaatt agtaaatgca gattccttaa gattcgagag ggtcgaatag taaaagaaat    840
atttccaaca ggaagagtag agcatactga agaatgcaca tgcggatttg ccagcaataa    900
aaccatagaa tgtgcctgta gagataacag ttacacagca aaaagaccct ttgtcaaatt    960
aaatgtggaa actgatacag cagaaataag attgatgtgc acagagactt atttggacac   1020
ccccagacca gatgatggaa gcataacagg gccttgcgaa tctaatgggg acaaagggag   1080
tggaggtatc aagggaggat ttgtccatca aagaatggca tccaagattg gaagatggta   1140
ctctcgaacg atgtctaaaa ctaaaagaat ggggatggaa ctgtatgtca agtatgatgg   1200
agacccatgg actgacagtg atgcccttgc tcctagtgga gtaatggtct caatagaaga   1260
acctggttgg tattctttcg gcttcgaaat aaaagataag aaatgcgatg tcccctgtat   1320
tgggatagag atggtacacg atggtggaaa aacaacttgg cactcagcag caacagccat   1380
ttactgttta atgggctcag gacagttgct atgggacact atcacaggtg ttgatatggc   1440
tctgtaatgg aggaatggtt gaatctgttc taaacccttt gttcctattt tgtttgaaca   1500
attgtcctta ctggacttaa ttgtttctga aaaatgctct tgtt                    1544
```

<210> SEQ ID NO 31
<211> LENGTH: 1885
<212> TYPE: DNA
<213> ORGANISM: influenza B virus

<400> SEQUENCE: 31

| | | | | |
|---|---|---|---|---|
| agcagaagca | gagcattttc | taatatccac | aaaatgaagg | caataattgt actactcatg | 60 |
| gtagtaacat | ccaatgcaga | tcgaatctgc | actgggataa | catcgtcaaa ctcacccat | 120 |
| gtggtcaaaa | ctgctactca | aggggaggtc | aatgtgactg | gtgtgatacc actgacaaca | 180 |
| acacccacca | aatctcattt | tgcaaatctc | aaaggaacaa | aaaccagagg gaaactatgc | 240 |
| ccaaaatgcc | tcaactgcac | agatctggac | gtggccttgg | gcagaccaaa atgcacgggg | 300 |
| aacatacccct | cggcaaaagt | ttcaatactc | catgaagtca | gacctgttac atctgggtgc | 360 |
| tttcctataa | tgcacgacag | aacaaaaatt | agacagctgc | ccaatcttct cagaggatac | 420 |
| gaacatatca | ggttatcaac | tcataacgtt | atcaatgcag | aaaaggcacc aggaggaccc | 480 |
| tacaaaattg | gaacctcagg | gtcttgccct | aacgttacca | atggaaacgg atttttcgca | 540 |
| acaatggctt | gggccgtccc | aaaaaacgac | aacaacaaaa | cagcaacaaa ttcattaaca | 600 |
| atagaagtac | catacatttg | tacagaagga | gaagaccaaa | ttaccgtttg ggggttccac | 660 |
| tctgataacg | aagcccaaat | ggcaaaactc | tatgggact | caaagcccca gaagttcacc | 720 |
| tcatctgcca | acggagtgac | cacacattac | gtttcacaga | ttggtggctt cccaaatcaa | 780 |
| acagaagacg | gaggactacc | acaaagtggt | agaattgttg | ttgattacat ggtgcaaaaa | 840 |
| tctgggaaaa | caggaacaat | tacctatcaa | agaggtattt | tattgcctca aaaagtgtgg | 900 |
| tgcgcaagtg | gcaggagcaa | ggtaataaaa | ggatccttgc | cttaattgg agaagcagat | 960 |
| tgcctccacg | aaaaatacgg | tggattaaac | aaaagcaagc | cttactacac aggggaacat | 1020 |
| gcaaaggcca | taggaaaattg | cccaatatgg | gtgaaaacac | ccttgaagct ggccaatgga | 1080 |
| accaaatata | gacctcctgc | aaaactatta | aaggaaagag | gtttcttcgg agctattgct | 1140 |
| ggtttcttag | aaggaggatg | ggaaggaatg | attgcaggtt | ggcacggata cacatcccat | 1200 |
| ggggcacatg | gagtagcagt | ggcagcagac | cttaagagta | ctcaagaagc cataaacaag | 1260 |
| ataacaaaaa | atctcaactc | tttgagtgag | ctggaagtaa | agaatcttca agactaagc | 1320 |
| ggtgccatgg | atgaactcca | caacgaaata | ctagaactag | acgagaaagt ggatgatctc | 1380 |
| agagctgata | caataagctc | acaaatagaa | ctcgcagtct | tgctttccaa tgaaggaata | 1440 |
| ataaacagtg | aagatgagca | tctcttggcg | cttgaaagaa | agctgaagaa atgctgggc | 1500 |
| ccctctgctg | tagagatagg | gaatggatgc | ttcgaaacca | acacaagtg caaccagacc | 1560 |
| tgtctcgaca | gaatagctgc | tggtacctt | gatgcaggag | aattttctct ccccactttt | 1620 |
| gattcactga | atattactgc | tgcatcttta | aatgacgatg | gattggataa tcatactata | 1680 |
| ctgctttact | actcaactgc | tgcctccagt | ttggctgtaa | cattgatgat agctatcttt | 1740 |
| gttgtttata | tggtctccag | agacaatgtt | tcttgctcca | tctgtctata aggaaagtta | 1800 |
| agccctgtat | tttcctttat | tgtagtgctt | gtttgcttgt | taccattaca aaaaacgtt | 1860 |
| attgaaaaat | gctcttgtta | ctact | | | 1885 |

<210> SEQ ID NO 32
<211> LENGTH: 1557
<212> TYPE: DNA
<213> ORGANISM: influenza B virus

<400> SEQUENCE: 32

-continued

| | |
|---|---|
| agcagaagca gagcatcttc tcaaaactga ggcaaatagg ccaaaaatga acaatgctac | 60 |
| cttcaactat acaaacgtta accctatttc tcacatcagg gggagtatta ttatcactat | 120 |
| atgtgtcagc ttcattgtca tacttactat attcggatat attgctaaaa ttctcaccaa | 180 |
| cagaaataac tgcaccaaca atgccattgg attgtgcaaa cgcatcaaat gttcaggctg | 240 |
| tgaaccgttc tgcaacaaaa ggggtgacac ttcttctccc agaaccagag tggacatacc | 300 |
| cgcgtttatc ttgcccgggc tcaacctttc agaaagcact cctaattagc cctcatagat | 360 |
| tcggagaaac caaggaaac tcagctccct tgataataag ggaacctttt attgcttgtg | 420 |
| gaccaaagga atgcaaacac tttgctctaa cccattatgc agcccaacca ggggatact | 480 |
| acaatggaac aagaggagac agaaacaagc tgaggcatct aatttcagtc aaattgggca | 540 |
| aaatcccaac agtagaaaac tccatttcc acatggcagc atggagcggg tccgcatgcc | 600 |
| atgatggtaa agaatggaca tatatcgag ttgatggccc tgacaataat gcattgctca | 660 |
| aaataaaata tggagaagca tatactgaca cataccattc ctatgcaaac aacatcctaa | 720 |
| gaacacaaga aagtgcctgc aattgcatcg ggggaaattg ttatcttatg ataactgatg | 780 |
| gctcagcttc aggtattagt gaatgcagat ttcttaaaat tcgagagggc cgaataataa | 840 |
| aagaaatatt tccaacagga agagtaaaac atactgaaga atgcacatgc ggatttgcca | 900 |
| gcaataagac catagaatgt gcctgtagag ataacagtta cacagcaaaa agacctttg | 960 |
| tcaaattaaa cgtggagact gatacagcag aaataagatt gatgtgcaca gagacttatt | 1020 |
| tggacacccc cagaccagat gatggaagca taacaggccc ttgtgaatct aatgggggaca | 1080 |
| aagggagtgg aggcatcaag ggaggatttg ttcatcaaag aatggcatcc aagattggaa | 1140 |
| ggtggtactc tcgaacgatg tctaaaacta aaaggatggg gatgggactg tatgtcaagt | 1200 |
| atgatggaga cccatgggct gacagtgatg cccttgctct tagtggagta atggtttcaa | 1260 |
| tggaagaacc tggttggtac tcctttggct tcgaaataaa agataagaaa tgtgatgtcc | 1320 |
| cctgtattgg aatagagatg gtacatgatg gtggaaaaga gacttggcac tcagcagcaa | 1380 |
| cagccatta ctgtttaatg ggctcaggac agctgctgtg ggacactgtc acaggtgttg | 1440 |
| atatggctct gtaatggagg aatggttgag tctgttctaa acccttgtt cctattttgt | 1500 |
| ttgaacaatt gtccttactg aacttaattg tttctgaaaa atgctcttgt tactact | 1557 |

<210> SEQ ID NO 33
<211> LENGTH: 1853
<212> TYPE: DNA
<213> ORGANISM: influenza B virus

<400> SEQUENCE: 33

| | |
|---|---|
| tctaatatcc acaaaatgaa ggcaataatt gtactactca tggtagtaac atccaatgca | 60 |
| gatcgaatct gcactgggat aacatcttca aactcacctc atgtggtcaa acagctact | 120 |
| caaggggagg tcaatgtgac tggtgtaata ccactgacaa caacaccaac aaaatcttat | 180 |
| tttgcaaatc tcaaggaac aaggaccaga gggaaactat gtccagactg tctcaactgt | 240 |
| acagatctgg atgtggcctt gggcagacca atgtgtgtgg ggaccacacc ttcggcaaaa | 300 |
| gcttcaatac tccacgaagt cagacctgtt acatccgggt gctttcctat aatgcacgac | 360 |
| agaacaaaaa tcagacaact acccaatctt ctcagaggat atgaaaatat cagattatca | 420 |
| acccaaaacg ttatcgatgc agaaaatgca ccaggaggac cctacagact ggaacctca | 480 |
| ggatcttgcc ctaacgctac cagtaaaagc ggatttttcg caacaatggc ttgggctgtc | 540 |

| | |
|---|---|
| ccaaaggaca acaacaaaaa tgcaacgaac ccactaacag tagaagtacc atacgtttgt | 600 |
| acagaagggg aagaccaaat tactgtttgg gggttccatt cagataacaa accccaatg | 660 |
| aagaacctct atggagactc aaatcctcaa aagttcacct catctgctaa tggagtaacc | 720 |
| acacattatg tttctcagat tggcggcttc ccagctcaaa cagaagacga aggactacca | 780 |
| caaagcggca gaattgttgt tgattacatg gtgcaaaaac ctaggaaaac aggaacaatt | 840 |
| gtctatcaaa gaggtgtttt gttgcctcaa aaggtgtggt gcgcgagtgg caggagcaaa | 900 |
| gtaataaaag gtccttgcc tttaattggt gaagcagatt gccttcatga aaaatacggt | 960 |
| ggattaaaca aaagcaagcc ttactacaca ggagaacatg caaaagccat aggaaattgc | 1020 |
| ccaatatggg tgaaaacacc tttgaagctt gccaatggaa ccaaatatag acctcctgca | 1080 |
| aaactattaa aggaaggggg tttcttcgga gctattgctg gtttcctaga aggaggatgg | 1140 |
| gaaggaatga ttgcaggttg gcacggatac acatctcacg gagcacatgg agtggcagtg | 1200 |
| gcggcagacc ttaagagtac gcaagaagct ataaacaaga taacaaaaaa tctcaattct | 1260 |
| ttgagtgagc tagaagtaaa gaatcttcaa agactaagtg gtgccatgga tgaactccac | 1320 |
| aacgaaatac tcgagctgga tgagaaagtg gatgatctca gagctgacac tataagctcg | 1380 |
| caaatagaac ttgcagtctt gctttccaat gaaggaataa taaacagtga agatgagcat | 1440 |
| ctattggcac ttgagagaaa actaaagaaa atgctgggtc cctctgctgt agacatagga | 1500 |
| aatggatgct tcgaaaccaa acacaagtgc aaccagacct gcttagacag gatagctgct | 1560 |
| ggcacctta atgcaggaga attttctctc cccacttttg attcactgaa cattactgct | 1620 |
| gcatctttaa atgatgatgg attggataac catactatac tgctctatta ctcaactgct | 1680 |
| gcttctagtt tggctgtaac attgatgcta gctattttta ttgtttatat ggtctccaga | 1740 |
| gacaacgttt catgctccat ctgtctataa ggaagattaa gccttgtatt ttcctttatt | 1800 |
| gtagtgcttg tttgcttgtc atcattacaa agaaacgtta ttgaaaaatg ctc | 1853 |

```
<210> SEQ ID NO 34
<211> LENGTH: 1529
<212> TYPE: DNA
<213> ORGANISM: influenza B virus

<400> SEQUENCE: 34
```

| | |
|---|---|
| tctcaaaact gaggcaaata ggccaaaaat gaacaatgct accctcaact atacaaacgt | 60 |
| taacccctatt cctcacatca gggggagtgt tattatcact atatgtgtca gcttcactgt | 120 |
| catacttact atattcggat atattgctaa aattttcaac aacagaaata actgcaccaa | 180 |
| caatgccatt ggattgtgca aacgcatcaa atgttcaggc tgtgaaccgt tctgcaacaa | 240 |
| aagggggtgac acttcttctc ccagaaccgg agtggacata cccgcgttta tcttgcccgg | 300 |
| gctcaacctt tcagaaagca ctcctaatta gccctcatag attcggagaa accaaaggaa | 360 |
| actcagctcc cttgataata agggaacctt ttattgcttg tggaccaaag gaatgcaaac | 420 |
| actttgctct aacccattat gcagcccaac caggggata ctacaatgga acaaagaag | 480 |
| acagaaacaa gctgaggcat ctaatttcag tcaaattggg caaatccca acagtagaaa | 540 |
| actccatttt ccacatggca gcatggagcg ggtccgcatg ccatgatggt aagaatgga | 600 |
| catatatcgg agttgatggc cctgacagta atgcattgct caaataaaa tatggagaag | 660 |
| catatactga cacataccat tcctatgcaa acaacatcct aagaacacaa gaaagtgcct | 720 |
| gcaattgcat cggggaaat tgttatctta tgataactga tggctcagct tcaggtatta | 780 |
| gtgagtgcag atttcttaag attcgagagg gccgaataat aaaagaaata tttccaacag | 840 |

```
gaagagtaaa acatactgaa gaatgcacat gcggatttgc cagcaataaa accatagaat      900
gtgcctgtag agataacagt tacacagcaa aaagacccttt tgtcaaatta aatgtggaga      960
ctgatacagc agaaataaga ttgatgtgca cagagactta tttggacacc cccagaccag     1020
atgatggaag cataacaggg ccttgtgaat ctaatgggaa taaagggagt ggaggcatca     1080
agggaggatt tgttcatcaa agaatggcat ccaaaattgg aagtggtac tctcgaacaa      1140 tgtctaaaac caaaaggatg ggaatgggac tgtatgtcaa gtatgatgga gacccatgga     1200
ctgacagtga tgcccttgct cttagtggag taatggtttc aatggaagaa cctggttggt     1260
actcatttgg cttcgaaata aaagataaga aatgtgatgt cccctgtatt gggatagaga     1320
tggtacatga tggtggaaag gagacttggc actcagcagc aacagccatt tactgtttaa     1380
tgggctcagg acaactgttg tgggacactg tcacaggtgt tgatatggct ctgtaatggg     1440
ggaatggttg agtctgttct aaaccctttg ttcctatttt gtttgaacaa ttgtccttgc     1500
tgaacttaat tgtttctgaa aaatgctct                                        1529

<210> SEQ ID NO 35
<211> LENGTH: 1721
<212> TYPE: DNA
<213> ORGANISM: influenza A virus

<400> SEQUENCE: 35
ctattaacca tgaagactat cattgctttg agctacattc tatgtctggt tttcgctcaa       60
aaacttcccg gaaatgacaa cagcacggca acgctgtgcc ttgggcacca tgcagtacca      120
aacggaacga tagtgaaaac aatcacgaat gaccaaattg aagttactaa tgctactgag      180
ctggttcaga gttcctcaac aggtggaata tgcgacagtc ctcatcagat ccttgatgga      240
gaaaactgca cactaataga tgctctattg ggagaccctc agtgtgatgg cttccaaaat      300
aagaaatggg accttttgt tgaacgcagc aaagcctaca gcaactgtta cccttatgat      360
gtgccggatt atgcctccct taggtcacta gttgcctcat ccggcacact ggagtttaac      420
aatgaaagct tcaattggac tggagtcact caaaatggaa caagctcttc ttgcaaaagg      480
agatctaata acagttttct tagtagattg aattggttga cccatttaaa attcaaatac      540
ccagcattga acgtgactat gccaaacaat gaaaaatttg acaaattgta catttggggg      600
gttcaccacc cgggtacgaa caatgaccaa atcagcctat atactcaagc atcaggaaga      660
atcacagtct ctaccaaaag aagccaacaa actgtaatcc cgaatatcgg atctagaccc      720
agggtaaggg atatccccag cagaataagc atctattgga caatagtaaa accgggagac      780
atacttttga ttaacagcac agggaatcta attgctcctc ggggttactt caaaatacga      840
agtgggaaaa gctcaataat gagatcagat gcacccattg gcaaatgcaa ttctgaatgc      900
atcactccaa atggaagcat tcccaatgac aaaccatttc aaaatgtaaa caggatcaca      960 tatgggcct gtcccagata tgttaagcaa aacactctga aattggcaac agggatgcga     1020
aatgtaccag agaaacaaac tagaggcata tttggcgcaa tcgcgggttt catagaaaat     1080
ggttgggagg gaatggtgga tggttggtac ggtttcaggc atcaaaattc tgagggaata     1140
ggacaagcag cagatctcaa aagcactcaa gcagcaatca accaaatcaa tgggaagctg     1200
aataggttga tcgggaaaac caacgagaaa ttccatcaga ttgaaaaaga attctcagaa     1260
gtagaaggga gaattcagga cctcgagaaa tatgttgagg acactaaaat agatctctgg     1320
tcatacaacg cggagcttct tgttgccctg gagaaccaac atacaattga tctaactgac     1380
```

-continued

| | |
|---|---|
| tcagaaatga acaaactgtt tgaaagaaca agaagcaac tgagggaaaa tgctgaggat | 1440 |
| atgggcaatg gttgtttcaa aatataccac aaatgtgaca atgcctgcat agggtcaatc | 1500 |
| agaaatggaa cttatgacca tgatgtatac agagatgaag cattaaacaa ccggttccag | 1560 |
| atcaaaggtg ttgagctgaa gtcaggatac aaagattgga tcctatggat ttcctttgcc | 1620 |
| atatcatgtt ttttgctttg tgttgctttg ttggggttca tcatgtgggc ctgccaaaaa | 1680 |
| ggcaacatta ggtgcaacat ttgcatttga gtgcattaat t | 1721 |

<210> SEQ ID NO 36
<211> LENGTH: 1426
<212> TYPE: DNA
<213> ORGANISM: influenza A virus

<400> SEQUENCE: 36

| | |
|---|---|
| atgaatccaa atcaaaagat aataacgatt ggctctgttt ctctcaccat ttccacaata | 60 |
| tgcttcttta tgcaaattgc catcttgata actactgtaa cattgcattt caagcaatat | 120 |
| gaattcaact ccccccccaaa caaccaagtg atgctgtgtg aaccaacaat aatagaaaga | 180 |
| aacataacag atagtgtta tctgaccaac accaccatag agaaggaaat atgccccaaa | 240 |
| ctagcagaat acagaaattg gtcaaagccg caatgtgaca ttacaggatt tgcaccttt | 300 |
| tctaaggaca attcgattag ctttccgct ggtggggaca tctgggtgac aagagaacct | 360 |
| tatgtgtcat gcgatcctga caaatgttat caatttgccc ttggacaggg aacaacacta | 420 |
| aacaacgtgc attcaaatga cacagtacat gataggaccc cttatcggac cctattgatg | 480 |
| aatgagttag gtgttccatt tcatctgggg actaagcaag tgtgcatagc atggtccagc | 540 |
| tcaagttgtc acgatggaaa agcatggctg catgtttgtg taacggggga tgataaaaat | 600 |
| gcaactgcta gcttcattta caatgggagg cttgtagata gtattgtttc atggtccaaa | 660 |
| gaaatcctca gaacccagga gtcagaatgc gtttgtatca atggaacttg tacagtagta | 720 |
| atgactgatg ggagtgcttc aggaaaagct gatactaaaa tactattcat tgaggagggg | 780 |
| aaaatcgttc atactagcac attgtcagga agtgcccagc atgtcgagga gtgctcctgc | 840 |
| tatcctcgat atcctggtgt cagatgtgtc tgcagagaca actggaaagg ctccaatagg | 900 |
| cccatcgtag atataaacat aaaggattat agcattgttt ccagttatgt gtgctcagga | 960 |
| cttgttggag acacacccag aaaaaacgac agctccagca gtagccattg cttggatcct | 1020 |
| aacaatgaag aaggtggtca tggagtgaaa ggctgggcct tgatgatgg aaatgacgtg | 1080 |
| tggatgggaa gaacgatcag cgagaagtta cgctcaggat atgaaacctt caaagtcatt | 1140 |
| gaaggctggt ccaaccctaa ttccaaattg cagataaata ggcaagtcat agttgacaga | 1200 |
| ggtaataggt ccggttattc tggtattttc tctgttgaag gcaaaagctg catcaatcgg | 1260 |
| tgcttttatg tggagttgat aaggggaaga aagaggaaa ctgaagtctt gtggacctca | 1320 |
| aacagtattg ttgtgtttg tggcacctca ggtacatatg aacaggctc atggcctgat | 1380 |
| ggggcggaca tcaatctcat gcctatataa gctttcgcaa ttttag | 1426 |

<210> SEQ ID NO 37
<211> LENGTH: 1736
<212> TYPE: DNA
<213> ORGANISM: influenza A virus

<400> SEQUENCE: 37

| | |
|---|---|
| gataattcta ttaaccatga agactatcat tgctttgagc tacattctat gtctggtttt | 60 |
| cgctcaaaag cttcccggaa atgacaacag cacggcaacg ctgtgccttg gcaccatgc | 120 |

```
agtaccaaac ggaacgatag tgaaaacaat cacgaatgac caaattgaag ttactaatgc    180
tactgagctg gttcagagtt cctcaacagg tggaatatgc gacagccctc atcagatcct    240
tgatggagaa aactgcacac taatagatgc tctattggga gaccctcagt gtgatggctt    300
ccaaaataag aaatgggacc ttttttgttga acgcagcaaa gcctacagca actgttaccc    360
ttatgatgtg ccggattatg cctcccttag gtcactagtt gcctcatccg gcacactgga    420
gtttaacaat gaaagcttca attggactgg agtcactcag aatggaacaa gctctgcttg    480
caaaaggaga tctaataaaa gtttctttag tagattgaat tggttgaccc acttaaaata    540 caaatacccca gcattgaacg tgactatgcc aaacaatgaa aaatttgaca aattgtacat    600 ttgggggtt caccacccgg gtacggacag tgaccaaatc agcctatatg ctcaagcatc    660
aggaagaatc acagtctcta ccaaaagaag ccaacaaact gtaatcccga atatcggatc    720
tagacccagg gtaagggatg tctccagcag aataagcatc tattggacaa tagtaaaacc    780
gggagacata cttttgatta acagcacagg gaatctaatt gctcctcggg gttacttcaa    840
aatacgaagt gggaaaagct caataatgag atcagatgca cccattggca aatgcaattc    900
tgaatgcatc actccaaatg gaagcattcc caatgacaaa ccatttcaaa atgtaaacag    960
gatcacatat ggggcctgtc ccagatatgt taagcaaaac actctgaaat tggcaacagg   1020
gatgcgaaat gtaccagaga acaaactaga aggcatattt ggcgcaatcg cgggtttcat   1080
agaaaatggt tgggagggaa tggtggacgg ttggtacggt ttcaggcatc aaaattctga   1140
gggcacagga caagcagcag atctcaaaag cactcaagca gcaatcaacc aaatcaatgg   1200
gaaactgaat aggttaatcg ggaaaacaaa cgagaaattc catcagattg aaaaagaatt   1260
ctcagaagta gaagggagaa ttcaggacct cgagaaatat gttgaggaca ctaaaataga   1320
tctctggtca tacaacgcgg agcttcttgt tgccctggag aaccaacata caattgatct   1380
aactgactca gaaatgaaca aactgtttga aagaacaaag aagcaactga gggaaaatgc   1440
tgaggatatg ggcaatggtt gtttcaaaat ataccacaaa tgtgacaatg cctgcataga   1500
gtcaatcaga aatggaactt atgaccatga tgtatacaga gatgaagcat taacaaccg    1560 gttccagatc aaaggtgttg agctgaagtc aggatacaaa gattggatcc tatggatttc   1620
ctttgccata tcatgttttt tgctttgtgt gctttgttg gggttcatca gtgtgggcctg   1680 ccaaaaaggc aacattaggt gcaacatttg catttgagtg cattaattaa aaacac        1736
```

<210> SEQ ID NO 38
<211> LENGTH: 1438
<212> TYPE: DNA
<213> ORGANISM: influenza A virus

<400> SEQUENCE: 38

```
atgaatccaa atcaaaagat aataacgatt ggctctgttt ccctcaccat ttccacaata     60
tgcttcttca tgcaaattgc catcctgata actactgtaa cattgcattt caagcaatat    120
gaattcaact ccccccccaaa caaccaagtg atgctgtgtg aaccaacaat aatagaaaga    180
aacataacag agatagtgta tctgaccaac accaccatag agaaggaaat atgccccaaa    240
ctagcagaat acagaaattg gtcaaagccg caatgtaaca ttacaggatt tgcacctttt    300
tctaaggaca attcgattcg gctttccgct ggtggggaca tctgggtgac aagacaacct    360
tatgtgtcat gcgatcctga caagtgttat caatttgccc ttggaaaggg aacaacacta    420
aacaacgtgc attcaaatga cacagtacat gataggaccc cttatcggac cctattgatg    480
```

```
aatgagttgg gtgttccatt tcatctgggg accaagcaag tgtgcatagc atggtccagc    540
tcaagttgtc acgatggaaa agcatggctg catgtttgtg taacggggga tgatgaaaat    600
gcaactgcta gcttcattta caatgggagg cttgtagata gtattgtttc atggtccaaa    660
aaaatcctca ggacccagga gtcagaatgc gtttgtatca atggaacttg tacagtagta    720
atgactgatg ggagtgcttc aggaaaagct gatactaaaa tactattcat tgaggagggg    780
aaaattgttc atactagcac attatcagga agtgctcagc atgtcgagga gtgctcctgt    840
tatcctcgat atcctggtgt cagatgtgtc tgcagagaca actggaaagg ctccaatagg    900
cccatcgtag atataaacat aaaggattat agcattgttt ccagttatgt gtgctcagga    960
cttgttggag acacacccag aaaaaacgac agctccagca gtagccattg cttggatcca   1020
aacaatgagg aaggtggtta tggagtgaaa ggctgggctt tgatgatgg aaatgacgtg    1080 tggatgggaa gaacgatcag cgagaagtta cgctcaggat atgaaacctt caaagtcatt   1140
gaaggctggt ccaaccctaa ctccaaattg cagataaata gcaagtcat agttgacaga    1200 ggtaacaggt ccggttattc tggtattttc tctgttgaag gcaaaagctg catcaatcgg   1260
tgcttttatg tggagttgat aaggggaaga aaacaggaaa ctgaagtctt gtggacctca   1320
aacagtattg ttgtgttttg tggcacctca ggtacatatg gaacaggctc atggcctgat   1380
ggggcggaca tcaatctcat gcctatataa gctttcgcaa ttttagaaaa aaactcct    1438

<210> SEQ ID NO 39
<211> LENGTH: 1723
<212> TYPE: DNA
<213> ORGANISM: influenza A virus

<400> SEQUENCE: 39
ttctattaac catgaagact atcattgctt tgagctacat tctatgtctg gttttcgctc     60
aaaaacttcc cggaaatgac aacagcacgg caacgctgtg ccttgggcac catgcagtac    120
caaacggaac gatagtgaaa acaatcacga atgaccaaat tgaagttact aatgctactg    180
agctggttca gagttcctca acaggtggaa tatgcgacag tcctcatcag atccttgatg    240
gagaaaactg cacactaata gatgctctat gggagaccc tcagtgtgat ggcttccaaa    300
ataagaaatg ggaccttttt gttgaacgca gcaaagccta cagcaactgt tacccttatg    360
atgtgccgga ttatgcctcc cttaggtcac tagttgcctc atccggcaca ctggagttta    420
acaatgaaag cttcaattgg actggagtca ctcaaaatgg aacaagctct gcttgcaaaa    480
ggagatctaa taaaagtttc tttagtagat tgaattggtt gacccactta aaattcaaat    540
acccagcatt gaacgtgact atgccaaaca atgaaaaatt tgacaaattg tacatttggg    600
gggttcacca cccgggtacg gacaatgacc aaatcaacct atatgttcaa gcatcaggaa    660
gaatcacagt ctctaccaaa agaagccaac aaactgtaat cccgaatatc ggatctagac    720
ccagagtaag ggatgtcccc agcagaataa gcatctattg gacaatagta aaaccgggag    780
acatactttt gattagcagc acagggaatc taattgctcc tcgggttac ttcaaaatac    840 gaagtgggaa aagctcaata atgagatcag atgcacccat tggcaaatgc aattctgaat    900
gcatcactcc aaatggaagc attcccaatg acaaaccatt tcaaaatgta acaggatca    960 catatgggc ctgtcccaga tatgttaagc aaaacactct gaaattggca acagggatgc   1020
gaaatgtacc agagaaacaa actagaggca tatttggcgc aatcgcgggt ttcatagaaa   1080
atggttggga gggaatggtg gacgttggt acgtttcag gcatcaaaat tctgagggaa   1140
caggacaagc agcagatctc aaaagcactc aagcagcaat caaccaaatc aatgggaagc   1200
```

```
tgaataggtt gatcgggaaa acaaacgaga aattccatca gattgaaaaa gaattctcag    1260
aagtagaagg gagaattcag gacctcgaga atatgttga ggacactaaa atagatctct    1320
ggtcatacaa cgcggagctt cttgttgccc tggagaacca acatacaatt gatctaactg    1380
actcagaaat gaacaaactg tttgaaagaa caaagaagca actgagggaa aatgctgagg    1440
atatgggcaa tggttgtttc aaaatatacc acaaatgtga caatgcctgc atagggtcaa    1500
tcagaaatgg aacttatgac catgatgtat acagagatga agcattaaac aaccggttcc    1560
agatcaaagg tgttgagctg aagtcaggat acaaagattg gatcctatgg atttcctttg    1620
ccatatcatg ttttttgctt tgtgttgctt tgttggggtt catcatgtgg gcctgccaaa    1680
aaggcaacat taggtgcaac atttgcattt gagtgcatta att    1723

<210> SEQ ID NO 40
<211> LENGTH: 1428
<212> TYPE: DNA
<213> ORGANISM: influenza A virus

<400> SEQUENCE: 40
aaatgaatcc aaatcaaaag ataataacga ttggctctgt ttctctcacc atttccacaa      60
tatgcttctt catgcaaatt gccatcttga taactactgt aacattgcat ttcaagcaat    120
atgaattcaa ctcccccccca aacaaccaag tgatgctgtg tgaaccaaca ataatagaaa    180
gaaacataac agagatagtg tatctgacca caccaccat agagaaggaa atatgcccca    240
aactagcaga atacagaaat tggtcaaagc cgcaatgtga cattacagga tttgcacctt    300
tttctaagga caattcgatt aggctttccg ctggtgggga catctgggtg acaagagaac    360
cttatgtgtc atgcgatcct gacaagtgtt atcaatttgc ccttggacag ggaacaacac    420
taaacaacgt gcattcaaat gacacagtac atgataggac cccttatcgg accctattga    480
tgaatgagtt aggtgttcca tttcatctgg ggaccaagca agtgtgcata gcatggtcca    540
gctcaagttg tcacgatgga aaagcatggc tgcatgtttg tgtaacgggg gatgataaaa    600
atgcaactgc tagcttcatt tacaatggga ggcttgtaga tagtattgtt tcatggtcca    660
aaaaaatcct caggacccag gagtcagaat gcgtttgtat caatggaact tgtacagtag    720
taatgactga tgggagtgct tcaggaaaag ctgatactaa aatactattc attgaggagg    780
ggaaaatcgt tcatactagc acattgtcag gaagtgctca gcatgtcgag gagtgctcct    840
gctatcctcg atatcctggt gtcagatgtg tctgcagaga caactggaaa ggctccaata    900
ggcccatcgt agatataaac ataaaggatt atagcattgt ttccagttat gtgtgctcag    960
gacttgttgg agacacaccc agaaaaaacg acagctccag cagtagccat tgcttggatc    1020
ctaacaatga gaaggtggt catggagtga aaggctgggc ctttgatgat ggaaatgacg    1080
tgtggatggg aagaacgatc agcgagaagt acgctcagg atatgaaacc ttcaaagtca    1140
ttgaaggctg gtccaaccct aattccaaat gcagataaa taggcaagtc atagttgaca    1200
gaggtaatag gtccggttat tctggtattt tctctgttga aggcaaaagc tgcatcaatc    1260 ggtgcttta tgttggagttg ataaggggaa gaaaagagga aactaaagtc ttgtggacct    1320
caaacagtat tgttgtgttt tgtggcacct caggtacata tggaacaggc tcatggcctg    1380
atggggcgga catcaatctc atgcctatat aagctttcgc aattttag    1428

<210> SEQ ID NO 41
<211> LENGTH: 1724
<212> TYPE: DNA
```

<213> ORGANISM: influenza A virus

<400> SEQUENCE: 41
attctattaa ccatgaagac tatcattgct ttgagctaca ttctatgtct ggttttcgct 60
caaaaacttc ccggaaatga caacagcacg gcaacgctgt gccttgggca ccatgcagta 120
ccaaacggaa caatagtgaa aacaatcacg aatgaccaaa ttgaagttac taatgctact 180
gagctggttc agaattcctc aacaggtgga atatgcgaca gtcctcatca gatccttgat 240
ggagaaaact gcacactaat agatgctcta ttgggagacc ctcagtgtga tggcttccaa 300
aataagaaat gggacctttt tgttgaacgc agcaaggcct acagcaactg ttacccttat 360
gatgtgccgg attatgcctc ccttaggtca ctagttgcct catccggcac actggagttt 420
aacaatgaaa gcttcaattg gactggagtc actcaaaatg gaacaagctc tgcttgcaaa 480
aggagatcta ataaaagttt ctttagtaga ttgaattggt tgacccactt aaaattcaaa 540
tacccagcat tgaacgtgac tatgccaaac aatgaaaaat ttgacaaatt gtacatttgg 600
ggggttcacc acccgggtac ggactatgac caaatccgcc tatatgctca agcatcagga 660
agaatcacag tctctaccaa aagaagccaa caaactgtaa tcccgaatat cggatctaga 720
cccagggtaa gggatatccc cagcagaata agcatctatt ggacaatagt aaaaccggga 780
gacatacttt tgattaacag cacagggaat ctaattgctc ctcggggtta cttcaaaata 840
cgaagtggga aaagctcaat aatgagatca gatgcaccca ttggcaaatg caattctgaa 900
tgcatcactc caaatggaag cattcccaat gacaaaccat ttcaaaatgt aaacaggatc 960
acatatgggg cctgtcccag atatgttaag caaaacactc tgaaattggc aacagggatg 1020
cgaaacgtac cagagaaaca aactagaggc atatttggcg caatcgcggg tttcatagaa 1080
aatggttggg agggaatggt ggacggttgg tacggtttca ggcatcaaaa ttctgaggga 1140
acaggacaag cagcagatct caaaagcact caagcagcaa tcaaccaaat caatgggaag 1200
ctgaataggt tgatcgggaa aacaaacgag aaattccatc agattgaaaa agaattctca 1260
gaagtagaag ggagaattca ggacctcgag aaatatgttg aggacactaa aatagatctc 1320
tggtcataca acgcggagct tcttgttgcc ctggagaacc aacatacaat tgatctaact 1380
gactcagaaa tgaacaaact gtttgaaaga acaaagaagc aactgaggga aaatgctgag 1440
gatatgggca atggttgttt caaaatatac cacaaatgtg acaatgcctg catagggtca 1500
atcagaaatg gaacttatga ccatgatgta tacagagatg aagcattaaa caaccggttc 1560
cagatcaaag gtgttgagct gaagtcagga tacaaagatt ggatcctatg gatttccttt 1620
gccatatcat gtttttttgct ttgtgttgct ttgtcggggt tcatcatgtg ggcctgccaa 1680
aaaggcaaca ttaggtgcaa catttgcatt tgagtgcatt aatt 1724

<210> SEQ ID NO 42
<211> LENGTH: 1426
<212> TYPE: DNA
<213> ORGANISM: influenza A virus

<400> SEQUENCE: 42
atgaatccaa atcaaaagat aataacgatt ggctctgttt ctctcaccat ttccacaata 60
tgcttcttca tgcaaattgc catcttgata actactgtaa cattgcattt caagcaatat 120
gaattcaact cccccccaaa caaccaagtg atgctgtgtg aaccaacaat aatagaaaga 180
aacataacag agatagtgta tctgaccaac accaccatag agaaggaaat atgccccaaa 240
ctagcagaat acagaaattg gtcaaagccg caatgtgaca ttacaggatt tgcacctttt 300

```
tctaaggaca attcgattag gctttccgct ggtggggaca tctgggtgac aagagaacct      360
tatgtgtcat gcgatcctga caagtgttat caatttgccc ttggacaggg aacaacacta      420
aacaacgtgc attcaaatga cacagtacat gataggaccc cttatcggac cctattgatg      480
aatgagttag gtgttccatt tcatctgggg accaagcaag tgtgcatagc atggtccagc      540
tcaagttgtc acgatggaaa agcatggctg catgtttgtg taacggggga tgataaaaat      600
gcaactgcta gcttcattta caatgggagg cttgtagata gtattgtttc atggtccaaa      660
aaaatcctca ggacccagga gtcagaatgc gtttgtatca atggaacttg tacagtagta      720
atgactgatg ggagtgcttc aggaaaagct gatactaaaa tactattcat tgaggagggg      780
aaaatcgttc atactagcac attgtcagga agtgctcagc atgtcgagga gtgctcctgc      840
tatcctcgat atcctggtgt cagatgtgtc tgcagagaca actggaaagg ctccaatagg      900
cccatcgtag atataaacat aaaggattat agcattgttt ccagttatgt gtgctcagga      960
cttgttggag acacacccag aaaaaacgac agctccagca gtagccattg cttggatcct     1020
aacaatgaag aaggtggtca tggagtgaaa ggctgggcct ttgatgatgg aaatgacgtg     1080
tggatgggaa gaacgatcag cgagaagtta cgctcaggat atgaaacctt caaagtcatt     1140
gaaggctggt ccaaccctaa ttccaaattg cagataaata ggcaagtcat agttgacaga     1200
ggtaataggt ccggttactc tggtattttc tctgttgaag gcaaaagctg catcaatcgg     1260
tgcttttatg tggagttgat aaggggaaga aaagagaaaa ctgaagtctt gtggacctca     1320
aacagtattg ttgtgttttg tggcacctca ggtacatatg gaacaggctc atggcctgat     1380
ggggcggaca tcaatctcat gcctatataa gctttcgcaa ttttag              1426

<210> SEQ ID NO 43
<211> LENGTH: 1724
<212> TYPE: DNA
<213> ORGANISM: influenza A virus

<400> SEQUENCE: 43
attctattaa ccatgaagac tatcattgct ttgagctaca ttctatgtct ggttttcgct       60
caaaaacttc ccggaaatga caacagcacg gcaacgctgt gccttgggca ccatgcagta      120
ccaaacggaa caatagtgaa aacaatcacg aatgaccaaa ttgaagttac taatgctact      180
gagctggttc agaattcctc aacaggtgga atatgcgaca gtcctcatca gatccttgat      240
ggagaaaact gcacactaat agatgctcta ttgggagacc ctcagtgtga tggcttccaa      300
aataagaaat gggacctttt tgttgaacgc agcaaggcct acagcaactg ttaccctat       360 gatgtgccgg attatgcctc ccttaggtca ctagttgcct catccggcac actggagttt      420
aacaatgaaa gcttcaattg gactggagtc actcaaaatg gaacaagctc tgcttgcaaa      480
aggagatcta ataaagtttt ctttagtaga ttgaattggt tgacccactt aaaattcaaa      540
tacccagcat tgaacgtgac tatgccaaac aatgaaaaat ttgacaaatt gtacatttgg      600
ggggttcacc acccggttac ggactatgac caaatcagcc tatatgctca agcatcagga      660
agaatcacag tctctaccaa aagaagccaa caaactgtaa tcccgaatat cggatctaga      720
cccagggtaa gggatatccc cagcagaata agcatctatt ggacaatagt aaaaccggga      780
gacatacttt tgattaacag cacagggaat ctaattgctc tcggggtta cttcaaaata      840 cgaagtggga aaagctcaat aatgagatca gatgcaccca ttggcaaatg caattctgaa      900
tgcatcactc caaatggaag cattcccaat gacaaaccat ttcaaaatgt aaacaggatc      960
```

```
acatatgggg cctgtcccag atatgttaag caaaacactc tgaaattggc aacaggatg    1020 cgaaacgtac cagagaaaca aactagaggc atatttggcg caatcgcggg tttcatagaa   1080
aatggttggg agggaatggt ggacggttgg tacggtttca ggcatcaaaa ttctgaggga   1140
acaggacaag cagcagatct caaaagcact caagcagcaa tcaaccaaat caatgggaag   1200
ctgaataggt tgatcgggaa aacaaacgag aaattccatc agattgaaaa agaattctca   1260
gaagtagaag ggagaattca ggacctcgag aaatatgttg aggacactaa aatagatctc   1320
tggtcataca acgcggagct tcttgttgcc ctggagaacc aacatacaat tgatctaact   1380
gactcagaaa tgaacaaact gtttgaaaga caaagaagc aactgaggga aaatgctgag    1440
gatatgggca atggttgttt caaaatatac cacaaatgtg acaatgcctg cataggtca   1500 atcagaaatg gaacttatga ccatgatgta tacagagatg aagcattaaa caaccggttc   1560
cagatcaaag gtgttgagct gaagtcagga tacaaagatt ggatcctatg gatttccttt   1620
gccatatcat gttttttgct ttgtgttgct ttgtcggggt tcatcatgtg ggcctgccaa   1680
aaaggcaaca ttaggtgcaa catttgcatt tgagtgcatt aatt                   1724

<210> SEQ ID NO 44
<211> LENGTH: 1427
<212> TYPE: DNA
<213> ORGANISM: influenza A virus

<400> SEQUENCE: 44
aatgaatcca atcaaaaga taataacgat tggctctgtt tctctcacca tttccacaat    60
atgcttcttc atgcaaattg ccatcttgat aactactgta acattgcatt tcaagcaata   120
tgaattcaac tccccccccaa acaaccaagt gatgctgtgt gaaccaacaa taatagaaag   180
aaacataaca gagatagtgt atctgaccaa caccaccata gagaaggaaa tatgccccaa   240
actagcagaa tacagaaatt ggtcaaagcc gcaatgtgac attacaggat ttgcaccttt   300
ttctaaggac aattcgatta ggcttttccgc tggtggggac atctgggtga aagagaacc    360 ttatgtgtca tgcgatcctg acaagtgtta tcaatttgcc cttggacagg gaacaacact   420
aaacaacgtg cattcaaatg acacagtaca tgataggacc ccttatcgga ccctattgat   480
gaatgagtta ggtgttccat ttcatctggg gaccaagcaa gtgtgcatag catggtccag   540
ctcaagttgt cacgatggaa aagcatggct gcatgtttgt gtaacggggg atgataaaaa   600
tgcaactgct agcttcattt acaatgggag gcttgtagat agtattgttt catggtccaa   660
aaaaatcctc aggacccagg agtcagaatg cgtttgtatc aatggaactt gtacagtagt   720
aatgactgat gggagtgctt caggaaaagc tgatactaaa atactattca ttgaggaggg   780
gaaaatcgtt catactagca cattgtcagg aagtgctcag catgtcgagg agtgctcctg   840
ctatcctcga tatcctggtg tcagatgtgt ctgcagagac aactggaaag ctccaatag    900 gcccatcgta gatataaaca taaggatta tagcattgtt ccagttatg tgtgctcagg    960 acttgttgga gacacaccca gaaaaacga cagctccagc agtagccatt gcttggatcc   1020
taacaatgaa gaaggtggtc atggagtgaa aggctgggcc tttgatgatg gaaatgacgt   1080
gtggatggga agaacgatca gcgagaagtt acgctcagga tatgaaacct tcaaagtcat   1140
tgaaggctgg tccaacccta attccaaatt gcagataaat aggcaagtca tagttgacag   1200
aggtaatagg tccggttact ctggtatttt ctctgttgaa ggcaaaagct gcatcaatcg   1260
gtgcttttat gtggagttga taggggaag aaaagagaaa actgaagtct tgtggaccct    1320
aaacagtatt gttgtgtttt gtggcacctc aggtacatat ggaacaggct catggcctga    1380
```

-continued

```
tggggcggac atcaatctca tgcctatata agctttcgca attttag                1427

<210> SEQ ID NO 45
<211> LENGTH: 1870
<212> TYPE: DNA
<213> ORGANISM: influenza B virus

<400> SEQUENCE: 45
gcagaagcag agcatttttct aatatccaca aaatgaaggc aataattgta ctactcatgg      60
tagtaacatc caatgcagat cgaatctgca ctgggataac atcttcaaac tcacctcatg     120
tggtcaaaac agctactcaa ggggaggtca atgtgactgg tgtaatacca ctgacaacaa     180
caccaacaaa atcttatttt gcaaatctca aaggaacaag gaccagaggg aaactatgtc     240
cagactgtct caactgtaca gatctggatg tggccttggg cagaccaatg tgtgtgggga     300
ccacaccttc ggcaaaagct tcaatactcc acgaagtcag acctgttaca tccgggtgct     360
ttcctataat gcacgacaga acaaaaatca gacaactacc caatcttctc agaggatatg     420
aaaatatcag attatcaacc caaaacgtta tcgatgcaga aaatgcacca ggaggaccct     480
acagacttgg aacctcaaga tcttgcccta acgctaccag taaaagcgga tttttcgcaa     540
caatggcttg ggctgtccca aaggacaaca acaaaaatgc aacgaaccca ctaacagtag     600
aagtaccata cgtttgtaca gaaggggaag accaaattac tgtttggggg ttccattcag     660
ataacaaaac ccaaatgaag aacctctatg gagactcaaa tcctcaaaag ttcacctcat     720
ctgctaatgg agtaaccaca cattatgttt ctcagattgg cggcttccca gctcaaacag     780
aagacgaagg actaccacaa agcggcagaa ttgttgttga ttacatggtg caaaaaccta     840
gaaaaacagg aacaattgtc tatcaaagag gtgttttgtt gcctcaaaag gtgtggtgcg     900
cgagtggcag gagcaaagta ataaaagggt ccttgccttt aattggtgaa gcagattgcc     960
ttcatgaaaa atacggtgga ttaaacaaaa gcaagcctta ctacacagga gaacatgcaa    1020
aagccatagg aaattgccca atatgggtga aaacaccttt gaagcttgcc aatggaacca    1080
aatatagacc tcctgcaaaa ctattaaagg aaaggggttt cttcggagct attgctggtt    1140
tcctagaagg aggatgggaa ggaatgattg caggttggca cggatacaca tctcacggag    1200
cacatggagt ggcagtggcg gcagaccctta agagtacgca agaagctata aacaagataa    1260
caaaaaatct caattctttg agtgagctag aagtaaagaa tcttcaaaga ctaagtggtg    1320
ccatggatga actccacaac gaaatactcg agctggatga gaaagtggat gatctcagag    1380
ctgacactat aagctcgcaa atagaacttg cagtcttgct ttccaatgaa ggaataataa    1440
acagtgaaga tgagcatcta ttggcacttg agagaaaact aaagaaaatg ctgggtccct    1500
ctgctgtaga cataggaaat ggatgcttcg aaaccaaaca caagtgcaac cagacctgct    1560
tagacaggat agctgctggc acctttaatg caggagaatt ttctctcccc acttttgatt    1620
cactgaacat tactgctgca tctttaaatg atgatggatt ggataaccat actatactgc    1680
tctattactc aactgctgct tctagtttgg ctgtaacatt gatgctagct atttttattg    1740
tttatatggt ctccagagac aacgtttcat gctccatctg tctataagga agattaagcc    1800
ttgtattttc ctttattgta gtgcttgttt gcttgtcatc attacaaaga aacgttattg    1860
aaaaatgctc                                                          1870

<210> SEQ ID NO 46
<211> LENGTH: 1536
<212> TYPE: DNA
```

<213> ORGANISM: influenza B virus

<400> SEQUENCE: 46

```
aagcagagca tcttctcaaa actgaggcaa ataggccaaa aatgaacaat gctaccctca      60
actatacaaa cgttaaccct attcctcaca tcaggggag tgttattatc actatatgtg      120
tcagcttcac tgtcatactt actatattcg gatatattgc taaaattttc aacaacagaa     180
acaactgcac caacaatgcc attggattgt gcaaacgcat caaatgttca ggctgtgaac     240
cgttctgcaa caaaagggt gacacttctt ctcccagaac cggagtggac atacccgcgt       300
ttatcttgcc cgggctcaac ctttcagaaa gcactcctaa ttagccctca tagattcgga      360
gaaaccaaag gaaactcagc tcccttgata taagggaac cttttattgc ttgtggacca       420
aaggaatgca aacactttgc tctaacccat tatgcagccc aaccagggg atactacaat        480
ggaacaagag aagacagaaa caagctgagg catctaattt cagtcaaatt gggcaaaatc       540
ccaacagtag aaaactccat tttccacatg gcagcatgga gcgggtccgc atgccatgat      600
ggtaaagaat ggacatatat cggagttgat ggccctgaca gtaatgcatt gctcaaaata      660
aaatatggag aagcatatac tgacacatac cattcctatg caaacaacat cctaagaaca     720
caagaaagtg cctgcaattg catcggggga aattgttatc ttatgataac tgatggctca      780
gcttcaggta ttagtgagtg cagatttctt aagattcgag agggccgaat aataaaagaa      840
atatttccaa caggaagagt aaaacatact gaagaatgca catgcggatt tgccagcaat    900
aaaaccatag aatgtgcctg tagagataac agttacacag caaaaagacc ctttgtcaaa     960
ttaaatgtgg agactgatac agcagaaata agattgatgt gcacagagac ttatttggac   1020
accccagac cagatgatgg aagtataaca gggccttgtg aatctaatgg gaataaaggg    1080
agtggaggca tcaagggagg atttgttcat caaagaatgg catccaaaat tggaaggtgg    1140
tactctcgaa caatgtctaa aaccaaaagg atgggaatgg gactgtatgt caagtatgat    1200
ggagaccccat ggactgacag tgatgcccct tgctcttagtg gagtaatggt ttcaatggaa   1260
gaacctggtt ggtactcatt tggcttcgaa ataaaagata gaaatgtgaa tgtcccctgt   1320
attgggatag agatggtaca tgatggtgga aaggagactt ggcactcagc agcaacagcc    1380
atttactgtt taatgggctc aggacaactg ttgtgggaca ctgtcacagg tgttgatatg   1440
gctctgtaat gggggaatgg ttgagtctgt tctaaaccct tgttcctat tttgtttgaa    1500
caattgtcct tgctgaactt aattgtttct gaaaaa                              1536
```

<210> SEQ ID NO 47
<211> LENGTH: 1846
<212> TYPE: DNA
<213> ORGANISM: influenza B virus

<400> SEQUENCE: 47

```
tctaatatcc acaaaatgaa ggcaataatt gtactactca tggtagtaac atccaacgca      60
gatcgaatct gcactgggat aacatcttca aactcacctc atgtggtcaa aacagctact      120
caaggggagg tcaatgtgac tggtgtgata ccactgacaa caactccaat aaaatctcat     180
tttgcaaatc tcaaaggaac aaggactaga gggaaactat gcccagattg tctcaactgc    240
acagatctgg atgtggcctt gggcagacca atgtgtgtgg gaccacacc ttcggcaaaa      300
gcttcaatac tccacgaagt cagacctgtt acatccgggt gctttcctat aatgcacgac   360
agaacaaaaa tcagacaact acccaatctt ctcagaggat atgaaaatat caggttatca    420
acccaaaacg ttatcgatgc agaaaaggcc ctaggaggac cctacagact tggaacctca    480
```

-continued

```
ggatcttgcc ctaacgccac cagtaaaagc ggattttttcg caacaatggc ttgggctgtc      540
ccaaaggaca acaacaaaaa tgcaacgaac ccactaacag tagaagtacc atacatctgt      600
acagaagggg aagaccaaat tactgttttgg gggttccatt cagatgacaa aacccaaatg     660
aaaaacctct atggagactc aaatcctcaa aagttcacct catctgctaa tggagtaacc      720
acacattatg tttctcagat tggcggcttc ccagatcaaa cagaagacgg aggactacca     780
caaagcggca gaattgttgt tgattacatg gtgcaaaaac ctgggaaaac aggaacaatt     840
gtctatcaaa gaggtgtttt gttgcctcaa aaggtgtggt gcgcgagtgg caggagcaaa      900
gtaataaaag ggtccttgcc tttaattggt gaagcagatt gccttcatga aaaatacggt      960
gggttaaaca aaagcaagcc ttactacaca ggagaacatg caaaagccat aggaaattgc     1020
ccaatatggg tgaaaacacc tttgaagctt gccaatggaa ccaaatatag acctcctgca     1080
aaactattaa aggaaggggg tttcttcgga gctattgctg gtttcctaga aggaggatgg     1140
gaaggaatga ttgcaggttg gcacggatac acatctcacg gagcacatgg agtggcagtg     1200
gcggcagacc ttaagagtac gcaagaagct ataaacaaga taacaaaaaa tctcaattct     1260
ttgagtgagc tagaagtaaa gaatcttcaa agactaagtg gtgccatgga tgaactccac     1320
aacgaaatac tcgagctgga tgagaaagtg gatgatctca gagctgacac tataagctcg     1380
caaatagaac ttgcagtctt gctttccaac gaaggaataa taaacagtga agatgagcat     1440
ctattggcac ttgagagaaa actaaagaaa atgctgggtc cctctgctgt agacatagga     1500
aatggatgct tcgaaaccaa acacaagtgc aaccagacct gcttagacag gatagctgct     1560 ggcacccttta atgcaggaga attttctctc cccacttttg attcactgaa cattactgct     1620
gcatctttaa atgatgatgg attggataac catactctat tgctctatta ctcaactgct     1680
gcttctagtt tggctgtaac attgatgcta gctattttta ttgtttatat ggtctccaga     1740
gacaacgttt catgctccat ctgtctataa gggagattaa gccttgtatt ttcctttatt     1800
gtagtgcttg tttgcttgtc atcattacaa agaaacgtta ttgaaa                   1846
```

<210> SEQ ID NO 48
<211> LENGTH: 1520
<212> TYPE: DNA
<213> ORGANISM: influenza B virus

<400> SEQUENCE: 48

```
ctcaaaactg aggcaaatag gccaaaaatg aacaatgcta ccctcaacta tacaaacgtt       60
aaccctattc ctcacatcag ggggagtgtt attatcacta tatgtgtcag cttcactgtc     120
atacttacta tattcggata tattgctaaa attttcaaca acagaaataa ctgcaccaac    180
aatgccattg gattgtgcaa acgcatcaaa tgttcaggct gtgaaccgtt ctgcaacaaa   240 agggtgaca cttcttctcc cagaaccgga gtggacatac ccgcgtttat cttgcccggg    300
ctcaaccttt cagaaagcac tcctaattag ccctcataga ttcggagaaa ccaaaggaaa   360
ctcagctccc ttgataataa gggaaccttt tattgcttgt ggaccaaagg aatgcaaaca   420 cttttgctcta acccattatg cagcccaacc aggggggatac tacaatggaa caagaagaga   480
caggaacaag ctgaggcatc taatttcagt caaattgggc aaaatcccaa cagtagaaaa   540
ctccattttc cacatggcag catggagcgg gtccgcatgc catgatggta agaatggac     600 atatatcgga gttgatggcc ctgacagtaa tgcattgctc aaaataaaat atggagaagc   660
atatactgac acataccatt cctatgcaaa caacatccta agaacacaag aaagtgcctg   720
```

```
caattgcatc gggggaaatt gttatcttat gataactgat ggctcagctt caggtattag    780
tgagtgcaga tttcttaaga ttcgagaggg ccgaataata aaagaaatat tccaacagg     840
aagagtaaaa catactgaag aatgcacatg cggatttgcc agcaataaaa ccatagaatg    900
tgcctgtagg gataacagtt acacagcaaa aagaccctt gtcaaattaa atgtggagac    960
tgatacagca gaaataagat tgatgtgcac agagacttat ttggacaccc ccagaccaga  1020
tgatggaagc ataacagggc cttgtgaatc taatgggaat aaagggagtg gaggcatcaa  1080
gggaggattt gttcatcaaa gaatggcatc caaaattgga aggtggtact ctcgaacaat  1140
gtctaaaacc aaaaggatgg aatgggact gtatgtcaag tatgatggag acccatggat  1200
tgacagtgat gcccttgctc ttagtggagt aatggtttca atggaagaac ctggttggta  1260
ctcatttggc ttcgaaataa agataagaa atgtgatgtc ccctgtattg ggatagagat  1320
ggtacatgat ggtggaaagg agacttggca ctcagcagca acagccattt actgtttaat  1380
gggctcagga cagctgctgt gggacactgt cacaggtgtt gatatggctc tgtaatggag  1440
gaatggttga gtctgttcta aacccttgt tcctattttg tttgaacaat tgtccttact  1500
gaacttaatt gtttctgaaa                                                1520
```

<210> SEQ ID NO 49
<211> LENGTH: 566
<212> TYPE: PRT
<213> ORGANISM: influenza A virus

<400> SEQUENCE: 49

```
Met Lys Thr Ile Ile Ala Leu Ser Tyr Ile Leu Cys Leu Val Phe Ala
1               5                  10                  15

Gln Lys Leu Pro Gly Asn Asp Asn Ser Thr Ala Thr Leu Cys Le

-continued

```
                225                 230                 235                 240
Gly Gln Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Asn Gly Lys Ser Ser Ile Met Arg Ser Asp Ala
                275                 280                 285

Pro Ile Gly Asn Cys Ser Ser Glu Cys Ile Thr Pro Asn Gly Ser Ile
                290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Thr Gly Gln Ala Ala Asp Leu Lys
                370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
                530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 50
<211> LENGTH: 436
<212> TYPE: PRT
<213> ORGANISM: influenza A virus

<400> SEQUENCE: 50

Met Gln Ile Ala Ile Leu Val Thr Val Thr Leu His Phe Lys Gln
1               5                   10                  15

Tyr Glu Cys Asn Ser Pro Pro Asn Asn Gln Val Met Leu Cys Glu Pro
                20                  25                  30
```

-continued

```
Thr Ile Ile Glu Arg Asn Ile Thr Glu Ile Val Tyr Leu Thr Asn Thr
             35                  40                  45
Thr Ile Glu Lys Glu Ile Cys Pro Lys Leu Ala Glu Tyr Arg Asn Trp
         50                  55                  60
Ser Lys Pro Gln Cys Lys Ile Thr Gly Phe Ala Pro Phe Ser Lys Asp
65                  70                  75                  80
Asn Ser Ile Arg Leu Ser Ala Gly Gly Asp Ile Trp Val Thr Arg Glu
                 85                  90                  95
Pro Tyr Val Ser Cys Asp Pro Gly Lys Cys Tyr Gln Phe Ala Leu Gly
            100                 105                 110
Gln Gly Thr Thr Leu Asn Asn Arg His Ser Asn Asp Thr Val His Asp
            115                 120                 125
Arg Thr Pro Tyr Arg Thr Leu Leu Met Asn Glu Leu Gly Val Pro Phe
        130                 135                 140
His Leu Gly Thr Lys Gln Val Cys Ile Ala Trp Ser Ser Ser Ser Cys
145                 150                 155                 160
His Asp Gly Lys Ala Trp Leu His Val Cys Val Thr Gly His Asp Glu
                165                 170                 175
Asn Ala Thr Ala Ser Phe Ile Tyr Asp Gly Arg Leu Val Asp Ser Ile
            180                 185                 190
Gly Ser Trp Ser Lys Asn Ile Leu Arg Thr Gln Glu Ser Glu Cys Val
        195                 200                 205
Cys Ile Asn Gly Thr Cys Thr Val Val Met Thr Asp Gly Ser Ala Ser
210                 215                 220
Glu Arg Ala Asp Thr Lys Ile Leu Phe Ile Glu Gly Lys Ile Val
225                 230                 235                 240
His Ile Ser Pro Leu Ser Gly Ser Ala Gln His Val Glu Glu Cys Ser
                245                 250                 255
Cys Tyr Pro Arg Tyr Pro Gly Val Arg Cys Val Cys Arg Asp Asn Trp
            260                 265                 270
Lys Gly Ser Asn Arg Pro Ile Val Asp Ile Asn Val Lys Asp Tyr Ser
        275                 280                 285
Ile Val Ser Ser Tyr Val Cys Ser Gly Leu Val Gly Asp Thr Pro Arg
290                 295                 300
Lys Asn Asp Ser Ser Ser Ser Tyr Cys Arg Asn Pro Asn Glu
305                 310                 315                 320
Lys Gly Ser His Gly Val Lys Gly Trp Ala Phe Asp Asp Gly Asn Asp
            325                 330                 335
Val Trp Met Gly Arg Thr Ile Ser Glu Glu Leu Arg Ser Gly Tyr Glu
        340                 345                 350
Thr Phe Lys Val Ile Gly Gly Trp Ser Lys Pro Asn Ser Lys Leu Gln
    355                 360                 365
Ile Asn Arg Gln Val Ile Val Asp Arg Gly Asn Arg Ser Gly Tyr Ser
    370                 375                 380
Gly Ile Phe Ser Val Glu Gly Lys Ser Cys Ile Asn Arg Cys Phe Tyr
385                 390                 395                 400
Val Glu Leu Ile Arg Gly Arg Lys Gln Glu Thr Glu Val Trp Trp Thr
                405                 410                 415
Ser Asn Ser Ile Val Val Phe Cys Gly Thr Ser Gly Thr Tyr Gly Thr
            420                 425                 430
Gly Ser Trp Pro
        435
```

<210> SEQ ID NO 51
<211> LENGTH: 566
<212> TYPE: PRT
<213> ORGANISM: influenza A virus

<400> SEQUENCE: 51

| Met | Lys | Thr | Ile | Ile | Ala | Leu | Ser | Tyr | Ile | Leu | Cys | Leu | Val | Phe | Ala |
|---|---|---|---|---|---|---|---|---|---|---|---|---|---|---|---|
| 1 | | | | 5 | | | | | 10 | | | | | 15 | |

| Gln | Lys | Leu | Pro | Gly | Asn | Asp | Asn | Ser | Thr | Ala | Thr | Leu | Cys | Leu | Gly |
| | | | 20 | | | | | 25 | | | | | 30 | | |

| His | His | Ala | Val | Pro | Asn | Gly | Thr | Leu | Val | Lys | Thr | Ile | Thr | Asn | Asp |
| | | 35 | | | | | 40 | | | | | 45 | | | |

| Gln | Ile | Glu | Val | Thr | Asn | Ala | Thr | Glu | Leu | Val | Gln | Ser | Ser | Pro | Thr |
| 50 | | | | | 55 | | | | | 60 | | | | | |

| Gly | Arg | Ile | Cys | Asp | Ser | Pro | His | Arg | Ile | Leu | Asp | Gly | Lys | Asn | Cys |
| 65 | | | | | 70 | | | | | 75 | | | | | 80 |

| Thr | Leu | Ile | Asp | Ala | Leu | Leu | Gly | Asp | Pro | His | Cys | Asp | Gly | Phe | Gln |
| | | | | 85 | | | | | 90 | | | | | 95 | |

| Asn | Lys | Glu | Trp | Asp | Leu | Phe | Val | Glu | Arg | Ser | Lys | Ala | Tyr | Ser | Asn |
| | | | 100 | | | | | 105 | | | | | 110 | | |

| Cys | Tyr | Pro | Tyr | Asp | Val | Pro | Asp | Tyr | Ala | Ser | Leu | Arg | Ser | Leu | Val |
| | | 115 | | | | | 120 | | | | | 125 | | | |

| Ala | Ser | Ser | Gly | Thr | Leu | Glu | Phe | Ile | Asn | Glu | Asn | Phe | Asn | Trp | Thr |
| 130 | | | | | 135 | | | | | 140 | | | | | |

| Gly | Val | Ala | Gln | Asp | Gly | Lys | Ser | Tyr | Ala | Cys | Lys | Arg | Gly | Ser | Val |
| 145 | | | | | 150 | | | | | 155 | | | | | 160 |

| Asn | Ser | Phe | Phe | Ser | Arg | Leu | Asn | Trp | Leu | His | Lys | Leu | Glu | Tyr | Lys |
| | | | | 165 | | | | | 170 | | | | | 175 | |

| Tyr | Pro | Ala | Leu | Asn | Val | Thr | Met | Pro | Asn | Asn | Gly | Lys | Phe | Asp | Lys |
| | | | 180 | | | | | 185 | | | | | 190 | | |

| Leu | Tyr | Ile | Trp | Gly | Val | His | His | Pro | Ser | Thr | Asp | Ser | Val | Gln | Thr |
| | | 195 | | | | | 200 | | | | | 205 | | | |

| Ser | Leu | Tyr | Val | Arg | Ala | Ser | Gly | Arg | Val | Thr | Val | Ser | Thr | Lys | Arg |
| 210 | | | | | 215 | | | | | 220 | | | | | |

| Ser | Gln | Gln | Thr | Val | Ile | Pro | Asp | Ile | Gly | Tyr | Arg | Pro | Trp | Val | Arg |
| 225 | | | | | 230 | | | | | 235 | | | | | 240 |

| Gly | Gln | Ser | Ser | Arg | Ile | Ser | Ile | Tyr | Trp | Thr | Ile | Val | Lys | Pro | Gly |
| | | | | 245 | | | | | 250 | | | | | 255 | |

| Asp | Ile | Leu | Leu | Ile | Asn | Ser | Thr | Gly | Asn | Leu | Ile | Ala | Pro | Arg | Gly |
| | | | 260 | | | | | 265 | | | | | 270 | | |

| Tyr | Phe | Lys | Ile | Arg | Asn | Gly | Lys | Ser | Ser | Ile | Met | Arg | Ser | Asp | Ala |
| | | 275 | | | | | 280 | | | | | 285 | | | |

| Pro | Ile | Gly | Asn | Cys | Ser | Ser | Glu | Cys | Ile | Thr | Pro | Asn | Gly | Ser | Ile |
| 290 | | | | | 295 | | | | | 300 | | | | | |

| Pro | Asn | Asp | Lys | Pro | Phe | Gln | Asn | Val | Asn | Arg | Ile | Thr | Tyr | Gly | Ala |
| 305 | | | | | 310 | | | | | 315 | | | | | 320 |

| Cys | Pro | Arg | Tyr | Val | Lys | Gln | Asn | Thr | Leu | Lys | Leu | Ala | Thr | Gly | Met |
| | | | | 325 | | | | | 330 | | | | | 335 | |

| Arg | Asn | Val | Pro | Glu | Lys | Gln | Thr | Arg | Gly | Ile | Phe | Gly | Ala | Ile | Ala |
| | | | 340 | | | | | 345 | | | | | 350 | | |

| Gly | Phe | Ile | Glu | Asn | Gly | Trp | Glu | Gly | Met | Val | Asp | Gly | Trp | Tyr | Gly |
| | | 355 | | | | | 360 | | | | | 365 | | | |

| Phe | Arg | His | Gln | Asn | Ser | Glu | Gly | Thr | Gly | Gln | Ala | Ala | Asp | Leu | Lys |
| 370 | | | | | 375 | | | | | 380 | | | | | |

```
Ser Thr Gln Ala Ala Ile Asp Gln Ile Asn Gly Lys Leu Asn Arg Leu
385                 390                 395                 400

Val Glu Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
    435                 440                 445

Asn Gln His Thr Ile Asp Leu Thr Asp Ser Glu Met Asn Lys Leu Phe
450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 52
<211> LENGTH: 451
<212> TYPE: PRT
<213> ORGANISM: influenza A virus

<400> SEQUENCE: 52

Lys Met Asn Pro Asn Gln Lys Ile Ile Thr Ile Gly Ser Val Ser Leu
1               5                   10                  15

Thr Ile Ala Thr Ile Cys Phe Leu Met Gln Ile Ala Ile Leu Val Thr
            20                  25                  30

Thr Val Thr Leu His Phe Lys Gln Tyr Glu Cys Asn Ser Pro Pro Asn
        35                  40                  45

Asn Gln Val Met Leu Cys Glu Pro Thr Ile Ile Glu Arg Asn Ile Thr
    50                  55                  60

Glu Ile Val Tyr Leu Thr Asn Thr Thr Ile Glu Lys Glu Ile Cys Pro
65                  70                  75                  80

Lys Leu Ala Glu Tyr Arg Asn Trp Ser Lys Pro Gln Cys Lys Ile Thr
                85                  90                  95

Gly Phe Ala Pro Phe Ser Lys Asp Asn Ser Ile Arg Leu Ser Ala Gly
            100                 105                 110

Gly Asp Ile Trp Val Thr Arg Glu Pro Tyr Val Ser Cys Asp Pro Gly
        115                 120                 125

Lys Cys Tyr Gln Phe Ala Leu Gly Gln Gly Thr Thr Leu Asn Asn Arg
    130                 135                 140

His Ser Asn Asp Thr Val His Asp Arg Thr Pro Tyr Arg Thr Leu Leu
145                 150                 155                 160

Met Asn Glu Leu Gly Val Pro Phe His Leu Gly Thr Lys Gln Val Cys
                165                 170                 175

Ile Ala Trp Ser Ser Ser Ser Cys His Asp Gly Lys Ala Trp Leu His
            180                 185                 190
```

-continued

```
Val Cys Val Thr Gly His Asp Glu Asn Ala Thr Ala Ser Phe Ile Tyr
            195                 200                 205

Asp Gly Arg Leu Val Asp Ser Ile Gly Ser Trp Ser Lys Asn Ile Leu
    210                 215                 220

Arg Thr Gln Glu Ser Glu Cys Val Cys Ile Asn Gly Thr Cys Thr Val
225                 230                 235                 240

Val Met Thr Asp Gly Ser Ala Ser Glu Arg Ala Asp Thr Lys Ile Leu
                245                 250                 255

Phe Ile Glu Glu Gly Lys Ile Val His Ile Ser Pro Leu Ser Gly Ser
            260                 265                 270

Ala Gln His Val Glu Glu Cys Ser Cys Tyr Pro Arg Tyr Pro Gly Val
        275                 280                 285

Arg Cys Val Cys Arg Asp Asn Trp Lys Gly Ser Asn Arg Pro Ile Val
    290                 295                 300

Asp Ile Asn Val Lys Asp Tyr Ser Ile Val Ser Ser Tyr Val Cys Ser
305                 310                 315                 320

Gly Leu Val Gly Asp Thr Pro Arg Lys Asn Asp Ser Ser Ser Ser Ser
                325                 330                 335

Tyr Cys Trp Asn Pro Asn Asn Glu Lys Gly Gly His Gly Val Lys Gly
            340                 345                 350

Trp Ala Phe Asp Asp Gly Asn Asp Val Trp Met Gly Arg Thr Ile Ser
        355                 360                 365

Glu Glu Leu Arg Ser Gly Tyr Glu Thr Phe Lys Val Ile Gly Gly Trp
    370                 375                 380

Ser Lys Pro Asn Ser Lys Leu Gln Ile Asn Arg Gln Val Ile Val Asp
385                 390                 395                 400

Arg Gly Asn Arg Ser Gly Tyr Ser Gly Ile Phe Ser Val Glu Gly Lys
                405                 410                 415

Ser Cys Ile Asn Arg Cys Phe Tyr Val Glu Leu Ile Arg Gly Arg Lys
            420                 425                 430

Gln Glu Thr Glu Val Trp Trp Thr Ser Asn Ser Ile Val Val Phe Cys
        435                 440                 445

Gly Thr Ser
    450

<210> SEQ ID NO 53
<211> LENGTH: 566
<212> TYPE: PRT
<213> ORGANISM: influenza A virus

<400> SEQUENCE: 53

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
```

-continued

```
                100                 105                 110
Cys Tyr Pro Tyr Asp Val Pro Asp Tyr Ala Ser Leu Arg Ser Leu Val
            115                 120                 125
Ala Ser Ser Gly Thr Leu Glu Phe Thr Asn Glu Gly Phe Asn Trp Thr
        130                 135                 140
Gly Val Ala Gln Asp Gly Thr Ser Tyr Ala Cys Lys Arg Gly Ser Val
145                 150                 155                 160
Lys Ser Phe Phe Ser Arg Leu Asn Trp Leu His Lys Leu Glu Tyr Lys
                165                 170                 175
Tyr Pro Ala Leu Asn Val Thr Met Pro Asn Asn Asp Lys Phe Asp Lys
            180                 185                 190
Leu Tyr Ile Trp Gly Val His His Pro Ser Thr Asp Ser Asp Gln Thr
        195                 200                 205
Ser Ile Tyr Val Gln Ala Ser Gly Arg Val Thr Val Ser Thr Lys Arg
        210                 215                 220
Ser Gln Gln Thr Val Ile Pro Asn Ile Gly Ser Arg Pro Trp Val Arg
225                 230                 235                 240
Gly Ile Ser Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Arg Ser Gly Lys Ser Ser Ile Met Arg Ser Asp Ala
        275                 280                 285
Pro Ile Gly Asn Cys Asn Ser Glu Cys Ile Thr Pro Asn Gly Ser Ile
290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Thr Gly Gln Ala Ala Asp Leu Lys
        370                 375                 380
Ser Thr Gln Ala Ala Ile Asn Gln Ile Asn Gly Lys Leu Asn Arg Leu
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
        450                 455                 460
Glu Arg Thr Arg Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
```

-continued

```
Asp Trp Ile Leu Trp Ile Ser Phe Ala Ile Ser Cys Phe Leu Leu Cys
    530                 535                 540

```
                325                 330                 335
Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
            355                 360                 365

Lys Leu Arg Ser Gly Tyr Glu Thr Phe Lys Val Ile Gly Gly Trp Ser
            370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Trp Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
            450                 455                 460

Asn Leu Met Pro Ile
465

<210> SEQ ID NO 55
<211> LENGTH: 566
<212> TYPE: PRT
<213> ORGANISM: influenza A virus

<400> SEQUENCE: 55

Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Tyr Ala Cys Lys Arg Ser Ser Ile
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Asn Asp Lys Phe Asp Lys
            180                 185                 190

Leu Tyr Ile Trp Gly Val His His Pro Ser Thr Asp Ser Asp Gln Thr
        195                 200                 205

Ser Ile Tyr Ala Gln Ala Ser Gly Arg Val Thr Val Ser Thr Lys Arg
    210                 215                 220
```

Ser Gln Gln Thr Val Ile Pro Asn Ile Gly Ser Arg Pro Trp Val Arg
225                 230                 235                 240

Gly Ile Ser Ser Arg Ile Ser Ile His Trp Thr Ile Val Lys Pro Gly
            245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 56
<211> LENGTH: 469
<212> TYPE: PRT
<213> ORGANISM: influenza A virus

<400> SEQUENCE: 56

Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

```
Val Thr Leu His Phe Lys Gln Tyr Glu Cys Ser Ser Pro Asn Asn
        35                  40                  45

Gln Val Met Leu Cys Glu Pro Thr Ile Ile Glu Arg Asn Ile Thr Glu
 50                  55                  60

Ile Val Tyr Leu Thr Asn Thr Thr Ile Glu Lys Glu Ile Cys Pro Lys
 65                  70                  75                  80

Leu Ala Glu Tyr Arg Asn Trp Ser Lys Pro Gln Cys Lys Ile Thr Gly
                 85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Arg His
            130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly His Asp Glu Asn Ala Thr Ala Ser Phe Ile Tyr Asp
            195                 200                 205

Gly Arg Leu Val Asp Ser Ile Gly Ser Trp Ser Lys Lys Ile Leu Arg
            210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Ile Val Asp
            290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
            355                 360                 365

Lys Phe Arg Ser Gly Tyr Glu Thr Phe Lys Val Ile Glu Gly Trp Ser
            370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Trp Trp Thr Ser Asn Ser Ile Val Val Phe Cys Gly
            435                 440                 445
```

```
Thr Ser Gly Thr Tyr Gly Thr Gly Ser Trp Pro Asp Gly Ala Asp Ile
    450                 455                 460

Asn Leu Met Pro Ile
465

<210> SEQ ID NO 57
<211> LENGTH: 566
<212> TYPE: PRT
<213> ORGANISM: influenza A virus

<400> SEQUENCE: 57

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Ser Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Gln Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Ser Ala Cys Lys Arg Gly Ser Asn
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val Leu His Pro Ser Thr Asp Ser Asp Gln Ile
        195                 200                 205

Ser Leu Tyr Ala Gln Ala Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350
```

-continued

```
Gly Phe Ile Glu Asn Gly Trp Glu Gly Met Val Asp Gly Trp Tyr Gly
            355                 360                 365

Phe Arg His Gln Asn Ser Glu Gly Thr Gly Gln Ala Ala Asp Leu Lys
        370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 58
<211> LENGTH: 469
<212> TYPE: PRT
<213> ORGANISM: influenza A virus

<400> SEQUENCE: 58

Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Cys Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Arg His
    130                 135                 140

Ser Asn Asp Thr Val His Asp Arg Thr Pro Tyr Arg Thr Leu Leu Met
```

```
            145                 150                 155                 160
Asn Glu Leu Gly Val Pro Phe His Leu Gly Thr Lys Gln Val Cys Ile
                165                 170                 175
Ala Trp Ser Ser Ser Cys His Asp Gly Lys Ala Trp Leu His Val
            180                 185                 190
Cys Val Thr Gly His Asp Glu Asn Ala Thr Ala Ser Phe Ile Tyr Asp
            195                 200                 205
Gly Arg Leu Val Asp Ser Ile Gly Ser Trp Ser Lys Lys Ile Leu Arg
            210                 215                 220
Thr Gln Glu Ser Glu Cys Val Cys Ile Asn Gly Thr Cys Thr Val Val
225                 230                 235                 240
Met Thr Asp Gly Ser Ala Ser Gly Arg Ala Asp Thr Lys Ile Leu Phe
                245                 250                 255
Ile Glu Glu Gly Lys Ile Val His Thr Ser Lys Leu Ser Gly Ser Ala
            260                 265                 270
Gln His Val Glu Glu Cys Ser Cys Tyr Pro Arg Tyr Pro Gly Val Arg
            275                 280                 285
Cys Val Cys Arg Asp Asn Trp Lys Gly Ser Asn Arg Pro Ile Val Asp
            290                 295                 300
Ile Asn Val Lys Asp Tyr Ser Ile Val Ser Ser Tyr Val Cys Ser Gly
305                 310                 315                 320
Leu Val Gly Asp Thr Pro Arg Lys Asn Asp Ser Ser Ser Ser His
                325                 330                 335
Cys Leu Asp Pro Asn Asn Glu Glu Gly Gly His Gly Val Lys Gly Trp
            340                 345                 350
Ala Phe Asp Asp Gly Asn Asp Val Trp Met Gly Arg Thr Ile Ser Glu
            355                 360                 365
Lys Ser Arg Ser Gly Tyr Glu Thr Phe Lys Val Ile Glu Gly Trp Ser
            370                 375                 380
Lys Pro Asn Ser Lys Leu Gln Ile Asn Arg Gln Val Ile Val Glu Arg
385                 390                 395                 400
Gly Asn Met Ser Gly Tyr Ser Gly Ile Phe Ser Val Glu Gly Lys Ser
                405                 410                 415
Cys Ile Asn Arg Cys Phe Tyr Val Glu Leu Ile Arg Gly Arg Lys Gln
            420                 425                 430
Glu Thr Glu Val Trp Trp Thr Ser Asn Ser Ile Val Val Phe Cys Gly
            435                 440                 445
Thr Ser Gly Thr Tyr Gly Thr Gly Ser Trp Pro Asp Gly Ala Asp Ile
            450                 455                 460
Asn Leu Met Pro Ile
465

<210> SEQ ID NO 59
<211> LENGTH: 566
<212> TYPE: PRT
<213> ORGANISM: influenza A virus

<400> SEQUENCE: 59

Met Lys Thr Ile Ile Ala Leu Ser Tyr Ile Leu Cys Leu Val Phe Ser
1               5                   10                  15
Gln Lys Leu Pro Gly Asn Asp Asn Ser Thr Ala Thr Leu Cys Leu Gly
            20                  25                  30
His His Ala Val Pro Asn Gly Thr Ile Val Lys Thr Ile Thr Asn Asp
        35                  40                  45
```

```
Gln Ile Glu Val Thr Asn Ala Thr Glu Leu Val Gln Ser Ser Ser Thr
 50                  55                  60

Gly Gly Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Ala
130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Ser Asp Gln Ile
            195                 200                 205

Ser Leu Tyr Ala Gln Ala Ser Gly Arg Ile Thr Val Ser Thr Lys Arg
210                 215                 220

Ser Gln Gln Thr Val Ile Pro Asn Ile Gly Tyr Arg Pro Arg Val Arg
225                 230                 235                 240

Asp Ile Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Thr Gly Gln Ala Ala Asp Leu Lys
370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
450                 455                 460

Glu Arg Thr Lys Lys Gln Leu Arg Glu Asn Ala Glu Asp Met Gly Asn
```

```
                465                 470                 475                 480
        Gly Cys Phe Lys Ile Tyr His Lys Cys Asp Asn Ala Cys Ile Glu Ser
                        485                 490                 495
        Ile Arg Asn Gly Thr Tyr Asp His Asp Val Tyr Arg Asp Glu Ala Leu
                        500                 505                 510
        Asn Asn Arg Phe Gln Ile Lys Gly Val Glu Leu Lys Ser Gly Tyr Lys
                        515                 520                 525
        Asp Trp Ile Leu Trp Ile Ser Phe Ala Ile Ser Cys Phe Leu Leu Cys
                        530                 535                 540
        Val Ala Leu Leu Gly Phe Ile Met Trp Ala Cys Gln Lys Gly Asn Ile
        545                 550                 555                 560
        Arg Cys Asn Ile Cys Ile
                        565

<210> SEQ ID NO 60
<211> LENGTH: 469
<212> TYPE: PRT
<213> ORGANISM: influenza A virus

<400> SEQUENCE: 60

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
                20                  25                  30

Val Thr Leu His Phe Lys Gln Tyr Glu Phe Asn Ser Pro Pro Asn Asn
            35                  40                  45

Gln Val Met Leu Cys Glu Pro Thr Ile Ile Glu Arg Asn Ile Thr Glu
        50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Val His
        130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
                180                 185                 190

Cys Val Thr Gly Asp Asp Glu Asn Ala Thr Ala Ser Phe Ile Tyr Asn
            195                 200                 205

Gly Arg Leu Val Asp Ser Ile Val Ser Trp Ser Lys Lys Ile Leu Arg
        210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
                260                 265                 270
```

```
Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
            325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
            355                 360                 365

Lys Leu Arg Ser Gly Tyr Glu Thr Phe Lys Val Ile Glu Gly Trp Ser
        370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 61
<211> LENGTH: 566
<212> TYPE: PRT
<213> ORGANISM: influenza A virus

<400> SEQUENCE: 61

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Val Ala Gly Trp Ile Leu Gly
65                  70                  75                  80

Asn Pro Lys Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Thr Ser Cys Ser His Asn Gly Lys Ser Ser
145                 150                 155                 160

Phe Tyr Arg Asn Leu Leu Trp Leu Thr Lys Lys Asn Gly Leu Tyr Pro
                165                 170                 175
```

```
Asn Val Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Gly Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Gly Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 62
<211> LENGTH: 470
```

<212> TYPE: PRT
<213> ORGANISM: influenza A virus

<400> SEQUENCE: 62

```
Met Asn Pro Asn Gln Lys Ile Ile Ile Gly Ser Ile Ser Met Ala
1               5                   10                  15

Ile Gly Ile Ile Ser Leu Ile Leu Gln Ile Gly Asn Ile Ile Ser
            20                  25                  30

Trp Ala Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Pro Ile Arg Gly
                85                  90                  95

Trp Ala Ile Tyr Thr Lys Asp Asn Ser Ile Arg Ile Gly Ser Lys Gly
                100                 105                 110

Asp Val Phe Val Ile Arg Glu Pro Phe Ile Ser Cys Ser His Leu Glu
            115                 120                 125

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
                195                 200                 205

Asn Gly Ile Ile Thr Glu Thr Ile Lys Ser Trp Lys Lys Arg Ile Leu
210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Arg Ile Phe
                245                 250                 255

Lys Ile Glu Lys Gly Lys Val Thr Lys Ser Ile Glu Leu Asp Ala Pro
                260                 265                 270

Asn Tyr His Tyr Glu Glu Cys Ser Cys Tyr Pro Asp Thr Gly Thr Val
            275                 280                 285

Met Cys Val Cys Arg Asp Asn Trp His Gly Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Arg Leu Arg
            355                 360                 365

Lys Gly Phe Glu Met Ile Trp Asp Pro Asn Gly Trp Thr Asp Thr Asp
            370                 375                 380

Ser Asp Phe Ser Val Lys Gln Asp Val Val Ala Met Thr Asp Trp Ser
385                 390                 395                 400
```

```
Gly Tyr Ser Gly Ser Phe Val Gln His Pro Glu Leu Thr Gly Leu Asp
                405                 410                 415

Cys Met Arg Pro Cys Phe Trp Val Glu Leu Ile Arg Gly Arg Pro Arg
            420                 425                 430

Glu Asn Thr Thr Ile Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465                 470

<210> SEQ ID NO 63
<211> LENGTH: 562
<212> TYPE: PRT
<213> ORGANISM: influenza A virus

<400> SEQUENCE: 63

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Thr
    50                  55                  60

Ala Pro Leu Gln Leu Gly Asn Cys Ser Val Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Thr
    130                 135                 140

Val Thr Lys Gly Val Thr Ala Ser Cys Ser His Asn Gly Lys Ser Ser
145                 150                 155                 160

Phe Tyr Lys Asn Leu Leu Trp Leu Thr Glu Lys Asn Gly Leu Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Gly Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Thr Ala Ser
        275                 280                 285

Met Gly Glu Cys Asp Ala Lys Cys Gln Thr Pro Gln Gly Ala Ile Asn
```

```
                290             295             300
Ser Ser Leu Pro Phe Gln Asn Val His Pro Val Thr Ile Gly Glu Cys
305                 310             315                 320

Pro Lys Tyr Val Arg Ser Thr Lys Leu Arg Met Val Thr Gly Leu Arg
                325             330             335

Asn Ile Pro Ser Ile Gln Ser Arg Gly Leu Phe Gly Ala Ile Ala Gly
                340             345             350

Phe Ile Glu Gly Gly Trp Thr Gly Met Ile Asp Gly Trp Tyr Gly Tyr
            355             360             365

His His Gln Asn Glu Gln Gly Ser Gly Tyr Ala Ala Asp Gln Lys Ser
        370             375             380

Thr Gln Asn Ala Ile Asp Gly Ile Thr Asn Lys Val Asn Ser Val Ile
385             390             395                 400

Glu Lys Met Asn Thr Gln Phe Thr Ala Val Gly Lys Glu Phe Asn Lys
                405             410             415

Leu Glu Arg Arg Met Glu Asn Leu Asn Lys Lys Val Asp Asp Gly Phe
            420             425             430

Leu Asp Ile Trp Thr Tyr Asn Ala Glu Leu Leu Val Leu Leu Glu Asn
            435             440             445

Gly Arg Thr Leu Gly Phe His Asp Ser Asn Val Lys Asn Leu Tyr Glu
        450             455             460

Lys Val Lys Asn Gln Leu Lys Asn Asn Ala Lys Glu Ile Gly Asn Gly
465             470             475                 480

Cys Phe Glu Phe Tyr His Lys Cys Asn Asn Glu Cys Met Glu Ser Val
                485             490             495

Lys Asn Gly Thr Tyr Asp Tyr Pro Lys Tyr Ser Glu Glu Ser Lys Leu
            500             505             510

Asn Arg Glu Lys Ile Asp Gly Val Lys Leu Glu Ser Met Gly Val Tyr
        515             520             525

Gln Ile Leu Ala Ile Tyr Ser Thr Val Ala Ser Ser Leu Val Leu Leu
    530             535             540

Val Ser Leu Gly Ala Ile Ser Phe Trp Met Cys Ser Asn Gly Ser Leu
545             550             555                 560

Gln Cys

<210> SEQ ID NO 64
<211> LENGTH: 470
<212> TYPE: PRT
<213> ORGANISM: influenza A virus

<400> SEQUENCE: 64

Met Asn Pro Asn Gln Lys Ile Ile Thr Ile Gly Ser Ile Ser Ile Ala
1               5                   10                  15

Ile Gly Ile Ile Ser Leu Ile Leu Gln Ile Gly Asn Ile Ile Ser Ile
            20                  25                  30

Trp Ala Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
    50                  55                  60

Thr Tyr Val Asn Ile Asn Asn Thr Asn Val Val Ala Gly Lys Asp Lys
65                  70                  75                  80

Thr Ser Met Thr Leu Ala Gly Asn Ser Ser Leu Cys Pro Ile Arg Gly
                85                  90                  95

Trp Ala Ile Tyr Thr Lys Asp Asn Ser Ile Arg Ile Gly Ser Lys Gly
```

```
                  100                 105                 110
Asp Val Phe Val Ile Arg Glu Pro Phe Ile Ser Cys Ser His Leu Glu
            115                 120                 125

Cys Arg Thr Phe Phe Leu Thr Gln Gly Ala Leu Leu Asn Asp Lys His
            130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Arg Phe Glu Ser
                165                 170                 175

Val Ala Trp Ser Ala Ser Ala Cys His Asp Gly Leu Gly Trp Leu Thr
            180                 185                 190

Ile Gly Ile Ser Gly Pro Asp Asn Gly Ala Val Ala Val Leu Lys Tyr
            195                 200                 205

Asn Gly Ile Ile Thr Glu Thr Ile Lys Ser Trp Lys Lys Arg Ile Leu
            210                 215                 220

Arg Thr Gln Glu Ser Glu Cys Val Cys Met Asn Gly Ser Cys Phe Thr
225                 230                 235                 240

Ile Met Thr Asp Gly Pro Ser Asn Gly Ala Ala Ser Tyr Arg Ile Phe
                245                 250                 255

Lys Ile Glu Lys Gly Arg Val Thr Lys Ser Ile Glu Leu Asp Ala Pro
            260                 265                 270

Asn Tyr His Tyr Glu Glu Cys Ser Cys Tyr Pro Asp Thr Gly Thr Val
            275                 280                 285

Met Cys Val Cys Arg Asp Asn Trp His Gly Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Arg Leu Arg
            355                 360                 365

Lys Gly Phe Glu Met Ile Trp Asp Pro Asn Gly Trp Thr Asp Thr Asp
370                 375                 380

Ser Asp Phe Ser Met Lys Gln Asp Ile Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
            435                 440                 445

Val Asn Ser Asp Thr Ala Asn Trp Ser Trp Pro Asp Gly Ala Glu Leu
            450                 455                 460

Pro Phe Thr Ile Asp Lys
465                 470

<210> SEQ ID NO 65
<211> LENGTH: 565
<212> TYPE: PRT
<213> ORGANISM: influenza A virus

<400> SEQUENCE: 65
```

```
Met Lys Ala Lys Leu Leu Val Leu Leu Cys Thr Phe Thr Ala Thr Tyr
 1               5                  10                 15

Ala Asp Thr Ile Cys Ile Gly Tyr His Ala Asn Asn Ser Thr Asp Thr
             20                  25                 30

Val Asp Thr Val Leu Glu Lys Asn Val Thr Val Thr His Ser Val Asn
         35                  40                 45

Leu Leu Glu Asp Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                 80

Asn Pro Glu Cys Glu Ser Leu Ile Ser Lys Glu Ser Trp Ser Tyr Ile
                 85                  90                 95

Val Glu Thr Pro Asn Pro Glu Asn Gly Thr Cys Tyr Pro Gly Tyr Phe
             100                 105                110

Ala Asp Tyr Glu Glu Leu Arg Glu Gln Leu Ser Ser Val Ser Ser Phe
         115                 120                 125

Glu Arg Phe Glu Ile Phe Pro Lys Glu Ser Ser Trp Pro Lys His Thr
     130                 135                 140

Val Thr Gly Val Thr Ala Ser Cys Ser His Asn Gly Lys Ser Ser Phe
145                 150                 155                160

Tyr Arg Asn Leu Leu Trp Leu Thr Glu Lys Asn Gly Leu Tyr Pro Asn
                 165                 170                 175

Leu Ser Asn Ser Tyr Val Asn Asn Lys Glu Lys Glu Val Leu Val Leu
             180                 185                 190

Trp Gly Val His His Pro Ser Asn Ile Gly Asp Gln Arg Ala Ile Tyr
         195                 200                 205

His Thr Glu Asn Ala Tyr Val Ser Val Val Ser Ser His Tyr Ser Arg
     210                 215                 220

Arg Phe Thr Pro Glu Ile Ala Lys Arg Pro Lys Val Arg Gly Gln Glu
225                 230                 235                 240

Gly Arg Ile Asn Tyr Tyr Trp Thr Leu Leu Glu Pro Gly Asp Thr Ile
                 245                 250                 255

Ile Phe Glu Ala Asn Gly Asn Leu Ile Ala Pro Trp Tyr Ala Phe Ala
             260                 265                 270

Leu Ser Arg Gly Phe Gly Ser Gly Ile Ile Thr Ser Asn Ala Pro Met
         275                 280                 285

Asn Glu Cys Asp Ala Lys Cys Gln Thr Pro Gln Gly Ala Ile Asn Ser
     290                 295                 300

Ser Leu Pro Phe Gln Asn Val His Pro Val Thr Ile Gly Glu Cys Pro
305                 310                 315                 320

Lys Tyr Val Arg Ser Thr Lys Leu Arg Met Val Thr Gly Leu Arg Asn
                 325                 330                 335

Ile Pro Ser Ile Gln Ser Arg Gly Leu Phe Gly Ala Ile Ala Gly Phe
             340                 345                 350

Ile Glu Gly Gly Trp Thr Gly Met Met Asp Gly Trp Tyr Gly Tyr His
         355                 360                 365

His Gln Asn Glu Gln Gly Ser Gly Tyr Ala Ala Asp Gln Lys Ser Thr
     370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                 405                 410                 415

Glu Arg Arg Met Glu Asn Leu Asn Lys Lys Val Asp Asp Gly Phe Leu
```

-continued

```
                420             425             430
Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 66
<211> LENGTH: 470
<212> TYPE: PRT
<213> ORGANISM: influenza A virus

<400> SEQUENCE: 66

Met Asn Pro Asn Gln Lys Ile Ile Thr Ile Gly Ser Ile Ser Ile Val
1               5                   10                  15

Ile Gly Ile Ile Ser Leu Met Leu Gln Ile Gly Asn Ile Ile Ser Ile
            20                  25                  30

Trp Ala Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220
```

-continued

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Lys Ile Phe
            245                 250                 255

Lys Ile Glu Lys Gly Lys Val Thr Lys Ser Ile Glu Leu Asn Ala Pro
        260                 265                 270

Asn Ser His Tyr Glu Glu Cys Ser Cys Tyr Pro Asp Thr Gly Thr Val
    275                 280                 285

Met Cys Val Cys Arg Asp Asn Trp His Gly Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
            325                 330                 335

Pro Val Thr Val Asp Gly Ala Asp Gly Val Lys Gly Phe Ser Tyr Arg
        340                 345                 350

Tyr Gly Asn Gly Val Trp Ile Gly Arg Thr Lys Ser Asn Arg Leu Arg
    355                 360                 365

Lys Gly Phe Glu Met Ile Trp Asp Pro Asn Gly Trp Thr Asp Thr Asp
370                 375                 380

Ser Asp Phe Ser Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
            405                 410                 415

Cys Ile Arg Pro Cys Phe Trp Val Glu Leu Val Arg Gly Arg Pro Arg
        420                 425                 430

Glu Asn Thr Thr Ile Trp Thr Ser Gly Ser Ser Ile Ser Phe Cys Gly
    435                 440                 445

Val Asn Ser Asp Thr Ala Asn Trp Ser Trp Pro Asp Gly Ala Glu Leu
450                 455                 460

Pro Phe Thr Ile Asp Lys
465             470

<210> SEQ ID NO 67
<211> LENGTH: 565
<212> TYPE: PRT
<213> ORGANISM: influenza A virus

<400> SEQUENCE: 67

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

-continued

```
Glu Arg Phe Glu Ile Phe Pro Lys Glu Ser Ser Trp Pro Lys His Thr
    130                 135                 140
Val Thr Gly Val Ser Ala Ser Cys Ser His Asn Gly Lys Asn Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Val Asn Asn Lys Glu Lys Glu Val Leu Val Leu
            180                 185                 190
Trp Gly Val His His Pro Pro Asn Ile Gly Asp Gln Arg Ala Leu Tyr
        195                 200                 205
His Thr Glu Asn Ala Tyr Val Ser Val Val Ser Ser His Tyr Ser Arg
    210                 215                 220
Arg Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Trp Tyr Ala Phe Ala
            260                 265                 270
Leu Ser Arg Gly Phe Gly Ser Gly Ile Ile Thr Ser Asn Ala Pro Met
        275                 280                 285
Asp Glu Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
    370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asn Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Lys Ile Asp Gly Val Lys Leu Glu Ser Met Gly Val Tyr Gln
        515                 520                 525
Ile Leu Ala Ile Tyr Ser Thr Val Ala Ser Ser Leu Val Leu Leu Val
    530                 535                 540
```

```
Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 68
<211> LENGTH: 470
<212> TYPE: PRT
<213> ORGANISM: influenza A virus

<400> SEQUENCE: 68

Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
            20                  25                  30

Trp Ala Ser His Ser Ile Gln Thr Gly Ser Gln Asn His Thr Gly Val
        35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Phe His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Lys
            340                 345                 350
```

-continued

Tyr Gly Asn Gly Val Trp Ile Gly Arg Thr Lys Ser Asn Arg Leu Arg
            355                 360                 365

Lys Gly Phe Glu Met Ile Trp Asp Pro Asn Gly Trp Thr Asp Thr Asp
        370                 375                 380

Ser Asp Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
            435                 440                 445

Val Asn Ser Asp Thr Ala Asn Trp Ser Trp Pro Asp Gly Ala Glu Leu
450                 455                 460

Pro Phe Thr Ile Asp Lys
465                 470

<210> SEQ ID NO 69
<211> LENGTH: 583
<212> TYPE: PRT
<213> ORGANISM: influenza B virus

<400> SEQUENCE: 69

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Ile Gly Ile Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Arg
    130                 135                 140

Ala Pro Gly Gly Pro Tyr Arg Leu Gly Thr Ser Gly Ser Cys Pro Asn
145                 150                 155                 160

Val Thr Ser Arg Ser Gly Phe Phe Ala Thr Met Ala Trp Ala Val Pro
                165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
        195                 200                 205

Asp Asn Lys Ile Gln Met Lys Asn Leu Tyr Gly Asp Ser Asn Pro Gln
    210                 215                 220

Lys Phe Thr Ser Ser Ala Asn Gly Ile Thr Thr His Tyr Val Ser Gln
225                 230                 235                 240

Ile Gly Gly Phe Pro Asn Gln Thr Glu Asp Gly Gly Leu Pro Gln Ser

```
                       245                 250                 255
Gly Arg Ile Val Val Asp Tyr Met Val Gln Lys Pro Gly Lys Thr Gly
                260                 265                 270

Thr Ile Val Tyr Gln Arg Gly Val Leu Leu Pro Gln Lys Val Trp Cys
            275                 280                 285

Ala Ser Gly Arg Ser Lys Val Ile Lys Gly Ser Leu Pro Leu Ile Gly
        290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Lys Gly Phe Phe Gly Ala Ile Ala Gly
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
                580

<210> SEQ ID NO 70
<211> LENGTH: 465
<212> TYPE: PRT
<213> ORGANISM: influenza B virus

<400> SEQUENCE: 70

Met Leu Pro Ser Thr Ile Gln Thr Leu Thr Leu Phe Leu Thr Ser Gly
1               5                   10                  15

Gly Val Leu Leu Ser Leu Tyr Val Ser Ala Leu Leu Ser Tyr Leu Leu
            20                  25                  30
```

```
Tyr Ser Asp Ile Leu Leu Lys Phe Ser Pro Lys Ile Ile Ala Pro Thr
     35                  40                  45

Thr Ser Leu Asp Cys Ala Asn Ala Ser Asn Val Gln Ala Val Asn His
 50                  55                  60

Ser Ala Thr Lys Glu Met Lys Phe Leu Pro Pro Glu Pro Glu Trp Thr
65                   70                  75                  80

Tyr Pro Arg Leu Ser Cys Gln Gly Ser Thr Phe Gln Lys Ala Leu Leu
                 85                  90                  95

Ile Ser Pro His Arg Phe Gly Glu Ala Lys Gly Asn Ser Ala Pro Leu
            100                 105                 110

Ile Ile Arg Glu Pro Phe Ile Ala Cys Gly Pro Lys Glu Cys Lys His
            115                 120                 125

Phe Ala Leu Thr His Tyr Ala Ala Gln Pro Gly Gly Tyr Tyr Asn Gly
            130                 135                 140

Thr Arg Glu Asp Arg Asn Lys Leu Arg His Leu Ile Ser Val Asn Leu
145                 150                 155                 160

Gly Lys Ile Pro Thr Val Glu Asn Ser Ile Phe His Met Ala Ala Trp
                165                 170                 175

Ser Gly Ser Ala Cys His Asp Gly Arg Glu Trp Thr Tyr Ile Gly Val
            180                 185                 190

Asp Gly Pro Asp Ser Asn Ala Leu Ile Lys Ile Lys Tyr Gly Glu Ala
            195                 200                 205

Tyr Thr Asp Thr Tyr His Ser Tyr Ala Asn Asn Ile Leu Arg Thr Gln
            210                 215                 220

Glu Ser Ala Cys Asn Cys Ile Gly Gly Asp Cys Tyr Leu Met Ile Thr
225                 230                 235                 240

Asp Gly Ser Ala Ser Gly Ile Ser Lys Cys Arg Phe Leu Lys Ile Arg
                245                 250                 255

Glu Gly Arg Ile Ile Lys Glu Ile Phe Pro Thr Gly Arg Val Glu His
            260                 265                 270

Thr Glu Glu Cys Thr Cys Gly Phe Ala Ser Asn Lys Thr Ile Glu Cys
            275                 280                 285

Ala Cys Arg Asp Asn Ser Tyr Thr Ala Lys Arg Pro Phe Val Lys Leu
            290                 295                 300

Asn Val Glu Thr Asp Thr Ala Glu Ile Arg Leu Met Cys Thr Glu Thr
305                 310                 315                 320

Tyr Leu Asp Thr Pro Arg Pro Asp Asp Gly Ser Ile Thr Gly Pro Cys
                325                 330                 335

Glu Ser Asn Gly Asp Lys Gly Ser Gly Gly Val Lys Gly Gly Phe Val
            340                 345                 350

His Gln Arg Met Ala Ser Lys Ile Gly Arg Trp Tyr Ser Arg Thr Met
            355                 360                 365

Ser Lys Thr Lys Arg Met Gly Met Glu Leu Tyr Val Lys Tyr Asp Gly
370                 375                 380

Asp Pro Trp Thr Asp Ser Asp Ala Leu Ala Pro Ser Gly Val Met Val
385                 390                 395                 400

Ser Met Glu Glu Pro Gly Trp Tyr Ser Phe Gly Phe Glu Ile Lys Asp
                405                 410                 415

Lys Lys Cys Asp Val Pro Cys Ile Gly Ile Glu Met Val His Asp Gly
            420                 425                 430

Gly Lys Arg Thr Trp His Ser Ala Ala Thr Ala Ile Tyr Cys Leu Met
            435                 440                 445

Gly Ser Gly Gln Leu Leu Trp Asp Thr Val Thr Gly Val Asn Met Ala
```

```
                450                 455                 460
Leu
465

<210> SEQ ID NO 71
<211> LENGTH: 584
<212> TYPE: PRT
<213> ORGANISM: influenza B virus

<400> SEQUENCE: 71

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Thr Cys Leu Asn Cys Thr Asp Leu Asp Val
65                  70                  75                  80

Ala Leu Gly Arg Pro Met Cys Val Gly Val Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Lys Ile Arg Leu Ser Thr Gln Ile Val Ile Asn Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Arg Ser Gly Phe Phe Ala Thr Met Ala Trp Ala Val Pro
                165                 170                 175

Lys Asp Asn Asn Lys Thr Ala Thr Asn Pro Leu Thr Val Glu Val Pro
            180                 185                 190

His Ile Cys Thr Lys Glu Glu Asp Gln Ile Thr Val Trp Gly Phe His
        195                 200                 205

Ser Asp Asp Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350
```

```
Pro Pro Ala Lys Leu Leu Lys Glu Arg Gly Phe Phe Gly Ala Ile Ala
            355                 360                 365

Gly Phe Leu Glu Gly Gly Trp Glu Gly Met Ile Ala Gly Trp His Gly
        370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
            405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
        450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
            485                 490                 495

Gly Cys Phe Glu Thr Lys His Lys Cys Asn Gln Thr Cys Leu Asp Arg
        500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
        530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Ile Ser Arg Asp
            565                 570                 575

Asn Val Ser Cys Ser Ile Cys Leu
            580

<210> SEQ ID NO 72
<211> LENGTH: 466
<212> TYPE: PRT
<213> ORGANISM: influenza B virus

<400> SEQUENCE: 72

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asn Cys Ala Asn Ala Ser Asn Val Gln Ala Val Asn
    50                  55                  60

Arg Ser Ala Thr Lys Gly Val Thr Leu Pro Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Arg
        115                 120                 125

His Phe Ala Leu Thr His Tyr Ala Ala Gln Pro Gly Gly Tyr Tyr Asn
    130                 135                 140
```

```
Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
370                 375                 380

Gly Asp Pro Trp Ile Asp Ser Asp Ala Leu Thr Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Lys Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465

<210> SEQ ID NO 73
<211> LENGTH: 584
<212> TYPE: PRT
<213> ORGANISM: influenza B virus

<400> SEQUENCE: 73

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Ala Ile Pro Leu Thr
```

-continued

```
                    35                  40                  45
Thr Thr Pro Thr Lys Ser His Phe Ala Asn Leu Lys Gly Thr Lys Thr
 50                      55                  60

Arg Gly Lys Leu Cys Pro Thr Cys Leu Asn Cys Thr Asp Leu Asp Val
 65                  70                  75                  80

Ala Leu Gly Arg Pro Met Cys Val Gly Ile Thr Pro Ser Ala Lys Ala
                     85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu Lys Ile Arg Leu Ser Thr Gln Asn Val Ile Asn Ala Glu Lys
130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Arg Asp Asn Asn Lys Thr Ala Thr Asn Pro Leu Thr Val Glu Val Pro
            180                 185                 190

His Ile Cys Thr Lys Glu Glu Asp Gln Ile Thr Val Trp Gly Phe His
        195                 200                 205

Ser Asp Asp Lys Thr Gln Met Lys Asn Leu Tyr Gly Asp Ser Asn Pro
210                 215                 220

Gln Lys Phe Thr Ser Ala Asn Gly Ile Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
450                 455                 460
```

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Ile Asp Ile Gly Asn
            485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
            515                 520                 525

Asp Ser Leu Asn Ile Thr Ala Ala Ser Leu Asn Asp Asp Gly Leu Asp
            530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Ile Ser Arg Asp
            565                 570                 575

Asn Val Ser Cys Ser Ile Cys Leu
            580

<210> SEQ ID NO 74
<211> LENGTH: 466
<212> TYPE: PRT
<213> ORGANISM: influenza B virus

<400> SEQUENCE: 74

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
            35                  40                  45

Ala Met Pro Leu Asp Cys Ala Asn Ala Ser Asn Val Gln Ala Val Asn
            50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
            85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
            115                 120                 125

His Phe Ala Leu Thr His Tyr Ala Ala Gln Pro Gly Gly Tyr Tyr Asn
130                 135                 140

Gly Thr Arg Glu Asp Arg Asn Lys Leu Arg His Leu Ile Ser Val Lys
145                 150                 155                 160

Phe Gly Lys Ile Pro Thr Val Glu Asn Ser Ile Phe His Met Ala Ala
            165                 170                 175

Trp Ser Gly Ser Ala Cys His Asp Gly Lys Glu Trp Thr Tyr Ile Gly
            180                 185                 190

Val Asp Gly Pro Asp Ser Asn Ala Leu Leu Lys Ile Lys Tyr Gly Glu
            195                 200                 205

Ala Tyr Thr Asp Thr Tyr His Ser Tyr Ala Asn Asn Ile Leu Arg Thr
            210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile

```
                245                 250                 255
Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Thr Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465

<210> SEQ ID NO 75
<211> LENGTH: 583
<212> TYPE: PRT
<213> ORGANISM: influenza B virus

<400> SEQUENCE: 75

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Ile Gly Ile Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Arg
    130                 135                 140
```

-continued

```
Ala Pro Gly Gly Pro Tyr Arg Leu Gly Thr Ser Gly Ser Cys Pro Asn
145                 150                 155                 160

Val Thr Ser Arg Ser Gly Phe Phe Ala Thr Met Ala Trp Ala Val Pro
                165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
        195                 200                 205

Asp Asn Lys Ile Gln Met Lys Asn Leu Tyr Gly Asp Ser Asn Pro Gln
    210                 215                 220

Lys Phe Thr Ser Ser Ala Asn Gly Ile Thr Thr His Tyr Val Ser Gln
225                 230                 235                 240

Ile Gly Gly Phe Pro Asn Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Lys Gly Phe Phe Gly Ala Ile Ala Gly
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
```

Val Ser Cys Ser Ile Cys Leu
        580

<210> SEQ ID NO 76
<211> LENGTH: 465
<212> TYPE: PRT
<213> ORGANISM: influenza B virus

<400> SEQUENCE: 76

Met Leu Pro Ser Thr Ile Gln Thr Leu Thr Leu Phe Leu Thr Ser Gly
1               5                   10                  15

Gly Val Leu Leu Ser Leu Tyr Val Ser Ala Leu Leu Ser Tyr Leu Leu
            20                  25                  30

Tyr Ser Asp Ile Leu Leu Lys Phe Ser Pro Lys Ile Ile Ala Pro Thr
        35                  40                  45

Thr Ser Leu Asp Cys Ala Asn Ala Ser Asn Val Gln Ala Val Asn His
    50                  55                  60

Ser Ala Thr Lys Glu Met Lys Phe Leu Pro Pro Glu Pro Glu Trp Thr
65                  70                  75                  80

Tyr Pro Arg Leu Ser Cys Gln Gly Ser Thr Phe Gln Lys Ala Leu Leu
                85                  90                  95

Ile Ser Pro His Arg Phe Gly Glu Ala Lys Gly Asn Ser Ala Pro Leu
            100                 105                 110

Ile Ile Arg Glu Pro Phe Ile Ala Cys Gly Pro Lys Glu Cys Lys His
        115                 120                 125

Phe Ala Leu Thr His Tyr Ala Ala Gln Pro Gly Gly Tyr Tyr Asn Gly
    130                 135                 140

Thr Arg Glu Asp Arg Asn Lys Leu Arg His Leu Ile Ser Val Asn Leu
145                 150                 155                 160

Gly Lys Ile Pro Thr Val Glu Asn Ser Ile Phe His Met Ala Ala Trp
                165                 170                 175

Ser Gly Ser Ala Cys His Asp Gly Arg Glu Trp Thr Tyr Ile Gly Val
            180                 185                 190

Asp Gly Pro Asp Ser Asn Ala Leu Ile Lys Ile Lys Tyr Gly Glu Ala
        195                 200                 205

Tyr Thr Asp Thr Tyr His Ser Tyr Ala Asn Asn Ile Leu Arg Thr Gln
    210                 215                 220

Glu Ser Ala Cys Asn Cys Ile Gly Gly Asp Cys Tyr Leu Met Ile Thr
225                 230                 235                 240

Asp Gly Ser Ala Ser Gly Ile Ser Lys Cys Arg Phe Leu Lys Ile Arg
                245                 250                 255

Glu Gly Arg Ile Ile Lys Glu Ile Phe Pro Thr Gly Arg Val Glu His
            260                 265                 270

Thr Glu Glu Cys Thr Cys Gly Phe Ala Ser Asn Lys Thr Ile Glu Cys
        275                 280                 285

Ala Cys Arg Asp Asn Ser Tyr Thr Ala Lys Arg Pro Phe Val Lys Leu
    290                 295                 300

Asn Val Glu Thr Asp Thr Ala Glu Ile Arg Leu Met Cys Thr Glu Thr
305                 310                 315                 320

Tyr Leu Asp Thr Pro Arg Pro Asp Asp Gly Ser Ile Thr Gly Pro Cys
                325                 330                 335

Glu Ser Asn Gly Asp Lys Gly Ser Gly Gly Val Lys Gly Gly Phe Val
            340                 345                 350

```
His Gln Arg Met Ala Ser Lys Ile Gly Arg Trp Tyr Ser Arg Thr Met
        355                 360                 365

Ser Lys Thr Lys Arg Met Gly Met Glu Leu Tyr Val Lys Tyr Asp Gly
        370                 375                 380

Asp Pro Trp Thr Asp Ser Asp Ala Leu Ala Pro Ser Gly Val Met Val
385                 390                 395                 400

Ser Met Glu Glu Pro Gly Trp Tyr Ser Phe Gly Phe Glu Ile Lys Asp
                405                 410                 415

Lys Lys Cys Asp Val Pro Cys Ile Gly Ile Glu Met Val His Asp Gly
                420                 425                 430

Gly Lys Arg Thr Trp His Ser Ala Ala Thr Ala Ile Tyr Cys Leu Met
        435                 440                 445

Gly Ser Gly Gln Leu Leu Trp Asp Thr Val Thr Gly Val Asn Met Ala
        450                 455                 460

Leu
465

<210> SEQ ID NO 77
<211> LENGTH: 585
<212> TYPE: PRT
<213> ORGANISM: influenza B virus

<400> SEQUENCE: 77

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Lys Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
        115                 120                 125

Tyr Glu Arg Ile Arg Leu Ser Asn His Asn Val Ile Asn Ala Glu Lys
        130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Glu Asn Asn Lys Thr Ala Thr Asn Ser Leu Thr Ile Glu Val
        180                 185                 190

Pro Tyr Ile Cys Thr Glu Gly Glu Asp Gln Ile Thr Val Trp Gly Phe
        195                 200                 205

His Ser Asp Ser Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255
```

```
Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
370                 375                 380

Gly Tyr Thr Ser His Gly Ala His Gly Val Ala Val Ala Ala Asp Leu
                385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
        420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
        500                 505                 510

Arg Ile Ala Ala Gly Thr Phe Asn Ala Gly Glu Phe Ser Leu Pro Thr
            515                 520                 525

Phe Asp Ser Leu Asn Ile Thr Ala Ala Ser Leu Asn Asp Asp Gly Leu
        530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 78
<211> LENGTH: 466
<212> TYPE: PRT
<213> ORGANISM: influenza B virus

<400> SEQUENCE: 78

Met Leu Pro Ser Thr Ile Gln Thr Leu Thr Leu Phe Leu Thr Ser Gly
1               5                   10                  15

Gly Val Leu Leu Ser Leu Tyr Val Ser Ala Leu Leu Ser Tyr Leu Leu
            20                  25                  30

Tyr Ser Asp Ile Leu Leu Lys Phe Ser Pro Thr Lys Ile Ile Ala Pro
```

-continued

```
                    35                  40                  45
Thr Thr Ser Leu Asp Ser Ala Asn Ala Ser Asn Phe Gln Ala Val Asn
             50                  55                  60
His Ser Ala Thr Lys Glu Met Thr Phe Leu Leu Pro Glu Pro Glu Trp
 65                  70                  75                  80
Thr Tyr Pro Arg Leu Ser Cys Gln Gly Ser Thr Phe Gln Lys Ala Leu
                 85                  90                  95
Leu Ile Ser Pro His Arg Phe Gly Glu Ala Lys Gly Asn Ser Ala Pro
                100                 105                 110
Leu Ile Ile Arg Glu Pro Phe Ile Ala Cys Gly Pro Lys Glu Cys Lys
                115                 120                 125
His Phe Ala Leu Thr His Tyr Ala Ala Gln Pro Gly Gly Tyr Tyr Asn
            130                 135                 140
Gly Thr Arg Glu Asp Arg Asn Lys Leu Arg His Leu Ile Ser Val Asn
145                 150                 155                 160
Leu Gly Lys Ile Pro Thr Val Glu Asn Ser Ile Phe His Met Ala Ala
                165                 170                 175
Trp Ser Gly Ser Ala Cys His Asp Gly Arg Glu Trp Thr Tyr Ile Gly
            180                 185                 190
Val Asp Gly Pro Asp Ser Asn Ala Leu Ile Lys Ile Lys Tyr Gly Glu
        195                 200                 205
Ala Tyr Thr Asp Thr Tyr His Ser Tyr Ala Asn Asn Ile Leu Arg Thr
    210                 215                 220
Gln Glu Ser Ala Cys Asn Cys Ile Gly Gly Asp Cys Tyr Leu Met Ile
225                 230                 235                 240
Thr Asp Gly Ser Ala Ser Gly Ile Ser Lys Cys Arg Phe Leu Lys Ile
                245                 250                 255
Arg Glu Gly Arg Ile Val Lys Glu Ile Phe Pro Thr Gly Arg Val Glu
            260                 265                 270
His Thr Glu Glu Cys Thr Cys Gly Phe Ala Ser Asn Lys Thr Ile Glu
        275                 280                 285
Cys Ala Cys Arg Asp Asn Ser Tyr Thr Ala Lys Arg Pro Phe Val Lys
    290                 295                 300
Leu Asn Val Glu Thr Asp Thr Ala Glu Ile Arg Leu Met Cys Thr Glu
305                 310                 315                 320
Thr Tyr Leu Asp Thr Pro Arg Pro Asp Asp Gly Ser Ile Thr Gly Pro
                325                 330                 335
Cys Glu Ser Asn Gly Asp Lys Gly Ser Gly Gly Ile Lys Gly Gly Phe
            340                 345                 350
Val His Gln Arg Met Ala Ser Lys Ile Gly Arg Trp Tyr Ser Arg Thr
        355                 360                 365
Met Ser Lys Thr Lys Arg Met Gly Met Glu Leu Tyr Val Lys Tyr Asp
    370                 375                 380
Gly Asp Pro Trp Thr Asp Ser Asp Ala Leu Ala Pro Ser Gly Val Met
385                 390                 395                 400
Val Ser Ile Glu Glu Pro Gly Trp Tyr Ser Phe Gly Phe Glu Ile Lys
                405                 410                 415
Asp Lys Lys Cys Asp Val Pro Cys Ile Gly Ile Glu Met Val His Asp
            420                 425                 430
Gly Gly Lys Thr Thr Trp His Ser Ala Ala Thr Ala Ile Tyr Cys Leu
        435                 440                 445
Met Gly Ser Gly Gln Leu Leu Trp Asp Thr Ile Thr Gly Val Asp Met
    450                 455                 460
```

Ala Leu
465

<210> SEQ ID NO 79
<211> LENGTH: 585
<212> TYPE: PRT
<213> ORGANISM: influenza B virus

<400> SEQUENCE: 79

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Lys Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Lys
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Ala Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile

```
                355                 360                 365
Ala Gly Phe Leu Glu Gly Trp Glu Gly Met Ile Ala Gly Trp His
370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 80
<211> LENGTH: 466
<212> TYPE: PRT
<213> ORGANISM: influenza B virus

<400> SEQUENCE: 80

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140
```

```
Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Ala Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465

<210> SEQ ID NO 81
<211> LENGTH: 584
<212> TYPE: PRT
<213> ORGANISM: influenza B virus

<400> SEQUENCE: 81

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45
```

```
Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
 65                  70                  75                  80

Ala Leu Gly Arg Pro Met Cys Val Gly Thr Thr Pro Ser Ala Lys Ala
                     85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu Asn Ile Arg Leu Ser Thr Gln Asn Val Ile Asp Ala Glu Asn
        130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
                180                 185                 190

Tyr Val Cys Thr Glu Gly Glu Asp Gln Ile Thr Val Trp Gly Phe His
        195                 200                 205

Ser Asp Asn Lys Thr Pro Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Gly Phe Pro Ala Gln Thr Glu Asp Gly Leu Pro Gln
                245                 250                 255

Ser Gly Arg Ile Val Val Asp Tyr Met Val Gln Lys Pro Arg Lys Thr
                260                 265                 270

Gly Thr Ile Val Tyr Gln Arg Gly Val Leu Leu Pro Gln Lys Val Trp
            275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
            370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
                420                 425                 430

Glu Leu His Asn Glu Ile Leu Glu Leu Asp Glu Lys Val Asp Asp Leu
            435                 440                 445

Arg Ala Asp Thr Ile Ser Ser Gln Ile Glu Leu Ala Val Leu Leu Ser
450                 455                 460
```

```
Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 82
<211> LENGTH: 466
<212> TYPE: PRT
<213> ORGANISM: influenza B virus

<400> SEQUENCE: 82

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Thr Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Lys Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile
                245                 250                 255
```

```
Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
            275                 280                 285

Cys Ala Cys Arg Asp Asn Ser Tyr Thr Ala Lys Arg Pro Phe Val Lys
            290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
            325                 330                 335

Cys Glu Ser Asn Gly Asn Lys Gly Ser Gly Gly Ile Lys Gly Gly Phe
            340                 345                 350

Val His Gln Arg Met Ala Ser Lys Ile Gly Arg Trp Tyr Ser Arg Thr
            355                 360                 365

Met Ser Lys Thr Lys Arg Met Gly Met Gly Leu Tyr Val Lys Tyr Asp
            370                 375                 380

Gly Asp Pro Trp Thr Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
            405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
            435                 440                 445

Met Gly Ser Gly Gln Leu Leu Trp Asp Thr Val Thr Gly Val Asp Met
            450                 455                 460

Ala Leu
465

<210> SEQ ID NO 83
<211> LENGTH: 566
<212> TYPE: PRT
<213> ORGANISM: influenza A virus

<400> SEQUENCE: 83

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
            85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
        130                 135                 140

Gly Val Thr Gln Asn Gly Thr Ser Ser Ser Cys Lys Arg Arg Ser Asn
```

-continued

```
            145                 150                 155                 160
        Asn Ser Phe Phe Ser Arg Leu Asn Trp Leu Thr His Leu Lys Phe Lys
                        165                 170                 175
        Tyr Pro Ala Leu Asn Val Thr Met Pro Asn Asn Glu Lys Phe Asp Lys
                        180                 185                 190
        Leu Tyr Ile Trp Gly Val His His Pro Gly Thr Asn Asn Asp Gln Ile
                        195                 200                 205
        Ser Leu Tyr Thr Gln Ala Ser Gly Arg Ile Thr Val Ser Thr Lys Arg
                        210                 215                 220
        Ser Gln Gln Thr Val Ile Pro Asn Ile Gly Ser Arg Pro Arg Val Arg
        225                 230                 235                 240
        Asp Ile Pro Ser Arg Ile Ser Ile Tyr Trp Thr Ile Val Lys Pro Gly
                        245                 250                 255
        Asp Ile Leu Leu Ile Asn Ser Thr Gly Asn Leu Ile Ala Pro Arg Gly
                        260                 265                 270
        Tyr Phe Lys Ile Arg Ser Gly Lys Ser Ser Ile Met Arg Ser Asp Ala
                        275                 280                 285
        Pro Ile Gly Lys Cys Asn Ser Glu Cys Ile Thr Pro Asn Gly Ser Ile
                        290                 295                 300
        Pro Asn Asp Lys Pro Phe Gln Asn Val Asn Arg Ile Thr Tyr Gly Ala
        305                 310                 315                 320
        Cys Pro Arg Tyr Val Lys Gln Asn Thr Leu Lys Leu Ala Thr Gly Met
                        325                 330                 335
        Arg Asn Val Pro Glu Lys Gln Thr Arg Gly Ile Phe Gly Ala Ile Ala
                        340                 345                 350
        Gly Phe Ile Glu Asn Gly Trp Glu Gly Met Val Asp Gly Trp Tyr Gly
                        355                 360                 365
        Phe Arg His Gln Asn Ser Glu Gly Ile Gly Gln Ala Ala Asp Leu Lys
                        370                 375                 380
        Ser Thr Gln Ala Ala Ile Asn Gln Ile Asn Gly Lys Leu Asn Arg Leu
        385                 390                 395                 400
        Ile Gly Lys Thr Asn Glu Lys Phe His Gln Ile Glu Lys Glu Phe Ser
                        405                 410                 415
        Glu Val Glu Gly Arg Ile Gln Asp Leu Glu Lys Tyr Val Glu Asp Thr
                        420                 425                 430
        Lys Ile Asp Leu Trp Ser Tyr Asn Ala Glu Leu Leu Val Ala Leu Glu
                        435                 440                 445
        Asn Gln His Thr Ile Asp Leu Thr Asp Ser Glu Met Asn Lys Leu Phe
                        450                 455                 460
        Glu Arg Thr Lys Lys Gln Leu Arg Glu Asn Ala Glu Asp Met Gly Asn
        465                 470                 475                 480
        Gly Cys Phe Lys Ile Tyr His Lys Cys Asp Asn Ala Cys Ile Gly Ser
                        485                 490                 495
        Ile Arg Asn Gly Thr Tyr Asp His Asp Val Tyr Arg Asp Glu Ala Leu
                        500                 505                 510
        Asn Asn Arg Phe Gln Ile Lys Gly Val Glu Leu Lys Ser Gly Tyr Lys
                        515                 520                 525
        Asp Trp Ile Leu Trp Ile Ser Phe Ala Ile Ser Cys Phe Leu Leu Cys
                        530                 535                 540
        Val Ala Leu Leu Gly Phe Ile Met Trp Ala Cys Gln Lys Gly Asn Ile
        545                 550                 555                 560
        Arg Cys Asn Ile Cys Ile
                        565
```

<210> SEQ ID NO 84
<211> LENGTH: 469
<212> TYPE: PRT
<213> ORGANISM: influenza A virus

<400> SEQUENCE: 84

|

-continued

```
                    370                 375                 380
Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
                420                 425                 430

Glu Thr Glu Val Leu Trp Thr Ser Asn Ser Ile Val Val Phe Cys Gly
                435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 85
<211> LENGTH: 550
<212> TYPE: PRT
<213> ORGANISM: influenza A virus

<400> SEQUENCE: 85

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
                20                  25                  30

Gln Ile Glu Val Thr Asn Ala Thr Glu Leu Val Gln Ser Ser Ser Thr
            35                  40                  45

Gly Gly Ile Cys Asp Ser Pro His Gln Ile Leu Asp Gly Glu Asn Cys
        50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Asn Asn Glu Ser Phe Asn Trp Thr
            115                 120                 125

Gly Val Thr Gln Asn Gly Thr Ser Ser Ala Cys Lys Arg Arg Ser Asn
        130                 135                 140

Lys Ser Phe Phe Ser Arg Leu Asn Trp Leu Thr His Leu Lys Tyr Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asp Ser Asp Gln Ile
                180                 185                 190

Ser Leu Tyr Ala Gln Ala Ser Gly Arg Ile Thr Val Ser Thr Lys Arg
            195                 200                 205

Ser Gln Gln Thr Val Ile Pro Asn Ile Gly Ser Arg Pro Arg Val Arg
        210                 215                 220

Asp Val Ser Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
                260                 265                 270
```

```
Pro Ile Gly Lys Cys Asn Ser Glu Cys Ile Thr Pro Asn Gly Ser Ile
            275                 280                 285

Pro Asn Asp Lys Pro Phe Gln Asn Val Asn Arg Ile Thr Tyr Gly Ala
        290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asn Gln Ile Asn Gly Lys Leu Asn Arg Leu
370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Arg Thr Lys Lys Gln Leu Arg Glu Asn Ala Glu Asp Met Gly Asn
450                 455                 460

Gly Cys Phe Lys Ile Tyr His Lys Cys Asp Asn Ala Cys Ile Glu Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
530                 535                 540

Arg Cys Asn Ile Cys Ile
545                 550

<210> SEQ ID NO 86
<211> LENGTH: 469
<212> TYPE: PRT
<213> ORGANISM: influenza A virus

<400> SEQUENCE: 86

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95
```

```
Phe Ala Pro Phe Ser Lys Asp Asn Ser Ile Arg Leu Ser Ala Gly Gly
                100                 105                 110

Asp Ile Trp Val Thr Arg Gln Pro Tyr Val Ser Cys Asp Pro Asp Lys
            115                 120                 125

Cys Tyr Gln Phe Ala Leu Gly Lys Gly Thr Thr Leu Asn Asn Val His
        130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Val Asp Ser Ile Val Ser Trp Ser Lys Lys Ile Leu Arg
                210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
        290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly Tyr Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
        370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 87
<211> LENGTH: 550
<212> TYPE: PRT
<213> ORGANISM: influenza A virus
```

-continued

```
<400> SEQUENCE: 87

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Lys Arg Arg Ser Asn
    130                 135                 140

Lys Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asp Asn Asp Gln Ile
            180                 185                 190

Asn Leu Tyr Val Gln Ala Ser Gly Arg Ile Thr Val Ser Thr Lys Arg
        195                 200                 205

Ser Gln Gln Thr Val Ile Pro Asn Ile Gly Ser Arg Pro Arg Val Arg
    210                 215                 220

Asp Val Pro Ser Arg Ile Ser Ile Tyr Trp Thr Ile Val Lys Pro Gly
225                 230                 235                 240

Asp Ile Leu Leu Ile Ser Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asn Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415
```

```
Lys Ile Asp Leu Trp Ser Tyr Asn Ala Glu Leu Leu Val Ala Leu Glu
            420                 425                 430

Asn G

```
                225                 230                 235                 240
Met Thr Asp Gly Ser Ala Ser Gly Lys Ala Asp Thr Lys Ile Leu Phe
                245                 250                 255
Ile Glu Glu Gly Lys Ile Val His Thr Ser Thr Leu Ser Gly Ser Ala
                260                 265                 270
Gln His Val Glu Glu Cys Ser Cys Tyr Pro Arg Tyr Pro Gly Val Arg
                275                 280                 285
Cys Val Cys Arg Asp Asn Trp Lys Gly Ser Asn Arg Pro Ile Val Asp
                290                 295                 300
Ile Asn Ile Lys Asp Tyr Ser Ile Val Ser Ser Tyr Val Cys Ser Gly
305                 310                 315                 320
Leu Val Gly Asp Thr Pro Arg Lys Asn Asp Ser Ser Ser Ser Ser His
                325                 330                 335
Cys Leu Asp Pro Asn Asn Glu Glu Gly Gly His Gly Val Lys Gly Trp
                340                 345                 350
Ala Phe Asp Asp Gly Asn Asp Val Trp Met Gly Arg Thr Ile Ser Glu
                355                 360                 365
Lys Leu Arg Ser Gly Tyr Glu Thr Phe Lys Val Ile Glu Gly Trp Ser
                370                 375                 380
Asn Pro Asn Ser Lys Leu Gln Ile Asn Arg Gln Val Ile Val Asp Arg
385                 390                 395                 400
Gly Asn Arg Ser Gly Tyr Ser Gly Ile Phe Ser Val Glu Gly Lys Ser
                405                 410                 415
Cys Ile Asn Arg Cys Phe Tyr Val Glu Leu Ile Arg Gly Arg Lys Glu
                420                 425                 430
Glu Thr Lys Val Leu Trp Thr Ser Asn Ser Ile Val Val Phe Cys Gly
                435                 440                 445
Thr Ser Gly Thr Tyr Gly Thr Gly Ser Trp Pro Asp Gly Ala Asp Ile
        450                 455                 460
Asn Leu Met Pro Ile
465

<210> SEQ ID NO 89
<211> LENGTH: 550
<212> TYPE: PRT
<213> ORGANISM: influenza A virus

<400> SEQUENCE: 89

Gln Lys Leu Pro Gly Asn Asp Asn Ser Thr Ala Thr Leu Cys Leu Gly
1               5                   10                  15
His His Ala Val Pro Asn Gly Thr Ile Val Lys Thr Ile Thr Asn Asp
                20                  25                  30
Gln Ile Glu Val Thr Asn Ala Thr Glu Leu Val Gln Asn Ser Ser Thr
            35                  40                  45
Gly Gly Ile Cys Asp Ser Pro His Gln Ile Leu Asp Gly Glu Asn Cys
        50                  55                  60
Thr Leu Ile Asp Ala Leu Leu Gly Asp Pro Gln Cys Asp Gly Phe Gln
65                  70                  75                  80
Asn Lys Lys Trp Asp Leu Phe Val Glu Arg Ser Lys Ala Tyr Ser Asn
                85                  90                  95
Cys Tyr Pro Tyr Asp Val Pro Asp Tyr Ala Ser Leu Arg Ser Leu Val
                100                 105                 110
Ala Ser Ser Gly Thr Leu Glu Phe Asn Asn Glu Ser Phe Asn Trp Thr
            115                 120                 125
```

```
Gly Val Thr Gln Asn Gly Thr Ser Ser Ala Cys Lys Arg Arg Ser Asn
    130                 135                 140

Lys Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asp Tyr Asp Gln Ile
            180                 185                 190

Arg Leu Tyr Ala Gln Ala Ser Gly Arg Ile Thr Val Ser Thr Lys Arg
        195                 200                 205

Ser Gln Gln Thr Val Ile Pro Asn Ile Gly Ser Arg Pro Arg Val Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asn Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Arg Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Ser Gly Phe Ile Met Trp Ala Cys Gln Lys Gly Asn Ile
    530                 535                 540

Arg Cys Asn Ile Cys Ile
```

-continued

```
                545                 550

<210> SEQ ID NO 90
<211> LENGTH: 469
<212> TYPE: PRT
<213> ORGANISM: influenza A virus

<400> SEQUENCE: 90

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asp Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365
```

```
Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Lys Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 91
<211> LENGTH: 550
<212> TYPE: PRT
<213> ORGANISM: influenza A virus

<400> SEQUENCE: 91

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Asn Ser Ser Thr
        35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Lys Arg Arg Ser Asn
    130                 135                 140

Lys Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Val Thr Asp Tyr Asp Gln Ile
            180                 185                 190

Ser Leu Tyr Ala Gln Ala Ser Gly Arg Ile Thr Val Ser Thr Lys Arg
        195                 200                 205

Ser Gln Gln Thr Val Ile Pro Asn Ile Gly Ser Arg Pro Arg Val Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270
```

```
Pro Ile Gly Lys Cys Asn Ser Glu Cys Ile Thr Pro Asn Gly Ser Ile
            275                 280                 285

Pro Asn Asp Lys Pro Phe Gln Asn Val Asn Arg Ile Thr Tyr Gly Ala
        290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asn Gln Ile Asn Gly Lys Leu Asn Arg Leu
370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Arg Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Ser Gly Phe Ile Met Trp Ala Cys Gln Lys Gly Asn Ile
    530                 535                 540

Arg Cys Asn Ile Cys Ile
545                 550

<210> SEQ ID NO 92
<211> LENGTH: 469
<212> TYPE: PRT
<213> ORGANISM: influenza A virus

<400> SEQUENCE: 92

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asp Ile Thr Gly
```

```
                85                  90                  95
Phe Ala Pro Phe Ser Lys Asp Asn Ser Ile Arg Leu Ser Ala Gly Gly
            100                 105                 110
Asp Ile Trp Val Thr Arg Glu Pro Tyr Val Ser Cys Asp Pro Asp Lys
            115                 120                 125
Cys Tyr Gln Phe Ala Leu Gly Gln Gly Thr Thr Leu Asn Asn Val His
            130                 135                 140
Ser Asn Asp Thr Val His Asp Arg Thr Pro Tyr Arg Thr Leu Leu Met
145                 150                 155                 160
Asn Glu Leu Gly Val Pro Phe His Leu Gly Thr Lys Gln Val Cys Ile
                165                 170                 175
Ala Trp Ser Ser Ser Cys His Asp Gly Lys Ala Trp Leu His Val
            180                 185                 190
Cys Val Thr Gly Asp Asp Lys Asn Ala Thr Ala Ser Phe Ile Tyr Asn
            195                 200                 205
Gly Arg Leu Val Asp Ser Ile Val Ser Trp Ser Lys Lys Ile Leu Arg
            210                 215                 220
Thr Gln Glu Ser Glu Cys Val Cys Ile Asn Gly Thr Cys Thr Val Val
225                 230                 235                 240
Met Thr Asp Gly Ser Ala Ser Gly Lys Ala Asp Thr Lys Ile Leu Phe
                245                 250                 255
Ile Glu Glu Gly Lys Ile Val His Thr Ser Thr Leu Ser Gly Ser Ala
            260                 265                 270
Gln His Val Glu Glu Cys Ser Cys Tyr Pro Arg Tyr Pro Gly Val Arg
            275                 280                 285
Cys Val Cys Arg Asp Asn Trp Lys Gly Ser Asn Arg Pro Ile Val Asp
            290                 295                 300
Ile Asn Ile Lys Asp Tyr Ser Ile Val Ser Ser Tyr Val Cys Ser Gly
305                 310                 315                 320
Leu Val Gly Asp Thr Pro Arg Lys Asn Asp Ser Ser Ser Ser Ser His
                325                 330                 335
Cys Leu Asp Pro Asn Asn Glu Glu Gly Gly His Gly Val Lys Gly Trp
            340                 345                 350
Ala Phe Asp Asp Gly Asn Asp Val Trp Met Gly Arg Thr Ile Ser Glu
            355                 360                 365
Lys Leu Arg Ser Gly Tyr Glu Thr Phe Lys Val Ile Glu Gly Trp Ser
            370                 375                 380
Asn Pro Asn Ser Lys Leu Gln Ile Asn Arg Gln Val Ile Val Asp Arg
385                 390                 395                 400
Gly Asn Arg Ser Gly Tyr Ser Gly Ile Phe Ser Val Glu Gly Lys Ser
                405                 410                 415
Cys Ile Asn Arg Cys Phe Tyr Val Glu Leu Ile Arg Gly Arg Lys Glu
            420                 425                 430
Lys Thr Glu Val Leu Trp Thr Ser Asn Ser Ile Val Val Phe Cys Gly
            435                 440                 445
Thr Ser Gly Thr Tyr Gly Thr Gly Ser Trp Pro Asp Gly Ala Asp Ile
            450                 455                 460
Asn Leu Met Pro Ile
465

<210> SEQ ID NO 93
<211> LENGTH: 569
<212> TYPE: PRT
<213> ORGANISM: influenza B virus
```

<400> SEQUENCE: 93

```
Asp Arg Ile Cys Thr Gly Ile Thr Ser Ser Asn Ser Pro His Val Val
1               5                   10                  15
Lys Thr Ala Thr Gln Gly Glu Val Asn Val Thr Gly Val Ile Pro Leu
            20                  25                  30
Thr Thr Thr Pro Thr Lys Ser Tyr Phe Ala Asn Leu Lys Gly Thr Arg
        35                  40                  45
Thr Arg Gly Lys Leu Cys Pro Asp Cys Leu Asn Cys Thr Asp Leu Asp
    50                  55                  60
Val Ala Leu Gly Arg Pro Met Cys Val Gly Thr Pro Ser Ala Lys
65                  70                  75                  80
Ala Ser Ile Leu His Glu Val Arg Pro Val Thr Ser Gly Cys Phe Pro
                85                  90                  95
Ile Met His Asp Arg Thr Lys Ile Arg Gln Leu Pro Asn Leu Leu Arg
            100                 105                 110
Gly Tyr Glu Asn Ile Arg Leu Ser Thr Gln Asn Val Ile Asp Ala Glu
        115                 120                 125
Asn Ala Pro Gly Gly Pro Tyr Arg Leu Gly Thr Ser Arg Ser Cys Pro
    130                 135                 140
Asn Ala Thr Ser Lys Ser Gly Phe Phe Ala Thr Met Ala Trp Ala Val
145                 150                 155                 160
Pro Lys Asp Asn Asn Lys Asn Ala Thr Asn Pro Leu Thr Val Glu Val
                165                 170                 175
Pro Tyr Val Cys Thr Glu Gly Glu Asp Gln Ile Thr Val Trp Gly Phe
            180                 185                 190
His Ser Asp Asn Lys Thr Gln Met Lys Asn Leu Tyr Gly Asp Ser Asn
        195                 200                 205
Pro Gln Lys Phe Thr Ser Ser Ala Asn Gly Val Thr Thr His Tyr Val
    210                 215                 220
Ser Gln Ile Gly Gly Phe Pro Ala Gln Thr Glu Asp Glu Gly Leu Pro
225                 230                 235                 240
Gln Ser Gly Arg Ile Val Val Asp Tyr Met Val Gln Lys Pro Arg Lys
                245                 250                 255
Thr Gly Thr Ile Val Tyr Gln Arg Gly Val Leu Leu Pro Gln Lys Val
            260                 265                 270
Trp Cys Ala Ser Gly Arg Ser Lys Val Ile Lys Gly Ser Leu Pro Leu
        275                 280                 285
Ile Gly Glu Ala Asp Cys Leu His Glu Lys Tyr Gly Gly Leu Asn Lys
    290                 295                 300
Ser Lys Pro Tyr Tyr Thr Gly Glu His Ala Lys Ala Ile Gly Asn Cys
305                 310                 315                 320
Pro Ile Trp Val Lys Thr Pro Leu Lys Leu Ala Asn Gly Thr Lys Tyr
                325                 330                 335
Arg Pro Pro Ala Lys Leu Leu Lys Glu Arg Gly Phe Phe Gly Ala Ile
            340                 345                 350
Ala Gly Phe Leu Glu Gly Gly Trp Glu Gly Met Ile Ala Gly Trp His
        355                 360                 365
Gly Tyr Thr Ser His Gly Ala His Gly Val Ala Val Ala Ala Asp Leu
    370                 375                 380
Lys Ser Thr Gln Glu Ala Ile Asn Lys Ile Thr Lys Asn Leu Asn Ser
385                 390                 395                 400
Leu Ser Glu Leu Glu Val Lys Asn Leu Gln Arg Leu Ser Gly Ala Met
```

-continued

```
                405                 410                 415
Asp Glu Leu His Asn Glu Ile Leu Glu Leu Asp Glu Lys Val Asp Asp
                420                 425                 430

Leu Arg Ala Asp Thr Ile Ser Ser Gln Ile Glu Leu Ala Val Leu Leu
            435                 440                 445

Ser Asn Glu Gly Ile Ile Asn Ser Glu Asp Glu His Leu Leu Ala Leu
        450                 455                 460

Glu Arg Lys Leu Lys Lys Met Leu Gly Pro Ser Ala Val Asp Ile Gly
465                 470                 475                 480

Asn Gly Cys Phe Glu Thr Lys His Lys Cys Asn Gln Thr Cys Leu Asp
                485                 490                 495

Arg Ile Ala Ala Gly Thr Phe Asn Ala Gly Glu Phe Ser Leu Pro Thr
            500                 505                 510

Phe Asp Ser Leu Asn Ile Thr Ala Ala Ser Leu Asn Asp Asp Gly Leu
        515                 520                 525

Asp Asn His Thr Ile Leu Leu Tyr Tyr Ser Thr Ala Ala Ser Ser Leu
        530                 535                 540

Ala Val Thr Leu Met Leu Ala Ile Phe Ile Val Tyr Met Val Ser Arg
545                 550                 555                 560

Asp Asn Val Ser Cys Ser Ile Cys Leu
                565

<210> SEQ ID NO 94
<211> LENGTH: 466
<212> TYPE: PRT
<213> ORGANISM: influenza B virus

<400> SEQUENCE: 94

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Thr Thr Glu Thr Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Ser Asn Ala Leu Leu Lys Ile Lys Tyr Gly Glu
        195                 200                 205
```

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asn Lys Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Thr Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465

<210> SEQ ID NO 95
<211> LENGTH: 569
<212> TYPE: PRT
<213> ORGANISM: influenza B virus

<400> SEQUENCE: 95

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Ile Lys Ser His Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

```
Gly Tyr Glu Asn Ile Arg Leu Ser Thr Gln Asn Val Ile Asp Ala Glu
            115                 120                 125
Lys Ala Leu Gly Gly Pro Tyr Arg Leu Gly Thr Ser Gly Ser Cys Pro
    130                 135                 140
Asn Ala Thr Ser Lys Ser Gly Phe Phe Ala Thr Met Ala Trp Ala Val
145                 150                 155                 160
Pro Lys Asp Asn Lys Asn Ala Thr Asn Pro Leu Thr Val Glu Val
                165                 170                 175
Pro Tyr Ile Cys Thr Glu Gly Asp Gln Ile Thr Val Trp Gly Phe
            180                 185                 190
His Ser Asp Asp Lys Thr Gln Met Lys Asn Leu Tyr Gly Asp Ser Asn
            195                 200                 205
Pro Gln Lys Phe Thr Ser Ser Ala Asn Gly Val Thr Thr His Tyr Val
            210                 215                 220
Ser Gln Ile Gly Gly Phe Pro Asp Gln Thr Glu Asp Gly Gly Leu Pro
225                 230                 235                 240
Gln Ser Gly Arg Ile Val Val Asp Tyr Met Val Gln Lys Pro Gly Lys
                245                 250                 255
Thr Gly Thr Ile Val Tyr Gln Arg Gly Val Leu Leu Pro Gln Lys Val
            260                 265                 270
Trp Cys Ala Ser Gly Arg Ser Lys Val Ile Lys Gly Ser Leu Pro Leu
    275                 280                 285
Ile Gly Glu Ala Asp Cys Leu His Glu Lys Tyr Gly Gly Leu Asn Lys
    290                 295                 300
Ser Lys Pro Tyr Tyr Thr Gly Glu His Ala Lys Ala Ile Gly Asn Cys
305                 310                 315                 320
Pro Ile Trp Val Lys Thr Pro Leu Lys Leu Ala Asn Gly Thr Lys Tyr
                325                 330                 335
Arg Pro Pro Ala Lys Leu Leu Lys Glu Arg Gly Phe Phe Gly Ala Ile
            340                 345                 350
Ala Gly Phe Leu Glu Gly Gly Trp Glu Gly Met Ile Ala Gly Trp His
            355                 360                 365
Gly Tyr Thr Ser His Gly Ala His Gly Val Ala Val Ala Ala Asp Leu
    370                 375                 380
Lys Ser Thr Gln Glu Ala Ile Asn Lys Ile Thr Lys Asn Leu Asn Ser
385                 390                 395                 400
Leu Ser Glu Leu Glu Val Lys Asn Leu Gln Arg Leu Ser Gly Ala Met
                405                 410                 415
Asp Glu Leu His Asn Glu Ile Leu Glu Leu Asp Glu Lys Val Asp Asp
            420                 425                 430
Leu Arg Ala Asp Thr Ile Ser Ser Gln Ile Glu Leu Ala Val Leu Leu
    435                 440                 445
Ser Asn Glu Gly Ile Ile Asn Ser Glu Asp Glu His Leu Leu Ala Leu
    450                 455                 460
Glu Arg Lys Leu Lys Lys Met Leu Gly Pro Ser Ala Val Asp Ile Gly
465                 470                 475                 480
Asn Gly Cys Phe Glu Thr Lys His Lys Cys Asn Gln Thr Cys Leu Asp
            485                 490                 495
Arg Ile Ala Ala Gly Thr Phe Asn Ala Gly Glu Phe Ser Leu Pro Thr
            500                 505                 510
Phe Asp Ser Leu Asn Ile Thr Ala Ala Ser Leu Asn Asp Asp Gly Leu
            515                 520                 525
```

```
Asp Asn His Thr Ile Leu Leu Tyr Tyr Ser Thr Ala Ala Ser Ser Leu
    530                 535                 540

Ala Val Thr Leu Met Leu Ala Ile Phe Ile Val Tyr Met Val Ser Arg
545                 550                 555                 560

Asp Asn Val Ser Cys Ser Ile Cys Leu
                565

<210> SEQ ID NO 96
<211> LENGTH: 466
<212> TYPE: PRT
<213> ORGANISM: influenza B virus

<400> SEQUENCE: 96

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Thr Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335
```

-continued

```
Cys Glu Ser Asn Gly Asn Lys Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Ile Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
            405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
            435                 440                 445

Met Gly Ser Gly Gln Leu Leu Trp Asp Thr Val Thr Gly Val Asp Met
    450                 455                 460

Ala Leu
465
```

INFLUENZA HEMAGGLUTININ AND NEURAMINIDASE VARIANTS

CROSS-REFERENCE TO RELATED APPLICATIONS

This application claims priority to and benefit of U.S. Provisional Patent Application 60/659,832. filed on Mar. 8, 2005, the disclosures of which is incorporated herein in its entirety for all purposes.

REFERENCE TO A SEQUENCE LISTING

This application refers to a sequence listing, which is provided as an electronic document on each of two identical compact discs, labeled "Copy 1" and "Copy 2." Each compact disk contains a 320,100 byte file entitled "FL2550US2_seqlist.txt," created Mar. 6, 2006. This electronic sequence listing file is incorporated in its entirety herein.

BACKGROUND OF THE INVENTION

Vaccines against various and evolving strains of influenza are important from a community health standpoint, as well as commercially, since each year numerous individuals are infected with different strains and types of influenza virus. Infants, the elderly, those without adequate health care and immuno-compromised persons are at special risk of death from such infections. Compounding the problem of influenza infections is that novel influenza strains evolve readily and can spread between various species, thereby necessitating the continuous production of new vaccines.

Numerous vaccines capable of producing a protective immune response specific for different influenza viruses/virus strains have been produced for over 50 years and include whole virus vaccines, split virus vaccines, surface antigen vaccines and live attenuated virus vaccines. However, while appropriate formulations of any of these vaccine types are capable of producing a systemic immune response, live attenuated virus vaccines have the advantage of also being able to stimulate local mucosal immunity in the respiratory tract. Considerable work in the production of influenza viruses, and fragments thereof, for production of vaccines has been done by the present inventors and co-workers; see, e.g., U.S. Application No. 60/420,708, filed Oct. 23, 2002, U.S. application Ser. No.10/423,828, filed Apr. 25, 2003, and U.S. Application No. 60/574,117, filed May 24, 2004, all entitled "Multi-Plasmid System for the Production of Influenza Virus."

Because of the continual emergence (or re-emergence) or different influenza strains, new influenza vaccines are continually desired. Such vaccines typically are created using antigenic moieties of the newly emergent virus strains so, therefore, polypeptides and polynucleotides of novel, newly emergent, or newly re-emergent virus strains (especially sequences of antigenic genes) are highly desirable. Furthermore, such sequences within preferred vectors are also quite highly desired.

The present invention provides new and/or newly isolated influenza hemagglutinin and neuraminidase variants, optionally within preferred vectors, that are capable of use in production of numerous types of vaccines as well as in research, diagnostics, etc. Numerous other benefits will become apparent upon review of the following

SUMMARY OF THE INVENTION

In some aspects herein, the invention comprises an isolated or recombinant polypeptide that is selected from: the polypeptides encoded by any one of the sequences of the sequence listing, e.g., SEQ ID NO:1 through SEQ ID NO:48, any one of the polypeptides encoded by the sequence listing, e.g., SEQ ID NO:49 through SEQ ID NO:96; any polypeptide that is encoded by a polynucleotide sequence which hybridizes under highly stringent conditions over substantially the entire length of a polynucleotide sequence of the sequence listing; and, a fragment of any of the above wherein the sequence comprises a hemagglutinin or neuraminidase polypeptide, or a fragment of a hemagglutinin or neuraminidase polypeptide. In various embodiments, the isolated or recombinant polypeptides of the invention are substantially identical to about 300 contiguous amino acid residues of any of the above polypeptides. In yet other embodiments, the invention comprises isolated or recombinant polypeptides (comprising hemagglutinin or neuraminidase or fragments of hemagglutinin or neuraminidase), that comprise an amino acid sequence that is substantially identical over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids contiguous of any of the polypeptides of claim of any of the above polypeptides. In yet other embodiments, the invention comprises isolated or recombinant polypeptides (e.g., comprising neuraminidase, hemagglutinin or fragments of neuraminidase or hemagglutinin), that comprise an amino acid sequence that is substantially identical over at least about 350 amino acids; over at least about 400 amino acids; over at least about 436 amino acids; over at least about 450 amino acids; over at least about 451 amino acids; over at least about 465 amino acids; over at least about 466 amino acids; over at least about 469 amino acids; or over at least about 470 amino acids contiguous of any of the polypeptides of any of the above polypeptides. Of course, in some embodiments, the polypeptide sequence (e.g., as listed in the sequence listing herein, e.g., SEQ ID NO:49 through SEQ ID NO:96) comprises less than 565, 559, etc. amino acids. In such embodiments, the shorter listed polypeptides optionally comprise less than 565, 559, etc. amino acids. In yet other embodiments, the polypeptides of the invention optionally comprise fusion proteins, proteins with a leader sequence, a precursor polypeptide, proteins with a secretion signal or a localization signal, or proteins with an epitope tag, an E-tag, or a His epitope tag, etc. In still other embodiments, the invention comprises a polypeptide comprising a sequence having at least 95%, at least 96%, at least 97%, at least 98%, at least 98.5%, at least 99%, at least 99.2%, at least 99.4%, at least 99.6%, at least 99.8%, or at least 99.9% sequence identity to at least one polypeptide listed above (e.g., of SEQ ID NO: 49-96). In some embodiments, such polypeptides are immunogenic. The HA sequences of the invention can comprise both those sequences with unmodified and those with modified polybasic cleavage sites.

In other aspects, the invention comprises a composition with one or more polypeptide listed above, or fragments thereof. The invention also includes polypeptides that are specifically bound by a polyclonal antisera raised against at least 1 antigen that comprises at least one amino acid sequence described above (e.g., SEQ ID NO: 49-96), or a fragment thereof Such antibodies specific for the polypeptides described above are also features of the invention. The polypeptides of the invention are optionally immunogenic.

The invention also encompasses immunogenic compositions comprising an immunologically effective amount of one or more of any of the polypeptides described above as well as methods for stimulating the immune system of an individual to produce a protective immune response against influenza virus by administering to the individual an immunologically effective amount of any of the above polypeptides (e.g., SEQ ID NO: 49-96) in a physiologically acceptable carrier.

Additionally, the invention has reassortant influenza virus that encode one or more of the polypeptides above (e.g., SEQ ID NO: 49-96), in addition to immunogenic compositions comprising an immunologically effective amount of such recombinant influenza virus. Methods for stimulating the immune system of an individual to produce a protective immune response against influenza virus, through administering an immunologically effective amount of such recombinant influenza virus in a physiologically acceptable carrier are also part of the invention. Such virus can optionally comprise a 6:2 reassortant virus with 6 genes encoding regions from one or more donor virus (e.g. A/AA/6/60, B/Ann Arbor/1/66, A/Puerto Rico/8/34, which is more commonly known as PR8), B/Leningrad/14/17/55, B/14/5/1, B/USSR/60/69, B/Leningrad/179/86, B/Leningrad/14/55, or B/England/2608/76 and 2 gene encoding regions (typically and preferably encoding HA and NA or fragments thereof) selected from SEQ ID NO:1 through SEQ ID NO:48 or from similar strains, as defined herein, to those having SEQ ID NO:1-48, etc. Immunogenic compositions comprising such reassortant (recombinant) virus are also features of the invention.

In other aspects, the invention comprises an isolated or recombinant nucleic acid that is selected from: any one of the polynucleotide sequences of the sequence listing, e.g., SEQ ID NO:1 through SEQ ID NO:48 (or complementary sequences thereof), any one of the polynucleotide sequences encoding a polypeptide of the sequence listing, e.g., SEQ ID NO:49 through SEQ ID NO:96 (or complementary polynucleotide sequences thereof), a polynucleotide sequence which hybridizes under highly stringent conditions over substantially the entire length of any of the above polynucleotide sequences, and a polynucleotide sequence comprising all or a fragment of any of the above polynucleotide sequences wherein the sequence encodes a hemagglutinin or neuraminidase polypeptide or one or more HA or NA fragments. Such nucleic acids can be DNA, RNA, cRNA, DNA:RNA hybrids, single stranded nucleic acid, double stranded nucleic acid, etc. The invention also includes an isolated or recombinant nucleic acid (e.g., comprising hemagglutinin or fragments thereof), that encodes an amino acid sequence which is substantially identical over at least about 300 amino acids of any of the above nucleic acids, or over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids of any of the above nucleic acids. In yet other embodiments, the invention comprises isolated or recombinant nucleic acids (e.g., comprising neuraminidase or fragments thereof), that encode an amino acid sequence that is substantially identical over at least about 350 amino acids; over at least about 400 amino acids; over at least about 436 amino acids; over at least about 450 amino acids; over at least about 451 amino acids; over at least about 465 amino acids; over at least about 466 amino acids; over at least about 469 amino acids; or over at least about 470 amino acids contiguous of any of the polypeptides above. Again, in situations wherein the amino acid is less than, e.g., 566, 565, 559, etc. in length (e.g., see, Sequence Listing in FIG. 1) then it should be understood that the length is optionally less than 566, 565, 559, etc. The invention also includes any of the above nucleic acids that comprise a hemagglutinin or neuraminidase polypeptide, or one or hemagglutinin or neuraminidase fragments. Other aspects of the invention include isolated or recombinant nucleic acids that encode a polypeptide (optionally a hemagglutinin or neuraminidase polypeptide) whose sequence has at least 95% identity, at least 96% identity, at least 97% identity, at least 98% identity, at least 98.5% identity, at least 99% identity, at least 99.2% identity, at least 99.4% identity, at least 99.6% identity, at least 99.8% identity, or at least 99.9% identity to at least one of the above described polynucleotide. The invention also includes isolated or recombinant nucleic acids encoding a polypeptide of hemagglutinin or neuraminidase produced by mutating or recombining one or more above described polynucleotide sequence. The polynucleotide sequences of the invention can optionally comprise one or more of, e.g., a leader sequence, a precursor sequence, or an epitope tag sequence or the like, and can optionally encode a fusion protein (e.g., with one or more additional nucleic acid sequences). Such nucleic acids of the invention can optionally encode immunogenic polypeptides.

In yet other embodiments, the invention comprises a composition of matter having two or more above described nucleic acids or fragments thereof (e.g., a library comprising at least about 2, 5, 10, 50 or more nucleic acids). Such compositions can optionally be produced by cleaving one or more above described nucleic acid (e.g., mechanically, chemically, enzymatically with a restriction endonuclease/RNAse/DNAse, etc.). Other compositions of the invention include, e.g., compositions produced by incubating one or more above described nucleic acid in the presence of deoxyribonucleotide triphosphates and a thermostable nucleic acid polymerase. Immunogenic compositions having an immunologically effective amount of any of the above nucleic acids are also within the current invention.

Also within the invention are reassortant influenza viruses comprising any of the above nucleic acids. Such reassortant viruses can (and preferably are) 6:2 reassortant viruses with 6 gene encoding regions from one or more donor virus (e.g., A/AA/6/60, B/AA/1/66 (also sometimes referred to herein as B/Ann Arbor/1/66), B/Leningrad/14/17/55, B/14/5/1, B/USSR/60/69, B/Leningrad/179/86, B/Leningrad/14/55, or B/England/2608/76 or A/Puerto Rico/8/34) and 2 gene encoding regions from two sequences above (e.g., from SEQ ID NO:1-48, from similar strains to those encoded in SEQ ID NO:1-48, etc.). Preferably, such two regions encode hemagglutinin and/or neuraminidase. Immunogenic compositions with immunologically effective amounts of such reassortant/recombinant influenza virus are also within purview of the current invention.

Vectors comprising one or more nucleic acid from SEQ ID NO:1-48 (again, also from similar strains to those of the sequence identification numbers) or fragments thereof are also within the current invention. Such vectors (e.g., expression vectors) can optionally be plasmids, cosmids, phage, viruses, virus fragments, etc. Especially preferred embodiments comprise plasmid vectors useful in plasmid rescue methods to produce virus (e.g., typically reassortant/recombinant virus for use in vaccines). Such plasmid systems are exampled in, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"; Hoffmann, E., 2000, *PNAS,* 97(11): 6108-6113; U.S. Published Patent Application No. 20020164770 to Hoffmann; and U.S. Pat. No. 6,544,785 issued Apr. 8, 2003 to Palese, et al. Cells transduced, transformed, transfected, etc. with such vectors are also within the current invention.

The invention also encompasses cells comprising at least one above described nucleic acid, or a cleaved or amplified fragment or product thereof. Such cells can optionally express a polypeptide encoded by such nucleic acid. Other embodiments of the invention include vectors (e.g., plasmids, cosmids, phage, viruses, virus fragments, etc.) comprising any of above described nucleic acid. Such vectors can optionally comprise an expression vector. Cells transduced by such vectors are also within the current invention.

In some embodiments, the invention encompasses a virus (e.g., an influenza virus) comprising one or more above described nucleic acid (e.g., from SEQ ID NO:1-48 or from similar strains to such and optionally encoding hemagglutinin and/or neuraminidase), or one or more fragments thereof. Typically, such viruses are reassortant/recombinant viruses. Immunogenic compositions comprising such virus are also part of the current invention. Such viruses can comprises a reassortant virus such as a 6:2 reassortment virus (which comprises 6 gene encoding regions from one or more donor virus (e.g., a master donor virus or a backbone virus such as A/AA/6/60, B/AA/1/66, A/Puerto Rico/8/34, B/Leningrad/14/17/55, B/14/5/1, B[USSR/60/69, B/Leningrad/179/86, B/Leningrad/14/55, or B/England/2608/76, etc.) and 2 gene encoding regions from one or more above described nucleotide sequence, or one or more fragment thereof which can optionally comprise hemagglutinin and/or neuraminidase). Other reassortant/recombinant viruses can comprise 7:1 reassortments. Reassortment viruses (optionally live viruses) of the invention can include donor viruses that are one or more of, e.g., temperature-sensitive (ts), cold-adapted (ca), or attenuated (att). For example, reassortment viruses can comprise, e.g., A/Ann Arbor/6/60, B/Ann Arbor/1/66, A/Puerto Rico/8/34, B/Leningrad/14/17/55, B/14/5/1, B/USSR/60/69, B/Leningrad/179/86, B/Leningrad/14/55, or B/England/2608/76, etc. In many embodiments, the produced viruses are live viruses (e.g., to be used in vaccines, etc.). Other embodiments include dead or inactivated viruses (e.g., also capable of use in vaccines, etc.). Cells comprising any of the above viruses are also products of the invention.

Methods of producing reassortant/recombinant influenza virus through culturing a host cell harboring an influenza virus in a suitable culture medium under conditions permitting expression of nucleic acid; and, isolating or recovering the recombinant influenza virus from one or more of the host cell or the medium are also part of the invention. Thus, introducing a plurality of vectors having an influenza virus genome into a population of host cells wherein the vectors comprise at least 6 internal genome segments of a first influenza strain (again, e.g., A/AA/6/60, B/AA/1/66, A/PR/8/34, B/Leningrad/14/17/55, B/14/5/1, B/USSR/60/69, B/Leningrad/179/86, B/Leningrad/14/55, or B/England/2608/76, etc.) and at least one (and preferably two) genome segments are selected from a second influenza strain (e.g., preferably one or more nucleic acid as described above, e.g., from SEQ ID NO:1-48 or from a similar strain to such or optionally comprising a hemagglutinin and/or neuraminidase, etc.). is a feature of the invention. Preferably, the first strain of virus is cold-adapted and/or temperature sensitive and/or attenuated. Also preferably, such viruses are suitable for administration as part of an intranasal vaccine formulation. Of course, other embodiments are suitable for administration as killed or inactivated vaccine formulations, live/attenuated nonnasal vaccine formulations, etc. The vectors in such methods can comprise influenza A viruses and/or influenza B viruses. Host cells for such methods can optionally comprise, e.g., Vero cells, PerC6 cells, MDCK cells, 293T cells, COS cells, etc. Typical embodiments do not comprise helper viruses in the method and yet other typical embodiments comprise eight plasmid vectors to contain the influenza genome.

In other embodiments herein, the invention comprises immunogenic compositions having an immunologically effective amount of the above described recombinant influenza virus (e.g., a live virus). Other embodiments include methods for stimulating the immune system of an individual to produce a protective immune response against influenza virus by administering to the individual an immunologically effective amount of the recombinant influenza virus of described above (optionally in a physiologically effective carrier).

Other aspects of the invention include methods of producing an isolated or recombinant polypeptide by culturing any host cell above, in a suitable culture medium under conditions permitting expression of nucleic acid and, isolating the polypeptide from one or more of the host cell or the medium in which it is grown.

Immunogenic compositions are also features of the invention. For example, immunogenic compositions comprising one or more of the polypeptides and/or nucleic acids described above (e.g., a sequence from SEQ ID NO:1-96 or from similar strains to such, etc.) and, optionally, an excipient such as a pharmaceutically acceptable excipient or one or more pharmaceutically acceptable administration component. Immunogenic compositions of the invention can also comprise one or more above described virus as well (e.g., along with one or more pharmaceutically acceptable administration component).

Methods of producing an influenza virus vaccine are also included in the invention. For example, the invention includes introducing a plurality of vectors (e.g., plasmid vectors) comprising an influenza genome (e.g., influenza A or B) into a population of host cells that is capable of supporting replication of such virus, culturing the cells, recovering a plurality of influenza viruses and providing one or more pharmaceutically acceptable excipient with such virus to an individual (e.g., one in need of such treatment). Such viruses can optionally be cold-adapted and/or temperature sensitive and/or attenuated and preferably are suitable for administration in an intranasal vaccine formulation. Such methods can include wherein the vectors have at least 6 internal genome segments of a first influenza strain and at least one genome segment (and preferably 2 segments) from another influenza strain (e.g., with sequence selected from SEQ ID NO:1-48 or from similar strains to such, etc.) which segment optionally codes for an immunogenic influenza surface antigen of the second influenza strain.

Methods of producing immunogenic responses in a subject through administration of an effective amount of any of the above viruses to a subject are also within the current invention. Additionally, methods of prophylactic or therapeutic treatment of a viral infection (e.g., viral influenza) in a subject through administration of one or more above described virus in an amount effective to produce an immunogenic response against the viral infection are also part of the current invention. Subjects for such treatment can include mammals (e.g., humans). Such methods can also comprise in vivo administration to the subject as well as in vitro or ex vivo administration to one or more cells of the subject. Additionally, such methods can also comprise administration of a composition of the virus and a pharmaceutically acceptable excipient that is administered to the subject in an amount effect to prophylactically or therapeutically treat the viral infection.

The invention also comprises compositions of matter having one or more sequence selected from SEQ ID NO:1 through SEQ ID NO:48, and a selected master donor virus, typically wherein the selected sequence and the master donor virus comprise a 6:2 reassortment, i.e., the HA and NA herein reassorted with the other six influenza genes from the donor virus. Such donor viruses are typically ca, att, ts influenza strains. For example, typically donor strains can include, e.g., A/Ann Arbor/6/60, B/Ann Arbor/1/66, A/Puerto Rico/8/34, B/Leningrad/14/17/55, B/14/5/1, B/USSR/60/69, B/Leningrad/179/86, B/Leningrad/14/55, or B/England/2608/76 and variants thereof. Those of skill in the art will appreciate that typically donor strains can vary from reassortant to reassortant. Thus, those variations are also encompassed within the current invention. Another element of the invention comprises one or more live attenuated influenza vaccine comprising such compositions, e.g., those having sequences herein reasserted in a 6:2 manner with a selected master donor virus.

Other aspects of the invention include, compositions of matter comprising a hemagglutinin polynucleotide and/or a neuraminidase polynucleotide reassorted with one or more master donor virus, again typically a ca, att, ts influenza virus, wherein the polynucleotide comprises a same virus strain as one or more virus strain of SEQ ID NO:1 through SEQ ID NO:48. Such hemagglutinin and/or neuraminidase polynucleotide is typically determined to be "within the same strain" when it produces a titer that is within a four-fold range of another virus (e.g., ones having the sequences listed herein) as measured by a hemagglutinin inhibition assay. As described below, however, other common assays can also be utilized to determine whether polynucleotides (i.e., viruses comprising such) are within the same strain.

These and other objects and features of the invention will become more fully apparent when the following detailed description is read in conjunction with the accompanying figures and claims.

BRIEF DESCRIPTION OF THE FIGURES

FIG. 1 displays the Sequence Listing of variant hemagglutinin and neuraminidase nucleic acids and polypeptides of the invention.

FIG. 2 displays an alternative organization of variant hemagglutinin and neuraminidase sequences as found in FIG. 1.

DETAILED DESCRIPTION

The present invention includes polypeptide and polynucleotide sequences of influenza hemagglutinin and neuraminidase as well as vectors, viruses, vaccines, compositions and the like comprising such sequences and methods of their use. Additional features of the invention are described in more detail herein.

Definitions

Unless defined otherwise, all technical and scientific terms used herein have the same meaning as commonly understood by one of ordinary skill in the art to which the invention pertains. The following definitions supplement those in the art and are directed to the current application and are not necessarily to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting. Additional terms are defined and described throughout.

As used in this specification and the appended claims, the singular forms "a," "an," and "the" include plural referents unless the context clearly dictates otherwise. Thus, for example, reference to "a virus" includes a plurality of viruses; reference to a "host cell" includes mixtures of host cells, and the like.

The terms "nucleic acid," "polynucleotide," "polynucleotide sequence," and "nucleic acid sequence" refer to single-stranded or double-stranded deoxyribonucleotide or ribonucleotide polymers, chimeras or analogues thereof, or a character string representing such, depending on context. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences in addition to the sequence explicitly indicated. From any specified polynucleotide sequence, either the given nucleic acid or the complementary polynucleotide sequence (e.g., the complementary nucleic acid) can be determined.

The term "nucleic acid" or "polynucleotide" also encompasses any physical string of monomer units that can be corresponded to a string of nucleotides, including a polymer of nucleotides (e.g., a typical DNA or RNA polymer), PNAs, modified oligonucleotides (e.g., oligonucleotides comprising bases that are not typical to biological RNA or DNA in solution, such as 2'-O-methylated oligonucleotides), and the like. A nucleic acid can be e.g., single-stranded or double-stranded.

A "subsequence" is any portion of an entire sequence, up to and including the complete sequence. Typically, a subsequence comprises less than the full-length sequence. A "unique subsequence" is a subsequence that is not found in any previously determined influenza polynucleotide or polypeptide sequence The phrase "substantially identical," in the context of two nucleic acids or polypeptides (e.g., DNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection.

The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described herein.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

The "neuraminidase" polypeptides of the invention show immunological cross reactivity with one or more known neuraminidase molecule from an influenza virus. The literature is replete with examples of such known neuraminidases (e.g., in GenBank, in publications from the CDC, etc.). Similarly, the "hemagglutinin" polypeptides of the invention show immunological cross-reactivity with one or more known hemagglutinin molecule from an influenza virus. Again, the literature is replete with examples of such known hemagglutinin molecules.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type, or types.

"Expression of a gene" or "expression of a nucleic acid" typically means transcription of DNA into RNA (optionally including modification of the RNA, e.g., splicing) or transcription of RNA into mRNA, translation of RNA into a polypeptide (possibly including subsequent modification of the polypeptide, e.g., post-translational modification), or both transcription and translation, as indicated by the context.

An "open reading frame" or "ORF" is a possible translational reading frame of DNA or RNA (e.g., of a gene), which is capable of being translated into a polypeptide. That is, the reading frame is not interrupted by stop codons. However, it should be noted that the term ORF does not necessarily indicate that the polynucleotide is, in fact, translated into a polypeptide.

The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids.

An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

An "amino acid sequence" is a polymer of amino acid residues (a protein, polypeptide, etc.) or a character string representing an amino acid polymer, depending on context.

A "polypeptide" is a polymer comprising two or more amino acid residues (e.g., a peptide or a protein). The polymer can optionally comprise modifications such as glycosylation or the like. The amino acid residues of the polypeptide can be natural or non-natural and can be unsubstituted, unmodified, substituted or modified.

In the context of the invention, the term "isolated" refers to a biological material, such as a virus, a nucleic acid or a protein, which is substantially free from components that normally accompany or interact with it in its naturally occurring environment. The isolated biological material optionally comprises additional material not found with the biological material in its natural environment, e.g., a cell or wild-type virus. For example, if the material is in its natural environment, such as a cell, the material can have been placed at a location in the cell (e.g., genome or genetic element) not native to such material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

The term "chimeric" or "chimera," when referring to a virus, indicates that the virus includes genetic and/or polypeptide components derived from more than one parental viral strain or source. Similarly, the term "chimeric" or "chimera," when referring to a viral protein, indicates that the protein includes polypeptide components (i.e., amino acid subsequences) derived from more than one parental viral strain or source. As will be apparent herein, such chimeric viruses are typically reassortant/recombinant viruses. Thus, in some embodiments, a chimera can optionally include, e.g., a sequence (e.g., of HA and/or NA) from an A influenza virus placed into a backbone comprised of, or constructed/derived from a B influenza virus (e.g., B/AA/1/66, etc.) or a B influenza virus sequence placed into an A influenza virus backbone (i.e., donor virus) such as, e.g., A/AA/6/60, etc.

The term "recombinant" indicates that the material (e.g., a nucleic acid or protein) has been artificially or synthetically (non-naturally) altered by human intervention. The alteration can be performed on the material within, or removed from, its natural environment or state. Specifically, e.g., an influenza virus is recombinant when it is produced by the expression of a recombinant nucleic acid. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

The term "reassortant," when referring to a virus (typically herein, an influenza virus), indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding a hemagglutinin or neuraminidase such as those listed in the SEQ ID Tables herein (e.g., SEQ ID NO: 1-96). A 6:2 reassortant includes 6 genomic segments, most commonly the 6 internal genes from a first parental virus, and two complementary segments, e.g., hemagglutinin and neuraminidase, from one or more different parental virus. Reassortant viruses can also, depending upon context herein, be termed as "chimeric" and/or "recombinant."

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation," and "transduction." In the context of the invention a variety of methods can be employed to introduce nucleic acids into cells, including electroporation, calcium phosphate precipitation, lipid mediated transfection (lipofection), etc.

The term "host cell" means a cell that contains a heterologous nucleic acid, such as a vector or a virus, and supports the replication and/or expression of the nucleic acid. Host cells can be prokaryotic cells such as *E. coli,* or eukaryotic cells such as yeast, insect, amphibian, avian or mammalian cells, including human cells. Exemplary host cells can include, e.g., Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells), etc. In other embodiments, host cells can optionally include eggs (e.g., hen eggs, embryonated hen eggs, etc.).

An "immunologically effective amount" of influenza virus is an amount sufficient to enhance an individual's (e.g., a human's) own immune response against a subsequent exposure to influenza virus. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against influenza virus refers to an immune response exhibited by an individual (e.g., a human) that is protective against disease when the individual is subsequently exposed to and/or infected with wild-type influenza virus. In some instances, the wild-type (e.g., naturally circulating) influenza virus can still cause infection, but it cannot cause a serious or life-threatening infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see Fundamental Immunology, W. E. Paul, ed., Raven Press, N.Y. (1999) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Influenza Virus

The polypeptides and polynucleotides of the invention are variants of influenza HA and/or NA sequences. See, e.g., the Sequence Listing in FIGS. 1 and 2 below. In general, influenza viruses are made up of an internal ribonucleoprotein core containing a segmented single-stranded RNA genome and an outer lipoprotein envelope lined by a matrix protein. The genome of influenza viruses is composed of eight segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); non-structural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA). The hemagglutinin molecule consists of a surface glycoprotein and acts to bind to N-AcetylNeuraminic acid (NeuNAc), also known as sialic acid, on host cell surface receptors. In some embodiments herein, the polypeptides of the invention (and polypeptides encoded by the polynucleotides of the invention) can act to bind NeuNAc whether in vitro or in vivo. Such action can in some embodiments also be done by fragments of hemagglutinin which retain hemagglutinin activity. Hemagglutinin is made up of two subunits, HA1 and HA2 and the entire structure is about 550 amino acids in length and about 220 kD. Neuraminidase molecules cleave terminal sialic acid residues from cell surface receptors of influenza virus, thereby releasing virions from infected cells. Neuraminidase also removes sialic acid from newly made hemagglutinin and neuraminidase molecules. In some embodiments herein, the polypeptides of the invention (and polypeptides encoded by the polynucleotides of the invention) can act to cleave sialic acid residues whether in vitro or in vivo. This action can also be done in some embodiments by fragments of neuraminidase which retain neuraminidase activity. The neuraminidase polypeptides of the invention show immunological cross reactivity with one or more known neuraminidase molecule from an influenza virus. The literature is replete with examples of such known neuraminidases (e.g., in GenBank, in publications from the CDC, etc.). Similarly, the hemagglutinin polypeptides of the invention show immunological cross-reactivity with one or more known hemagglutinin molecule from an influenza virus. Again, the literature is replete with examples of such known hemagglutinin molecules.

Influenza is commonly grouped into influenza A and influenza B categories, as well as a typically less important C category. Influenza A and influenza B viruses each contain eight segments of single stranded RNA with negative polarity. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants. The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a bicistronic mRNA. Segment 7 of influenza B also encodes two proteins: M1 and BM2. The smallest segment encodes two products: NS1 is translated from the full length RNA, while NS2 is translated from a spliced mRNA variant.

Influenza types A and B are typically associated with influenza outbreaks in human populations. However, type A influenza also infects other creatures as well, e.g., birds, pigs, and other animals. The type A viruses are categorized into subtypes based upon differences within their hemagglutinin and neuraminidase surface glycoprotein antigens. Hemagglutinin in type A viruses has 14 known subtypes and neuraminidase has 9 known subtypes. In humans, currently only about 3 different hemagglutinin and 2 different neuraminidase subtypes are known, e.g., H1, H2, H3, N1, and N2. In particular, two major subtypes of influenza A have been active in humans, namely, H1N1 and H3N2. H1N2, however has recently been of concern. Influenza B viruses are not divided into subtypes based upon their hemagglutinin and neuraminidase proteins. As will be appreciated, the sequences contained within the sequence listing in FIG. 1 comprise a number of different subtypes of influenza. Thus, for example in the sequence listing A-H3N2 strains are exampled by ca A/Shandong/9/93, ca A/Johannesburg/33/94-like, ca A/Wuhan/395/95, ca A/Sydney/05/97, ca A/Panama/2007/99, ca A/Wyoming/03/2003. A-H1N1 strains are shown in ca A/Texas/36/91, ca A/Shenzhen/227/95, ca A/Beijing/262/95, and ca A/New Caledonia/20/99, while B-HANA strains include ca B/Ann Arbor/1/94, ca B/Yamanashi/166/98, ca B/Johannesburg/5/99, ca B/Victoria/504/2000, ca B/Hong Kong/330/2001, ca B/Brisbane/32/2002, and ca B/Jilin/20/2003, etc. The Figures also show the subtypes of the other specific strains as well. As can be seen from the Figures several sequences are A/Fujian-like strains (e.g., ca A/Wellington/01/2004 (for classical reassorted), ca A/Malaysia/1/2004_1 (186G, 193R in HA) (for plasmid-derived, ca A/Malaysia/1/2004_2 (186V, 193S in HA) (for both plasmid-derived and classical reassorted). Other sequences are ca B/Shanghai-like strains (e.g., ca B/Jiangshu/10/2003 (for both classical reassorted and plasmid-derived), ca B/Shanghai/361/2002 (for plasmid-derived).

Different strains of influenza can be categorized based upon, e.g., the ability of influenza to agglutinate red blood cells (RBCs or erythrocytes). Antibodies specific for particular influenza strains can bind to the virus and, thus, prevent such agglutination. Assays determining strain types based on such inhibition are typically known as hemagglutinin inhibition assays (HI assays or HAI assays) and are standard and well known methods in the art to characterize influenza strains. Of course, those of skill in the art will be familiar with other assays, e.g., ELISA, indirect fluorescent antibody assays, immunohistochemistry, Western blot assays, etc. with which to characterize influenza strains and the use of and discussion herein of HI assays should not be necessarily construed as limiting.

Briefly, in typical HI assays, sera to be used for typing or categorization, which is often produced in ferrets, is added to erythrocyte samples in various dilutions, e.g., 2-fold, etc. Optical determination is then made whether the erythrocytes are clumped together (i.e., agglutinated) or are suspended (i.e., non-agglutinated). If the cells are not clumped, then agglutination did not occur due to the inhibition from antibodies in the sera that are specific for that influenza. Thus, the types of influenza are defined as being within the same strain. In some cases, one strain is described as being "like" the other, e.g., strain x is a "y-like" strain, etc. For example, if two samples are within four-fold titer of one another as measured by an HI assay, then they can be described as belonging to the same strain (e.g., both belonging to the "New Caledonia" strain or both being "Moscow-like" strains, etc.). In other words, strains are typically categorized based upon their immunologic or antigenic profile. An HAI titer is typically defined as the highest dilution of a serum that completely inhibits hemagglutination. See, e.g., Schild, et al., *Bull. Wld Hlth Org.*, 1973, 48:269-278, etc. Again, those of skill in the art will be quite familiar with categorization and classification of influenza into strains and the methods to do so.

From the above it will be appreciated that the current invention not only comprises the specific sequences listed herein, but also such sequences within various vectors (e.g., ones used for plasmid reassortment and rescue, see below) as well as hemagglutinin and neuraminidase sequences within the same strains as the sequences listed herein. Also, such same strains that are within various vectors (e.g., typically ones used for plasmid reassortment and rescue such as A/Ann Arbor/6/60 or B/Ann Arbor/1/66, A/Puerto Rico/8/34, B/Leningrad/14/17/55, B/14/5/1, B/USSR/60/69, B/Leningrad/179/86, B/Leningrad/14/55, or B/England/2608/76, etc.) are also included.

As used herein, the term "similar strain" should be taken to indicate that a first influenza virus is of the same or related strain as a second influenza virus. In typical embodiments such relation is commonly determined through use of an HAI assay. Influenza viruses that fall within a four-fold titer of one another in an HAI assay are, thus, of a "similar strain." Those of skill in the art, however, will be familiar with other assays, etc. to determine similar strains, e.g., FRID, neutralization assays, etc. The current invention also comprises such similar strains (i.e., strains similar to the ones present in the sequence listing herein) in the various plasmids, vectors, viruses, methods, etc. herein. Thus, unless the context clearly dictates otherwise, descriptions herein of particular sequences (e.g., those in the sequence listing) or fragments thereof also should be considered to include sequences from similar strains to those (i.e., similar strains to those strains having the sequences in those plasmids, vectors, viruses, etc. herein). Also, it will be appreciated that the NA and HA polypeptides within such similar strains are, thus, "similar polypeptides" when compared between "similar strains."

Influenza Virus Vaccines

The sequences, compositions and methods herein are primarily, but not solely, concerned with production of influenza viruses for vaccines. Historically, influenza virus vaccines have primarily been produced in embryonated hen eggs using strains of virus selected or based on empirical predictions of relevant strains. More recently, reassortant viruses have been produced that incorporate selected hemagglutinin and/or neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines). Thus, it will be appreciated that HA and NA sequences (as in the current invention) are quite useful in constructing influenza vaccines.

Attempts at producing recombinant and reassortant vaccines in cell culture have been hampered by the inability of some of the strains approved for vaccine production to grow efficiently under standard cell culture conditions. However, prior work by the inventors and their coworkers provided a vector system, and methods for producing recombinant and reassortant viruses in culture, thus, making it possible to rapidly produce vaccines corresponding to one or many selected antigenic strains of virus, e.g., either A or B strains, various subtypes or substrains, etc., e.g., comprising the HA and NA sequences herein. See, U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus." Typically, the cultures are maintained in a system, such as a cell culture incubator, under controlled humidity and $CO_2$, at constant temperature using a temperature regulator, such as a thermostat to insure that the temperature does not exceed 35° C. Reassortant influenza viruses can be readily obtained by introducing a subset of vectors corresponding to genomic segments of a master influenza virus, in combination with complementary segments derived from strains of interest (e.g., HA and NA antigenic variants herein). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. As explained elsewhere herein and, e.g., in U.S. patent application Ser. No. 10/423,828, etc., various embodiments of the invention utilize A/Ann Arbor (AA)/6/60 or B/Ann Arbor/1/66 or A/Puerto Rico/8/34, or B/Leningrad/14/17/55, B/14/5/1, B/USSR/60/69, B/Leningrad/179/86, B/Leningrad/14/55, or B/England/2608/76 influenza strain as a "backbone" upon which to add HA and/or NA genes (e.g., such as those sequences listed herein, etc.) to create desired reassortant viruses. Thus, for example, in a 6:2 reassortant, 2 genes (i.e., NA and HA) would be from the influenza strain(s) against which an immunogenic reaction is desired, while the other 6 genes would be from the Ann Arbor strain, or other backbone strain, etc. The Ann Arbor virus is useful for its cold adapted, attenuated, temperature sensitive attributes. Of course, it will be appreciated that the HA and NA sequences herein are capable of reassortment with a number of other virus genes or virus types (e.g., a number of different "backbones" such as A/Puerto Rico/8/34, etc., containing the other influenza genes present in a reassortant, namely, the non-HA and non-NA genes). Live, attenuated influenza A virus vaccines against human influenza viruses were recently licensed in the United States. See above. Such vaccines are reassortant H1N1 and H1N2 viruses in which the internal protein genes of A/Ann Arbor (AA)/6/60 (H2N2) cold adapted (ca) virus confer the cold adapted, attenuation and temperature sensitive phenotypes of the AA ca virus on the reassortant viruses (i.e., the ones having the hemagglutinin and neuraminidase genes from the non-Ann Arbor strain). In some embodiments herein, the reassortants can also comprise 7:1 reassortants. In other words, only the HA or the NA is not from the backbone or MDV strain. Previous work has been reported with suitable backbone donor virus strains that optionally are within various embodiments of the current invention. See, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus"; Maassab et al., *J. of Inf. Dis.*, 1982, 146:780-790; Cox, et al., *Virology*, 1988, 167:554-567; Wareing et al., *Vaccine*, 2001, 19:3320-3330; Clements, et al., *J Infect Dis.*, 1990, 161(5):869-77, etc.

In some embodiments, the sequences herein can optionally have specific regions removed (both or either in the nucleic acid sequence or the amino acid sequence). For example, for those molecules having a polybasic cleavage site, such sites can optionally be removed. Such cleavage sites, in some embodiments herein, are, e.g., modified or altered in their sequences in comparison to the wild-type sequences from which such sequences are derived (e.g., to disable the cleavage or reduce the cleavage there, etc.). Such modifications/alterations can be different in different strains or sequences due to the various sequences of the cleavage sites in the starting sequences. For example, 4 polybasic residues (RRKK) are typically removed in some HA sequences. (as compared to wt). In various embodiments, such polybasic cleavage sites can be modified in a number of ways (all of which are contained within the invention). For example, the polybasic cleavage site can be removed one amino acid at a time (e.g., one R removed, two Rs removed, RRK removed, or RRKK removed). Additionally, an amino acid residue directly upstream of the cleavage site can also be removed or altered (e.g., from an R to a T, etc.); also, the nucleotides encoding the amino acid residue directly after the cleavage site can also be modified. Those of skill in the art will be familiar with various methods of removing such specific regions. The resulting shortened sequences are also contained within the current invention. See, e.g., Li et al., *J. of Infectious Diseases*, 179:1132-8, 1999

The terms "temperature sensitive," "cold adapted" and "attenuated" as applied to viruses (typically used as vaccines or for vaccine production) which optionally encompass the current sequences, are well known in the art. For example, the term "temperature sensitive" (ts) indicates, e.g., that the virus exhibits a 100 fold or greater reduction in titer at 39° C. relative to 33° C. for influenza A strains, or that the virus exhibits a 100 fold or greater reduction in titer at 37° C.

relative to 33° C. for influenza B strains. The term "cold adapted" (ca) indicates that the virus exhibits growth at 25° C. within 100 fold of its growth at 33° C., while the term "attenuated" (att) indicates that the virus replicates in the upper airways of ferrets but is not detectable in their lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), or exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses and can be used in conjunction with the HA and NA sequences herein.

Thus, the present invention can utilize growth, e.g., in appropriate culture conditions, of virus strains (both A strain and B strain influenza viruses) with desirable properties relative to vaccine production (e.g., attenuated pathogenicity or phenotype, cold adaptation, temperature sensitivity, etc.) in vitro in cultured cells. Influenza viruses can be produced by introducing a plurality of vectors incorporating cloned viral genome segments into host cells, and culturing the cells at a temperature not exceeding 35° C. When vectors including an influenza virus genome are transfected, recombinant viruses suitable as vaccines can be recovered by standard purification procedures. Using the vector system and methods of the invention, reassortant viruses incorporating the six internal gene segments of a strain selected for its desirable properties with respect to vaccine production, and the immunogenic HA and NA segments from a selected, e.g., pathogenic strain such as those in the sequence listing herein, can be rapidly and efficiently produced in tissue culture. Thus, the system and methods described herein are useful for the rapid production in cell culture of recombinant and reassortant influenza A and B viruses, including viruses suitable for use as vaccines, including live attenuated vaccines, such as vaccines suitable for intranasal administration.

In such embodiments, typically, a single Master Donor Virus (MDV) strain is selected for each of the A and B subtypes. In the case of a live attenuated vaccine, the Master Donor Virus strain is typically chosen for its favorable properties, e.g., temperature sensitivity, cold adaptation and/or attenuation, relative to vaccine production. For example, exemplary Master Donor Strains include such temperature sensitive, attenuated and cold adapted strains of A/Ann Arbor/6/60 and B/Ann Arbor/1/66, respectively, as well as others mentioned throughout.

For example, a selected master donor type A virus (MDV-A), or master donor type B virus (MDV-B), is produced from a plurality of cloned viral cDNAs constituting the viral genome. Embodiments include those wherein recombinant viruses are produced from eight cloned viral cDNAs. Eight viral cDNAs representing either the selected MDV-A or MDV-B sequences of PB2, PB1, PA, NP, HA, NA, M and NS are optionally cloned into a bi-directional expression vector, such as a plasmid (e.g., pAD3000), such that the viral genomic RNA can be transcribed from an RNA polymerase I (pol I) promoter from one strand and the viral mRNAs can be synthesized from an RNA polymerase II (pol II) promoter from the other strand. Optionally, any gene segment can be modified, including the HA segment (e.g., to remove the multi-basic cleavage site (also known as a polybasic cleavage site)).

Infectious recombinant MDV-A or MDV-B virus can be then recovered following transfection of plasmids bearing the eight viral cDNAs into appropriate host cells, e.g., Vero cells, co-cultured MDCK/293T or MDCK/COS7 cells. Using the plasmids and methods described herein and, e.g., in U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"; Hoffmann, E., 2000, *PNAS,* 97(11):6108-6113; U.S. Published Patent Application No. 20020164770 to Hoffmann; and U.S. Pat. No. 6,544,785 issued Apr. 8, 2003 to Palese, et al., the invention is useful, e.g., for generating 6:2 reassortant influenza vaccines by co-transfection of the 6 internal genes (PB1, PB2, PA, NP, M and NS) of the selected virus (e.g., MDV-A, MDV-B) together with the HA and NA derived from different corresponding type (A or B) influenza viruses e.g., as shown in the sequence listings herein. For example, the HA segment is favorably selected from a pathogenically relevant H1, H3 or B strain, as is routinely performed for vaccine production. Similarly, the HA segment can be selected from a strain with emerging relevance as a pathogenic strain such as those in the sequence listing herein. Reassortants incorporating seven genome segments of the MDV and either the HA or NA gene of a selected strain (7:1 reassortants) can also be produced. It will be appreciated, and as is detailed throughout, the molecules of the invention can optionally be combined in any desired combination. For example, the HA and/or NA sequences herein can be placed, e.g., into a reassortant backbone such as A/AA/6/60, B/AA/1/66, A/Puerto Rico/8/34 (i.e., PR8), etc., in 6:2 reassortants or 7:1 reassortants, etc. Thus, as explained more fully below, there would be 6 backbone gene regions from the donor virus (again, e.g., A/AA/6/60, etc.) and 2 genes regions from a second strain (e.g., a wild-type strain, not the backbone donor virus). Such 2 gene regions are preferably the HA and NA genes. A similar situation arises for 7:1 reassortants, in which however, there are 7 gene regions from the background donor virus and 1 gene (either HA or NA) from a different virus (typically wild-type or one to which an immune response is desired). Also, it will be appreciated that the sequences herein (e.g., those in the sequence listing of FIG. 1, etc.) can be combined in a number of means in different embodiments herein. Thus, any of the sequences herein can be present singularly in a 7:1 reassortant (i.e., the sequence of the invention present with 7 backbone donor virus gene regions) and/or can be present with another sequence of the invention in a 6:2 reassortant. Within such 6:2 reassortants, any of the sequences of the invention can optionally be present with any other sequence of the invention. Typical, and preferred, embodiments comprise HA and NA from the same original wild-type strains however (or modified wild-type strains such as those with modified polybasic cleavage sites). For example, typical embodiments can comprise a 6:2 reassortant having 6 gene regions from a backbone donor virus such as A/AA/6/60 and the HA and NA gene regions from the same strain such as ca A/Shandong/9/93 or both HA and NA from ca A/Wuhan/395/95 or both HA and NA from ca B/Ann Arbor/1/94 (which would typically, but not exclusively, be present within a B influenza backbone donor virus such as B/Ann Arbor/1/66, etc.), etc. Of course, it will again be appreciated that the invention also includes such reassortant viruses wherein the non-background gene regions (i.e., the HA and/or NA regions) are from similar strains (i.e., strains that are similar strains to influenza strains having the sequences found in SEQ ID NO:1-48. The above references are specifically incorporated herein in their entirety for all purposes, e.g., especially for their teachings regarding plasmids, plasmid rescue of virus (influenza virus), multi-plasmid systems for virus rescue/production, etc.

Again, the HA and NA sequences of the current invention are optionally utilized in such plasmid reassortment vaccines (and/or in other ts, cs, ca, and/or att viruses and vaccines). However, it should be noted that the HA and NA sequences, etc. of the invention are not limited to specific vaccine compositions or production methods, and can, thus, be utilized in substantially any vaccine type or vaccine production method which utilizes strain specific HA and NA antigens (e.g., the sequences of the invention).

FluMist™

As mentioned previously, numerous examples and types of influenza vaccine exist. An exemplary influenza vaccine is FluMist™ (MedImmune Vaccines Inc., Mt. View, Calif.) which is a live, attenuated vaccine that protects children and adults from influenza illness (Belshe et al. (1998) The efficacy of live attenuated, cold-adapted, trivalent, intranasal influenza virus vaccine in children *N Engl J Med* 338:1405-12; Nichol et al. (1999) Effectiveness of live, attenuated intranasal influenza virus vaccine in healthy, working adults: a randomized controlled trial *JAMA* 282:137-44). In typical, and preferred, embodiments, the methods and compositions of the current invention are preferably adapted to/used with production of FluMist™ vaccine. However, it will be appreciated by those skilled in the art that the sequences, methods, compositions, etc. herein are also adaptable to production of similar or even different viral vaccines.

FluMist™ vaccine strains contain, e.g., HA and NA gene segments derived from the wild-type strains to which the vaccine is addressed (or, in some instances, to related strains) along with six gene segments, PB1, PB2, PA, NP, M and NS, from a common master donor virus (MDV). The HA and NA sequences herein, thus, are optionally part of various FluMist™ formulations. The MDV for influenza A strains of FluMist™ (MDV-A), was created by serial passage of the wild-type A/Ann Arbor/6/60 (A/AA/6/60) strain in primary chicken kidney tissue culture at successively lower temperatures (Maassab (1967) Adaptation and growth characteristics of influenza virus at 25 degrees C. *Nature* 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) Principles underlying the development and use of live attenuated cold-adapted influenza A and B virus vaccines *Viral Immunol* 15:295-323).

Clinical studies in over 20,000 adults and children involving 12 separate 6:2 reassortant strains have shown that these vaccines are attenuated, safe and efficacious (Belshe et al. (1998) The efficacy of live attenuated, cold-adapted, trivalent, intranasal influenza virus vaccine in children *N Engl J Med* 338:1405-12; Boyce et al. (2000) Safety and immunogenicity of adjuvanted and unadjuvanted subunit influenza vaccines administered intranasally to healthy adults *Vaccine* 19:217-26; Edwards et al. (1994) A randomized controlled trial of cold adapted and inactivated vaccines for the prevention of influenza A disease *J Infect Dis* 169:68-76 ; Nichol et al. (1999) Effectiveness of live, attenuated intranasal influenza virus vaccine in healthy, working adults: a randomized controlled trial *JAMA* 282:137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) Evaluation of a cold-recombinant influenza virus vaccine in ferrets *J. Infect. Dis.* 146:780-900).

Production of such reassorted virus using B strains of influenza is more difficult, however, recent work (see, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus") has shown an eight plasmid system for the generation of influenza B virus entirely from cloned cDNA. Methods for the production of attenuated live influenza A and B virus suitable for vaccine formulations, such as live virus vaccine formulations useful for intranasal administration were also shown.

The system and methods described previously are useful for the rapid production in cell culture of recombinant and reassortant influenza A and B viruses, including viruses suitable for use as vaccines, including live attenuated vaccines, such as vaccines suitable for intranasal administration. The sequences, methods, etc. of the current invention, are optionally used in conjunction with, or in combination with, such previous work involving, e.g., reasserted influenza viruses for vaccine production to produce viruses for vaccines.

Methods and Compositions for Prophylactic Administration of Vaccines

As stated above, alternatively, or in addition to, use in production of FluMist™ vaccine, the current invention can be used in other vaccine formulations. In general, recombinant and reassortant viruses of the invention (e.g., those comprising polynucleotides of SEQ ID NO:1-48 or polypeptides of SEQ ID NO:49-96, or similar strains of the virus sequences within SEQ ID NO:1-96, or fragments of any of the previous) can be administered prophylactically in an immunologically effective amount and in an appropriate carrier or excipient to stimulate an immune response specific for one or more strains of influenza virus as determined by the HA and/or NA sequence. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected hen eggs (i.e., normal allantoic fluid or NAF), or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

A related aspect of the invention provides methods for stimulating the immune system of an individual to produce a protective immune response against influenza virus. In the methods, an immunologically effective amount of a recombinant influenza virus (e.g., an HA and/or an NA molecule of the invention), an immunologically effective amount of a polypeptide of the invention, and/or an immunologically effective amount of a nucleic acid of the invention is administered to the individual in a physiologically acceptable carrier.

Generally, the influenza viruses of the invention are administered in a quantity sufficient to stimulate an immune response specific for one or more strains of influenza virus (i.e., against the HA and/or NA strains of the invention). Preferably, administration of the influenza viruses elicits a protective immune response to such strains. Dosages and methods for eliciting a protective immune response against one or more influenza strains are known to those of skill in the art. See, e.g., U.S. Pat. No. 5,922,326; Wright et al., *Infect. Immun.* 37:397-400 (1982); Kim et al., *Pediatrics* 52:56-63 (1973); and Wright et al., *J. Pediatr.* 88:931-936 (1976). For example, influenza viruses are provided in the range of about 1-1000 $HID_{50}$ (human infectious dose), i.e., about $10^5$-$10^8$ pfu (plaque forming units) per dose administered. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. See above. While stimulation of a protective immune response with a single dose is preferred, additional dosages can be administered, by the same or different route, to achieve the desired prophylactic effect.

Typically, the attenuated recombinant influenza of this invention as used in a vaccine is sufficiently attenuated such that symptoms of infection, or at least symptoms of serious infection, will not occur in most individuals immunized (or otherwise infected) with the attenuated influenza virus. In some instances, the attenuated influenza virus can still be capable of producing symptoms of mild illness (e.g., mild upper respiratory illness) and/or of dissemination to unvaccinated individuals. However, its virulence is sufficiently abrogated such that severe lower respiratory tract infections do not occur in the vaccinated or incidental host.

Alternatively, an immune response can be stimulated by ex vivo or in vivo targeting of dendritic cells with influenza viruses comprising the sequences herein. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Optionally, the formulation for prophylactic administration of the influenza viruses also contains one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum,* and the synthetic adjuvants QS-21 and MF59.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein (e.g., an HA and/or NA polypeptide of the invention) or an expression vector encoding the protein can be administered to produce an immunostimulatory effect.

The above described methods are useful for therapeutically and/or prophylactically treating a disease or disorder, typically influenza, by introducing a vector of the invention comprising a heterologous polynucleotide encoding a therapeutically or prophylactically effective HA and/or NA polypeptide (or peptide) or HA and/or NA RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences, e.g., as described herein. Optionally, more than one heterologous coding sequence is incorporated into a single vector or virus. For example, in addition to a polynucleotide encoding a therapeutically or prophylactically active HA and/or NA polypeptide or RNA, the vector can also include additional therapeutic or prophylactic polypeptides, e.g., antigens, co-stimulatory molecules, cytokines, antibodies, etc., and/or markers, and the like.

Although vaccination of an individual with an attenuated influenza virus of a particular strain of a particular subgroup can induce cross-protection against influenza virus of different strains and/or subgroups, cross-protection can be enhanced, if desired, by vaccinating the individual with attenuated influenza virus from at least two, at least three, or at least four influenza virus strains or substrains, e.g., at least two of which may represent a different subgroup. For example, vaccinating an individual with at least four strains or substrains of attenuated influenza virus may include vaccinating the individual with at least two strains or substrains of influenza A virus and at least two strains or substrains of influenza B virus. Vaccinating the individual with the at least four strains or substrains of attenuated influenza virus may include vaccinating the individual with at least three strains or substrains of influenza A virus and at least one strain or substrain of influenza B virus. The vaccination of the individual with at least four influenza virus strains or substrains may require administration of a single tetravalent vaccine which comprises all of the at least four attenuated influenza virus strains or substrains. The vaccination may alternatively require administration of multiple vaccines, each of which comprises one, two, or three of the attenuated influenza virus strains or substrains. Additionally, vaccine combinations can optionally include mixes of pandemic vaccines and non-pandemic strains. Vaccine mixtures (or multiple vaccinations) can comprise components from human strains and/or non-human influenza strains (e.g., avian and human, etc.). Similarly, the attenuated influenza virus vaccines of this invention can optionally be combined with vaccines that induce protective immune responses against other infectious agents.

Polynucleotides of the Invention

Probes

The HA and NA polynucleotides of the invention, e.g., as shown in the sequences herein such as SEQ ID NO:1 through SEQ ID NO:48, and fragments thereof, are optionally used in a number of different capacities alternative to, or in addition to, the vaccines described above. Other exemplary uses are described herein for illustrative purpose and not as limitations on the actual range of uses, etc. Different methods of construction, purification, and characterization of the nucleotide sequences of the invention are also described herein.

In some embodiments, nucleic acids including one or more polynucleotide sequence of the invention are favorably used as probes for the detection of corresponding or related nucleic acids in a variety of contexts, such as in nucleic hybridization experiments, e.g., to find and/or characterize homologous influenza variants (e.g., homologues to sequences herein, etc.) infecting other species or in different influenza outbreaks, etc. The probes can be either DNA or RNA molecules, such as restriction fragments of genomic or cloned DNA, cDNAs, PCR amplification products, transcripts, and oligonucleotides, and can vary in length from oligonucleotides as short as about 10 nucleotides in length to full length sequences or cDNAs in excess of 1 kb or more. For example, in some embodiments, a probe of the invention includes a polynucleotide sequence or subsequence selected, e.g., from among SEQ ID NO:1-SEQ ID NO:48, or sequences complementary thereto. Alternatively, polynucleotide sequences that are variants of one of the above-designated sequences are used as probes. Most typically, such variants include one or a few conservative nucleotide variations. For example, pairs (or sets) of oligonucleotides can be selected, in which the two (or more) polynucleotide sequences are conservative variations of each other, wherein one polynucleotide sequence corresponds identically to a first variant or and the other(s) corresponds identically to additional variants. Such pairs of oligonucleotide probes are particularly useful, e.g., for specific hybridization experiments to detect polymorphic nucleotides or to, e.g., detect homologous influenza HA and NA variants, e.g., homologous to the current HA and NA sequences, infecting other species or present in different (e.g., either temporally and/or geographically different) influenza outbreaks. In other applications, probes are selected that are more divergent, that is probes that are at least about 91% (or about 92%, about 93%, about 94%, about 95%, about 96%, about 97%, about 98%, about 98.5%, about 98.7%, about 99%, about 99.1%, about 99.2%, about 99.3%, about 99.4%, about 99.5%, or about 99.6% or more about 99.7%, about 99.8%, about 99.9% or more) identical are selected.

The probes of the invention, e.g., as exemplified by sequences derived from the sequences herein, can also be used to identify additional useful polynucleotide sequences according to procedures routine in the art. In one set of embodiments, one or more probes, as described above, are utilized to screen libraries of expression products or chromosomal segments (e.g., expression libraries or genomic libraries) to identify clones that include sequences identical to, or with significant sequence similarity to, e.g., one or more probe of, e.g., SEQ ID NO:1-SEQ ID NO:48, i.e., variants, homologues, etc. It will be understood that in addition to such physical methods as library screening, computer assisted bioinformatic approaches, e.g., BLAST and other sequence homology search algorithms, and the like, can also be used for identifying related polynucleotide sequences. Polynucleotide sequences identified in this manner are also a feature of the invention.

Oligonucleotide probes are optionally produced via a variety of methods well known to those skilled in the art. Most typically, they are produced by well known synthetic methods, such as the solid phase phosphoramidite triester method described by Beaucage and Caruthers (1981) *Tetrahedron Letts* 22(20):1859-1862, e.g., using an automated synthesizer, or as described in Needham-Van Devanter et al. (1984) *Nucl Acids Res,* 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J Chrom* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560. Custom oligos can also easily be ordered from a variety of commercial sources known to persons of skill.

In other circumstances, e.g., relating to attributes of cells or organisms expressing the polynucleotides and polypeptides of the invention (e.g., those harboring virus comprising the sequences of the invention), probes that are polypeptides, peptides or antibodies are favorably utilized. For example, isolated or recombinant polypeptides, polypeptide fragments and peptides derived from any of the amino acid sequences of the invention and/or encoded by polynucleotide sequences of the invention, e.g., selected from SEQ ID NO:1 through SEQ ID NO:48, are favorably used to identify and isolate antibodies, e.g., from phage display libraries, combinatorial libraries, polyclonal sera, and the like.

Antibodies specific for any a polypeptide sequence or subsequence, e.g., of SEQ ID NO:49 through SEQ ID NO:96, and/or encoded by polynucleotide sequences of the invention, e.g., selected from SEQ ID NO:1 through SEQ ID NO:48, are likewise valuable as probes for evaluating expression products, e.g., from cells or tissues. In addition, antibodies are particularly suitable for evaluating expression of proteins comprising amino acid subsequences, e.g., of those given herein, or encoded by polynucleotides sequences of the invention, e.g., selected from those shown herein, in situ, in a tissue array, in a cell, tissue or organism, e.g., an organism infected by an unidentified influenza virus or the like. Antibodies can be directly labeled with a detectable reagent, or detected indirectly by labeling of a secondary antibody specific for the heavy chain constant region (i.e., isotype) of the specific antibody. Antibodies against specific amino acids sequences herein (e.g., SEQ ID NOs: 49-96) are also useful in determining whether other influenza viruses are within the same strain as the current sequences (e.g., through an HI assay, etc.). Additional details regarding production of specific antibodies are provided below.

Diagnostic Assays

The nucleic acid sequences of the present invention can be used in diagnostic assays to detect influenza (and/or hemagglutinin and/or neuraminidase) in a sample, to detect hemagglutinin-like and/or neuraminidase-like sequences, and to detect strain differences in clinical isolates of influenza using either chemically synthesized or recombinant polynucleotide fragments, e.g., selected from the sequences herein. For example, fragments of the hemagglutinin and/or neuraminidase sequences comprising at least between 10 and 20 nucleotides can be used as primers to amplify nucleic acids using polymerase chain reaction (PCR) methods well known in the art (e.g., reverse transcription-PCR) and as probes in nucleic acid hybridization assays to detect target genetic material such as influenza RNA in clinical specimens.

The probes of the invention, e.g., as exemplified by unique subsequences selected from, e.g., SEQ ID NO:1 through SEQ ID NO:48, can also be used to identify additional useful polynucleotide sequences (such as to characterize additional strains of influenza) according to procedures routine in the art. In one set of preferred embodiments, one or more probes, as described above, are utilized to screen libraries of expression products or cloned viral nucleic acids (i.e., expression libraries or genomic libraries) to identify clones that include sequences identical to, or with significant sequence identity to the sequences herein. In turn, each of these identified sequences can be used to make probes, including pairs or sets of variant probes as described above. It will be understood that in addition to such physical methods as library screening, computer assisted bioinformatic approaches, e.g., BLAST and other sequence homology search algorithms, and the like, can also be used for identifying related polynucleotide sequences.

The probes of the invention are particularly useful for detecting the presence and for determining the identity of influenza nucleic acids in cells, tissues or other biological samples (e.g., a nasal wash or bronchial lavage). For example, the probes of the invention are favorably utilized to determine whether a biological sample, such as a subject (e.g., a human subject) or model system (such as a cultured cell sample) has been exposed to, or become infected with influenza, or particular strain(s) of influenza. Detection of hybridization of the selected probe to nucleic acids originating in (e.g., isolated from) the biological sample or model system is indicative of exposure to or infection with the virus (or a related virus) from which the probe polynucleotide is selected.

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the lengths of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction, such as selecting against primer self-complementarity and the like.

Vectors, Promoters and Expression Systems

The present invention includes recombinant constructs incorporating one or more of the nucleic acid sequences described herein. Such constructs optionally include a vector, for example, a plasmid, a cosmid, a phage, a virus, a bacterial artificial chromosome (BAC), a yeast artificial chromosome (YAC), etc., into which one or more of the polynucleotide sequences of the invention, e.g., comprising any of SEQ ID NO:1 through SEQ ID NO:48, or a subsequence thereof etc., has been inserted, in a forward or reverse orientation. For example, the inserted nucleic acid can include a viral chromosomal sequence or cDNA including all or part of at least one of the polynucleotide sequences of the invention. In one embodiment, the construct further comprises regulatory sequences, including, for example, a promoter, operably linked to the sequence. Large numbers of suitable vectors and promoters are known to those of skill in the art, and are commercially available.

The polynucleotides of the present invention can be included in any one of a variety of vectors suitable for generating sense or antisense RNA, and optionally, polypeptide (or peptide) expression products (e.g., a hemagglutinin and/or neuraminidase molecule of the invention, or hemagglutinin or neuraminidase fragments). Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others (e.g., pCDL). Any vector that is capable of introducing genetic material into a cell, and, if replication is desired, which is replicable in the relevant host can be used.

In an expression vector, the HA and/or NA polynucleotide sequence of interest is physically arranged in proximity and orientation to an appropriate transcription control sequence (e.g., promoter, and optionally, one or more enhancers) to direct mRNA synthesis. That is, the polynucleotide sequence of interest is operably linked to an appropriate transcription control sequence. Examples of such promoters include: LTR or SV40 promoter, E. coli lac or trp promoter, phage lambda $P_L$ promoter, and other promoters known to control expression of genes in prokaryotic or eukaryotic cells or their viruses.

A variety of promoters are suitable for use in expression vectors for regulating transcription of influenza virus genome segments. In certain embodiments, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like.

Various embodiments of the current invention can comprise a number of different vector constructions. Such constructions are typically and preferably used in plasmid rescue systems to create viruses for use in vaccines (e.g., in live attenuated vaccines, in killed or inactivated vaccines, etc.). Thus, the invention includes recombinant DNA molecules having a transcription control element that binds a DNA-directed RNA polymerase that is operatively linked to a DNA sequence that encodes an RNA molecule, wherein the RNA molecule comprises a binding site specific for an RNA-directed RNA polymerase of a negative strand RNA virus, operatively linked to an RNA sequence comprising the reverse complement of a mRNA coding sequence of a negative strand RNA virus. Also, the invention includes a recombinant DNA molecule that, upon transcription yields an RNA template that contains an RNA sequence comprising the reverse complement of an mRNA coding sequence of a negative strand RNA virus, and vRNA terminal sequences. The invention also includes a recombinant DNA molecule that upon transcription yields a replicable RNA template comprising the reverse complement of an mRNA coding sequence of a negative strand RNA virus. Such above recombinant DNA molecules typically involve wherein the negative strand RNA virus is influenza (e.g., influenza A or B, etc.). Also, the RNA molecule in such embodiments is typically an influenza genome segment and the RNA template is typically an influenza genome segment. The recombinant DNA molecules typically comprise wherein the RNA template is replicable, wherein the negative strand RNA virus is influenza, and wherein the RNA template is an influenza genome segment. Thus, the nucleic acids influenza segments typically comprise HA and/or NA genes (the corresponding nucleic acid of which is, e.g., in FIG. 1, or within similar strains of the strains having the nucleic acids in, e.g., FIG. 1.

The invention also includes methods of preparing an RNA molecule comprising transcribing a recombinant DNA molecule with a DNA-directed RNA polymerase, wherein the DNA molecule comprises a transcription control element that binds a DNA-directed RNA polymerase that is operatively linked to a DNA sequence that encodes an RNA molecule, wherein the RNA molecule comprises a binding site specific for an RNA-directed RNA polymerase of a negative strand RNA virus, operatively linked to an RNA sequence comprising the reverse complement of an mRNA coding sequence of a negative strand RNA virus. The invention also includes a method of preparing an RNA molecule comprising transcribing a recombinant DNA molecule with a DNA-directed RNA polymerase, wherein the recombinant DNA molecule yields upon transcription an RNA molecule that contains an RNA sequence comprising the reverse complement of an mRNA coding sequence of a negative strand RNA virus, and vRNA terminal sequences. Furthermore, the invention includes a method of preparing an RNA molecule comprising transcribing a recombinant DNA molecule with a DNA-directed RNA polymerase, wherein the recombinant DNA molecule yields upon transcription a replicable RNA molecule comprising the reverse complement of an mRNA coding sequence of a negative strand RNA virus. Such methods typically comprise wherein the negative strand RNA virus is influenza, and wherein the RNA molecule is an influenza genome segment. Such methods preferably include wherein the DNA-directed RNA polymerase is pol I, pol II, T7 polymerase, T3 polymerase, or Sp6 polymerase. Thus, again, the influenza nucleic acid segments typically comprise HA and/or NA genes as described throughout.

Other methods within the invention include methods of constructing a DNA molecule comprising a transcription control element that binds a DNA-directed RNA polymerase that is operatively linked to a DNA sequence that encodes an RNA molecule, wherein the RNA molecule comprises a binding site specific for an RNA-directed RNA polymerase of an influenza virus, operatively linked to an RNA sequence comprising the reverse complement of an mRNA coding sequence of an influenza virus, wherein the DNA sequence comprises a nucleic acid corresponding to one or more of SEQ ID NO:1-48 or a fragment thereof or of one or more nucleic acid sequence of a similar strain (e.g., a strain similar to such strains having the sequences found in the sequences of FIG. 1, etc.). Also, the invention includes a method of constructing a DNA molecule comprising a DNA sequence that upon transcription yields an RNA template that contains an RNA sequence comprising the reverse complement of an mRNA coding sequence of an influenza virus, and vRNA terminal sequences, wherein the DNA sequence comprises a nucleic acid corresponding to one or more of SEQ ID NO:1-48 or a fragment thereof, or of one or more nucleic acid of a similar strain (e.g., a strain similar to such strains that have the sequences found in FIG. 1, etc.). Such methods also include wherein the RNA template is replicable. Other methods of the invention include those of constructing a DNA molecule comprising a DNA sequence that upon transcription yields a replicable RNA template comprising the reverse complement of an mRNA coding sequence of an influenza virus. These methods of the invention typically include wherein the RNA molecule is an influenza genome segment, wherein the DNA-directed RNA polymerase is pol I, pol II, T7 polymerase, T3 polymerase, or Sp6 polymerase.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) Heat stress promoters and transcription factors *Results Probl Cell Differ* 20:125-62; Kriegler et al. (1990) Assembly of enhancers, promoters, and splice signals to control expression of transferred genes *Methods in Enzymol* 185: 512-27). Optionally, the amplicon can also contain a ribosome binding site or an internal ribosome entry site (IRES) for translation initiation.

The vectors of the invention also favorably include sequences necessary for the termination of transcription and for stabilizing the mRNA, such as a polyadenylation site or a terminator sequence. Such sequences are commonly available from the 5' and, occasionally 3', untranslated regions of eukaryotic or viral DNAs or cDNAs. In one embodiment, the SV40 polyadenylation signal sequences can provide a bi-directional polyadenylation site that insulates transcription of (+) strand mRNA molecules from the PolI promoter initiating replication of the (−) strand viral genome.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate nucleic acid sequence as described above, as well as an appropriate promoter or control sequence, can be employed to transform a host cell permitting expression of the protein. While the vectors of the invention can be replicated in bacterial cells, most frequently it will be desirable to introduce them into mammalian cells, e.g., Vero cells, BHK cells, MDCK cell, 293 cells, COS cells, or the like, for the purpose of expression.

As described elsewhere, the HA and NA sequences herein, in various embodiments, can be comprised within plasmids involved in plasmid-rescue reassortment. See, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"; Hoffmann, E., 2000, PNAS, 97(11):6108-6113; U.S. Published Patent Application No. 20020164770 to Hoffmann; and U.S. Pat. No. 6,544,785 issued Apr. 8, 2003 to Palese, et al. The reassortants produced can include the HA and NA genes arranged with the 6 other influenza genes from the A/Ann Arbor/6/60 donor strain, the B/Ann Arbor/1/66 donor strain (and/or derivatives and modifications thereof), the A/Puerto Rico/8/34 donor strain, etc.

Additional Expression Elements

Most commonly, the genome segment encoding the influenza virus HA and/or NA protein includes any additional sequences necessary for its expression, including translation into a functional viral protein. In other situations, a minigene, or other artificial construct encoding the viral proteins, e.g., an HA and/or NA protein, can be employed. Again, in such case, it is often desirable to include specific initiation signals that aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Where translation of a polypeptide encoded by a nucleic acid sequence of the invention is desired, additional translation specific initiation signals can improve the efficiency of translation. These signals can include, e.g., an ATG initiation codon and adjacent sequences, an IRES region, etc. In some cases, for example, full-length cDNA molecules or chromosomal segments including a coding sequence incorporating, e.g., a polynucleotide sequence of the invention (e.g., as in the sequences herein), a translation initiation codon and associated sequence elements are inserted into the appropriate expression vector simultaneously with the polynucleotide sequence of interest. In such cases, additional translational control signals frequently are not required. However, in cases where only a polypeptide coding sequence, or a portion thereof, is inserted, exogenous translational control signals, including, e.g., an ATG initiation codon is often provided for expression of the relevant sequence. The initiation codon is put in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (see, e.g., Scharf D. et al. (1994) *Results Probl Cell Differ* 20:125-62; Bittner et al. (1987) *Methods in Enzymol* 153:516-544).

Production of Recombinant Virus

Negative strand RNA viruses can be genetically engineered and recovered using a recombinant reverse genetics approach (U.S. Pat. No. 5,166,057 to Palese et al.). Such method was originally applied to engineer influenza viral genomes (Luytjes et al. (1989) Cell 59:1107-1113; Enami et al. (1990) *Proc. Natl. Acad. Sci. USA* 92:11563-11567), and has been successfully applied to a wide variety of segmented and nonsegmented negative strand RNA viruses, e.g., rabies (Schnell et al. (1994) *EMBO J.* 13: 4195-4203); VSV (Lawson et al. (1995) *Proc. Natl. Acad. Sci. USA* 92: 4477-4481); measles virus (Radecke et al.(1995) *EMBO J.* 14:5773-5784); rinderpest virus (Baron & Barrett (1997) *J. Virol.* 71: 1265-1271); human parainfluenza virus (Hoffman & Banerjee (1997) *J. Virol.* 71: 3272-3277; Dubin et al. (1997) *Virology* 235:323-332); SV5 (He et al. (1997) *Virology* 237:249-260); canine distemper virus (Gassen et al. (2000) *J. Virol.* 74:10737-44); and Sendai virus (Park et al. (1991) *Proc. Natl. Acad. Sci. USA* 88: 5537-5541; Kato et al. (1996) Genes to Cells 1:569-579). Those of skill in the art will be familiar with these and similar techniques to produce influenza virus comprising the HA and NA sequences of the invention. Recombinant influenza viruses produced according to such methods are also a feature of the invention, as are recombinant influenza virus comprising one or more nucleic acids and/or polypeptides of the invention. Of course, as will be appreciated by those of skill in the art, influenza viruses in general (and those of the invention as well) are negative stranded RNA viruses. Thus, when the present invention describes influenza viruses as comprising, e.g., the sequences of FIG. 1, etc., it is to be understood to typically mean the corresponding negative stranded RNA version of the sequences. The nucleotide sequences in FIG. 1 comprise DNA versions (e.g., coding plus sense, etc.) of the genes (along with some untranslated regions in the nucleotide sequences). Those of skill in the art can easily convert between RNA and DNA sequences (e.g., changing U to T, etc.), and between complementary nucleotide sequences (whether RNA or DNA),etc. Thus, for example, those of skill in the art can easily convert from a nucleotide sequence (e.g., one given in FIG. 1 such as SEQ ID NO:1) to the corresponding amino acid sequence or to a corresponding complementary sequence (whether DNA or RNA), etc. Also, as will be evident, when such HA and/or NA sequences are described within DNA vectors, e.g., plasmids, etc., then the corresponding DNA version of the sequences are typically to be understood. Again, nucleic acids of the invention include the explicit sequences in the sequence listings herein, as well as the complements of such sequences (both RNA and DNA), the double stranded form of the sequences in the sequence listings, the corresponding RNA forms of the sequences in the sequence listings (either as the RNA complement to the explicit sequence in the sequence listing or as the RNA version of the sequence in the sequence listing, e.g., of the same sense, but comprised of RNA, with U in place of T, etc.). Thus, depending on context herein, the nucleic acid sequences of the invention can comprise the RNA versions of SEQ ID NO: 1-48 (either in positive stranded sense or in negative stranded sense).

Cell Culture and Expression Hosts

The present invention also relates to host cells that are introduced (transduced, transformed or transfected) with vectors of the invention, and the production of polypeptides of the invention by recombinant techniques. Host cells are genetically engineered (i.e., transduced, transformed or transfected) with a vector, such as an expression vector, of this invention. As described above, the vector can be in the form of a plasmid, a viral particle, a phage, etc. Examples of appropriate expression hosts include: bacterial cells, such as *E. coli, Streptomyces,* and *Salmonella typhimurium;* fungal cells, such as *Saccharomyces cerevisiae, Pichia pastoris,* and *Neurospora crassa;* or insect cells such as *Drosophila* and *Spodoptera frugiperda.*

Most commonly, mammalian cells are used to culture the HA and NA molecules of the invention. Suitable host cells for the replication of influenza virus (e.g., with the HA and/or NA sequences herein) include, e.g., Vero cells, BHK cells, MDCK cells, 293 cells and COS cells, including 293T cells, COS7 cells or the like. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

The engineered host cells can be cultured in conventional nutrient media modified as appropriate for activating promoters, selecting transformants, or amplifying the inserted polynucleotide sequences, e.g., through production of viruses. The culture conditions, such as temperature, pH and the like, are typically those previously used with the particular host cell selected for expression, and will be apparent to those skilled in the art and in the references cited herein, including, e.g., Freshney (1994) *Culture of Animal Cells, a Manual of Basic Technique*, 3$^{rd}$ edition, Wiley-Liss, New York and the references cited therein. Other helpful references include, e.g., Paul (1975) *Cell and Tissue Culture*, 5$^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. in Cohen and Shafferman (eds.) *Novel Strategies in Design and Production of Vaccines*, which is incorporated herein in its entirety for all purposes. Additionally, variations in such procedures adapted to the present invention are readily determined through routine experimentation and will be familiar to those skilled in the art.

Cells for production of influenza virus (e.g., having the HA and/or NA sequences of the invention) can be cultured in serum-containing or serum free medium. In some cases, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent multi plasmid systems (see, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some embodiments herein (e.g., wherein reassorted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reassorted viruses, etc. Thus, in one example, approximately 1 µg of each vector is introduced into a population of host cells with approximately 2 µl of TransIT-LT1 diluted in 160 µl medium, preferably serum-free medium, in a total volume of 200 µl. The DNA:transfection reagent mixtures are incubated at room temperature for 45 minuets followed by addition of 800 µl of medium. The transfection mixture is added to the host cells, and the cells are cultured as described via other methods well known to those skilled in the art. Accordingly, for the production of recombinant or reassortant viruses in cell culture, vectors incorporating each of the 8 genome segments, (PB2, PB1, PA, NP, M, NS, HA and NA, e.g., of the invention) are mixed with approximately 20 µl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza genome segments into host cells. For example, plasmid vectors incorporating an influenza A or influenza B virus are favorably introduced into Vero cells using electroporation according to the following procedure. In brief, approximately $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 µl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In mammalian host cells, a number of expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing the polypeptides of interest in infected host cells (Logan and Shenk (1984) *Proc Natl Acad Sci* 81:3655-3659). In addition, transcription enhancers, such as the rous sarcoma virus (RSV) enhancer, can be used to increase expression in mammalian host cells.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing, which cleaves a precursor form into a mature form, of the protein is sometimes important for correct insertion, folding and/or function. Additionally proper location within a host cell (e.g., on the cell surface) is also important. Different host cells such as COS, CHO, BHK, MDCK, 293, 293T, COS7, etc. have specific cellular machinery and characteristic mechanisms for such post-translational activities and can be chosen to ensure the correct modification and processing of the current introduced, foreign protein.

For long-term, high-yield production of recombinant proteins encoded by, or having subsequences encoded by, the polynucleotides of the invention, stable expression systems are optionally used. For example, cell lines, stably expressing a polypeptide of the invention, are transfected using expression vectors that contain viral origins of replication or endogenous expression elements and a selectable marker gene. For example, following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Thus, resistant clumps of stably transformed cells, e.g., derived from single cell type, can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The cells expressing said protein can be sorted, isolated and/or purified. The protein or fragment thereof produced by a recombinant cell can be secreted, membrane-bound, or retained intracellularly, depending on the sequence (e.g., depending upon fusion proteins encoding a membrane retention signal or the like) and/or the vector used.

Expression products corresponding to the nucleic acids of the invention can also be produced in non-animal cells such as plants, yeast, fungi, bacteria and the like. In addition to Sambrook, Berger and Ausubel, all infra, details regarding cell culture can be found in Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture; Fundamental Methods* Springer Lab Manual, Springer-Verlag (Berlin Heidelberg New York) and Atlas and Parks (eds.) *The Handbook of Microbiological Media* (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors that direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., sequences comprising those found herein, etc., can be ligated into the vector in-frame with sequences for the amino-terminal translation initiating methionine and the subsequent 7 residues of beta-galactosidase producing a catalytically active beta galactosidase fusion protein; pIN vectors (Van Heeke & Schuster (1989) *J Biol Chem* 264:5503-5509); pET vectors (Novagen, Madison Wis.); and the like. Similarly, in the yeast *Saccharomyces cerevisiae* a number of vectors containing constitutive or inducible promoters such as alpha factor, alcohol oxidase and PGH can be used for production of the desired expression products. For reviews, see Ausubel, infra, and Grant et al., (1987); *Methods in Enzymology* 153: 516-544.

Nucleic Acid Hybridization

Comparative hybridization can be used to identify nucleic acids of the invention, including conservative variations of nucleic acids of the invention. This comparative hybridization method is a preferred method of distinguishing nucleic acids of the invention. In addition, target nucleic acids which hybridize to the nucleic acids represented by, e.g., SEQ ID NO:1 through SEQ ID NO:48 under high, ultra-high and ultra-ultra-high stringency conditions are features of the invention. Examples of such nucleic acids include those with one or a few silent or conservative nucleic acid substitutions as compared to a given nucleic acid sequence.

A test target nucleic acid is said to specifically hybridize to a probe nucleic acid when it hybridizes at least one-half as well to the probe as to the perfectly matched complementary target, i.e., with a signal to noise ratio at least one-half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well-characterized physico-chemical forces, such as hydrogen bonding, solvent exclusion, base stacking and the like. Numerous protocols for nucleic acid hybridization are well known in the art. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in Ausubel, Sambrook, and Berger and Kimmel, all below. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions comprises a 0.2×SSC wash at 65° C. for 15 minutes (see, Sambrook, infra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

After hybridization, unhybridized nucleic acids can be removed by a series of washes, the stringency of which can be adjusted depending upon the desired results. Low stringency washing conditions (e.g., using higher salt and lower temperature) increase sensitivity, but can produce nonspecific hybridization signals and high background signals. Higher stringency conditions (e.g., using lower salt and higher temperature that is closer to the $T_m$) lower the background signal, typically with primarily the specific signal remaining. See, also, Rapley, R. and Walker, J. M. eds., *Molecular Biomethods Handbook* (Humana Press, Inc. 1998).

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra, and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the hybridization and wash conditions are gradually increased until a probe binds to a perfectly matched complementary target with a signal to noise ratio that is at least 5× as high as that observed for hybridization of the probe to an unmatched target.

In general, a signal to noise ratio of at least 2× (or higher, e.g., at least 5×, 10×, 20×, 50×, 100×, or more) than that observed for an unrelated probe in the particular hybridization assay indicates detection of a specific hybridization. Detection of at least stringent hybridization between two sequences in the context of the present invention indicates relatively strong structural similarity to, e.g., the nucleic acids of the present invention provided in the sequence listings herein.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any unmatched target nucleic acids. A target nucleic acid which hybridizes to a probe under such conditions, with a signal to noise ratio of at least one-half that of the perfectly matched complementary target nucleic acid is said to bind to the probe under ultra-high stringency conditions.

In determining stringent or highly stringent hybridization (or even more stringent hybridization) and wash conditions, the hybridization and wash conditions are gradually increased (e.g., by increasing temperature, decreasing salt concentration, increasing detergent concentration and/or increasing the concentration of organic solvents, such as formamide, in the hybridization or wash), until a selected set of criteria are met. For example, the hybridization and wash conditions are gradually increased until a probe comprising one or more polynucleotide sequences of the invention, e.g., sequences or unique subsequences selected from those given herein and/or complementary polynucleotide sequences, binds to a perfectly matched complementary target (again, a nucleic acid comprising one or more nucleic acid sequences or subsequences selected from those given herein and/or complementary polynucleotide sequences thereof), with a signal to noise ratio that is at least 2× (and optionally 5×, 10×, or 100× or more) as high as that observed for hybridization of the probe to an unmatched target (e.g., a polynucleotide sequence comprising one or more sequences or subsequences selected from known influenza sequences present in public databases such as GenBank at the time of filing, and/or complementary polynucleotide sequences thereof), as desired.

Using the polynucleotides of the invention, or subsequences thereof, novel target nucleic acids can be obtained; such target nucleic acids are also a feature of the invention. For example, such target nucleic acids include sequences that hybridize under stringent conditions to a unique oligonucleotide probe corresponding to any of the polynucleotides of the invention.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any unmatched target nucleic acids. The particular signal will depend on the label used in the relevant assay, e.g., a fluorescent label, a colorimetric label, a radioactive label, or the like. A target nucleic acid which hybridizes to a probe under such conditions, with a signal to noise ratio of at least one-half that of the perfectly matched complementary target nucleic acid, is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Cloning, Mutagenesis and Expression of Biomolecules of Interest

General texts which describe molecular biological techniques, which are applicable to the present invention, such as cloning, mutation, cell culture and the like, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related to, e.g., the generation of HA and/or NA molecules, etc.

Various types of mutagenesis are optionally used in the present invention, e.g., to produce and/or isolate, e.g., novel or newly isolated HA and/or NA molecules and/or to further modify/mutate the polypeptides (e.g., HA and NA molecules) of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications (and references cited within): Sieber, et al., *Nature Biotechnology*, 19:456-460 (2001); Ling et al., Approaches to DNA mutagenesis: an overview, *Anal Biochem* 254(2): 157-178 (1997); Dale et al., Oligonucleotide-directed random mutagenesis using the phosphorothioate method, *Methods Mol Biol* 57:369-374 (1996); I. A. Lorimer, I. Pastan, *Nucleic Acids Res* 23, 3067-8 (1995); W. P. C. Stemmer, *Nature* 370, 389-91 (1994); Arnold, Protein engineering for unusual environments, *Current Opinion in Biotechnology* 4:450-455 (1993); Bass et al., Mutant Trp repressors with new DNA-binding specificities, *Science* 242:240-245 (1988); Fritz et al., Oligonucleotide-directed construction of mutations: a gapped duplex DNA procedure without enzymatic reactions in vitro, *Nucl Acids Res* 16: 6987-6999 (1988); Kramer et al., Improved enzymatic in vitro reactions in the gapped duplex DNA approach to oligonucleotide-directed construction of mutations, *Nucl Acids Res* 16: 7207 (1988); Sakamar and Khorana, Total synthesis and expression of a gene for the a-subunit of bovine rod outer segment guanine nucleotide-binding protein (transducin), *Nucl Acids Res* 14: 6361-6372 (1988); Sayers et al., Y-T Exonucleases in phosphorothioate-based oligonucleotide-directed mutagenesis, *Nucl Acids Res* 16:791-802 (1988); Sayers et al., Strand specific cleavage of phosphorothioate-containing DNA by reaction with restriction endonucleases in the presence of ethidium bromide, (1988) *Nucl Acids Res* 16: 803-814; Carter, Improved oligonucleotide-directed mutagenesis using M13 vectors, *Methods in Enzymol* 154: 382-403 (1987); Kramer & Fritz Oligonucleotide-directed construction of mutations via gapped duplex DNA, *Methods in Enzymol* 154:350-367 (1987); Kunkel, The efficiency of oligonucleotide directed mutagenesis, in *Nucleic Acids & Molecular Biology* (Eckstein, F. and Lilley, D. M. J. eds., Springer Verlag, Berlin)) (1987); Kunkel et al., Rapid and efficient site-specific mutagenesis without phenotypic selection, *Methods in Enzymol* 154, 367-382 (1987); Zoller & Smith, Oligonucleotide-directed mutagenesis: a simple method using two oligonucleotide primers and a single-stranded DNA template, *Methods in Enzymol* 154: 329-350 (1987); Carter, Site-directed mutagenesis, *Biochem J* 237:1-7 (1986); Eghtedarzadeh & Henikoff, Use of oligonucleotides to generate large deletions, *Nucl Acids Res* 14: 5115 (1986); Mandecki, Oligonucleotide-directed double-strand break repair in plasmids of *Escherichia coli:* a method for site-specific mutagenesis, *Proc Natl Acad Sci USA*, 83:7177-7181 (1986); Nakamaye & Eckstein, Inhibition of restriction endonuclease Nci I cleavage by phosphorothioate groups and its application to oligonucleotide-directed mutagenesis, *Nucl Acids Res* 14: 9679-9698 (1986); Wells et al., Importance of hydrogen-bond formation in stabilizing the transition state of subtilisin, *Phil Trans R Soc Lond* A 317: 415-423 (1986); Botstein & Shortle, Strategies and applications of in vitro mutagenesis, *Science* 229:1193-1201(1985); Carter et al., Improved oligonucleotide site-directed mutagenesis using M13 vectors, *Nucl Acids Res* 13: 4431-4443 (1985); Grundström et al., Oligonucleotide-directed mutagenesis by microscale 'shot-gun' gene synthesis, *Nucl Acids Res* 13: 3305-3316 (1985); Kunkel, Rapid and efficient site-specific mutagenesis without phenotypic selection, *Proc Natl Acad Sci USA* 82:488-492 (1985); Smith, In vitro mutagenesis, *Ann Rev Genet* 19:423-462(1985); Taylor et al., The use of phosphorothioate-modified DNA in restriction enzyme reactions to prepare nicked DNA, *Nucl Acids Res* 13: 8749-8764 (1985); Taylor et al., The rapid generation of oligonucleotide-directed mutations at high frequency using phosphorothioate-modified DNA, *Nucl Acids Res* 13: 8765-8787 (1985); Wells et al., Cassette mutagenesis: an efficient method for generation of multiple mutations at defined sites, *Gene* 34:315-323 (1985); Kramer et al., The gapped duplex DNA approach to oligonucleotide-directed mutation construction, *Nucl Acids Res* 12: 9441-9456 (1984); Kramer et al., Point Mismatch Repair, *Cell* 38:879-887 (1984); Nambiar et al., Total synthesis and cloning of a gene coding for the ribonuclease S protein, *Science* 223: 1299-1301 (1984); Zoller & Smith, Oligonucleotide-directed mutagenesis of DNA fragments cloned into M13 vectors, *Methods in Enzymol* 100:468-500 (1983); and Zoller & Smith, Oligonucleotide-directed mutagenesis using M13-derived vectors: an efficient and general procedure for the production of point mutations in any DNA fragment, *Nucl Acids Res* 10:6487-6500 (1982). Additional details on many of the above methods can be found in *Methods in Enzymol Volume* 154, which also describes useful controls for trouble-shooting problems with various mutagenesis, gene isolation, expression, and other methods.

Oligonucleotides, e.g., for use in mutagenesis of the present invention, e.g., mutating libraries of the HA and/or NA molecules of the invention, or altering such, are typically synthesized chemically according to the solid phase phosphoramidite triester method described by Beaucage and Caruthers, *Tetrahedron Letts* 22(20):1859-1862, (1981) e.g., using an automated synthesizer, as described in Needham-VanDevanter et al., *Nucleic Acids Res,* 12:6159-6168(1984).

In addition, essentially any nucleic acid can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, peptides and antibodies can be custom ordered from any of a variety of sources, such as PeptidoGenic (available at pkim@ccnet.com), HTI Bio-products, Inc. (www.htibio.com), BMA Biomedicals Ltd. (U.K.), Bio. Synthesis, Inc., and many others.

The present invention also relates to host cells and organisms comprising a HA and/or NA molecule or other polypeptide and/or nucleic acid of the invention or such HA and/or NA or other sequences within various vectors such as 6:2 reassortant influenza viruses, plasmids in plasmid rescue systems, etc. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (see, From et al., *Proc Natl Acad Sci USA* 82, 5824 (1985), infection by viral vectors, high velocity ballistic penetration by small particles with the nucleic acid either within the matrix of small beads or particles, or on the surface (Klein et al., *Nature* 327, 70-73 (1987)). Berger, Sambrook, and Ausubel provide a variety of appropriate transformation methods. See, above.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr Purif* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds.) published by the ATCC. Additional basic procedures for sequencing, cloning and other aspects of molecular biology and underlying theoretical considerations are also found in Watson et al. (1992) *Recombinant DNA Second Edition* Scientific American Books, NY. See, above.

Polypeptide Production and Recovery

In some embodiments, following transduction of a suitable host cell line or strain and growth of the host cells to an appropriate cell density, a selected promoter is induced by appropriate means (e.g., temperature shift or chemical induction) and cells are cultured for an additional period. In some embodiments, a secreted polypeptide product, e.g., a HA and/or NA polypeptide as in a secreted fusion protein form, etc., is then recovered from the culture medium. In other embodiments, a virus particle containing one or more HA and/or NA polypeptide of the invention is produced from the cell. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art. Additionally, cells expressing a HA and/or a NA polypeptide product of the invention can be utilized without separating the polypeptide from the cell. In such situations, the polypeptide of the invention is optionally expressed on the cell surface and is examined thus (e.g., by having HA and/or NA molecules, or fragments thereof, e.g., comprising fusion proteins or the like) on the cell surface bind antibodies, etc. Such cells are also features of the invention.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems known to those skilled in the art), hydroxylapatite chromatography, and lectin chromatography. Protein refolding steps can be used, as desired, in completing configuration of the mature protein. Also, high performance liquid chromatography (HPLC) can be employed in the final purification steps. In addition to the references noted herein, a variety of purification methods are well known in the art, including, e.g., those set forth in Sandana (1997) *Bioseparation of Proteins*, Academic Press, Inc.; and Bollag et al. (1996) *Protein Methods, 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* $3^{rd}$ *Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

When the expressed polypeptides of the invention are produced in viruses, the viruses are typically recovered from the culture medium, in which infected (transfected) cells have been grown. Typically, crude medium is clarified prior to concentration of influenza viruses. Common methods include ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large-scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. Vaccine Production, in Nicholson et al. (eds.) *Textbook of Influenza* pp. 324-332; Merten et al. (1996) Production of influenza virus in cell cultures for vaccine preparation, in Cohen & Shafferman (eds.) *Novel Strategies in Design and Production of Vaccines* pp. 141-151, and U.S. Pat. No. 5,690,937. If desired, the recovered viruses can be stored at −80° C. in the presence of sucrose-phosphate-glutamate (SPG) as a stabilizer Alternatively, cell-free transcription/translation systems can be employed to produce polypeptides comprising an amino acid sequence or subsequence of, e.g., SEQ ID NO:49 through SEQ ID NO:96, or encoded by the polynucleotide sequences of the invention. A number of suitable in vitro transcription and translation systems are commercially available. A general guide to in vitro transcription and translation protocols is found in Tymms (1 995) *In vitro Transcription and Translation Protocols: Methods in Molecular Biology* Volume 37, Garland Publishing, NY.

In addition, the polypeptides, or subsequences thereof, e.g., subsequences comprising antigenic peptides, can be produced manually or by using an automated system, by direct peptide synthesis using solid-phase techniques (see, Stewart et al. (1969) *Solid-Phase Peptide Synthesis,* WH Freeman Co, San Francisco; Merrifield J (1963) *J Am Chem Soc* 85:2149-2154). Exemplary automated systems include the Applied Biosystems 431A Peptide Synthesizer (Perkin Elmer, Foster City, Calif.). If desired, subsequences can be chemically synthesized separately, and combined using chemical methods to provide full-length polypeptides.

Modified Amino Acids

Expressed polypeptides of the invention can contain one or more modified amino acids. The presence of modified amino acids can be advantageous in, for example, (a) increasing polypeptide serum half-life, (b) reducing/increasing polypeptide antigenicity, (c) increasing polypeptide storage stability, etc. Amino acid(s) are modified, for example, co-translationally or post-translationally during recombinant production (e.g., N-linked glycosylation at N-X-S/T motifs during expression in mammalian cells) or modified by synthetic means (e.g., via PEGylation).

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) *Protein Protocols on CD-ROM* Human Press, Towata, N.J.

Fusion Proteins

The present invention also provides fusion proteins comprising fusions of the sequences of the invention (e.g., encoding HA and/or NA polypeptides) or fragments thereof with, e.g., immunoglobulins (or portions thereof), sequences encoding, e.g., GFP (green fluorescent protein), or other similar markers, etc. Nucleotide sequences encoding such fusion proteins are another aspect of the invention. Fusion proteins of the invention are optionally used for, e.g., similar applications (including, e.g., therapeutic, prophylactic, diagnostic, experimental, etc. applications as described herein) as the non-fusion proteins of the invention. In addition to fusion with immunoglobulin sequences and marker sequences, the proteins of the invention are also optionally fused with, e.g., sequences which allow sorting of the fusion proteins and/or targeting of the fusion proteins to specific cell types, regions, etc.

Antibodies

The polypeptides of the invention can be used to produce antibodies specific for the polypeptides given herein and/or polypeptides encoded by the polynucleotides of the invention, e.g., those shown herein, and conservative variants thereof. Antibodies specific for the above mentioned polypeptides are useful, e.g., for diagnostic and therapeutic purposes, e.g., related to the activity, distribution, and expression of target polypeptides. For example, such antibodies can optionally be utilized to define other viruses within the same strain(s) as the HA/NA sequences herein.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production (e.g., full length functional hemagglutinin or neuraminidase is not required). However, the polypeptide or oligopeptide must be antigenic. Peptides used to induce specific antibodies typically have an amino acid sequence of at least about 4 amino acids, and often at least 5 or 10 amino acids. Short stretches of a polypeptide can be fused with another protein, such as keyhole limpet hemocyanin, and antibody produced against the chimeric molecule.

Numerous methods for producing polyclonal and monoclonal antibodies are known to those of skill in the art, and can be adapted to produce antibodies specific for the polypeptides of the invention, and/or encoded by the polynucleotide sequences of the invention, etc. See, e.g., Coligan (1991) *Current Protocols in Immunology* Wiley/Greene, NY; Paul (ed.) (1998) *Fundamental Immunology, Fourth Edition,* Lippincott-Raven, Lippincott Williams & Wilkins; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495-497. Other suitable techniques for antibody preparation include selection of libraries of recombinant antibodies in phage or similar vectors. See, Huse et al. (1989) *Science* 246: 1275-1281; and Ward, et al. (1989) *Nature* 341: 544-546. Specific monoclonal and polyclonal antibodies and antisera will usually bind with a $K_D$ of, e.g., at least about 0.1 μM, at least about 0.01 μM or better, and, typically and at least about 0.001 μM or better.

For certain therapeutic applications, humanized antibodies are desirable. Detailed methods for preparation of chimeric (humanized) antibodies can be found in U.S. Pat. No. 5,482,856. Additional details on humanization and other antibody production and engineering techniques can be found in Borrebaeck (ed.) (1995) *Antibody Engineering, $2^{nd}$ Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul). Additional details regarding specific procedures can be found, e.g., in Ostberg et al. (1983), *Hybridoma* 2: 361-367, Ostberg, U.S. Pat. No. 4,634,664, and Engelman et al., U.S. Pat. No. 4,634,666.

Defining Polypeptides by Immunoreactivity

Because the polypeptides of the invention provide a variety of new polypeptide sequences (e.g., comprising HA and NA molecules), the polypeptides also provide new structural features which can be recognized, e.g., in immunological assays. The generation of antisera which specifically bind the polypeptides of the invention, as well as the polypeptides which are bound by such antisera, are features of the invention.

For example, the invention includes polypeptides (e.g., HA and NA molecules) that specifically bind to or that are specifically immunoreactive with an antibody or antisera generated against an immunogen comprising an amino acid sequence selected from one or more of the sequences given herein such as in SEQ ID NOs: 49-96, etc. To eliminate cross-reactivity with other homologues, the antibody or antisera is subtracted with the HA and/or NA molecules found in public databases at the time of filing, e.g., the "control" polypeptide(s). Where the other control sequences correspond to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to the sequences herein, etc. or a substantial subsequence thereof (i.e., at least about 30% of the full length sequence provided). The set of potential polypeptide immunogens derived from the present sequences are collectively referred to below as "the immunogenic polypeptides." The resulting antisera is optionally selected to have low cross-reactivity against the control hemagglutinin and/or neuraminidase homologues and any such cross-reactivity is removed, e.g., by immunoabsorbtion, with one or more of the control hemagglutinin and neuraminidase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies A Laboratory Manual,* Cold Spring Harbor Publications, New York, for a standard description of antibody generation, immunoassay formats and conditions that can be used to determine specific immunoreactivity). Additional references and discussion of antibodies is also found herein and can be applied here to defining polypeptides by immunoreactivity. Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control hemagglutinin and/or neuraminidase polypeptide(s) to produce subtracted pooled titered polyclonal antisera.

The subtracted pooled titered polyclonal antisera are tested for cross reactivity against the control homologue(s) in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic polypeptides as compared to binding to the control homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control receptor homologues under discriminatory binding conditions, and at least about a ½ signal to noise ratio as compared to the immunogenic polypeptide(s), shares substantial structural similarity with the immunogenic polypeptide as compared to the known receptor, etc., and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control protein(s) to compete for binding to the pooled subtracted antisera is optionally determined as compared to the ability of the immunogenic polypeptide(s) to compete for binding to the antisera. Again, the percent cross-reactivity for the control polypeptide(s) is calculated, using standard calculations. Where the percent cross-reactivity is at least 5-10× as high for the test polypeptides as compared to the control polypeptide(s) and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptide(s)) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Nucleic Acid and Polypeptide Sequence Variants

As described herein, the invention provides for nucleic acid polynucleotide sequences and polypeptide amino acid sequences, e.g., hemagglutinin and neuraminidase sequences, and, e.g., compositions and methods comprising said sequences. Examples of said sequences are disclosed herein. However, one of skill in the art will appreciate that the invention is not necessarily limited to those sequences disclosed herein and that the present invention also provides many related and unrelated sequences with the functions described herein, e.g., encoding a HA and/or a NA molecule.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Silent Variations

Due to the degeneracy of the genetic code, any of a variety of nucleic acid sequences encoding polypeptides and/or viruses of the invention are optionally produced, some which can bear lower levels of sequence identity to the HA and NA nucleic acid and polypeptide sequences herein. The following provides a typical codon table specifying the genetic code, found in many biology and biochemistry texts.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |

TABLE 1-continued

Codon Table

| Amino acids | | | Codon |
|---|---|---|---|
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations," discussed below. One of skill will recognize that each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a hemagglutinin or a neuraminidase polypeptide of the invention. All such variations of every nucleic acid herein are specifically provided and described by consideration of the sequence in combination with the genetic code. One of skill is fully able to make these silent substitutions using the methods herein.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence of the invention which encodes an amino acid. Similarly, "conservative amino acid substitutions," in one or a few amino acids in an amino acid sequence are substituted with different amino acids with highly similar properties, are also readily identified as being highly similar to a disclosed construct such as those herein. Such conservative variations of each disclosed sequence are a feature of the present invention.

"Conservative variation" of a particular nucleic acid sequence refers to those nucleic acids which encode identical or essentially identical amino acid sequences, or, where the nucleic acid does not encode an amino acid sequence, to essentially identical sequences, see, Table 2 below. One of skill will recognize that individual substitutions, deletions or additions which alter, add or delete a single amino acid or a small percentage of amino acids (typically less than 5%, more typically less than 4%, 3%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 4%, 3%, 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

TABLE 2

| Conservative Substitution Groups | | | |
|---|---|---|---|
| 1 Alanine (A) | Serine (S) | Threonine (T) | |
| 2 Aspartic acid (D) | Glutamic acid (E) | | |
| 3 Asparagine (N) | Glutamine (Q) | | |
| 4 Arginine (R) | Lysine (K) | | |
| 5 Isoleucine (I) | Leucine (L) | Methionine (M) | Valine (V) |
| 6 Phenylalanine (F) | Tyrosine (Y) | Tryptophan (W) | |

Unique Polypeptide and Polynucleotide Subsequences

In one aspect, the invention provides a nucleic acid which comprises a unique subsequence in a nucleic acid selected from the sequence of HA and NA molecules disclosed herein (e.g., SEQ ID NO:1-48). The unique subsequence is unique as compared to a nucleic acids corresponding to nucleic acids such as, e.g., those found in GenBank or other similar public databases at the time of filing (e.g., other known or characterized hemagglutinin and/or neuraminidase nucleic acid molecules). Alignment can be performed using, e.g., BLAST set to default parameters. Any unique subsequence is useful, e.g., as a probe to identify the nucleic acids of the invention. See, above.

Similarly, the invention includes a polypeptide (e.g., from SEQ ID NO:49 through 96) which comprises a unique subsequence in a polypeptide selected from the sequence of HA and NA molecules disclosed herein. Here, the unique subsequence is unique as compared to a polypeptide corresponding to, e.g., the amino acid corresponding to polynucleotide sequences found in, e.g., GenBank or other similar public databases at the time of filing.

The invention also provides for target nucleic acids which hybridize under stringent conditions to a unique coding oligonucleotide which encodes a unique subsequence in a polypeptide selected from the sequences of HA and NA molecules of the invention wherein the unique subsequence is unique as compared to a polypeptide corresponding to any of the control polypeptides (sequences of, e.g., the nucleic acids corresponding to those found in, e.g., GenBank or other similar public databases at the time of filing). Unique sequences are determined as noted above. The polynucleotides of the invention also comprise RNA (both positive sense and negative sense) versions of the sequences of the sequence listing. See above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs and/or RNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the amino acid sequences that is at least about 200 residues in length, more preferably over a region of at least about 250 residues, and most preferably the sequences are substantially identical over at least about 300 residues, 350 residues, 400 residues, 425 residues, 450 residues, 475 residues, 480 residues, 490 residues, 495 residues, 499 residues, 500 residues, 502 residues, 559 residues, 565 residues, or 566 residues, or over the full length of the two sequences to be compared when the amino acids are hemagglutinin or hemagglutinin fragments or which is substantially identical over at least about 350 amino acids; over at least about 400 amino acids; over at least about over at least about 436 amino acids, over at least about 450 amino acids; over at least about 451 amino acids; over at least about 465 amino acids; over at least about 466 amino acids; over at least about 469 amino acids; over at least about 470 amino acids; or over at least about 566 amino acids contiguous when the amino acid is neuraminidase or a neuraminidase fragment.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv Appl Math* 2:482 (1981), by the homology alignment algorithm of Needleman & Wunsch, *J Mol Biol* 48:443 (1970), by the search for similarity method of Pearson & Lipman, *Proc Natl Acad Sci USA* 85:2444 (1988), by computerized implementations of algorithms such as GAP, BESTFIT, FASTA, and TFASTA in the Wisconsin Genetics Software Package, Genetics Computer Group, 575 Science Dr., Madison, Wis., or by visual inspection (see generally, Ausubel et al., supra).

One example of an algorithm that is suitable for determining percent sequence identity and sequence similarity is the BLAST algorithm, which is described in Altschul et al., *J Mol Biol* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (see, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc Natl Acad Sci USA* 89:10915).

In addition to calculating percent sequence identity, the BLAST algorithm also performs a statistical analysis of the similarity between two sequences (see, e.g., Karlin & Altschul, *Proc Natl Acad Sci USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) *CABIOS* 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple nucleic acid, or amino acid, sequence alignments is the CLUSTALW program (Thompson, J. D. et al. (1994) *Nucl. Acids. Res.* 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) *Proc. Natl. Acad. Sci. USA* 89: 10915-10919.

Digital Systems

The present invention provides digital systems, e.g., computers, computer readable media and integrated systems comprising character strings corresponding to the sequence information herein for the nucleic acids and isolated or recombinant polypeptides herein, including, e.g., the sequences shown herein, and the various silent substitutions and conservative substitutions thereof. Integrated systems can further include, e.g., gene synthesis equipment for making genes corresponding to the character strings.

Various methods known in the art can be used to detect homology or similarity between different character strings (see above), or can be used to perform other desirable functions such as to control output files, provide the basis for making presentations of information including the sequences and the like. Examples include BLAST, discussed supra. Computer systems of the invention can include such programs, e.g., in conjunction with one or more data file or data base comprising a sequence as noted herein.

Thus, different types of homology and similarity of various stringency and length between various HA or NA sequences or fragments, etc. can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among four principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.).

Thus, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™, Paradox™, GeneWorks™, or MacVector™ or other similar programs) can be adapted to the present invention by inputting a character string corresponding to one or more polynucleotides and polypeptides of the invention (either nucleic acids or proteins, or both). For example, a system of the invention can include the foregoing software having the appropriate character string information, e.g., used in conjunction with a user interface (e.g., a GUI in a standard operating system such as a Windows, Macintosh or LINUX system) to manipulate strings of characters corresponding to the sequences herein. As noted, specialized alignment programs such as BLAST can also be incorporated into the systems of the invention for alignment of nucleic acids or proteins (or corresponding character strings).

Systems in the present invention typically include a digital computer with data sets entered into the software system comprising any of the sequences herein. The computer can be, e.g., a PC (Intel x86 or Pentium chip-compatible DOS™, OS2™ WINDOWS™ WINDOWSNT™, WINDOWS95™, WINDOWS2000™, WINDOWS98™, LINUX based machine, a MACINTOSH™, Power PC, or a UNIX based (e.g., SUN™ work station) machine) or other commercially available computer that is known to one of skill. Software for aligning or otherwise manipulating sequences is available, or can easily be constructed by one of skill using a standard programming language such as Visualbasic, PERL, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation, e.g., of appropriate mechanisms or transport controllers to carry out the desired operation. The software can also include output elements for controlling nucleic acid synthesis (e.g., based upon a sequence or an alignment of sequences herein), comparisons of samples for differential gene expression, or other operations.

Kits and Reagents

The present invention is optionally provided to a user as a kit. For example, a kit of the invention contains one or more nucleic acid, polypeptide, antibody, or cell line described herein (e.g., comprising, or with, a HA and/or NA molecule of the invention). The kit can contain a diagnostic nucleic acid or polypeptide, e.g., antibody, probe set, e.g., as a cDNA microarray packaged in a suitable container, or other nucleic acid such as one or more expression vector. The kit typically further comprises, one or more additional reagents, e.g., substrates, labels, primers, for labeling expression products, tubes and/or other accessories, reagents for collecting samples, buffers, hybridization chambers, cover slips, etc. The kit optionally further comprises an instruction set or user manual detailing preferred methods of using the kit components for discovery or application of diagnostic sets, etc.

When used according to the instructions, the kit can be used, e.g., for evaluating a disease state or condition, for evaluating effects of a pharmaceutical agent or other treatment intervention on progression of a disease state or condition in a cell or organism, or for use as a vaccine, etc.

In an additional aspect, the present invention provides system kits embodying the methods, composition, systems and apparatus herein. System kits of the invention optionally comprise one or more of the following: (1) an apparatus, system, system component or apparatus component; (2) instructions for practicing methods described herein, and/or for operating the apparatus or apparatus components herein and/or for using the compositions herein. In a further aspect, the present invention provides for the use of any apparatus, apparatus component, composition or kit herein, for the practice of any method or assay herein, and/or for the use of any apparatus or kit to practice any assay or method herein.

Additionally, the kits can include one or more translation system as noted above (e.g., a cell) with appropriate packaging material, containers for holding the components of the kit, instructional materials for practicing the methods herein and/or the like. Similarly, products of the translation systems (e.g., proteins such as HA and/or NA molecules) can be provided in kit form, e.g., with containers for holding the components of the kit, instructional materials for practicing the methods herein and/or the like. Furthermore, the kits can comprise various vaccines (e.g., produced through plasmid rescue protocols) such as live attenuated vaccine (e.g., FluMist™) comprising the HA and/or NA sequences herein. 10197] To facilitate use of the methods and compositions of the invention, any of the vaccine components and/or compositions, e.g., reassorted virus in allantoic fluid, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A reassortant influenza virus comprising a polynucleic selected from the group consisting of:
   a) a polynucleotide sequence of one of SEQ ID NO:35, or a complementary sequence thereof; and
   b) a polynucleotide sequence encoding a polypeptide comprising the amino acid sequence of SEQ ID NO:83, or a complementary polynucleotide sequence thereof.

2. The virus of claim 1, wherein the virus is a 6:2 reassortant virus.

3. The virus of claim 2, wherein the donor virus is A/Ann Arbor/6/60, or A/Puerto Rico/8/34.

4. An immunogenic composition comprising an immunologically effective amount of the recombinant influenza virus of claim 2.

5. The virus of claim 1, wherein the virus is a 7:1 reassortment virus, which virus comprises 7 genomic segments from one or more donor virus and 1 genomic segment comprising a polynucleotide comprising the nucleotide sequence of SEQ ID NO:35.

6. The virus of claim 1, wherein the virus is one or more of: a temperature-sensitive virus, a cold-adapted virus, or an attenuated virus.

7. The virus of claim 5, wherein the donor virus is A/Ann Arbor/6/60, or A/Puerto Rico/8/34.

8. The virus of claim 2, wherein the 6:2 reassortant virus is a live virus.

9. A method for producing the reassortant influenza virus of claim 1 comprising:
   introducing a plurality of vectors comprising nucleic acids corresponding to an influenza virus genome into a population of host cells, which plurality comprises at least 6 internal genomic segments of a first influenza strain, and at least one genomic segment of a second influenza strain, wherein the at least one genomic segment of the second influenza strain comprises a polynucleotide comprising the nucleotide sequence of SEQ ID NO:35, and wherein the population of host cells is capable of supporting replication of influenza virus;
   culturing the population of host cells; and
   recovering a plurality of influenza viruses.

10. The method of claim 9, wherein the first influenza virus strain is at least one of: an attenuated influenza virus strain, a cold-adapted influenza virus strain, and a temperature-sensitive influenza virus strain.

11. The method of claim 9, wherein the influenza viruses are suitable for administration in an intranasal vaccine formulation.

12. The method of claim 9, wherein the plurality of vectors comprising the influenza genome comprise genomic segments of an influenza A genome.

13. The method of claim 9, wherein the first influenza strain is selected from the group consisting of A/Ann Arbor/6/60, or A/Puerto Rico/8/34.

14. The method of claim 9, wherein the plurality of vectors are plasmid vectors.

15. The method of claim 9, wherein the population of host cells comprises one or more of: Vero cells, PerC6 cells, MDCK cells, 293T cells, or COS cells.

16. The method of claim 9, wherein the method does not comprise use of a helper virus.

17. The method of claim 9, wherein the plurality of vectors consists of eight vectors.

18. A vaccine comprising the immunogenic composition of claim 4.

* * * * *

UNITED STATES PATENT AND TRADEMARK OFFICE
CERTIFICATE OF CORRECTION

PATENT NO. : 7,459,162 B2  Page 1 of 1
APPLICATION NO. : 11/368246
DATED : December 2, 2008
INVENTOR(S) : Chin-Fen Yang et al.

It is certified that error appears in the above-identified patent and that said Letters Patent is hereby corrected as shown below:

Column 6 at Line 5:

"PerC6 cells," should read -- PER.C6 cells (deposited under ECACC No. 96022940), --

Claim 1 at Column 259, Line 31:

"a polynucleotide sequence of one of SEQ ID NO:35" should read -- a polynucleotide comprising the nucleotide sequence of SEQ ID NO:35 --

Claim 15 at Column 260, Line 51:

"PerC6 cells" should read -- cells deposited under ECACC No. 96022940 --

Signed and Sealed this

Twenty-seventh Day of January, 2009

JOHN DOLL
*Acting Director of the United States Patent and Trademark Office*